US012466809B2

(12) United States Patent
Gray et al.

(10) Patent No.: US 12,466,809 B2
(45) Date of Patent: Nov. 11, 2025

(54) CDK2/5 DEGRADERS AND USES THEREOF

(71) Applicant: DANA-FARBER CANCER INSTITUTE, INC., Boston, MA (US)

(72) Inventors: Nathanael Gray, Stanford, CA (US); Nicholas Kwiatkowski, Brookline, MA (US); Eric Fischer, Chestnut Hill, MA (US); Katherine Donovan, Boston, MA (US); Tinghu Zhang, Brookline, MA (US); Mingxing Teng, Boston, MA (US); Jie Jiang, Brookline, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 1023 days.

(21) Appl. No.: 17/442,923

(22) PCT Filed: Apr. 2, 2020

(86) PCT No.: PCT/US2020/026411

§ 371 (c)(1),
(2) Date: Sep. 24, 2021

(87) PCT Pub. No.: WO2020/206137

PCT Pub. Date: Oct. 8, 2020

(65) Prior Publication Data

US 2022/0153722 A1 May 19, 2022

Related U.S. Application Data

(60) Provisional application No. 62/981,334, filed on Feb. 25, 2020, provisional application No. 62/829,302, filed on Apr. 4, 2019.

(51) Int. Cl.
*C07D 401/14* (2006.01)
*A61K 47/55* (2017.01)
*C07D 417/12* (2006.01)

(52) U.S. Cl.
CPC ............ *C07D 401/14* (2013.01); *A61K 47/55* (2017.08); *C07D 417/12* (2013.01)

(58) Field of Classification Search
CPC ..... C07D 417/12; C07D 401/14; A61K 47/55
USPC .......................................................... 514/275
See application file for complete search history.

(56) References Cited

U.S. PATENT DOCUMENTS

| | | | | |
|---|---|---|---|---|
| 7,598,260 B2 * | 10/2009 | Brumby | ............... | C07D 405/12 544/323 |
| 10,865,204 B2 * | 12/2020 | Gray | ....................... | A61P 37/00 |
| 2003/0149064 A1 | 8/2003 | Pease et al. | | |
| 2006/0111378 A1 | 5/2006 | Cleve et al. | | |
| 2017/0065719 A1 | 3/2017 | Qian et al. | | |
| 2017/0121321 A1 | 5/2017 | Crews et al. | | |

FOREIGN PATENT DOCUMENTS

| | | | | |
|---|---|---|---|---|
| WO | 2003076437 A1 | 9/2003 | | |
| WO | 2006034872 A1 | 4/2006 | | |
| WO | WO2015031666 * | 3/2015 | ........... | A61K 31/519 |
| WO | 2017185023 A1 | 10/2017 | | |
| WO | 2017185034 A1 | 10/2017 | | |
| WO | WO-2017185031 A1 * | 10/2017 | ........... | C07D 471/04 |
| WO | 2017197055 A1 | 11/2017 | | |

OTHER PUBLICATIONS

Locking et al., "The lab oddity prevails: discovery of pan-CDK inhibitor (R)-S-cyclopropyl-S-(4-{[4-{[(1R,2R)-2-hydroxy-1-methylpropyl]oxy}-5-(trifluoromethyl)pyrimidin-2-yl]amino}phenyl)sulfoximide (BAY 1000394) for the treatment of cancer," ChemMedChem, 2013, vol. 8, pp. 1067-1085.
Huang, et al., "A Chemoproteomic Approach to Query the Degradable Kinome Using a Multi-Kinase Degrader," Cell Chemical Biology, 2018, vol. 25, pp. 88-99.
Teng, M. et al., "Development of CDK2 and CDK5 Dual Degrader TMX-2172", Angew. Chem. Int. Ed. Engl., 2020, vol. 59, No. 33, pp. 13865-13870.
Bekes, M., et al. "PROTAC targetes protein degraders: the past is prologue", Nature Reviews Drug Discovery, 2022, vol. 21, pp. 181-200.
Bondeson, D. P., et al., "Lesson in PROTAC design from selective degradation with promiscuous warhead", Cell Chem. Biol., 2018, vol. 25, No. 1, pp. 78-87.
Li, X., et al., "Protrolysis-targeting chimera (PROTAC) for targeted protein degradation and cancer therapy", Journal of Hematology & Oncology, 2020, vol. 13, No. 50, 14 pages.
Tan, L. et al., "When Kinases Meet PROTACs", Chin. J. Chem., 2018, vol. 36, pp. 971-977.

* cited by examiner

*Primary Examiner* — Jeffrey H Murray
*Assistant Examiner* — Rilla Marie Samsell
(74) *Attorney, Agent, or Firm* — ArentFox Schiff LLP; Daniel W. Clarke; Shawn P. Foley

(57) ABSTRACT

The present invention relates to bifunctional compounds, compositions, and methods for treating diseases or conditions mediated by dysfunctional cyclin-dependent kinase 2 (CDK2) and CDK5 activity.

27 Claims, 6 Drawing Sheets

CDK2/5 DEGRADERS AND USES THEREOF

RELATED APPLICATIONS

This application is a national stage application, filed under 35 U.S.C. § 371, of International Application No. PCT/US2020/026411, filed Apr. 2, 2020, which claims the benefit of priority under 35 U.S.C. § 119 (e) to U.S. Provisional Application No. 62/829,302, filed Apr. 4, 2019 and U.S. Provisional Application No. 62/981,334, filed Feb. 25, 2020, each of which are incorporated herein by reference in their entireties.

GOVERNMENT LICENSE RIGHTS

This invention was made with government support under grant numbers R01 CA218278-02 and P01 CA154303-08 awarded by the National Institutes of Health. The government has certain rights in the invention.

BACKGROUND OF THE INVENTION

Cyclin-dependent kinases (CDK/Cyclins) form a family of heterodimeric kinases that play central roles in regulation of cell cycle progression, transcription, and other major biological processes including neuronal differentiation and metabolism (Malumbres et al., Nat. Rev. Cancer 9:153-166 (2009)). Constitutive or deregulated hyperactivity of these kinases due to amplification, overexpression, or mutation of CDK/cyclins contributes to proliferation of cancer cells. Aberrant activity of these kinases has been reported in a wide variety of human cancers (Peyressatre et al., Cancers 7:179-237 (2015)). These kinases therefore constitute biomarkers of proliferation and attractive pharmacological targets for the development of anticancer therapeutics. The human genome encodes 21 CDKs, although only seven (CDK1-4, CDK6, CDK10, and CDK11) have been shown to have a direct role in the cell cycle progression. Other CDKs play an indirect role via activation of other CDKs (CDK3), regulation of transcription (CDK7-9), and neuronal function (CDK5) (Sinchez-Martinez et al., Bioorganic Med. Chem. Lett. 25:3420-3435 (2015)).

CDK2 functions through a heterodimer composed of its catalytic subunit and one of two activating subunits, cyclin E or cyclin A. The two isoforms of the CDK2 complex have distinct roles during the cell cycle. CDK2/cyclin E is mainly involved in progression through G1/S, centrosome duplication, and DNA replication. CDK2/cyclin A is a key regulator of G2/M progression. Either over-expression of CDK2 or inactivation of its endogenous inhibitors (CIP/KIP family of proteins) is linked to various cancers (Tadesse et al., J. Med. Chem. 10.1021/acs.jmedchem.8b01469 (2018); Lim et al., Development 140:3079-3093 (2013)). One hypothesis is that cancer cells may use CDK2 to take over the function of CDK4/CDK6, which might account for the resistance of current CDK4/CDK6 targeted therapy (Guha, Nat. Rev. Drug Discov. 11:892-894 (2012)).

CDK5 is an atypical cyclin-dependent kinase, best known for its role in the central nervous system (CNS) and regulates development, axon elongation, and neuronal migration. Unlike other CDKs which are activated by cyclins, CDK5 is activated by regulatory proteins p35, p39, and their respective truncated products p25 and p29. The ubiquitously distributed CDK5 is a vital kinase in postmitotic neurons, where it is intrinsically important for various functions and the development of CNS, including neuronal migration, synaptic plasticity, and neuronal survival (Shupp et al., Oncotarget 8:17373-17382 (2017)). Aberrant expression of CDK5 and its activators has been observed in multiple solid and hematological malignancies, but not in normal tissues (Lenjisa et al., Future Med. Chem. 9:1939-1962 (2017); Pozo et al., Trends in Cancer 2:606-618 (2016)). In particular, CDK5 disruption has been shown to attenuate medulloblastoma PD-L1 expression and promote antitumor immunity (Dorand et al., Science 353:399-403 (2016)). Beyond cancer, CDK5 has been demonstrated to play a role in the pathophysiology of common cancer-related co-morbidities such as pain (Pareek et al., Cell Cycle 5:585-588 (2016)), diabetes (Ubeta et al., J. Biol. Chem. 281:28858-28864 (2006)), and neurodegenerative disorders (Su et al., Annu. Rev. Cell Dev. Bio. 27:465-491 (2011)).

Inhibition of CDK activity by small molecules for the treatment of cancer has been widely investigated (Sinchez-Martinez et al., Bioorganic Med. Chem. Lett. 25:3420-3435 (2015); Tadesse et al., J. Med. Chem. 10.1021/acs.jmedchem.8b01469 (2018); Kalra et al., Eur. J. Med. Chem. 142:424-458 (2017)). The common approach to targeting CDKs is through the use of ATP-competitive inhibitors that bind within the catalytic sites of CDKs and outcompete the binding of ATP. Given the fact that CDKs are highly homologous and contain a conserved catalytic core (for example, CDK2 and CDK5 share a sequence homology of 60%, with the substrate binding pocket alone showing nearly 93% sequence similarity), the previously disclosed CDK inhibitors are pan-CDK inhibitors that target most, if not all the members of the family. While they have showed promise in targeting CDKs, the broader-spectrum CDK inhibitors are compromised by significant dose-limited toxicity. CDK1 has proved especially hard to eliminate as an off-target and the resulting CDK1-dependent toxicity narrows the therapeutic window. Many clinical trials of CDK inhibitors were halted in development (Guha, Nat. Rev. Drug Discov. 11:892-894 (2012)).

Accordingly, there is a need for compounds that inhibit specific CDKs while minimizing off-target toxicity, for use in treating diseases such as cancer.

SUMMARY OF THE INVENTION

A bifunctional compound having a structure represented by formula:

(I)

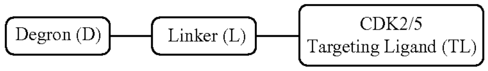

, wherein the targeting ligand represents a moiety that binds cyclin-dependent kinase 2 (CDK2) and cyclin-dependent kinase 5 (CDK5), the degron represents a moiety that binds an E3 ubiquitin ligase, and the linker represents a moiety that covalently connects the degron and the targeting ligand, or a pharmaceutically acceptable salt or stereoisomer thereof.

Another aspect of the present invention is directed to a pharmaceutical composition containing a therapeutically effective amount of the bifunctional compound or a pharmaceutically acceptable salt or stereoisomer thereof, and a pharmaceutically acceptable carrier.

In another aspect of the present invention, methods of making the bifunctional compounds are provided.

A further aspect of the present invention is directed to a method of treating a disease or disorder mediated by dysregulated (e.g., dysfunctional) CDK2 and CDK5 activity, that includes administering a therapeutically effective amount of the bifunctional compound or a pharmaceutically acceptable salt or stereoisomer thereof, to a subject in need thereof.

Without intending to be bound by any particular theory of operation, the bifunctional compounds of formula (I) (also referred to herein as degraders) are believed to promote the dual degradation of CDK2 and CDK5 while substantially sparing other CDK isoforms. By conjugating low nanomole potency of pan-CDK ligands with a E3 ligase binder, these bifunctional compounds are able to fast recruit E3 ligase, and therefore promote the dual degradation of CDK2/5. The degraders achieve high target selectivity beyond that expected from the constitutive binding ligands, thus greatly reducing off-target effect.

Accordingly, the bifunctional compounds of the present invention may serve as a set of new chemical tools for CDK2/5 knockdown, exemplify a broadly applicable approach to arrive at degraders that are selective over non-selective binding ligands, and may provide effective treatments for CDK2/5-mediated diseases and disorders including cancer.

DETAILED DESCRIPTION

Figure 1A:
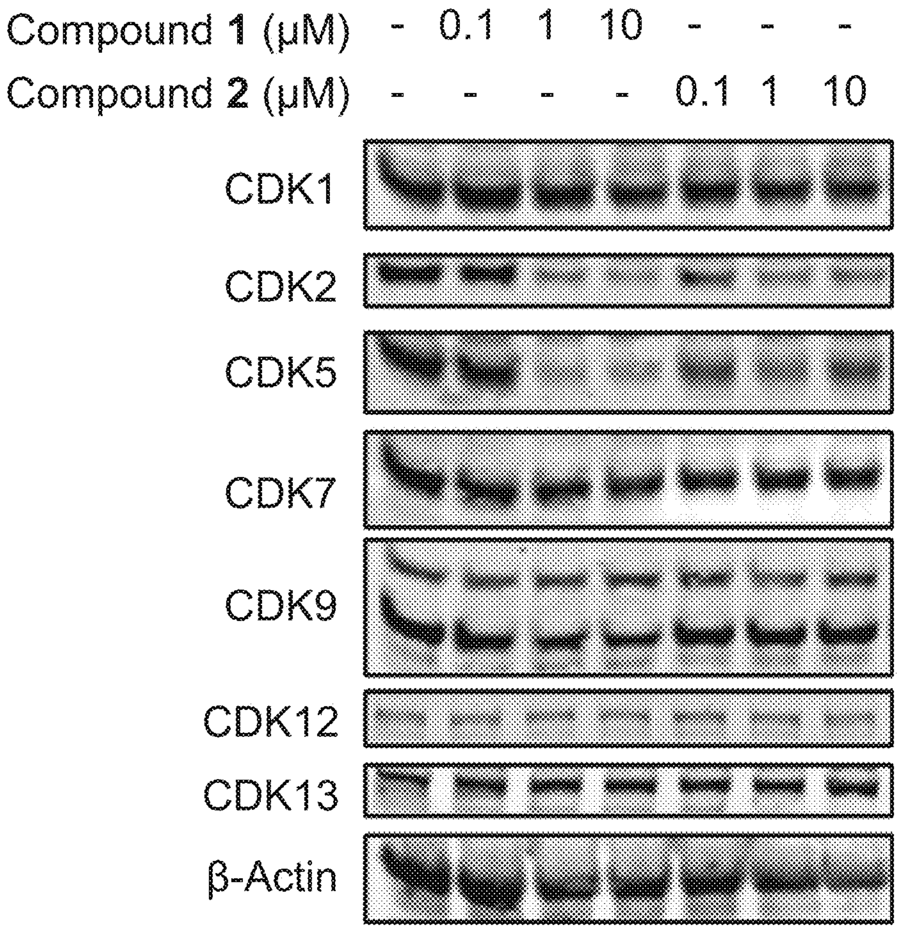
FIG. 1A-FIG. 1C are immunoblots that show the selective knockdown of CDK2/5 in Jurkat cells after 6 hours at various concentrations for inventive compounds 1-4.

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to compounds of the present invention, and to the extent the following terms are used herein to further describe them, the following definitions apply.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

As used herein, the term "alkynyl" refers to a linear or branched monovalent hydrocarbon radical with at least one carbon-carbon triple bond. In one example, the alkynyl radical is a $C_2$-$C_{18}$ group. In other examples, the alkynyl radical is $C_2$-$C_{12}$, $C_2$-$C_{10}$, $C_2$-$C_8$, $C_2$-$C_6$ or $C_2$-$C_3$. Examples include ethynyl prop-1-ynyl, prop-2-ynyl, but-1-ynyl, but-2-ynyl and but-3-ynyl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

As used herein, the term “carbocyclic” (also “carbocyclyl”) refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term “aryl” used alone or as part of a larger moiety (e.g., “aralkyl”, wherein the terminal carbon atom on the alkyl group is the point of attachment, e.g., a benzyl group, “aralkoxy” wherein the oxygen atom is the point of attachment, or “aroxyalkyl” wherein the point of attachment is on the alkyl group) refers to a group that includes monocyclic, bicyclic or tricyclic, carbon ring system, that includes fused rings, wherein at least one ring in the system is aromatic. In some embodiments, the aralkoxy group is a benzoxy group. The term “aryl” may be used interchangeably with the term “aryl ring”. In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term “heterocyclyl” refers to a “carbocyclyl” that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or $S(O)_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$— heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tricyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —$R^c$-heteroaryl, wherein $R^c$ is an alkylene chain as defined above. The term heteroaryl also embraces heteroaralkoxy (or heteroarylalkoxy) groups which as used herein refer to a group bonded through an oxygen atom of the formula —O—$R^c$-heteroaryl, where $R^c$ is an alkylene group as defined above.

Any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1, 2, 3, or 4) heteroatoms such as oxygen, sulfur, and nitrogen grouped in a linear, branched, or cyclic structural format.

Representative examples of substituents may include alkyl, substituted alkyl (e.g., $C_1$-$C_6$, $C_1$-$C_5$, $C_1$-$C_4$, $C_1$-$C_3$, $C_1$-$C_2$, $C_1$), alkoxy (e.g., $C_1$-$C_6$, $C_1$-$C_5$, $C_1$-$C_4$, $C_1$-$C_3$, $C_1$-$C_2$, $C_1$), substituted alkoxy (e.g., $C_1$-$C_6$, $C_1$-$C_5$, $C_1$-$C_4$, $C_1$-$C_3$, $C_1$-$C_2$, $C_1$), haloalkyl (e.g., $CF_3$), alkenyl (e.g., $C_2$-$C_6$, $C_2$-$C_5$, $C_2$-$C_4$, $C_2$-$C_3$, $C_2$), substituted alkenyl (e.g., $C_2$-$C_6$, $C_2$-$C_5$, $C_2$-$C_4$, $C_2$-$C_3$, $C_2$), alkynyl (e.g., $C_2$-$C_6$, $C_2$-$C_5$, $C_2$-$C_4$, $C_2$-$C_3$, $C_2$), substituted alkynyl (e.g., $C_2$-$C_6$, $C_2$-$C_5$, $C_2$-$C_4$, $C_2$-$C_3$, $C_2$), cyclic (e.g., $C_3$-$C_{12}$, $C_5$-$C_6$), substituted cyclic (e.g., $C_3$-$C_{12}$, $C_5$-$C_6$), carbocyclic (e.g., $C_3$-$C_{12}$, $C_5$-$C_6$), substituted carbocyclic (e.g., $C_3$-$C_{12}$, $C_5$-$C_6$), heterocyclic (e.g., $C_3$-$C_{12}$, $C_5$-$C_6$), substituted heterocyclic (e.g., $C_3$-$C_{12}$, $C_5$-$C_6$), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., $C_6$-$C_{12}$, $C_6$), substituted aryloxy (e.g., $C_6$-$C_{12}$, $C_6$), alkylthio (e.g., $C_1$-$C_6$), substituted alkylthio (e.g., C1-C6), arylthio (e.g., $C_6$-$C_{12}$, $C_6$), substituted arylthio (e.g., $C_6$-$C_{12}$, $C_6$), cyano, carbonyl, substituted carbonyl, carboxyl, substituted carboxyl, amino, substituted amino, amido, substituted amido, sulfonyl, substituted sulfonyl, urea, substituted urea, carbamate, substituted carbamate, amino acid, and peptide groups.

The term "binding" as it relates to interaction between the targeting ligand and the targeted protein or proteins, which in this invention are CDK2 and CDK5, refers to an inter-molecular interaction that is substantially specific in that binding of the targeting ligand with other proteinaceous entities present in the cell, including other CDK isoforms, is functionally insignificant. The present bifunctional compounds may preferentially bind and recruit CDK2 and CDK5 for targeted degradation.

The term "binding" as it relates to interaction between the degron and the E3 ubiquitin ligase, typically refers to an inter-molecular interaction that may or may not exhibit an affinity level that equals or exceeds that affinity between the targeting ligand and the target protein, but nonetheless wherein the affinity is sufficient to achieve recruitment of the ligase to the targeted degradation and the selective degradation of the targeted protein.

Broadly, the bifunctional compounds have a structure represented by formula:

(I)

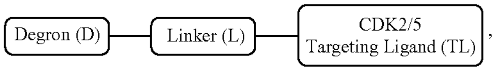

, wherein the targeting ligand represents a moiety that binds cyclin-dependent kinase 2 (CDK2) and cyclin-dependent kinase 5 (CDK5), the degron represents a moiety that binds an E3 ubiquitin ligase, and the linker represents a moiety that covalently connects the degron and the targeting ligand, or a pharmaceutically acceptable salt or stereoisomer thereof.

CDK2/5 Targeting Ligands

In some embodiments, the targeting ligand has a structure represented by formula (TL-1):

(TL-1)

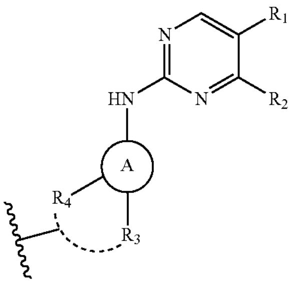

wherein:

$R_1$ represents Br or $CF_3$;

$R_2$ represents $OR_5$, $NHR_5$,

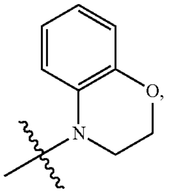
, or
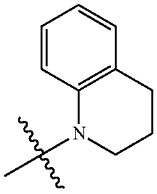
;

$R_5$ represents

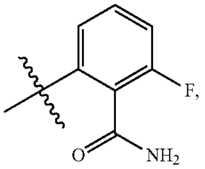
,
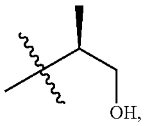
,
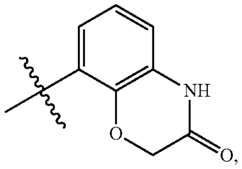
,
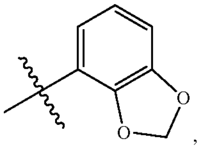
,
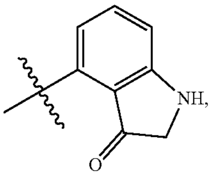
, or
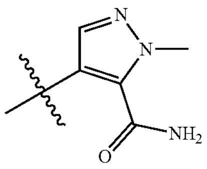
;

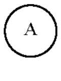

represents optionally substituted cyclopentyl, optionally substituted cyclohexyl, optionally substituted phenyl, optionally substituted pyridinyl, optionally substituted pyrrolidinyl, or optionally substituted piperidinyl.

$R_3$ represents

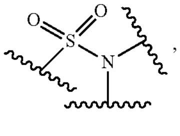
,
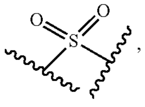
,

-continued

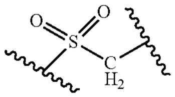

, or

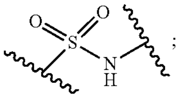

;

and $R_4$ represents H, C(O), or

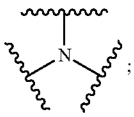 [SMILES: *N(*)*]

;

provided that when $R_3$ represents

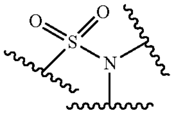

or

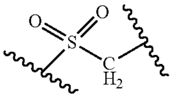

and $R_4$ represents C(O) or

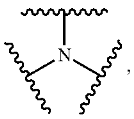 [SMILES: *N(*)*]

, $R_3$ and $R_4$ together with the atoms to which they are bound form a 5-membered cyclic sulfonamide.

Thus, in some embodiments, the compounds of the present invention have a structure represented by formula (I-1):

(I-1)

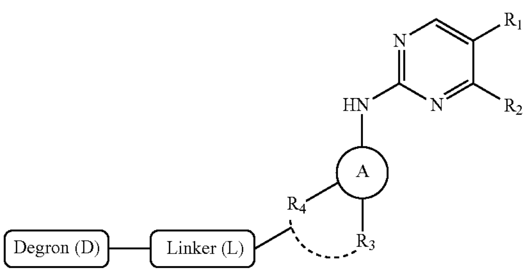

wherein:

$R_1$ represents Br or $CF_3$;

$R_2$ represents $OR_5$, $NHR_5$,

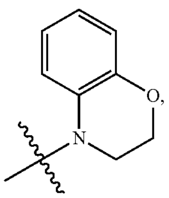

or

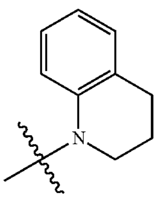

;

$R_5$ represents

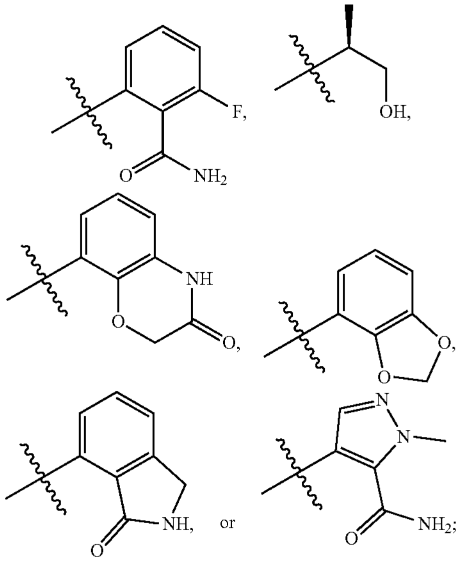

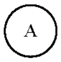

represents optionally substituted cyclopentyl, optionally substituted cyclohexyl, optionally substituted phenyl, optionally substituted pyridinyl, optionally substituted pyrrolidinyl, or optionally substituted piperidinyl;

$R_3$ represents

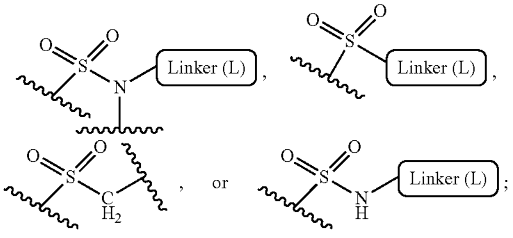

and $R_4$ represents H, C(O), or

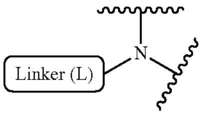

;

provided that when $R_3$ represents

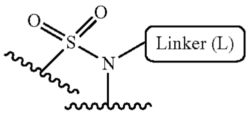

or

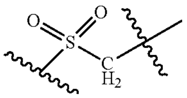

, and $R_4$ represents C(O) or

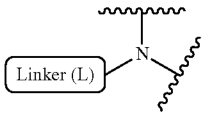

$R_3$ and $R_4$ together with the atoms to which they are bound form a 5-membered cyclic sulfonamide; or a pharmaceutically acceptable salt or stereoisomer thereof.

Thus, in some embodiments, when $R_1$ is Br, $R_2$ is $NHR_5$, $R_5$ is

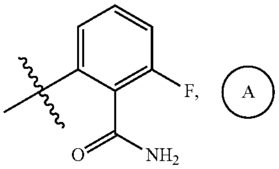

is piperidinyl, and $R_3$ is

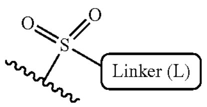

the compounds of the present invention have a structure represented by formula (I-1a):

(I-1a)

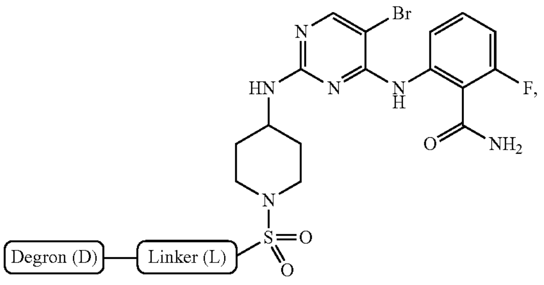

or a pharmaceutically acceptable salt or stereoisomer thereof.

Thus, in some embodiments, when $R_1$ is Br, $R_2$ is $NHR_5$, $R_5$ is

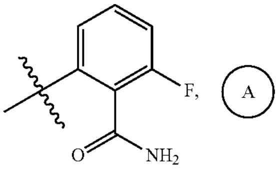

piperidinyl, and $R_3$ is

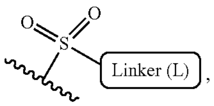 [SMILES: *S(C)(=O)=O]

the compounds of the present invention have a structure represented by formula (I-1b):

(I-1b)

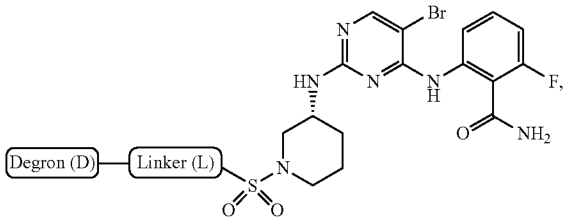

or a pharmaceutically acceptable salt or stereoisomer thereof.

Thus, in some embodiments, when $R_1$ is Br, $R_2$ is $NHR_5$, $R_5$ is

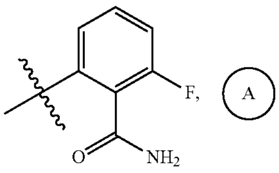

is phenyl, and $R_3$ is

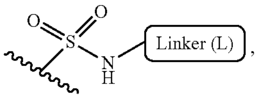 [SMILES: *S(=O)(=O)NC]

the compounds of the present invention have a structure represented by formula I-1c):

(I-1c)

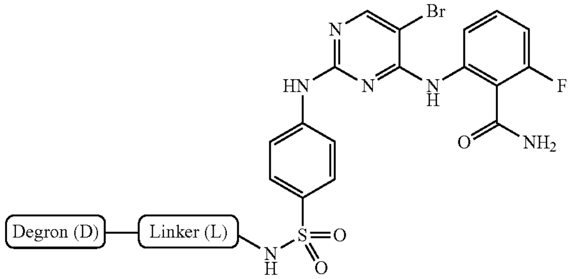

or a pharmaceutically acceptable salt or stereoisomer thereof.

Thus, in some embodiments, when $R_1$ is Br, $R_2$ is $NHR_5$, $R_5$ is

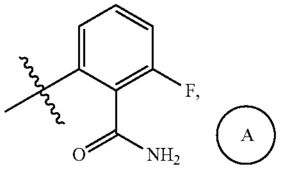

is phenyl, $R_3$ is

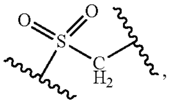 [SMILES: *CS(*)(=O)=O]

and $R_4$ is

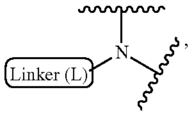

the compounds of the present invention have a structure represented by formula (I-1d):

(I-1d)

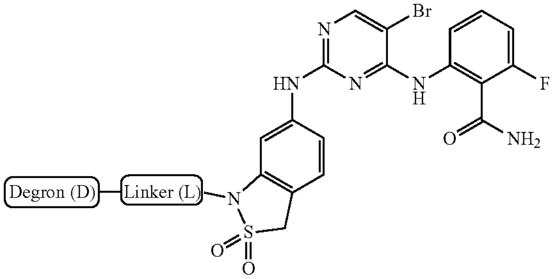

or a pharmaceutically acceptable salt or stereoisomer thereof.

Thus, in some embodiments, when $R_1$ is Br, $R_2$ is $NHR_5$, $R_5$ is

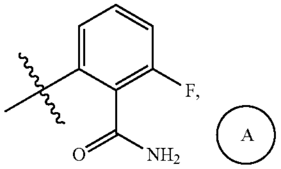

is phenyl, $R_3$ is

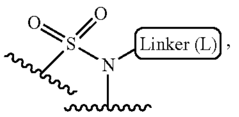

and $R_4$ is C(O), the compounds of the present invention have a structure represented by formula (I-1e):

(I-1e)

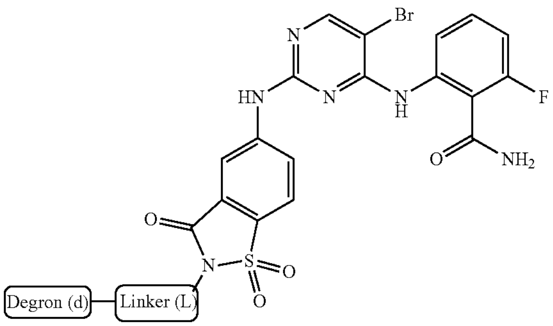

or a pharmaceutically acceptable salt or stereoisomer thereof.

Thus, in some embodiments, when $R_1$ is $CF_3$, $R_2$ is $NHR_5$, $R_5$ is

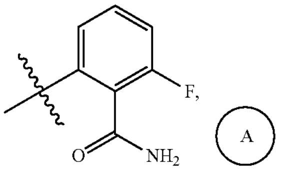

is piperidinyl, and $R_3$ is

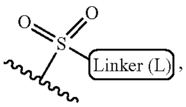

the compounds of the present invention have a structure represented by formula (I-1f):

(I-1f)

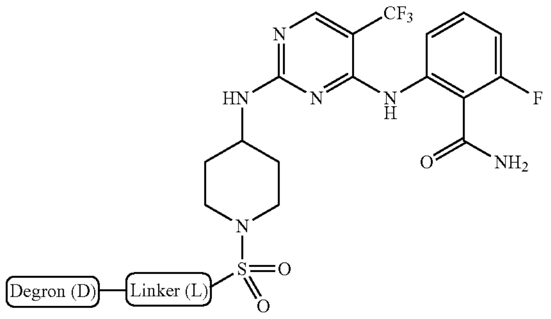

or a pharmaceutically acceptable salt or stereoisomer thereof.

Thus, in some embodiments, when $R_1$ is Br, $R_2$ is $NHR_5$, $R_5$ is

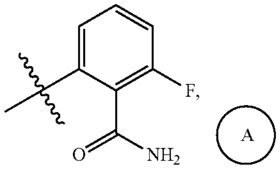

is substituted piperidinyl, and $R_3$ is

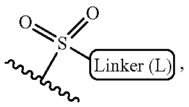

the compounds of the present invention have a structure represented by formula (I-1g):

(I-1g)

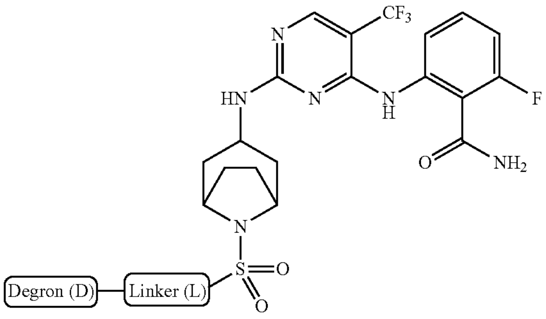

or a pharmaceutically acceptable salt or stereoisomer thereof.

Thus, in some embodiments, when $R_1$ is Br, $R_2$ is $OR_5$, $R_5$ is

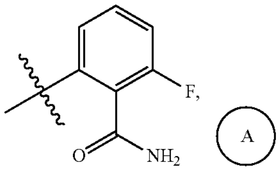

is piperidinyl, and $R_3$ is

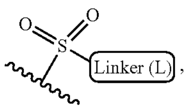

the compounds of the present invention have a structure represented by formula (I-1h):

(I-1h)

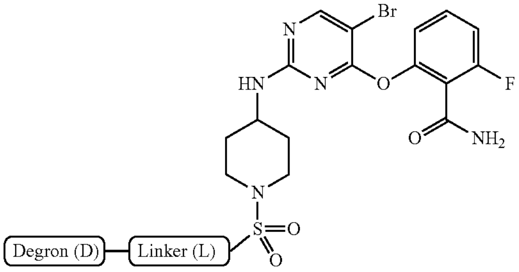

or a pharmaceutically acceptable salt or stereoisomer thereof.

Thus, in some embodiments, when $R_1$ is Br, $R_2$ is

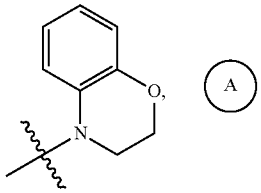

is piperidinyl, and $R_3$ is

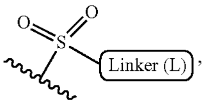 [SMILES: *S(C)(=O)=O]

the compounds of the present invention have a structure represented by formula (I-1i):

(I-1i)

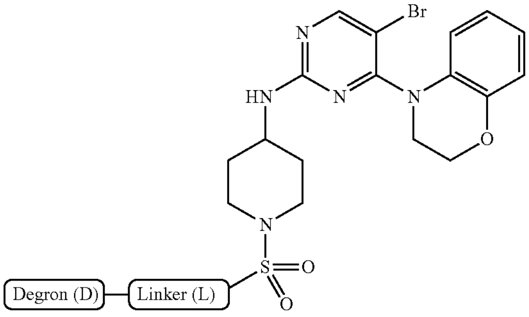

or a pharmaceutically acceptable salt or stereoisomer thereof.

Thus, in some embodiments, when $R_1$ is Br, $R_2$ is $NHR_5$, $R_5$ is

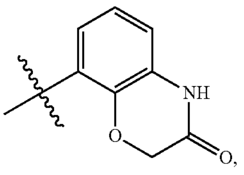

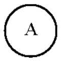

is piperidinyl, and $R_3$ is

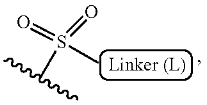 [SMILES: *S(C)(=O)=O]

the compounds of the present invention have a structure represented by formula (I-1j):

(I-1j)

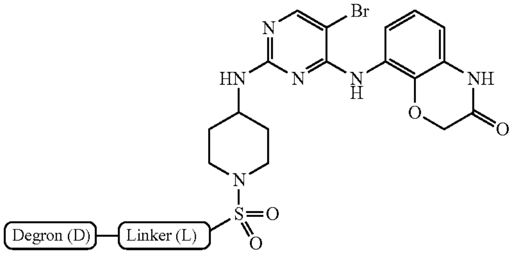

or a pharmaceutically acceptable salt or stereoisomer thereof.

Thus, in some embodiments, when $R_1$ is Br, $R_2$ is $NHR_5$, $R_5$ is

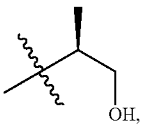

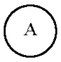

is piperidinyl, and $R_3$ is

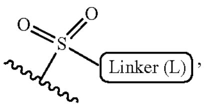

the compounds of the present invention have a structure represented by formula (I-1k):

(I-1k)

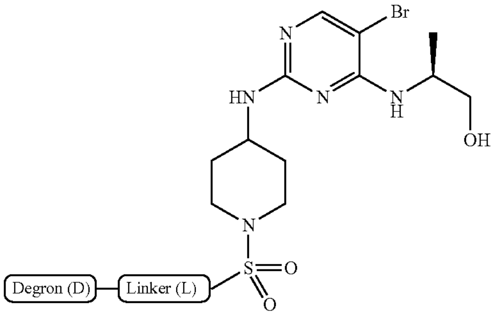

or a pharmaceutically acceptable salt or stereoisomer thereof.

Thus, in some embodiments, when $R_1$ is Br, $R_2$ is $NHR_5$, $R_5$ is

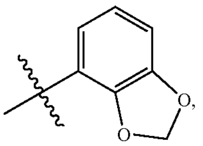

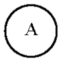

is piperidinyl, and $R_3$ is

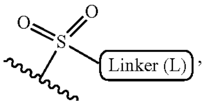 [SMILES: *S(C)(=O)=O]

the compounds of the present invention have a structure represented by formula (I-1l):

(I-1l)

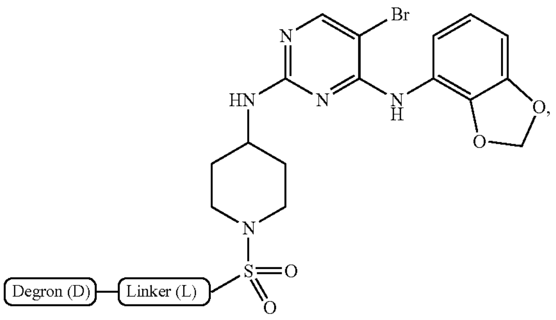

or a pharmaceutically acceptable salt or stereoisomer thereof.

Thus, in some embodiments, when $R_1$ is Br, $R_2$ is $NHR_5$, $R_5$ is

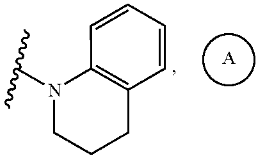

is piperidinyl, and $R_3$ is

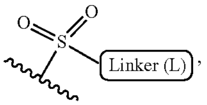

the compounds of the present invention have a structure represented by formula (I-1m):

(I-1m)

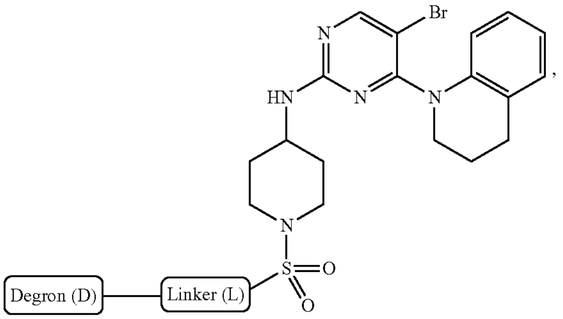

or a pharmaceutically acceptable salt or stereoisomer thereof.

Thus, in some embodiments, when $R_1$ is Br, $R_2$ is $NHR_5$, $R_5$ is

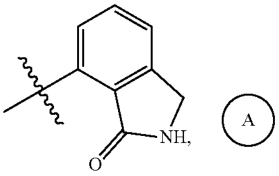

is piperidinyl, and $R_3$ is

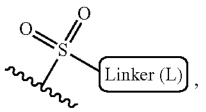 [SMILES: *S(C)(=O)=O]

the compounds of the present invention have a structure represented by formula (I-1n):

(I-1n)

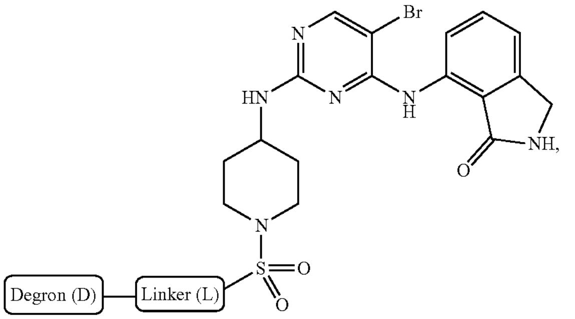

or a pharmaceutically acceptable salt or stereoisomer thereof.

Thus, in some embodiments, when $R_1$ is Br, $R_2$ is $NHR_5$, $R_5$ is

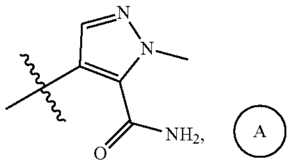

is piperidinyl, and $R_3$ is

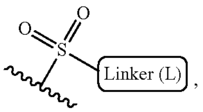 [SMILES: *S(C)(=O)=O]

the compounds of the present invention have a structure represented by formula (I-1o):

(I-1o)

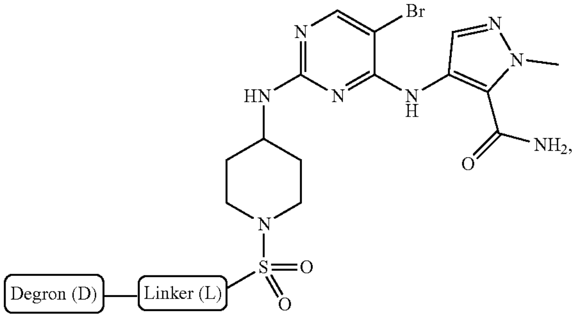

or a pharmaceutically acceptable salt or stereoisomer thereof.

In some embodiments,

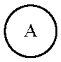

is optionally substituted phenyl or optionally substituted piperidinyl. In certain embodiments, the substitutent is methyl or cyclopropyl.

Thus, in some embodiments, when $R_1$ is Br, $R_2$ is $NHR_5$, $R_5$ is

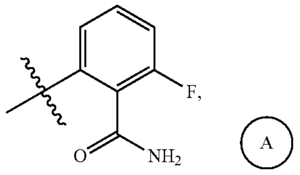

is optionally substituted piperidinyl, and $R_3$ is

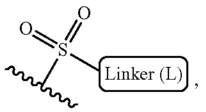 [SMILES: *S(C)(=O)=O]

the compounds of the present invention have a structure represented by formula (I-1p):

(I-1p)

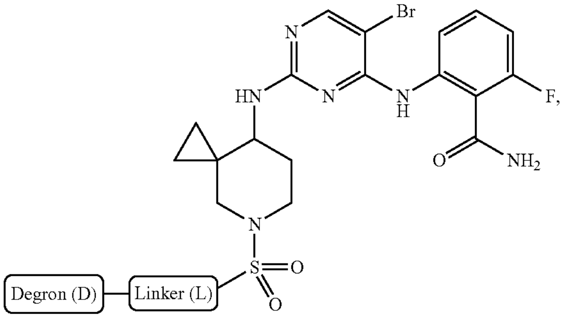

or a pharmaceutically acceptable salt or stereoisomer thereof.

In some embodiments, when $R_1$ is Br, $R_2$ is $NHR_5$, $R_5$ is

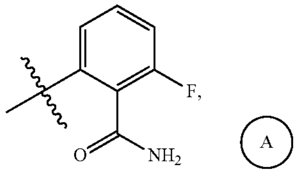

is optionally substituted phenyl, and $R_3$ is

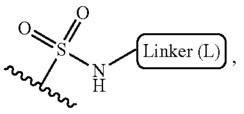 [SMILES: *S(=O)(=O)NC]

the compounds of the present invention have a structure represented by formula (I-1q):

(I-1q)

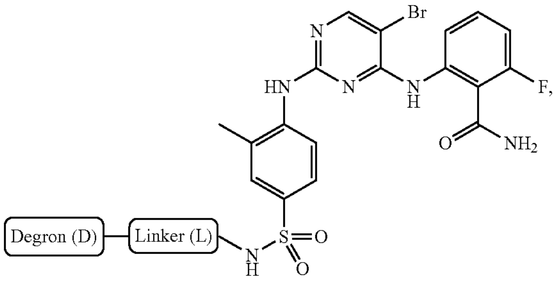

or a pharmaceutically acceptable salt or stereoisomer thereof.

In some embodiments, when $R_1$ is Br, $R_2$ is $NHR_5$, $R_5$ is

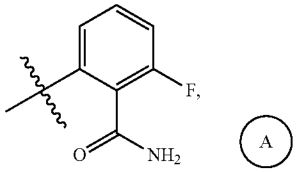

is optionally substituted phenyl, and $R_3$ is

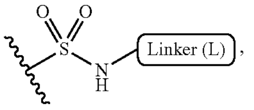 [SMILES: *S(=O)(=O)NC]

the compounds of the present invention have a structure represented by formula (I-1r):

(I-1r)

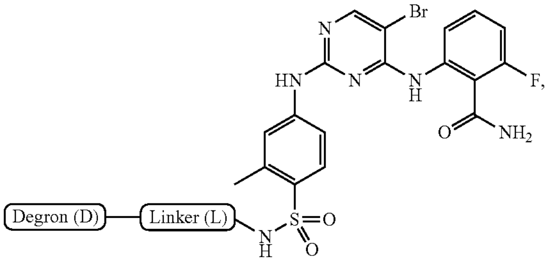

or a pharmaceutically acceptable salt or stereoisomer thereof.

Linkers

In some embodiments, the linker may be an alkylene chain or a bivalent alkylene chain, either of which may be interrupted by, and/or terminate (at either or both termini) in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, $—S(O)_2—$, —OS(O)—, —S(O)

O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_3$-$C_{12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different.

In some embodiments, the linker is an alkylene chain having 1-10 alkylene units and terminating in

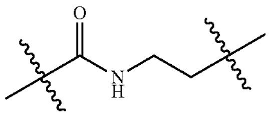
,
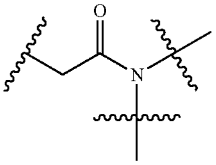
,
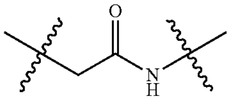
,
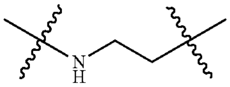
, or
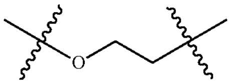
.

In some embodiments, the linker is an alkylene chain having 1-10 alkylene units and terminating in

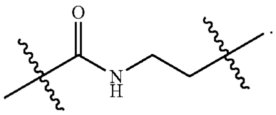 [SMILES: *CCNC(*)=O]
.

"Carbocyclene" refers to a bivalent carbocycle radical, which is optionally substituted.

"Heterocyclene" refers to a bivalent heterocyclyl radical which may be optionally substituted.

"Heteroarylene" refers to a bivalent heteroaryl radical which may be optionally substituted.

Representative examples of linkers that may be suitable for use in the present invention include alkylene chains:

(L1)

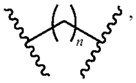
, wherein n is an integer of 1-12 ("of" meaning inclusive), e.g., 1-12, 1-11, 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10 and 1, 2, 3, 4, 5, 6, 7, 8, 9 and 10, examples of which include:

(L1-a)

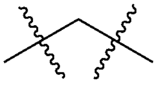
;

(L1-b)

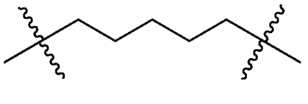
;

-continued (L1-c)

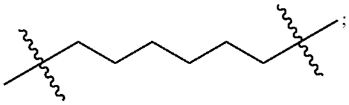
;

(L1-d)

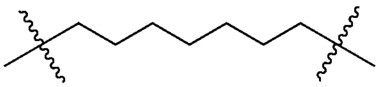
; and (L1-e)

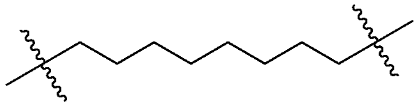
;

alkylene chains terminating in various functional groups (as described above), examples of which are as follows:

(L2-a)

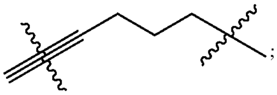
;

(L2-b)

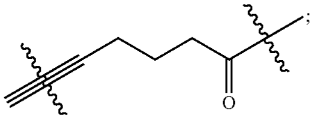
;

(L2-c)

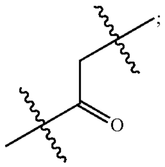
;

(L2-d)

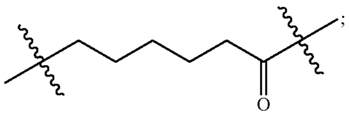
;

(L2-e)

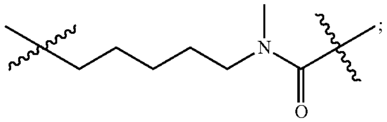
;

(L2-f)

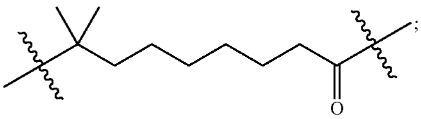
; and (L2-g)

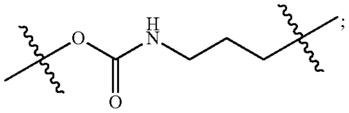
;

alkylene chains interrupted by various functional groups (as described above), examples of which are as follows:

(L3-a)

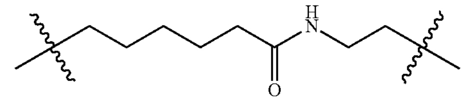

;

(L3-b)

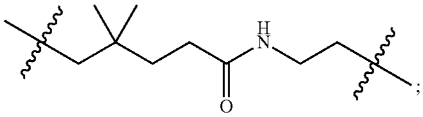

;

(L3-c)

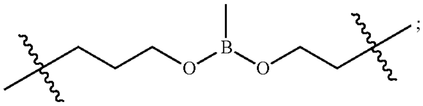

; and (L3-d)

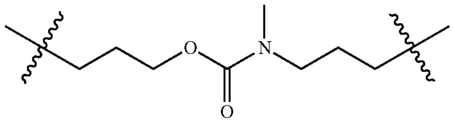

;

alkylene chains interrupted by or terminating with heterocyclene groups, e.g., (L4)

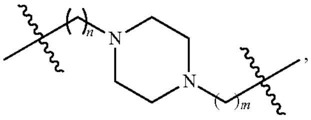

, wherein m and n are independently integers of 0-10, examples of which include:

(L4-a)

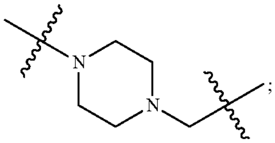

;

(L4-b)

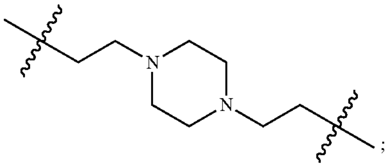

;

(L4-c)

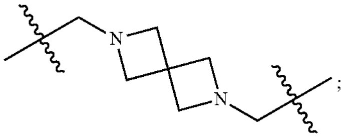

;

(L4-d)

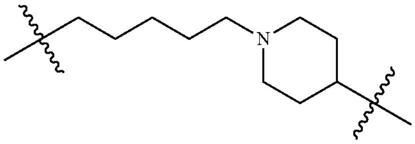

; and

-continued (L4-e)

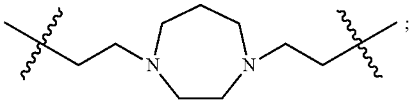

;

alkylene chains interrupted by amide, heterocyclene and/or aryl groups, examples of which include:

(L5-a)

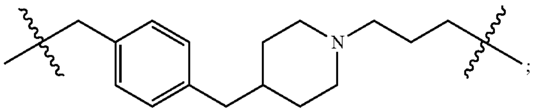

; and (L5-b)

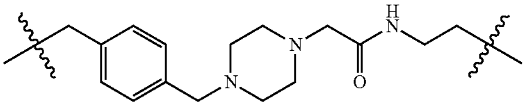

;

alkylene chains interrupted by heterocyclene and aryl groups, and a heteroatom, examples of which include:

(L6-a)

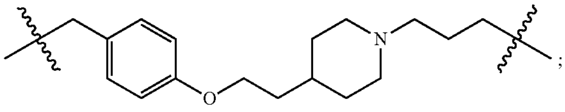

;

(L6-b)

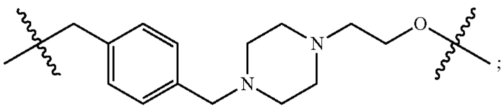

; and (L6-c)

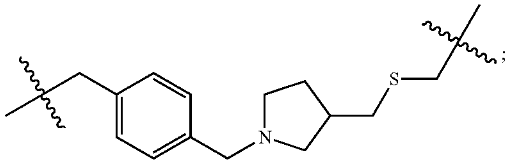

;

and alkylene chains interrupted by and/or terminating in a heteroatom such as N, O or B, e.g., (L7)

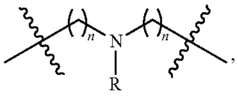

, wherein each n is independently an integer of 1-10, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10, and 1, 2, 3, 4, 5, 6, 7, 8, 9 and 10, and R is H or C1 to C4 alkyl, an example of which is (L7-a)

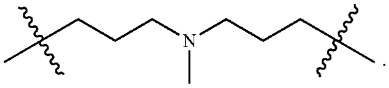

In some embodiments, the linker may be a polyethylene glycol chain which may terminate (at either or both termini) in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, $—S(O)_2—$, —OS(O)—, —S(O)O—, —S(O)—, $—OS(O)_2—$, $—S(O)_2O—$, $—N(R')S(O)_2—$, $—S(O)_2N(R')—$, —N(R')S(O)—, —S(O)N(R')—, $—N(R')S(O)_2N(R')—$, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different.

In some embodiments, the linker is a polyethylene glycol linker having 2-8 PEG units and terminating in

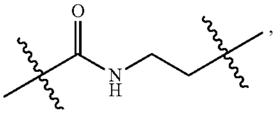
,
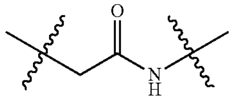
, or
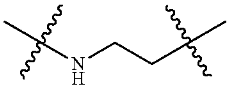
.

In some embodiments, the linker is a polyethylene glycol linker having 2-8 PEG units and terminating in

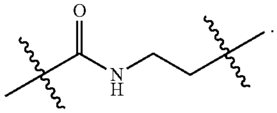 [SMILES: *CCNC(*)=O]
.

In some embodiments, the linker is a polyethylene glycol chain, examples of which include:

(L8)

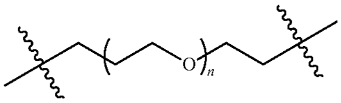
, wherein n is an integer of 2-10, examples of which include:

(L8-a)

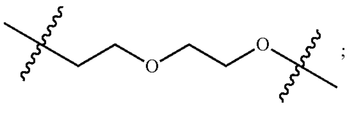
;

-continued (L8-b)

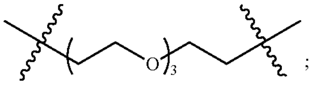
;

(L8-c)

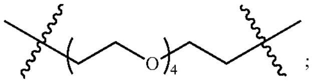
; and (L8-d)

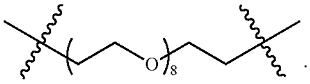
.

In some embodiments, the polyethylene glycol chain may terminate in a functional group, examples of which are as follows:

(L9-a)

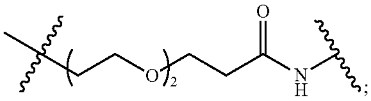
;

(L9-b)

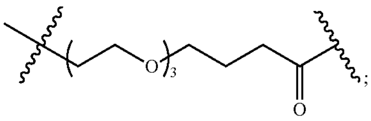
;

(L9-c)

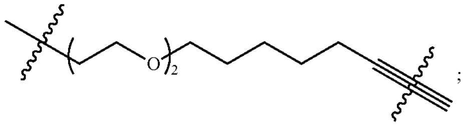
;

(L9-d)

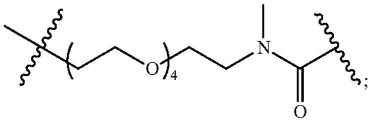
; and (L9-e)

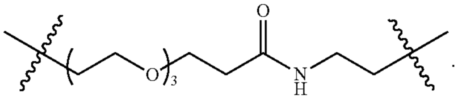
.

In some embodiments, the linker is represented by any one of the following structures:

(L10-a)

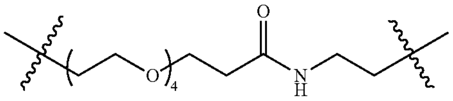
, (L10-b)

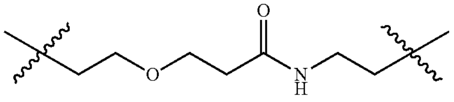
, (L10-c)

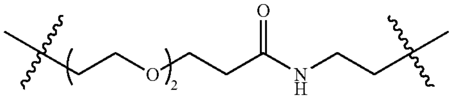
,

-continued
(L10-d)
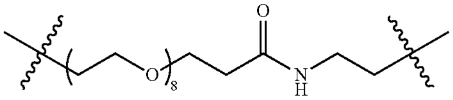,
(L10-e)
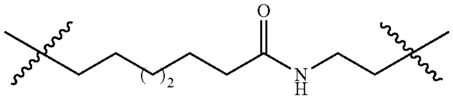,
(L10-f)
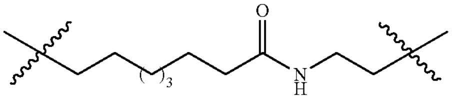,
(L10-g)
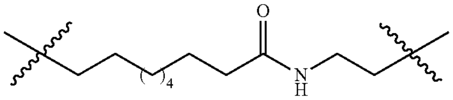,
(L10-h)
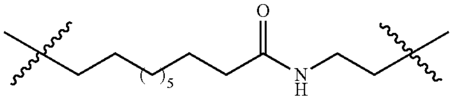,
(L10-i)
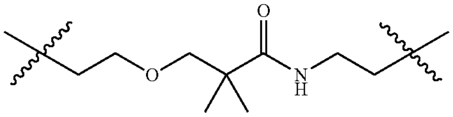,
(L10-j)
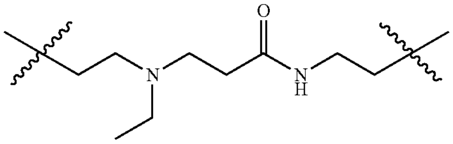,
(L10-k)
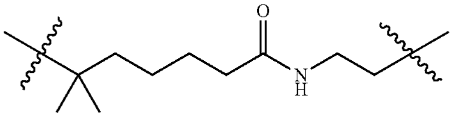,
(L10-l)
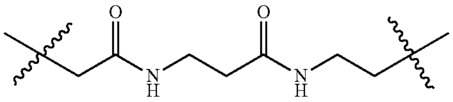,
(L10-m)
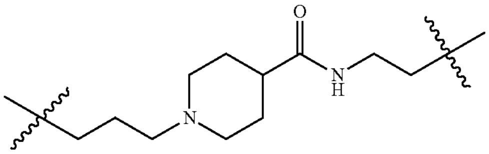,
(L10-n)
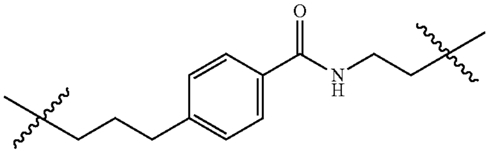,
-continued
(L10-o)
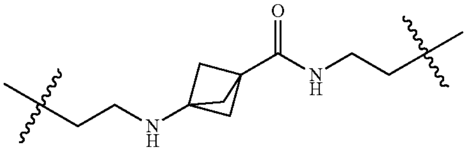,
(L10-p)
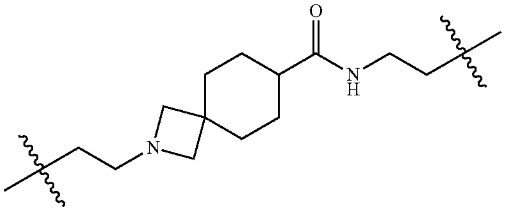
(L10-q)
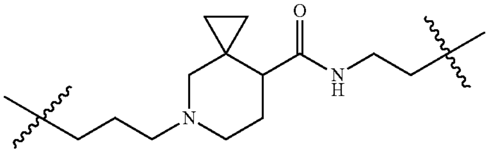,
(L10-r)
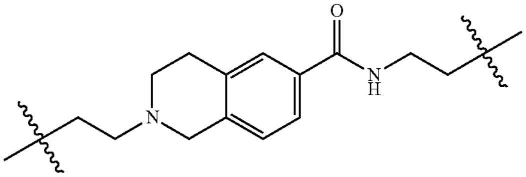,
(L10-s)
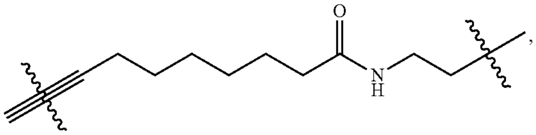,
(L10-t)
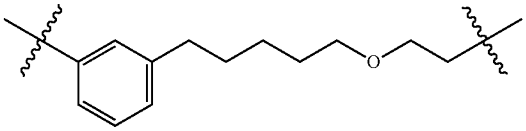,
(L10-u)
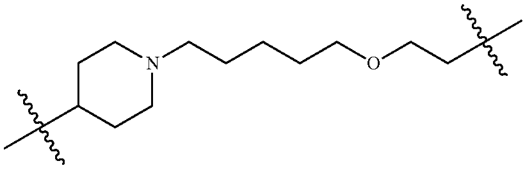,
(L10-v)
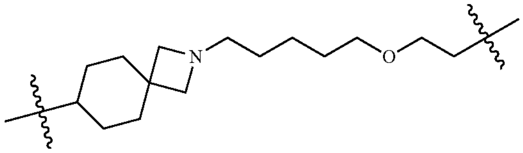, -continued (L10-w)

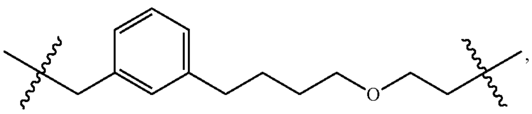, (L10-x)

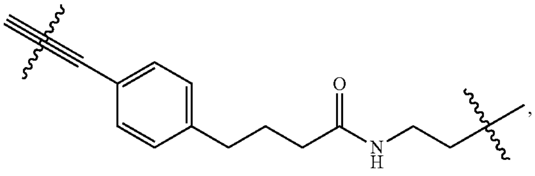, (L10-y)

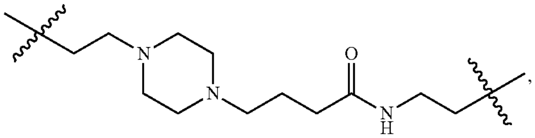, (L10-z)

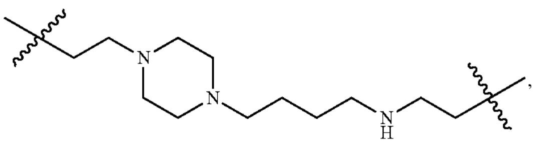, (L10-aa)

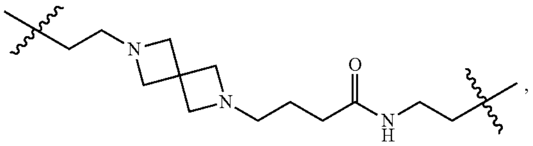, (L10-bb)

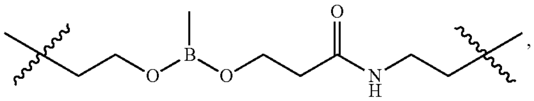, (L10-cc)

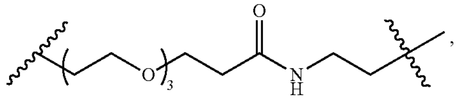,

-continued (L10-dd)

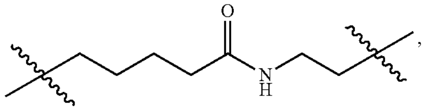, (L10-ee)

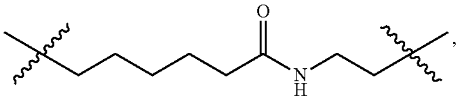, (L10-ff)

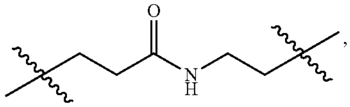, (L10-gg)

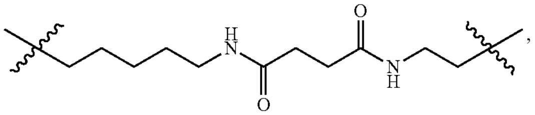, (L10-hh)

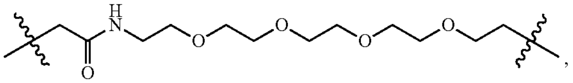, (L10-ii)

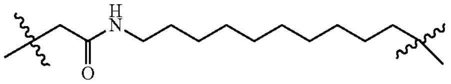, and (L10-jj)

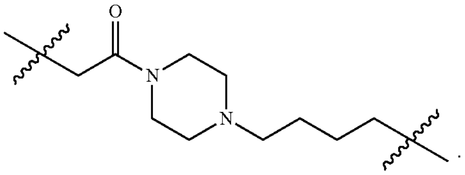.

In some embodiments, bifunctional compounds of the present invention may include a TL linked to a degron via a PEG linker that terminates in a functional group. Representative examples of bifunctional compounds include:

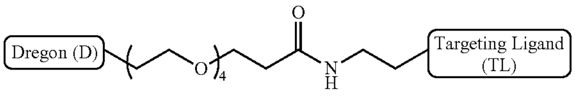,

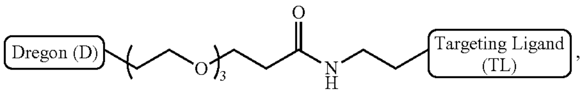,

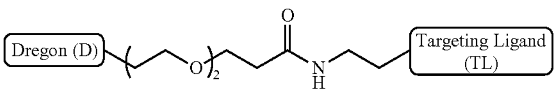,

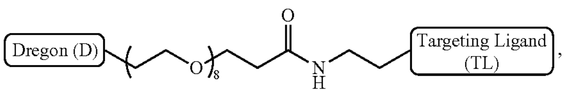, and

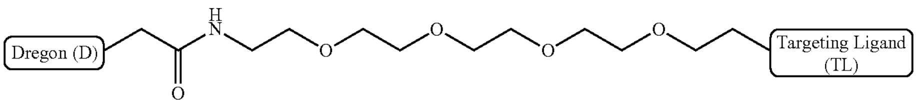, or a pharmaceutically acceptable salt or stereoisomer thereof.

In some embodiments, bifunctional compounds of the present invention may include a TL linked to a degron via an alkylene linker that is interrupted by and/or terminating in one or more cyclic or non-cyclic functional groups containing one or more heteroatoms, such as ether and amide groups. Representative examples of bifunctional compounds include:
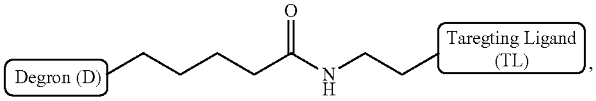
,
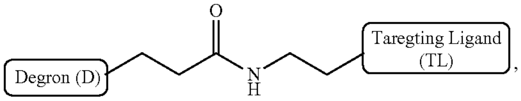
,
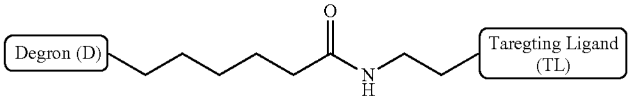
,
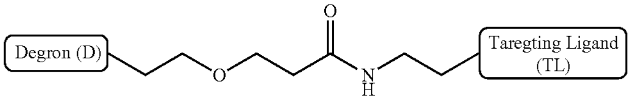
,
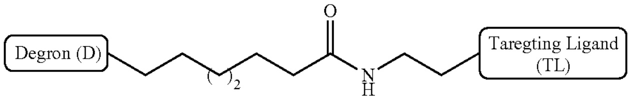
,
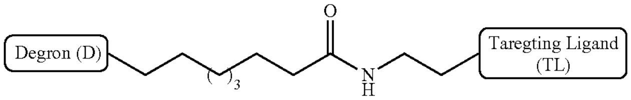
,
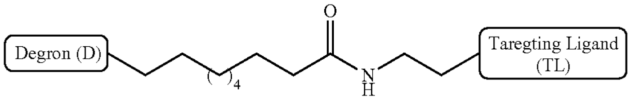
,
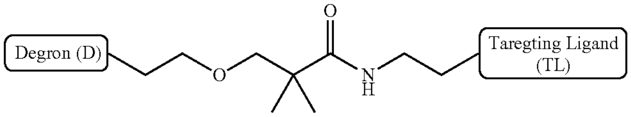
,
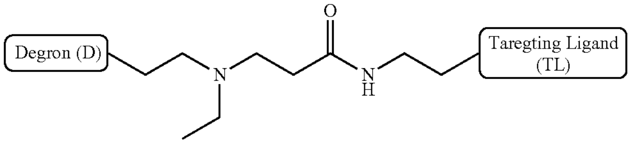
,
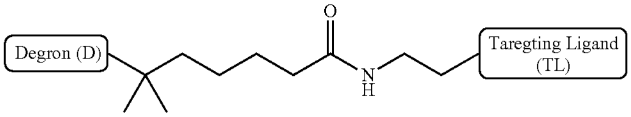
,
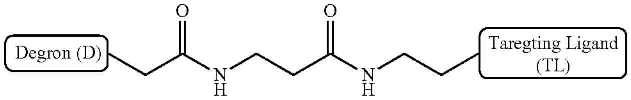
,
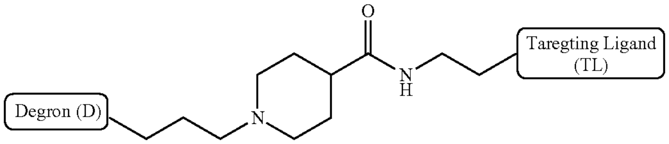
,
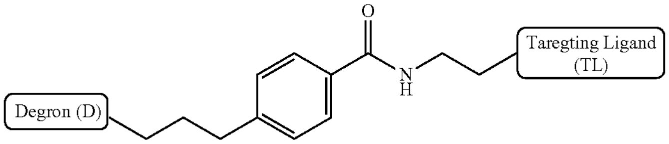
,
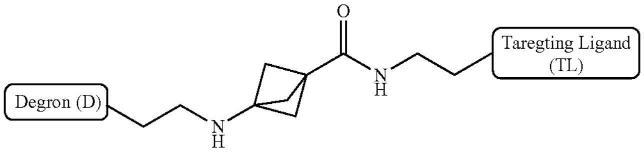
, -continued
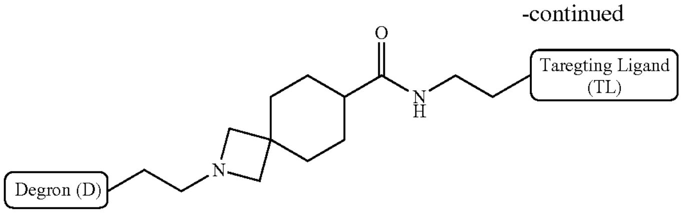
,
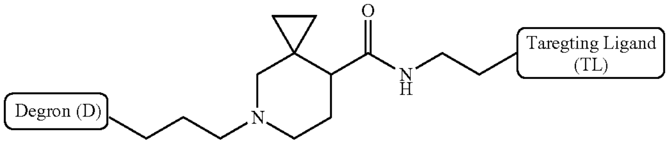
,
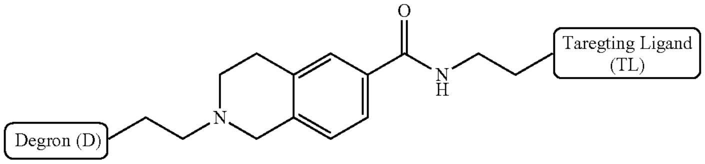
,
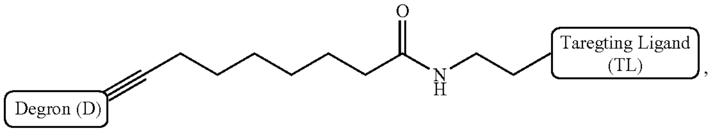
,
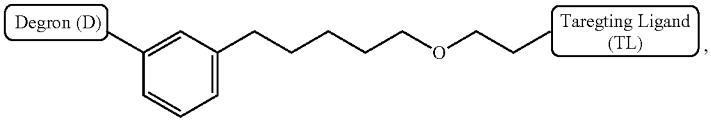
,
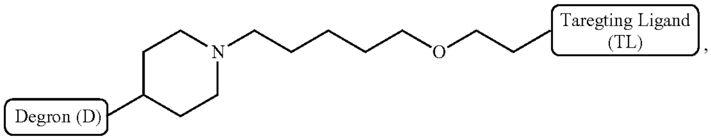
,
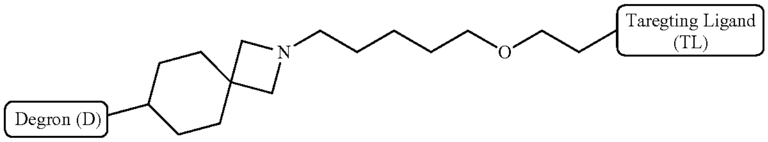
,
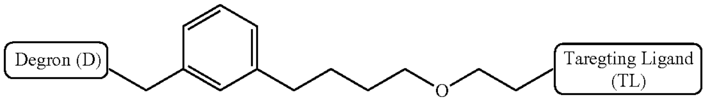
,
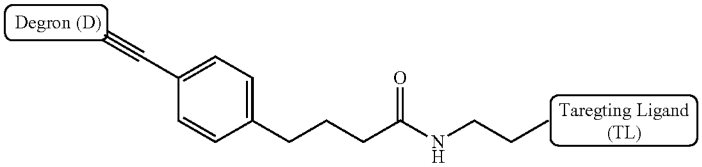
,
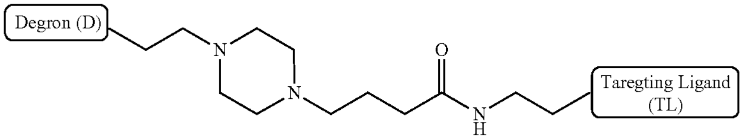
,
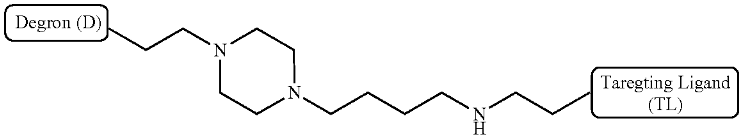
,
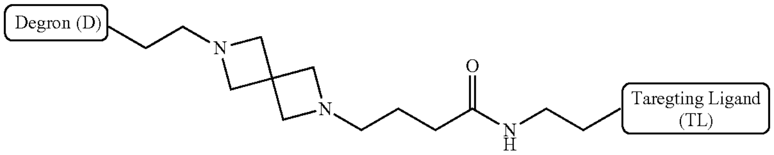
, -continued
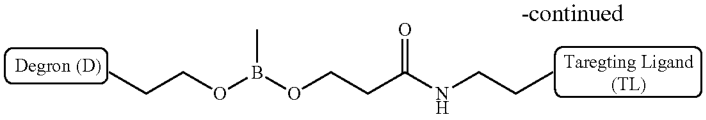
,
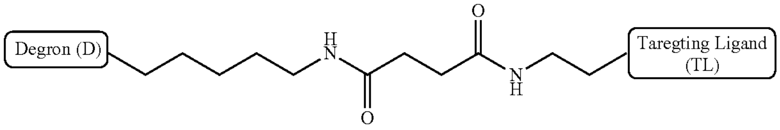
,
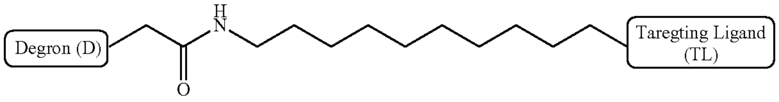
, and
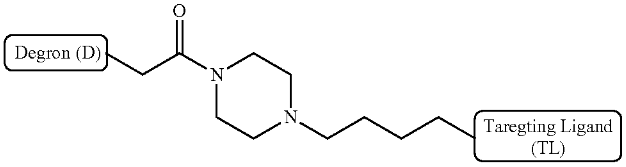
,
or a pharmaceutically acceptable salt or stereoisomer thereof.
In some embodiments, the bifunctional compounds of the present invention are represented by any of the following structures (with the Degron shown generically):
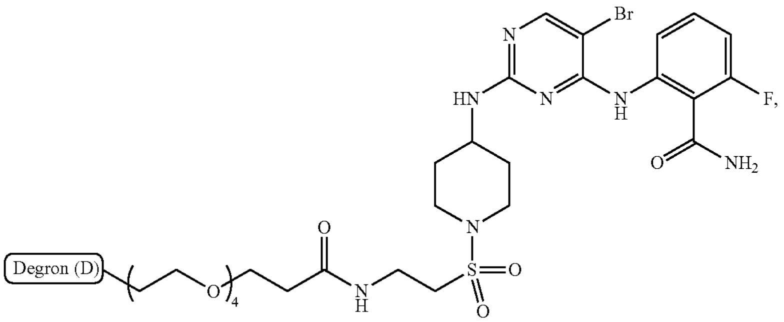
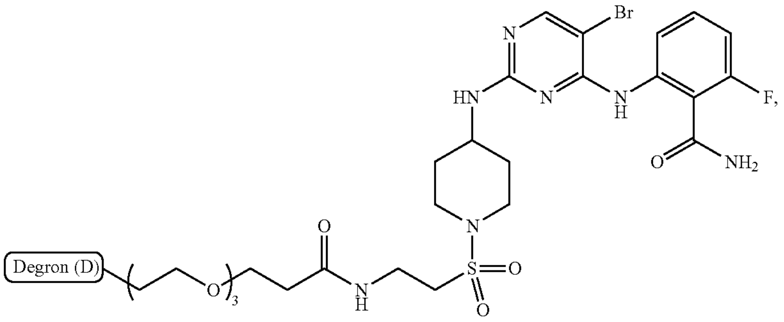
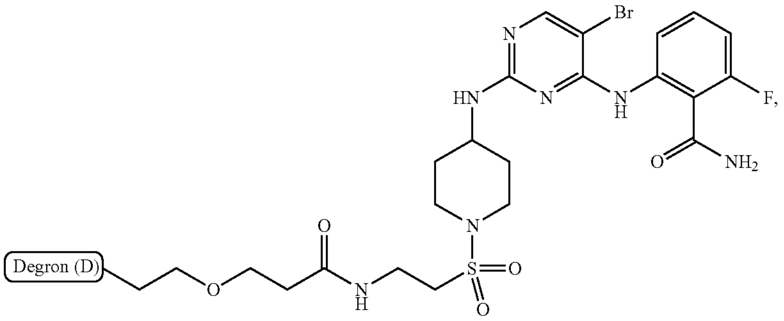

-continued
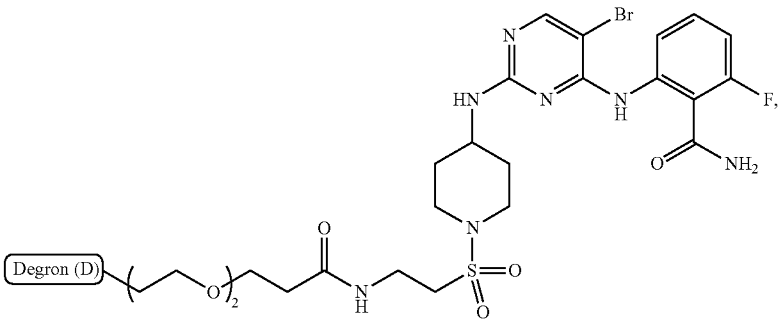
,
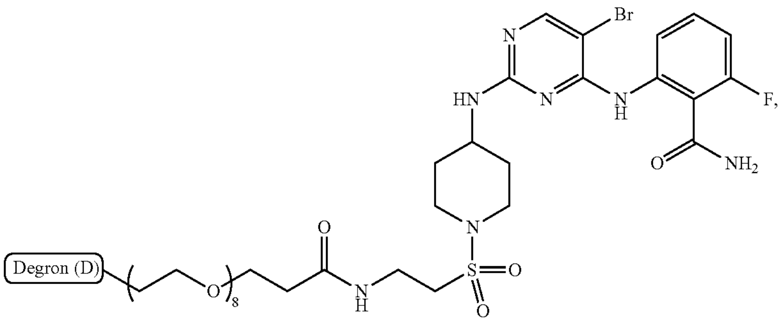
,
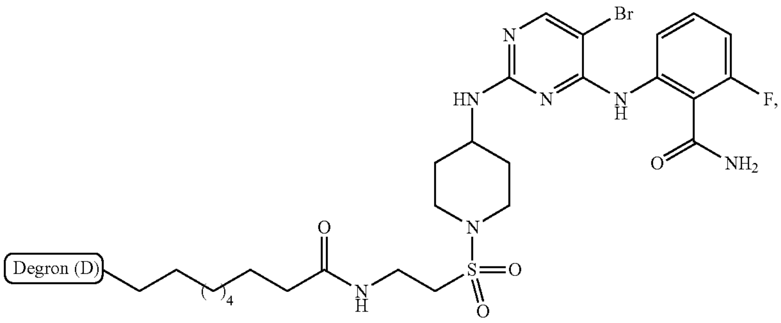
,
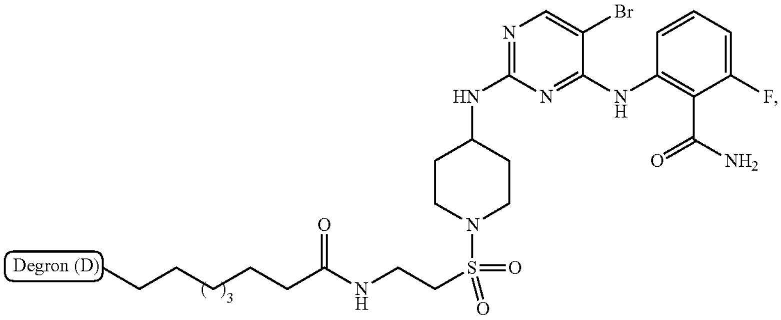
,
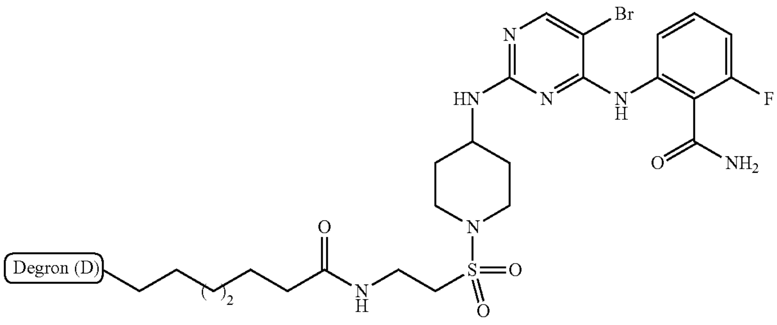

-continued
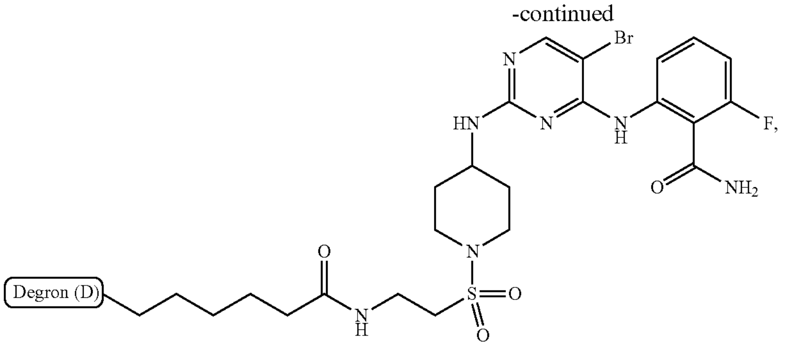
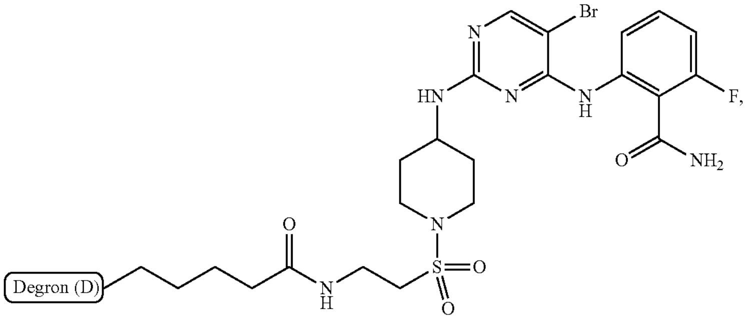
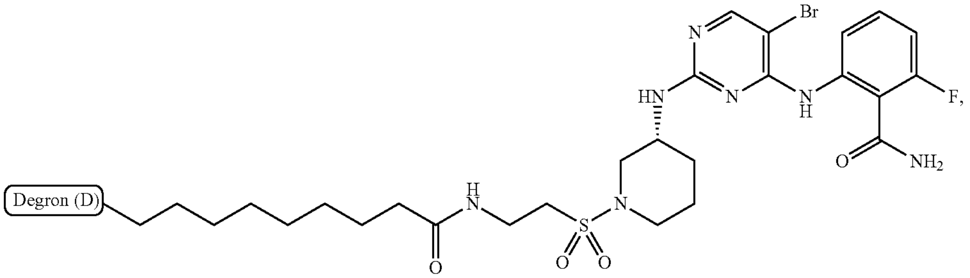
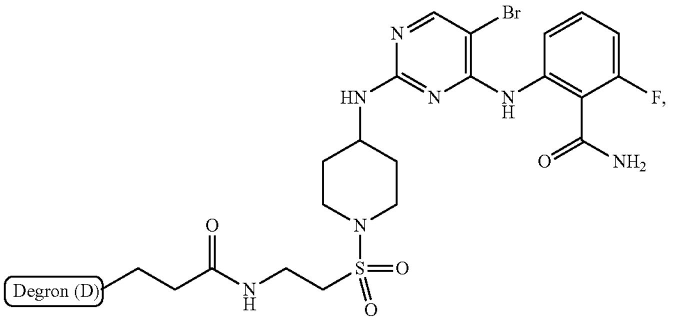
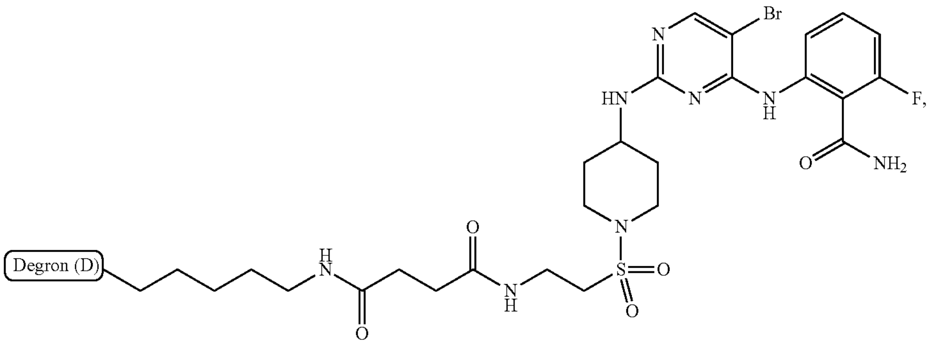

-continued
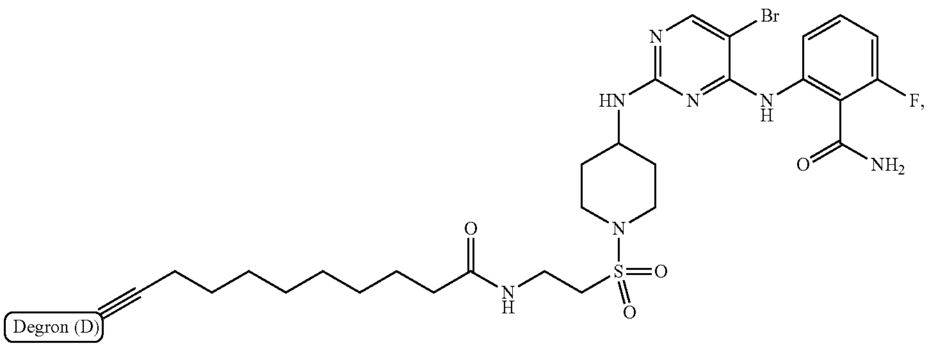
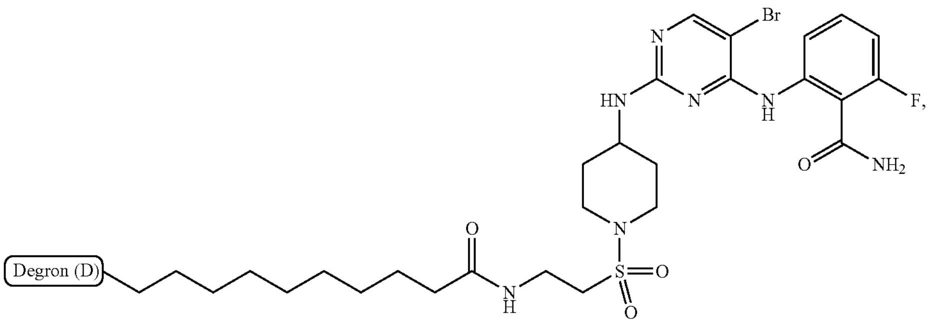
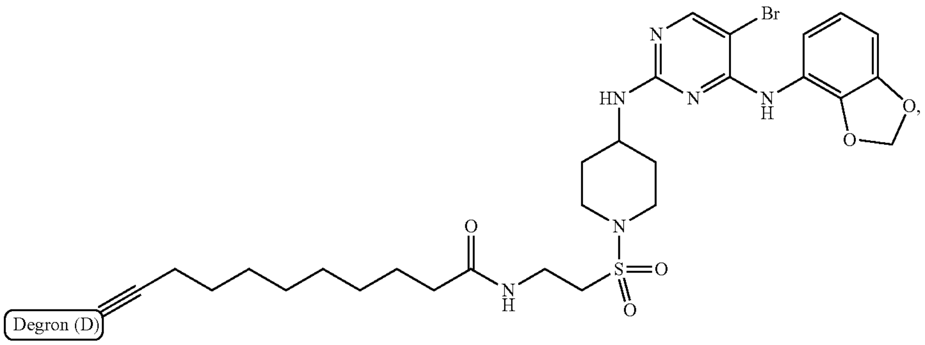
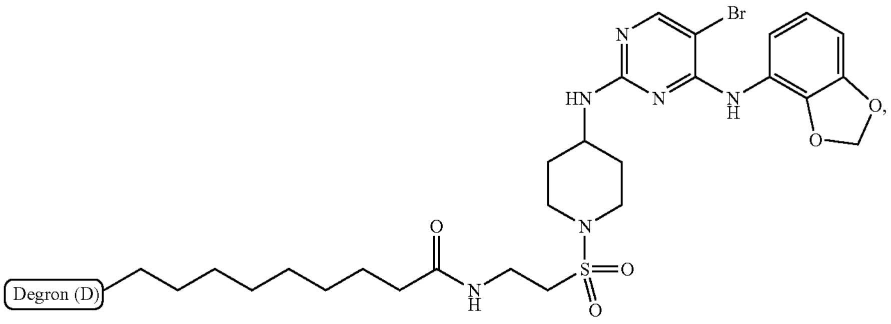
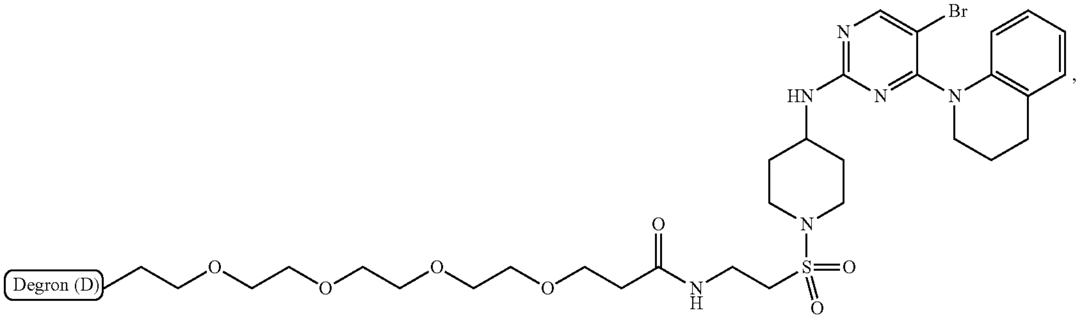

-continued
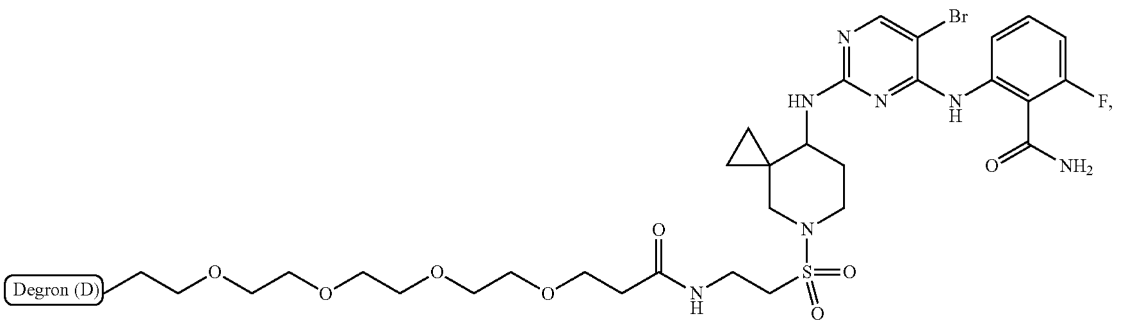
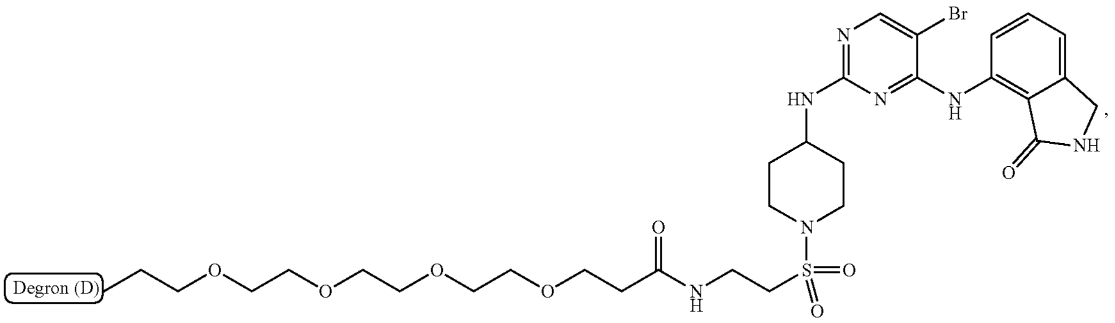
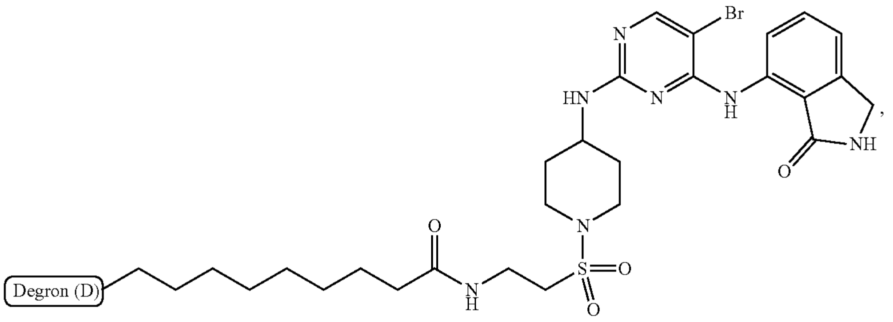
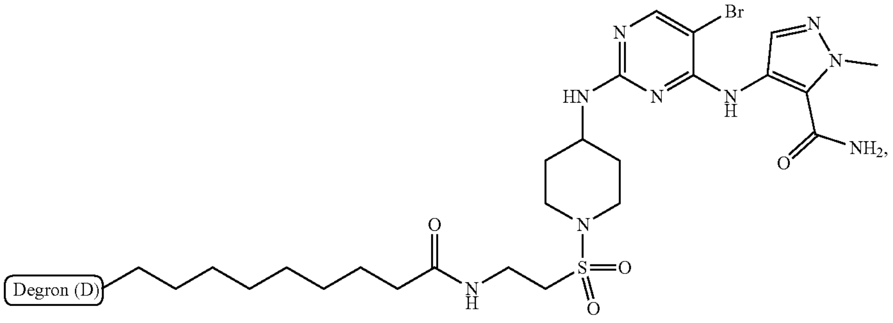
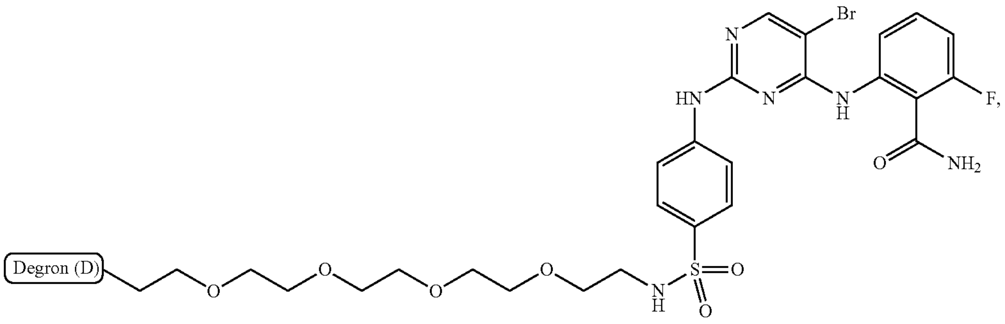

-continued
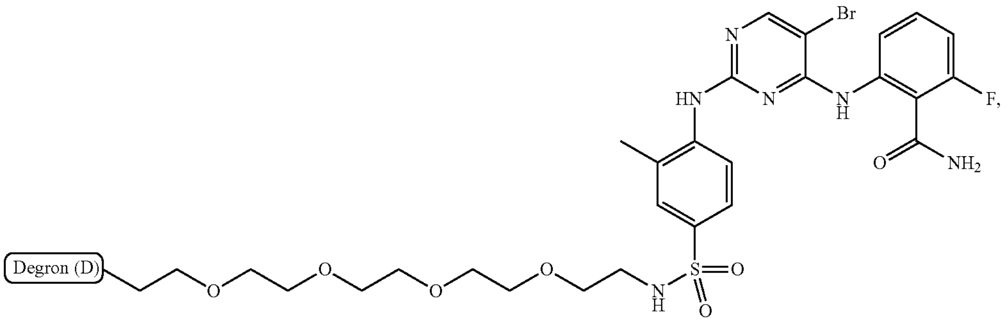
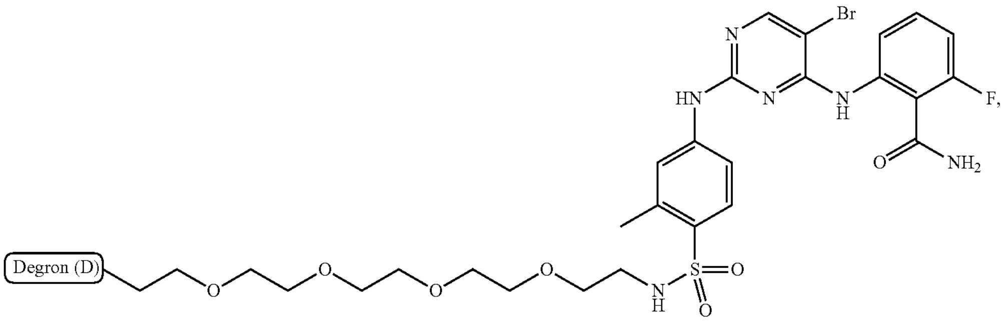
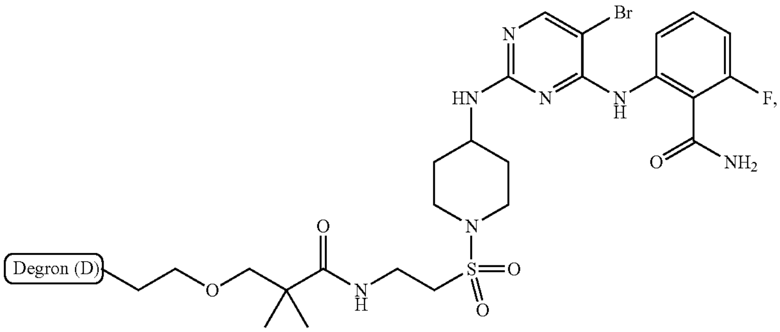
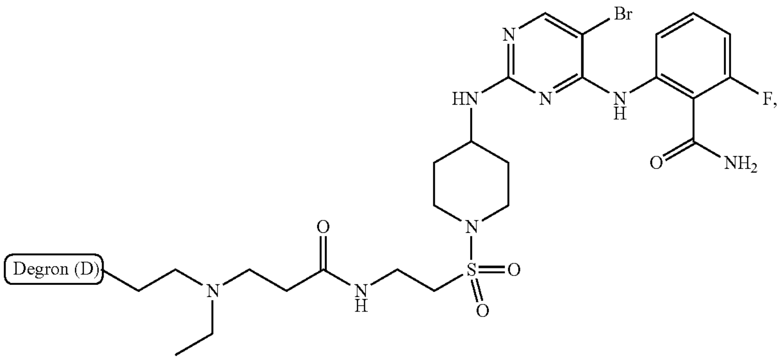
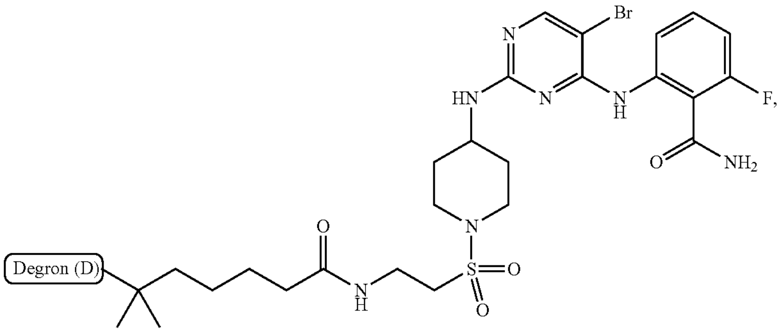

-continued
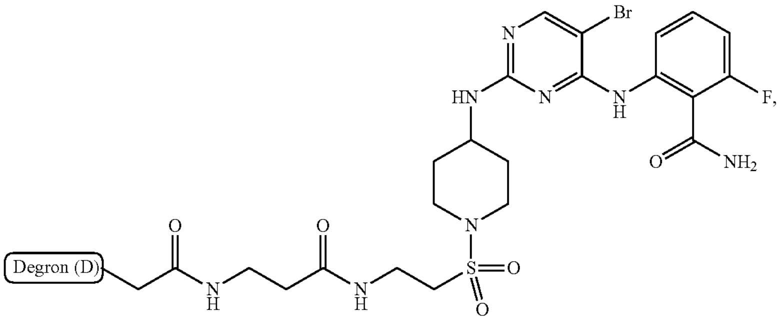
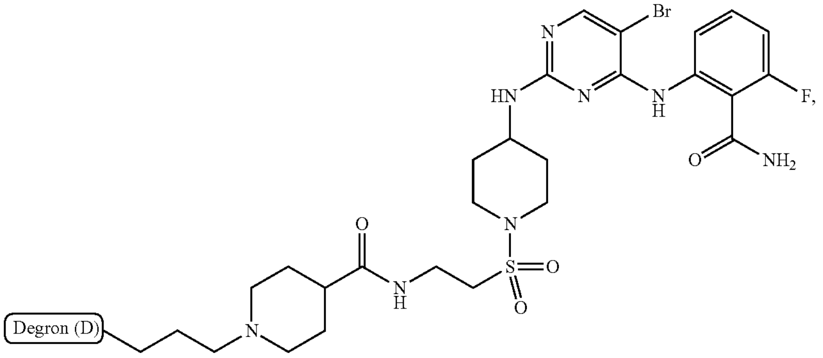
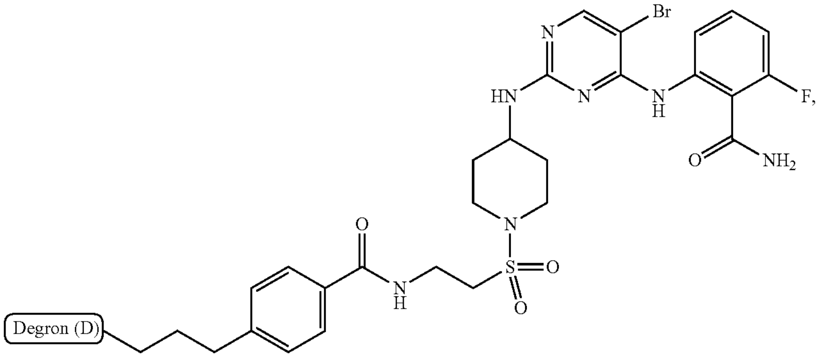
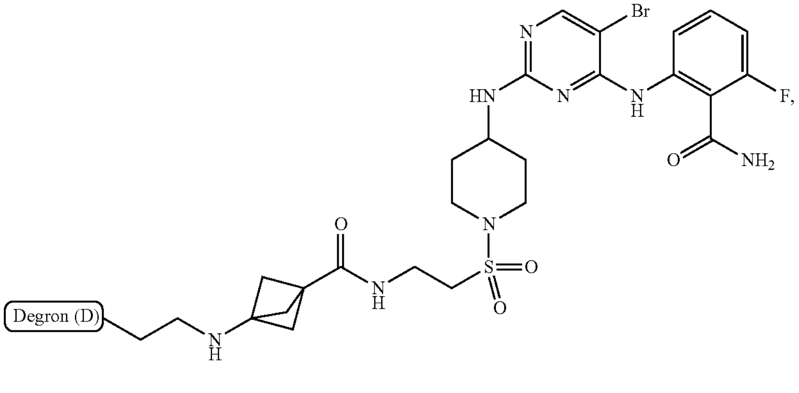

-continued
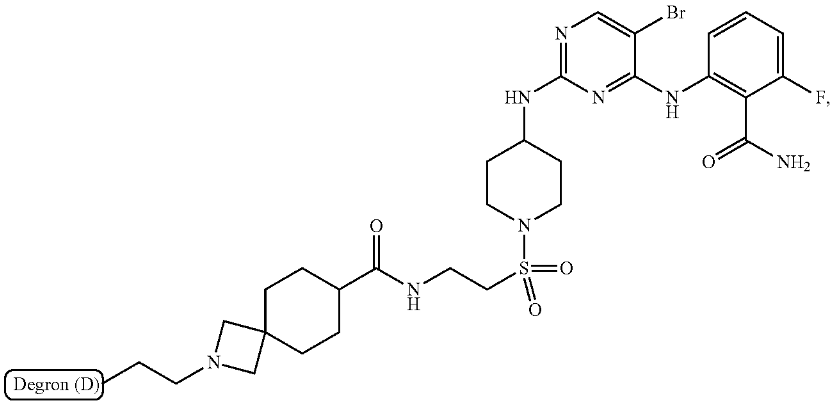
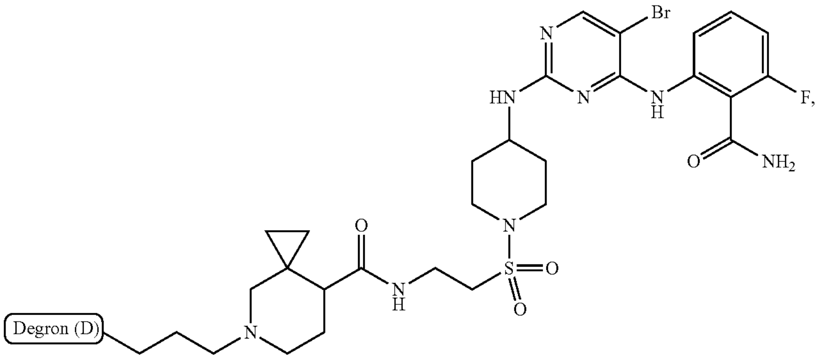
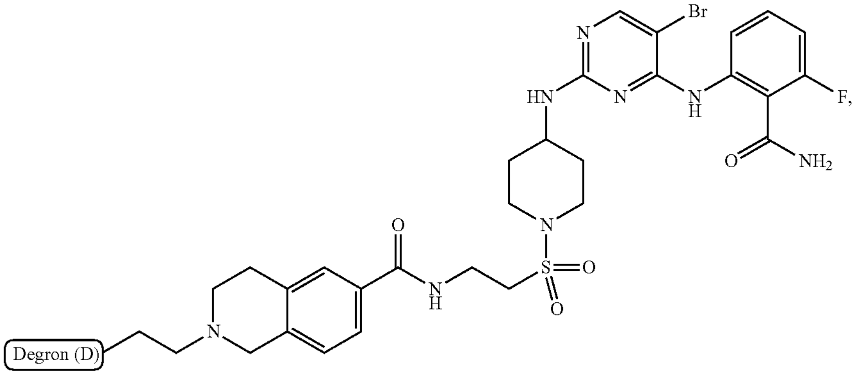
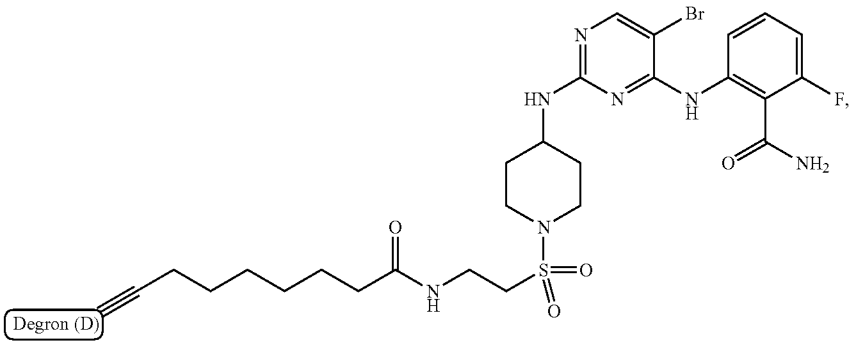

-continued
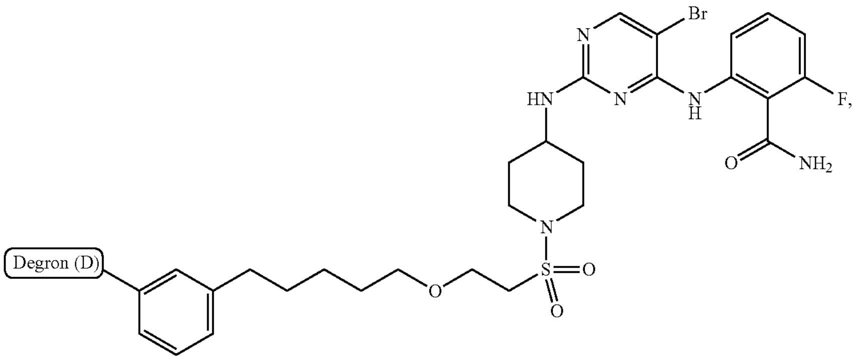
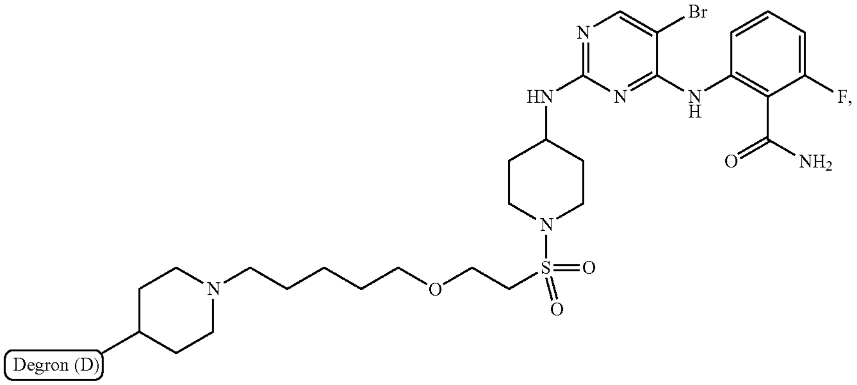
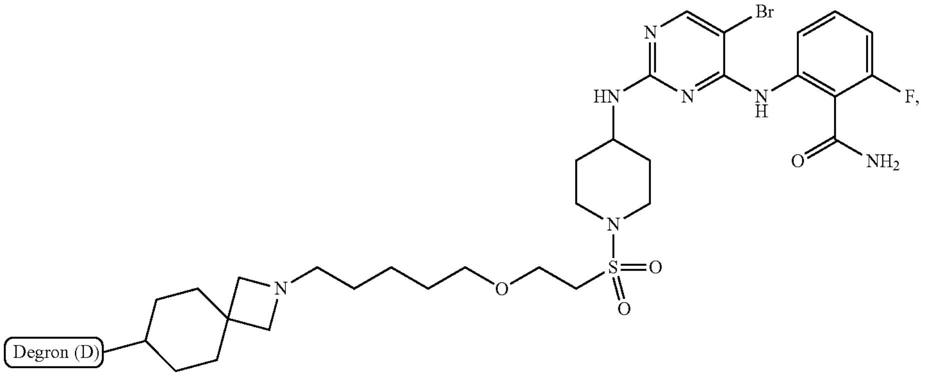
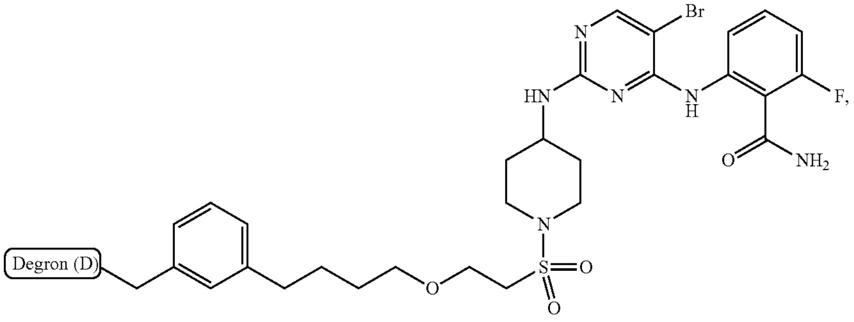

-continued
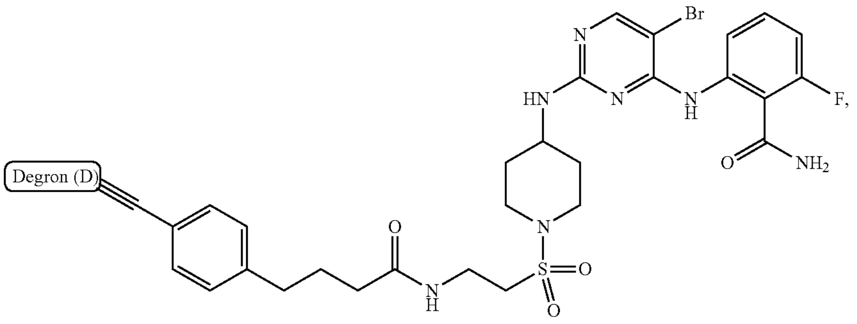
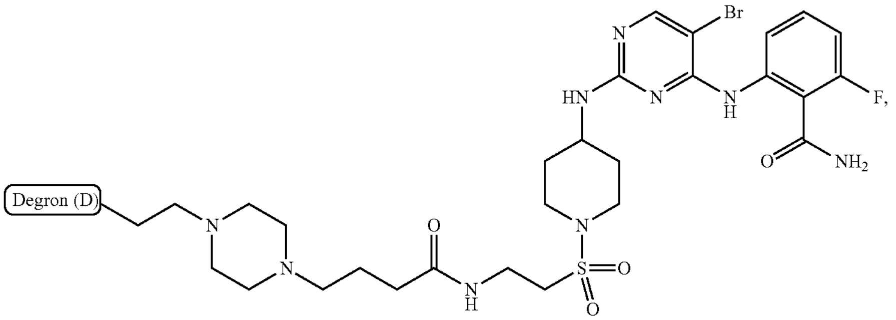
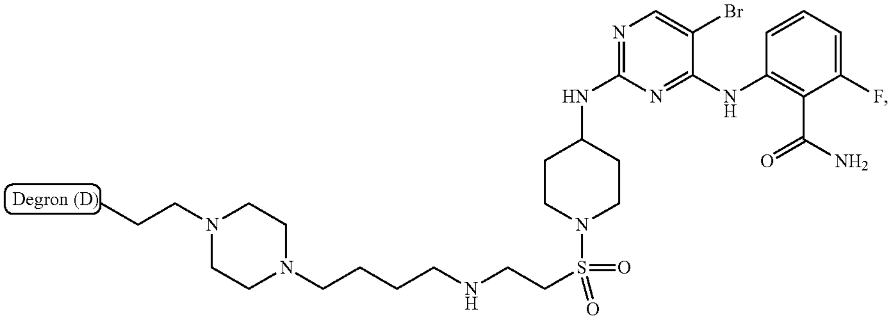
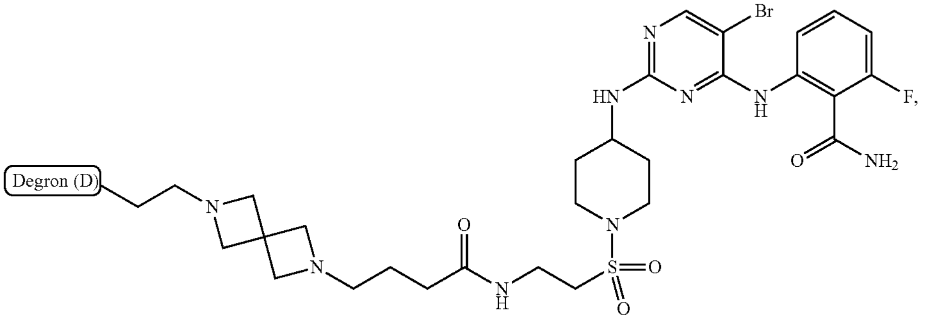
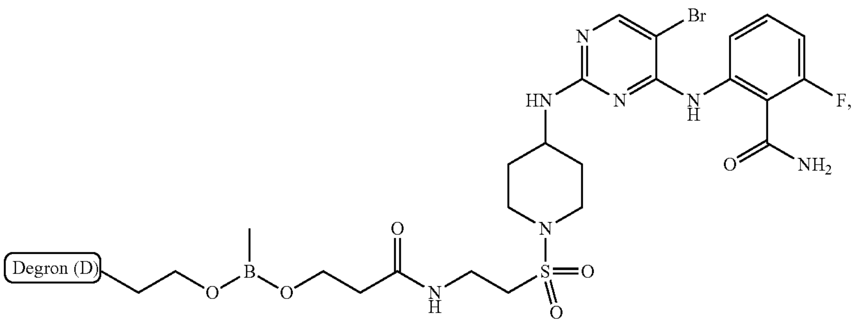

-continued

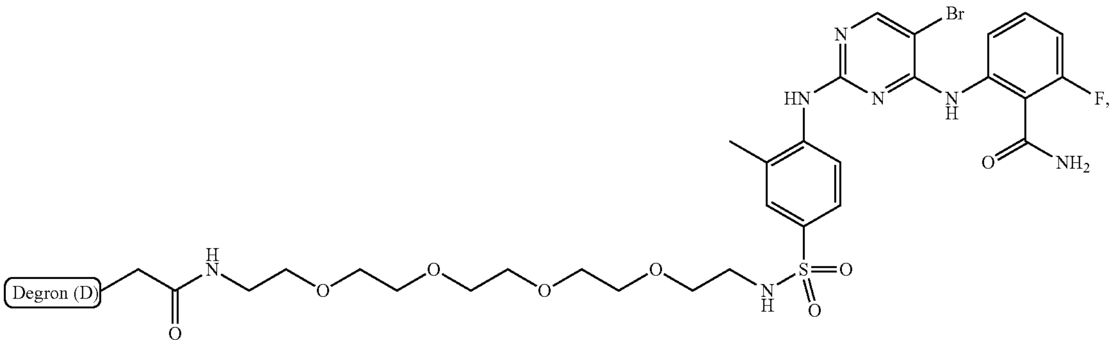

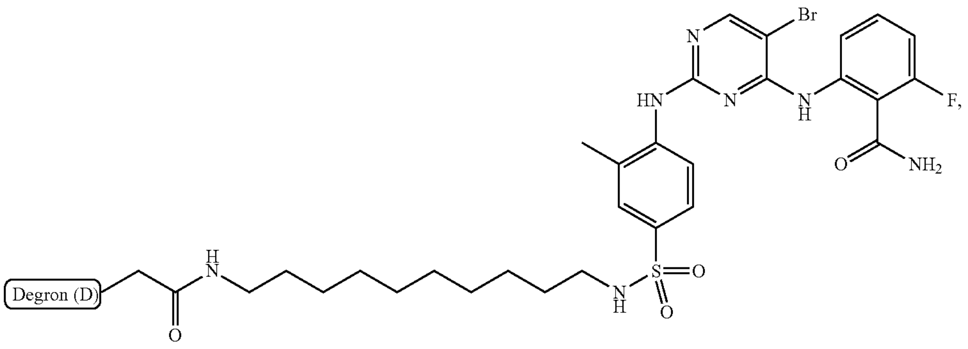

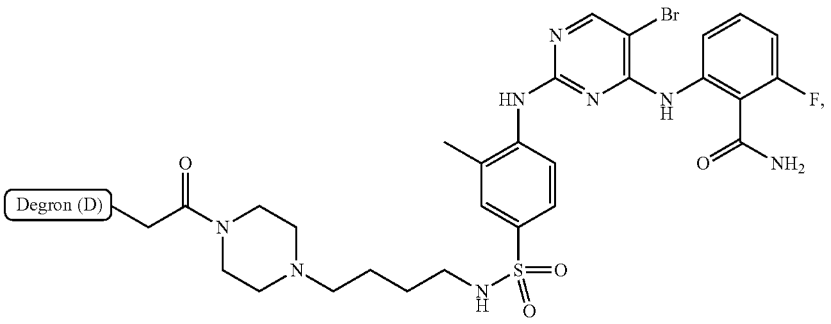 [SMILES: CCC(=O)N1CCN(CCCCNS(=O)(=O)c2ccc(Nc3ncc(Br)c(Nc4cccc(F)c4C(N)=O)n3)c(C)c2)CC1]

or a pharmaceutically acceptable salt or stereoisomer thereof.

Degrons

The Ubiquitin-Proteasome Pathway (UPP) is a critical cellular pathway that regulates key regulator proteins and degrades misfolded or abnormal proteins. UPP is central to multiple cellular processes. The covalent attachment of ubiquitin to specific protein substrates is achieved through the action of E3 ubiquitin ligases. These ligases include over 500 different proteins and are categorized into multiple classes defined by the structural element of their E3 functional activity.

In some embodiments, the degron binds the E3 ubiquitin ligase which is cereblon (CBRN), and is represented by D1 or D2:

(D1)

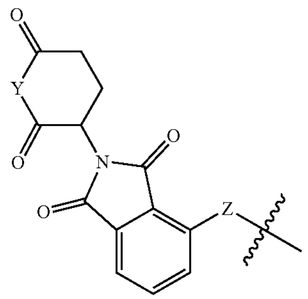

or

-continued
(D2)
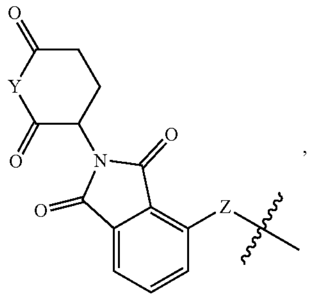
,
wherein
Y is NH, NMe, or O.
Z is $CH_2$, NH, O, or C≡.
Thus, in some embodiments, the compounds of this invention are represented by any one of the following formulas:
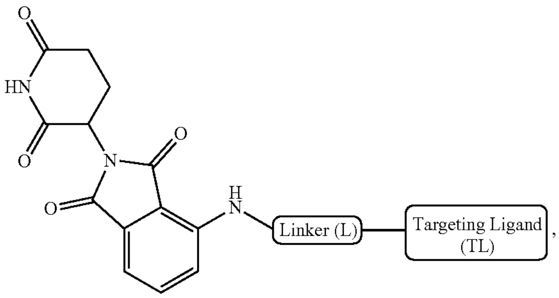
,
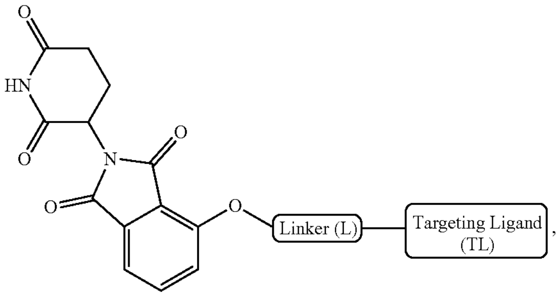
,
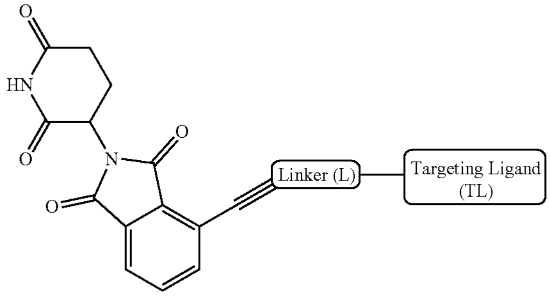
,
-continued
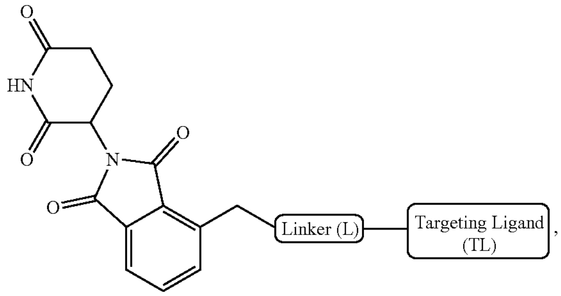
,
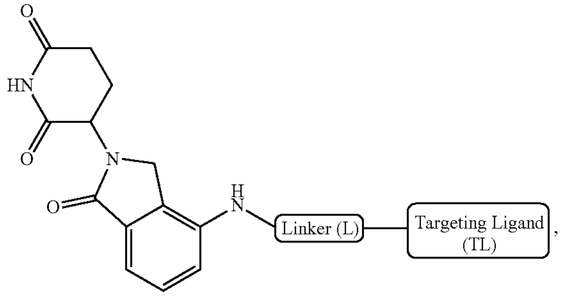
,
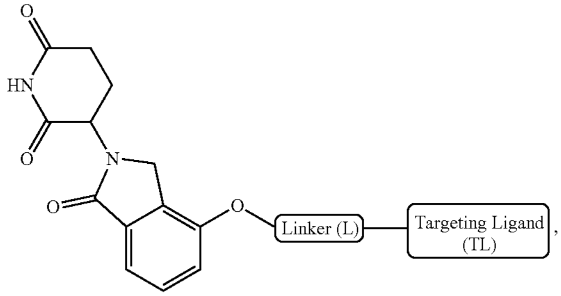
,
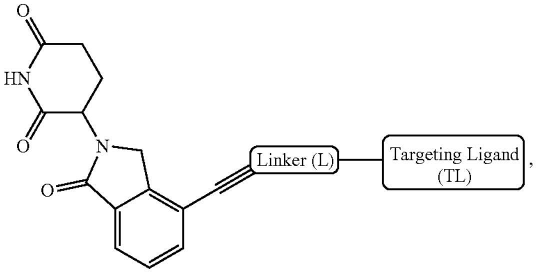
, and
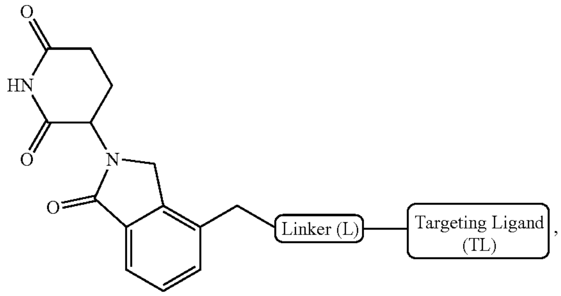
,
or a pharmaceutically acceptable salt or stereoisomer thereof.
Thus in some embodiments, the compounds of the present invention are represented by any one of the following formulas:

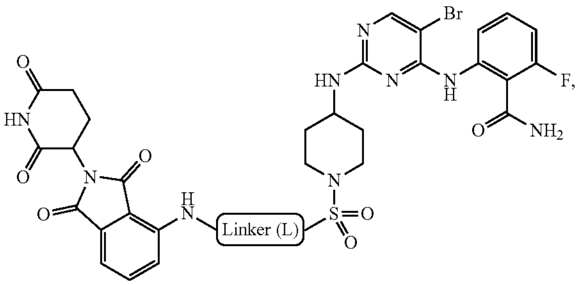
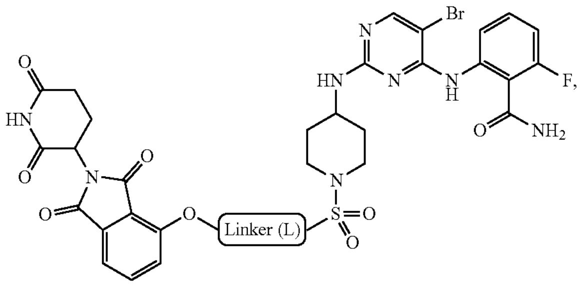
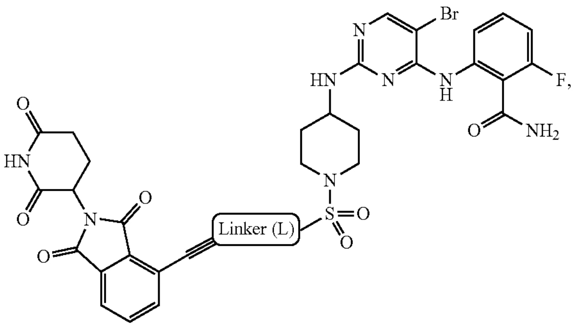
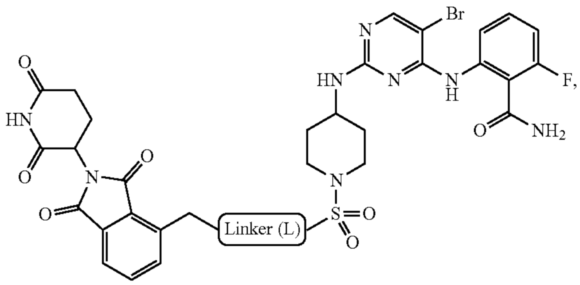
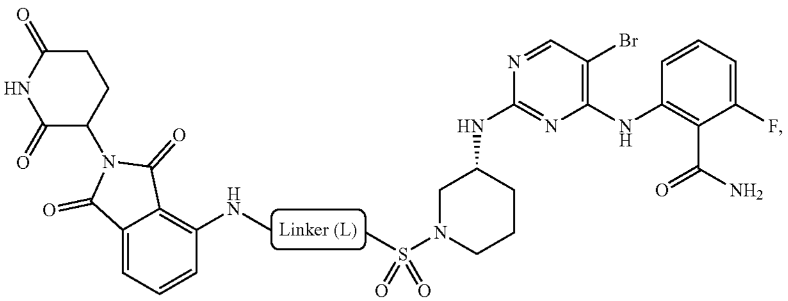
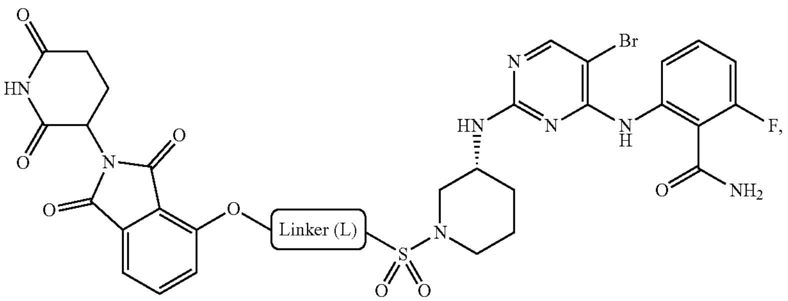
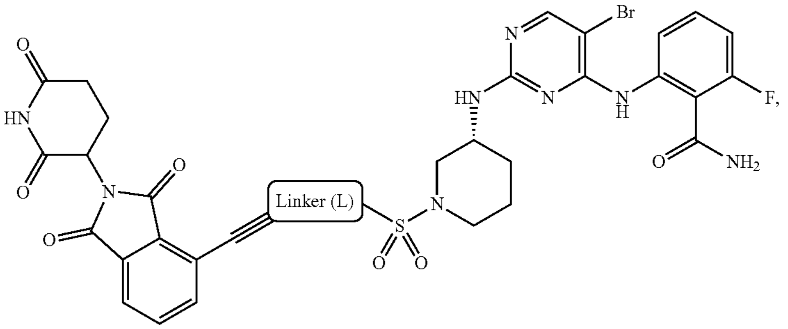

-continued
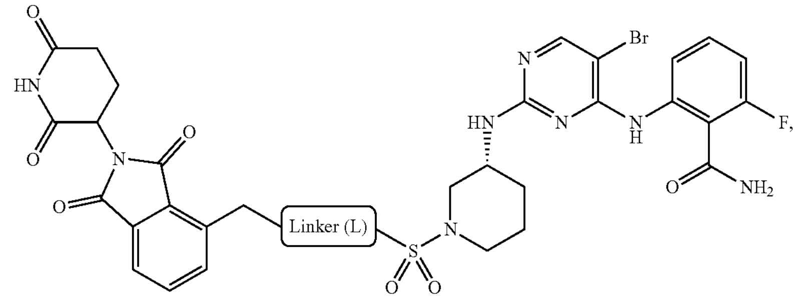,
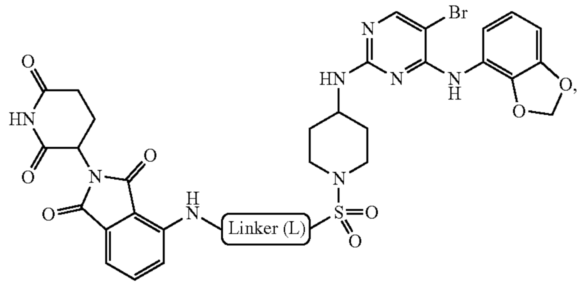,
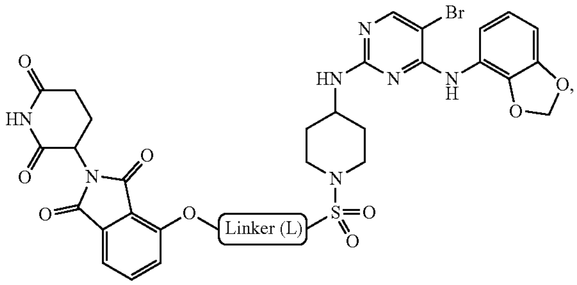,
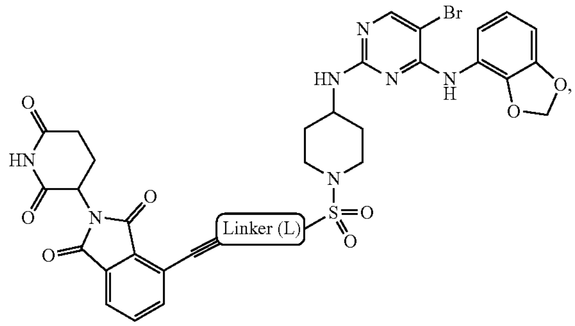,
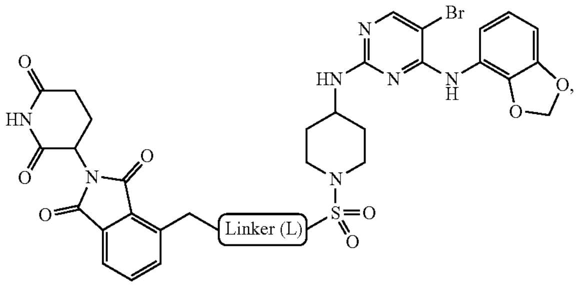,
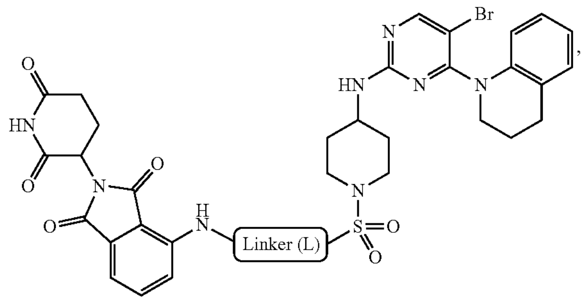,
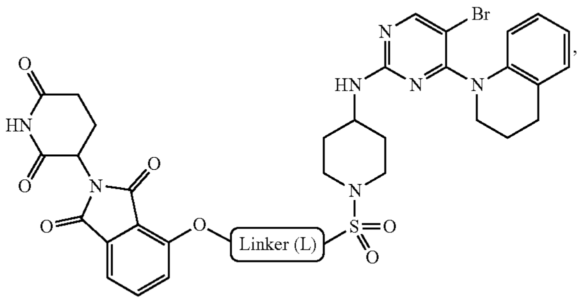,
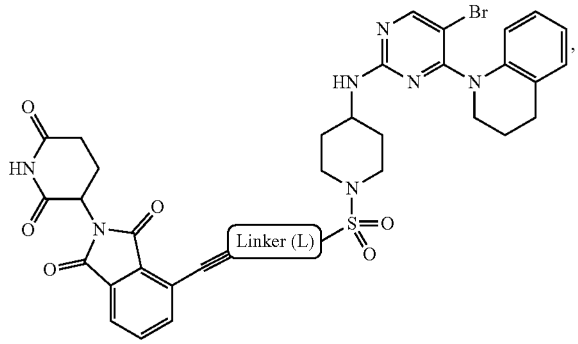,
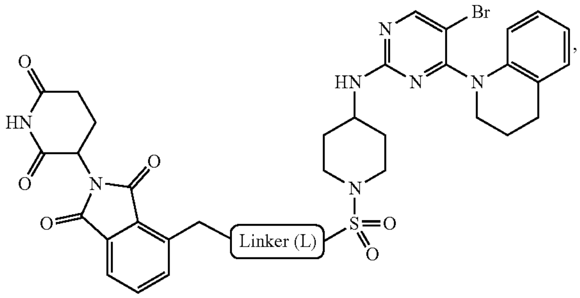, -continued
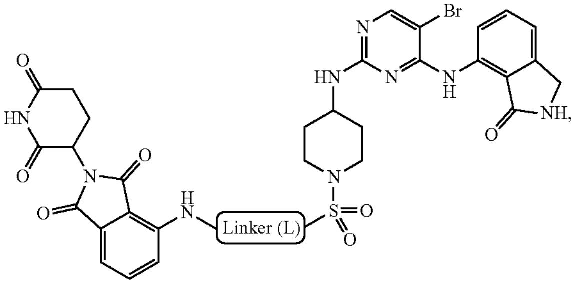
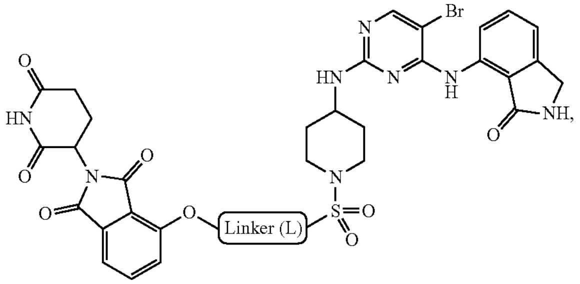
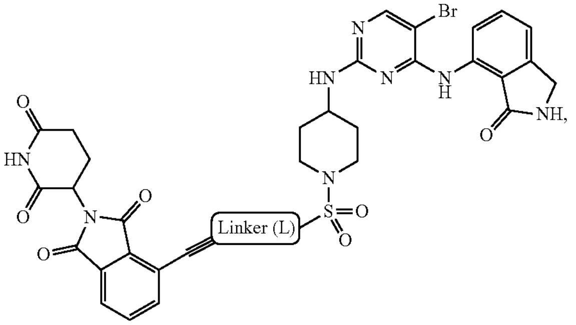
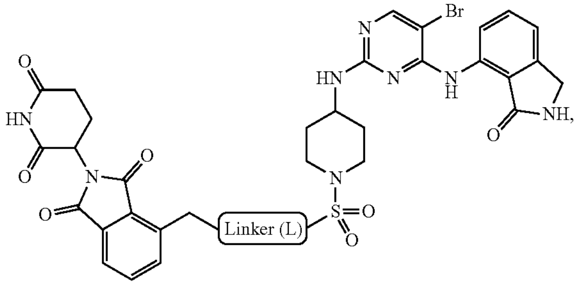
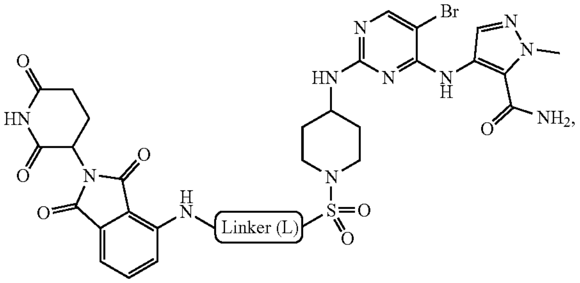
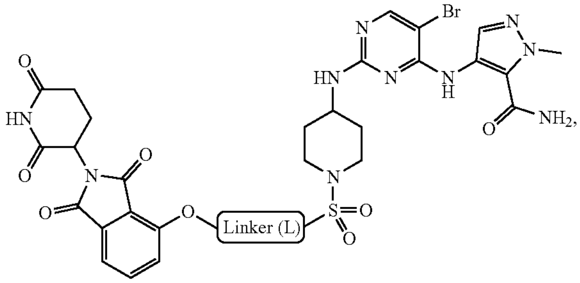
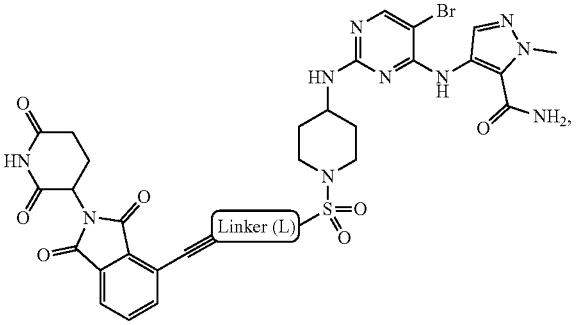
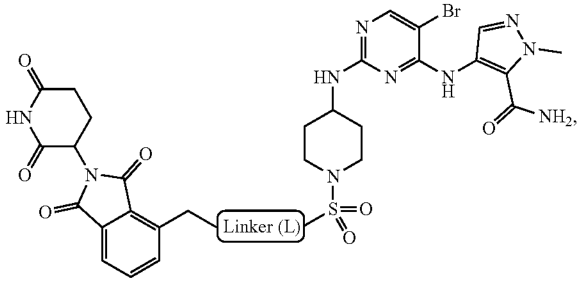
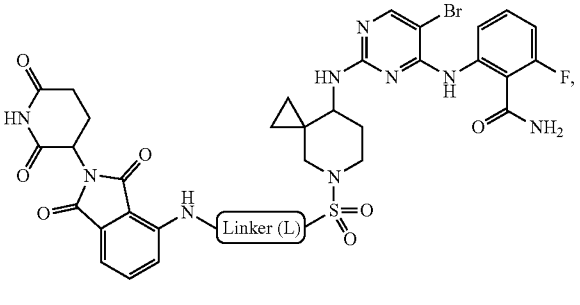
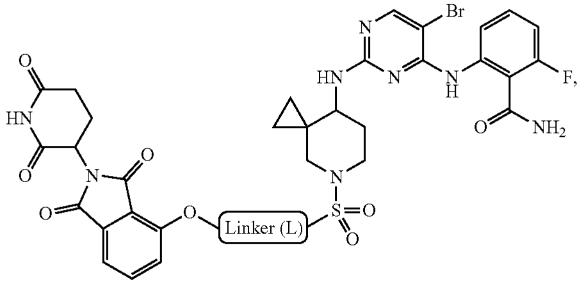

-continued
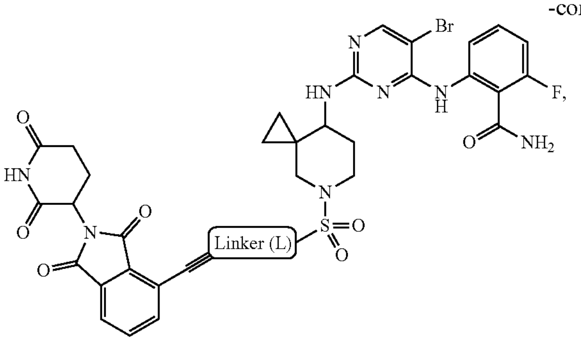
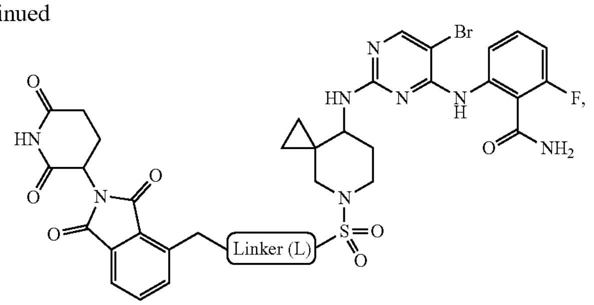
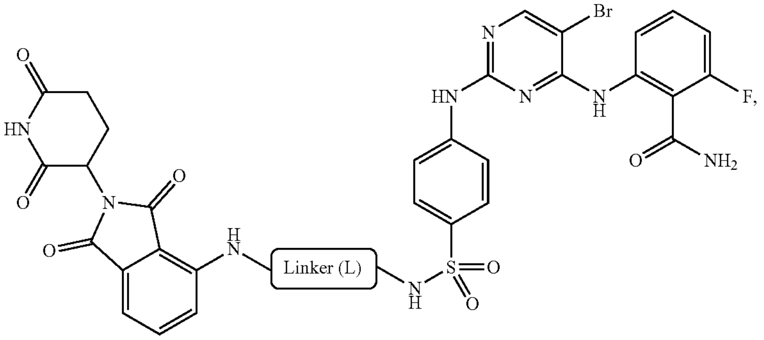
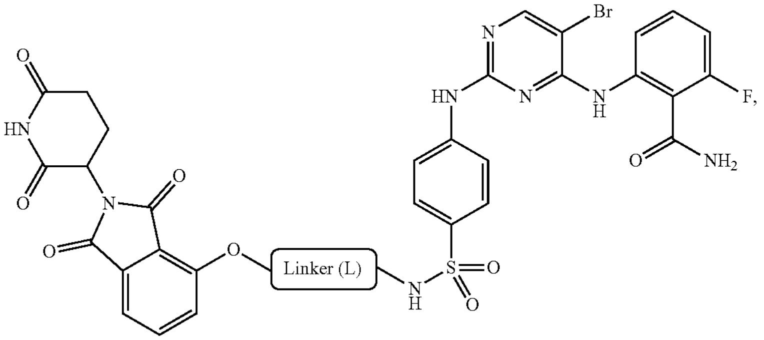
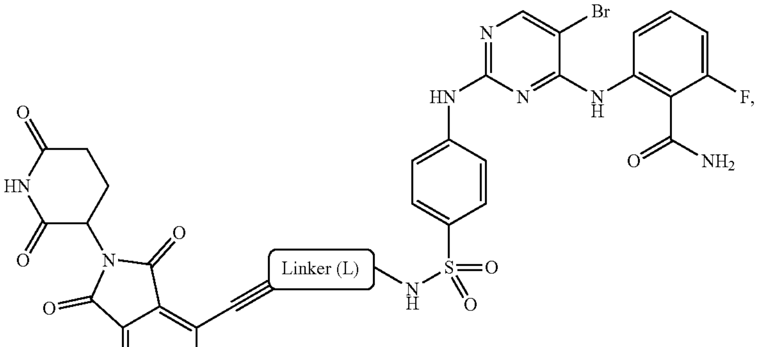
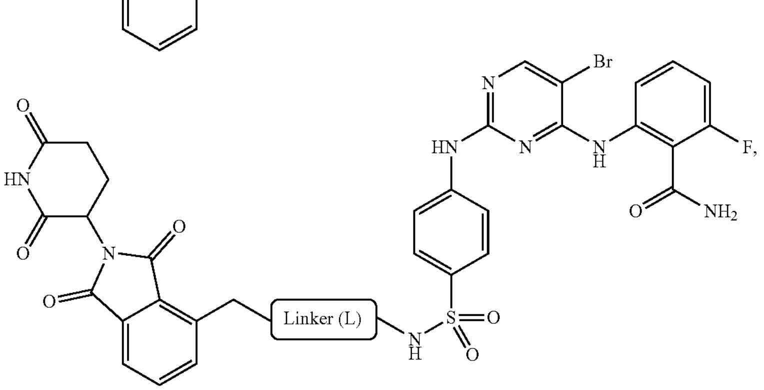

-continued
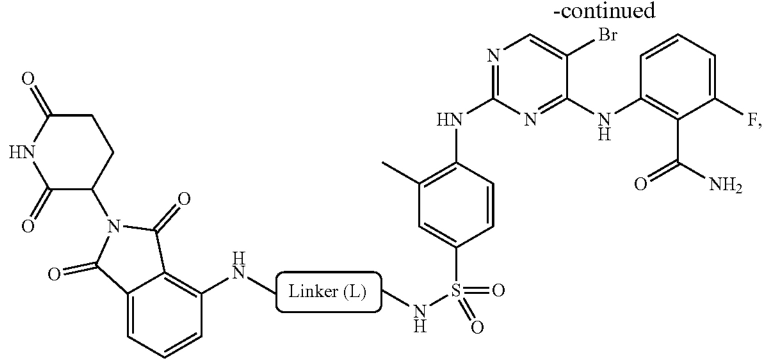
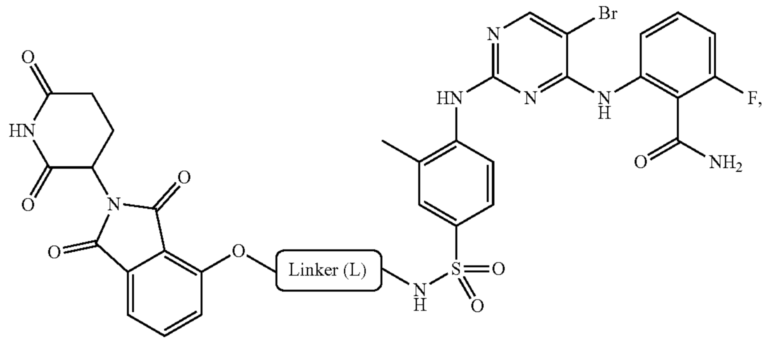
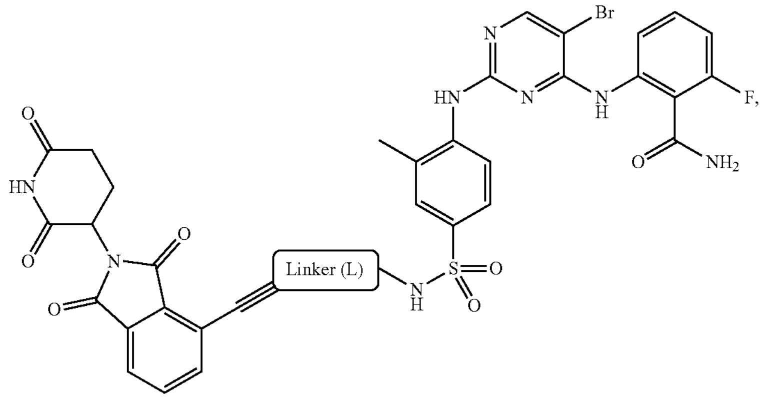
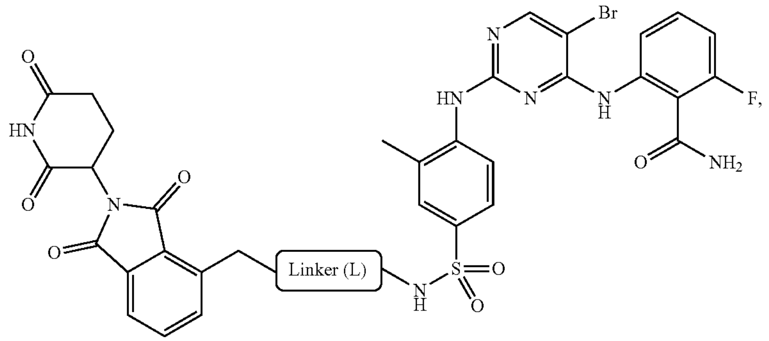

-continued
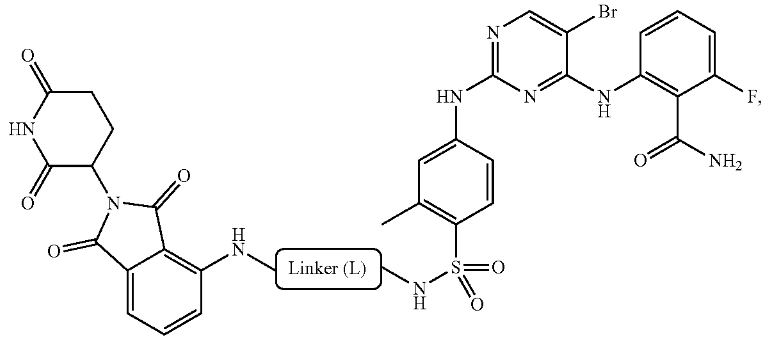
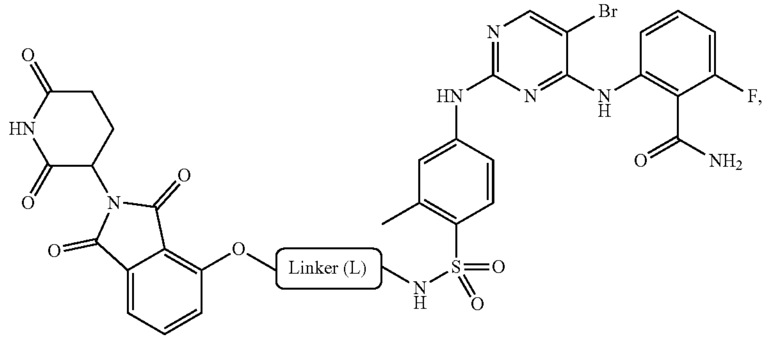
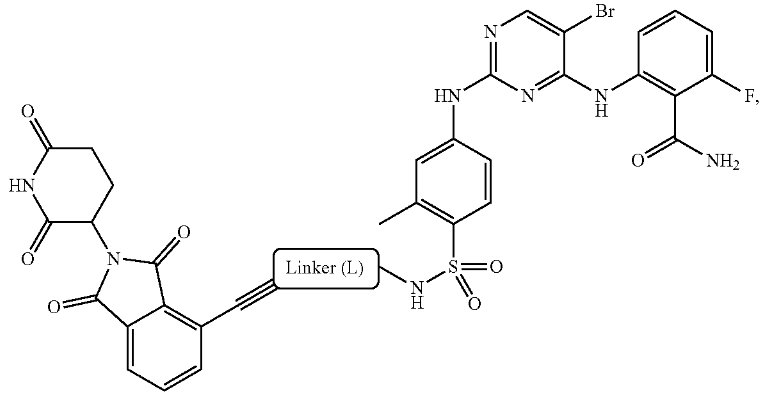
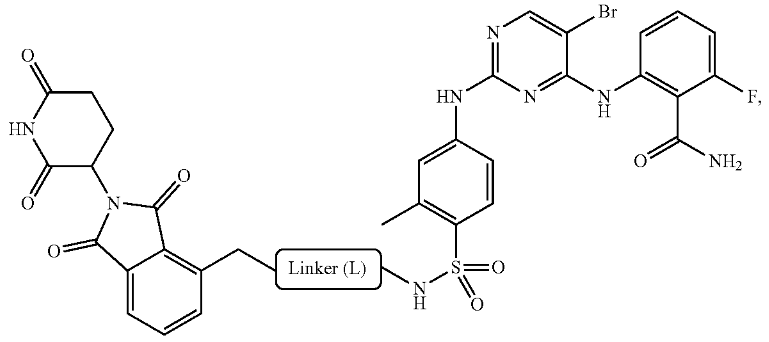
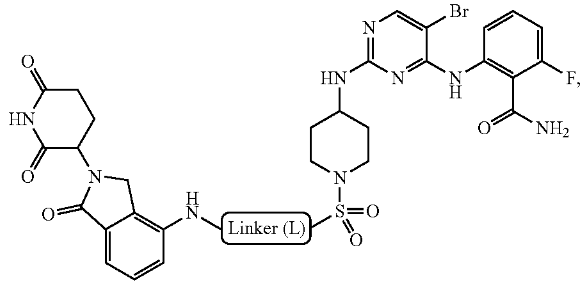
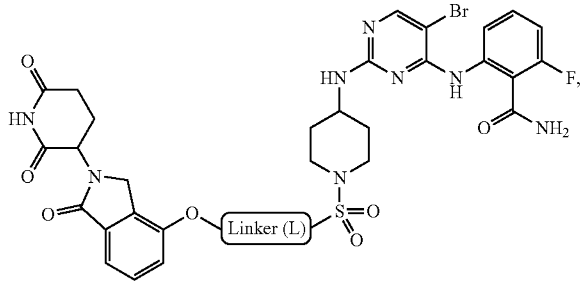

-continued
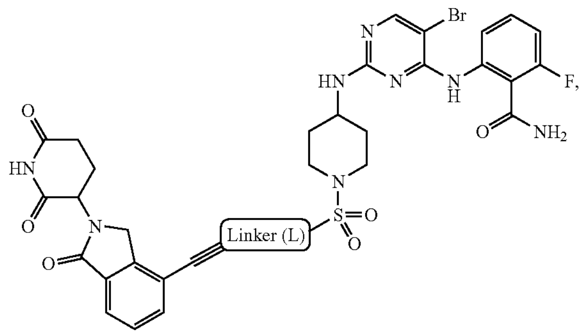
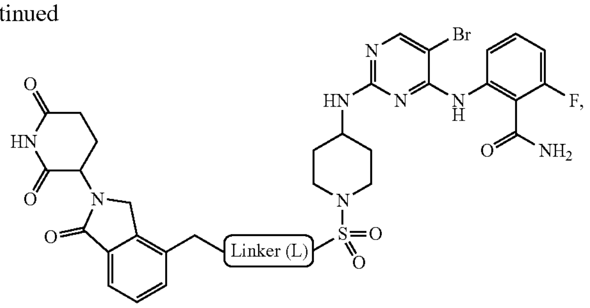
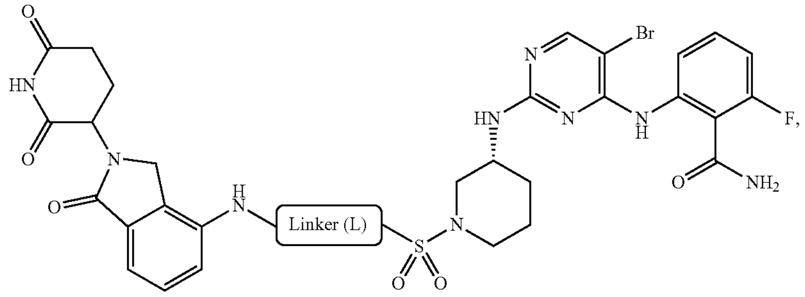
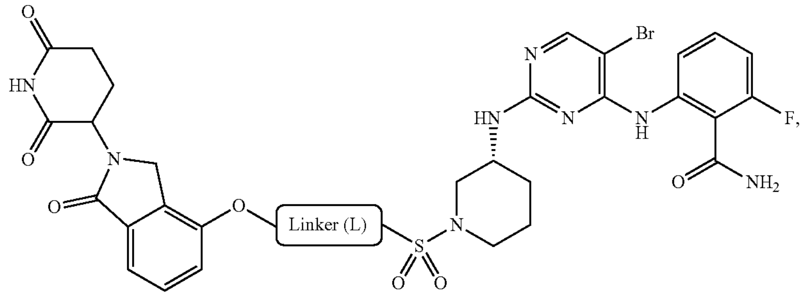
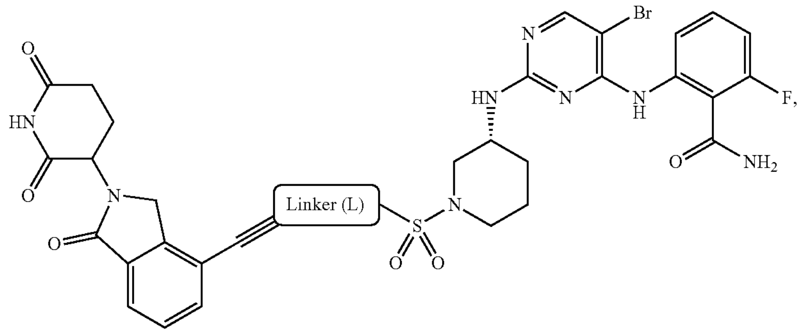
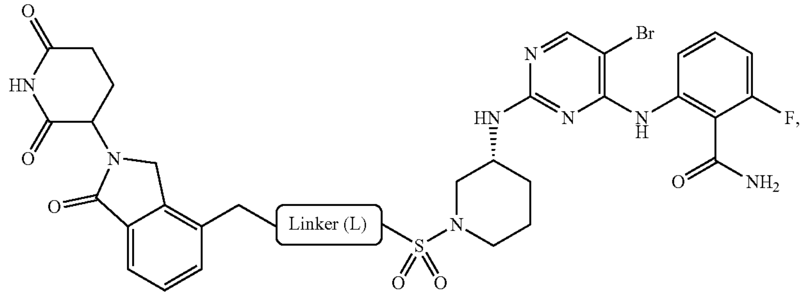

-continued
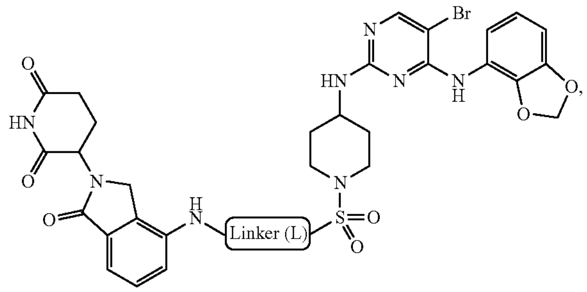
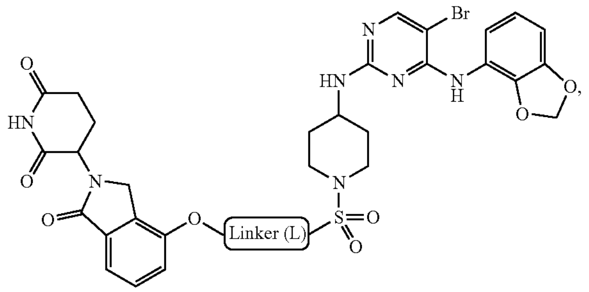
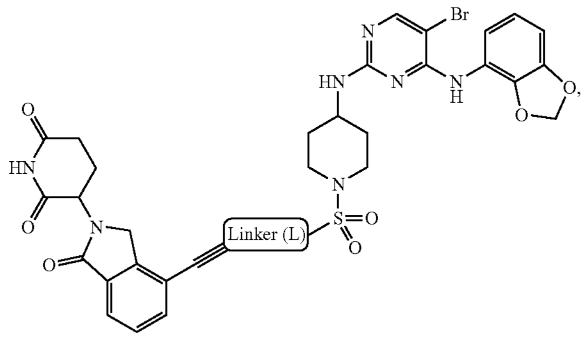
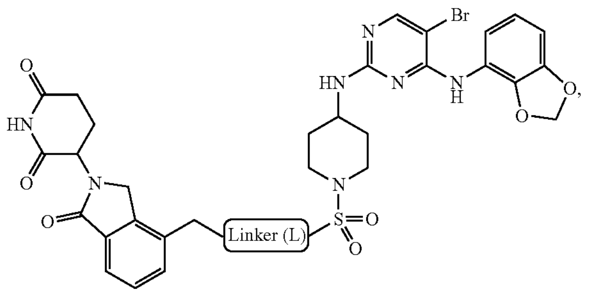
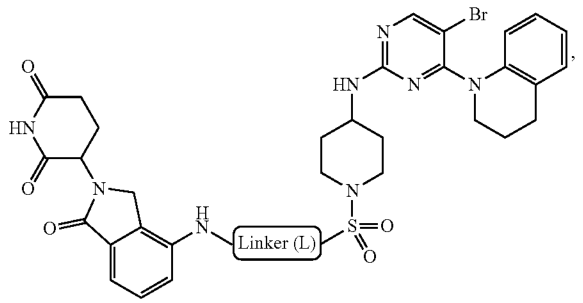
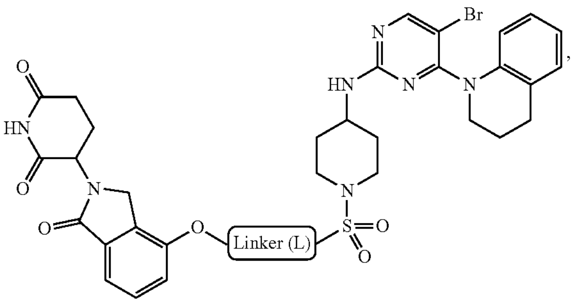
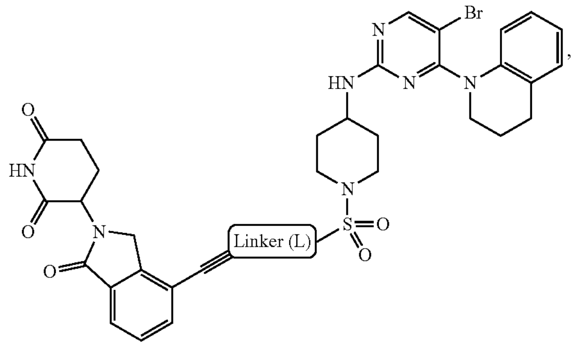
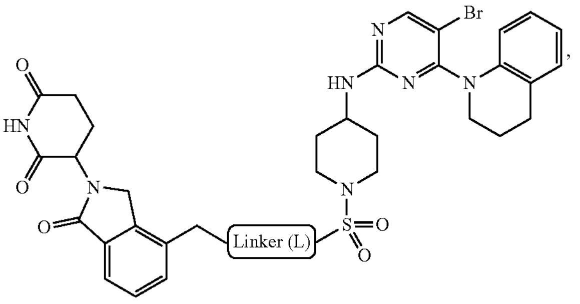
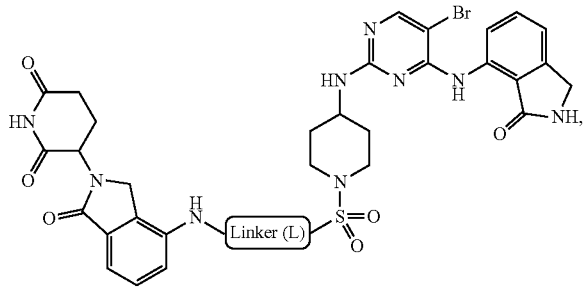
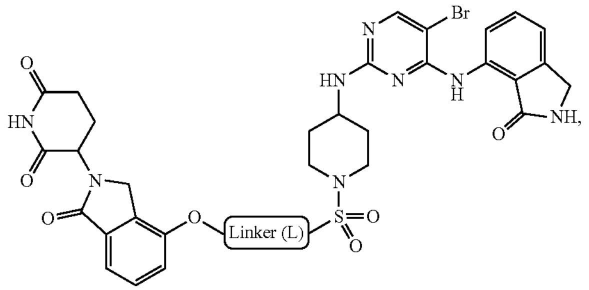

-continued
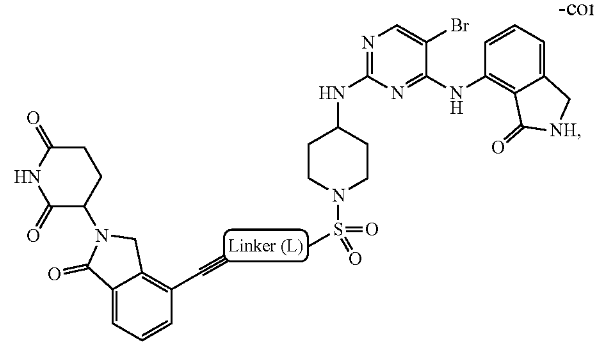
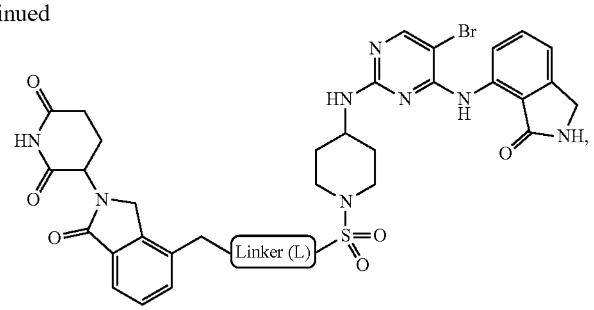
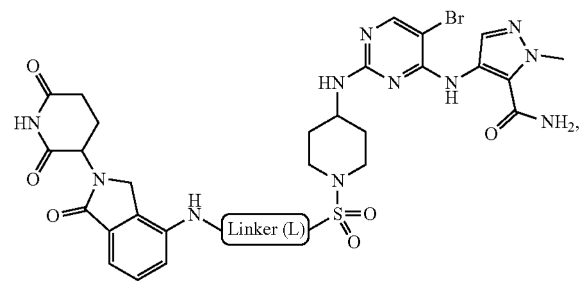
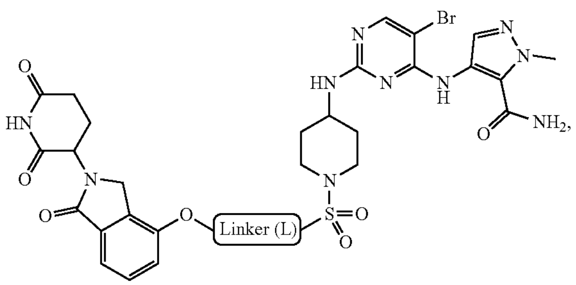
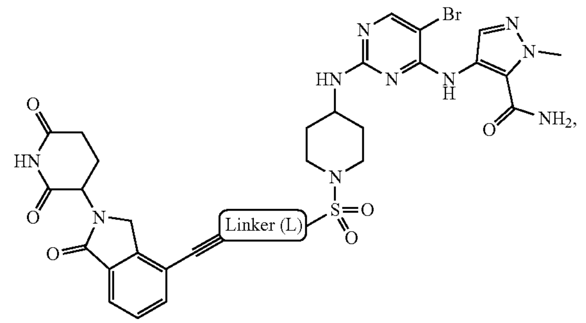
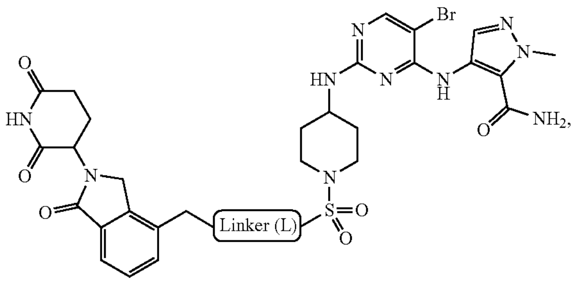
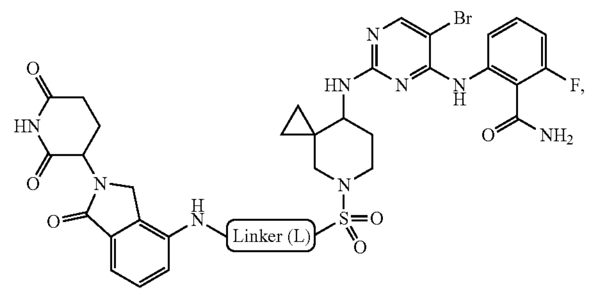
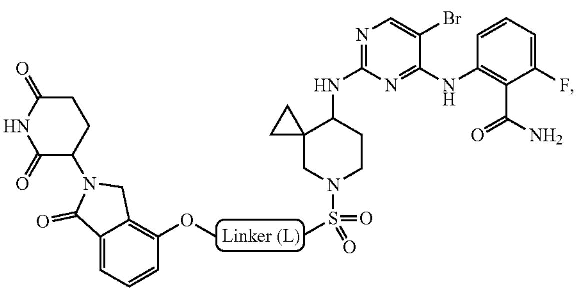
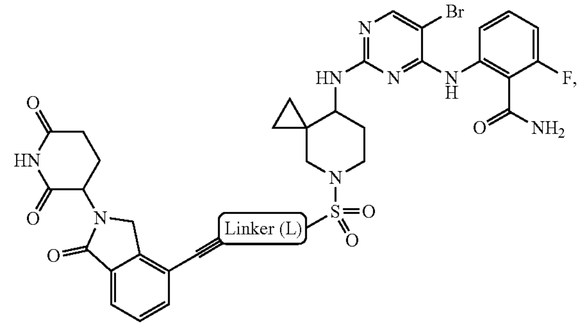
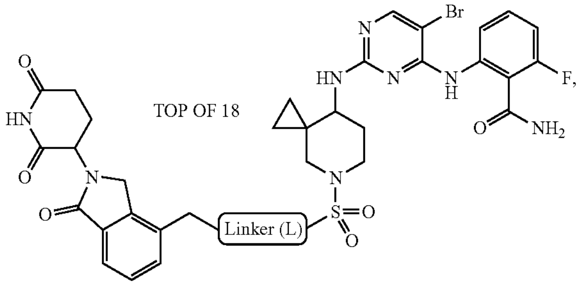
TOP OF 18

-continued
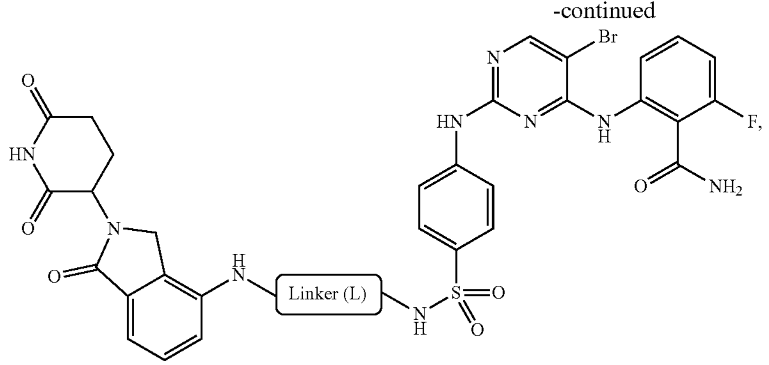
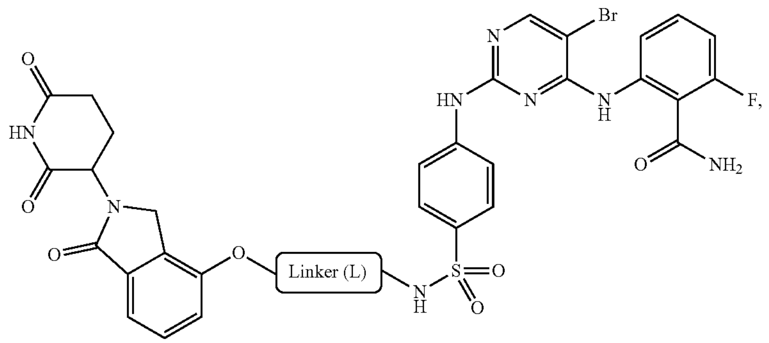
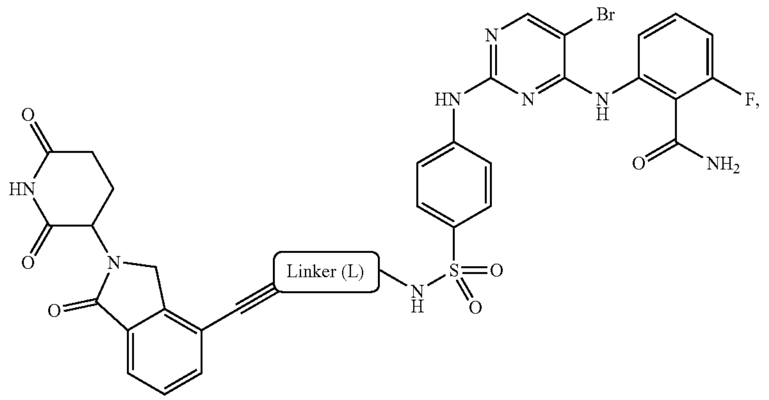
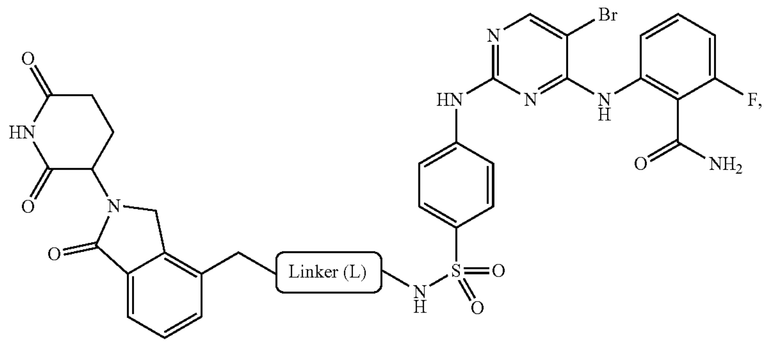

-continued
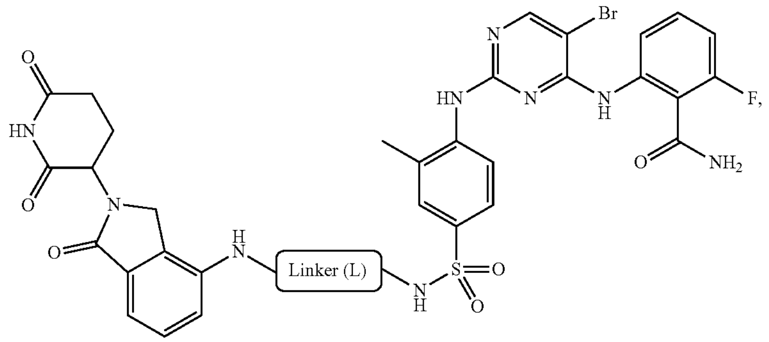
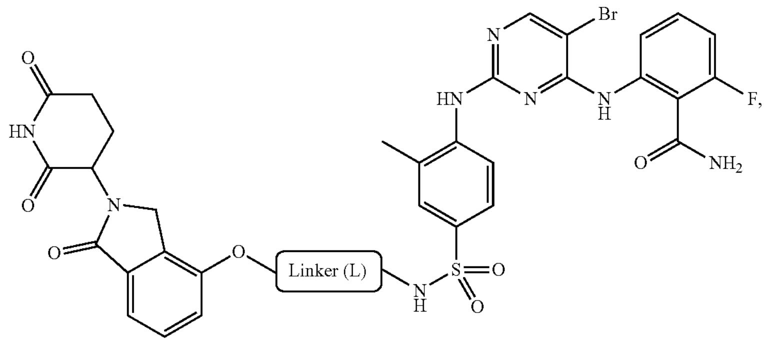
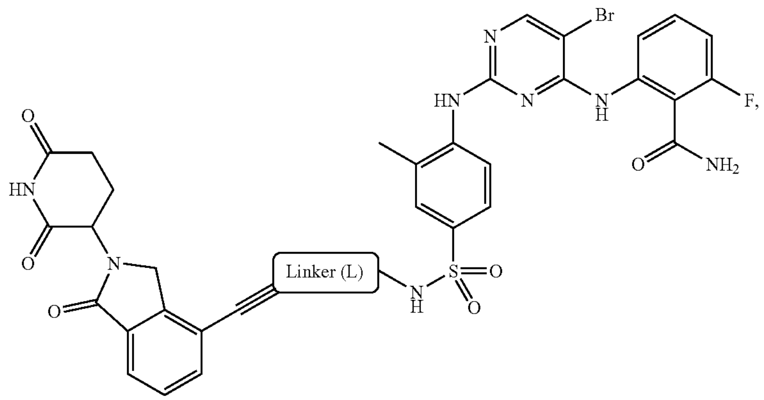
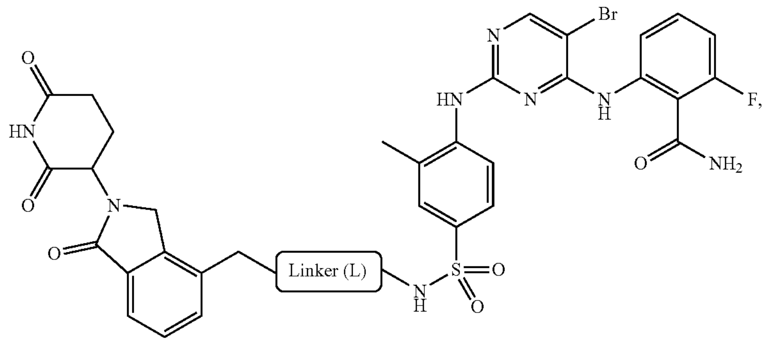

-continued

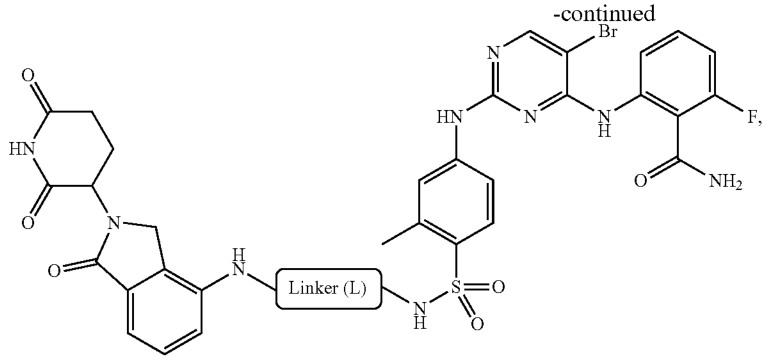

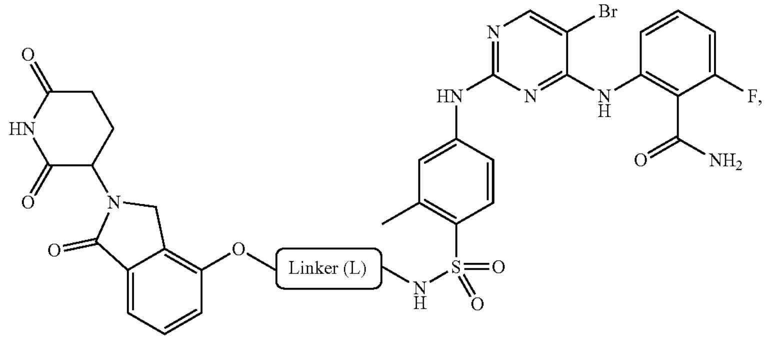

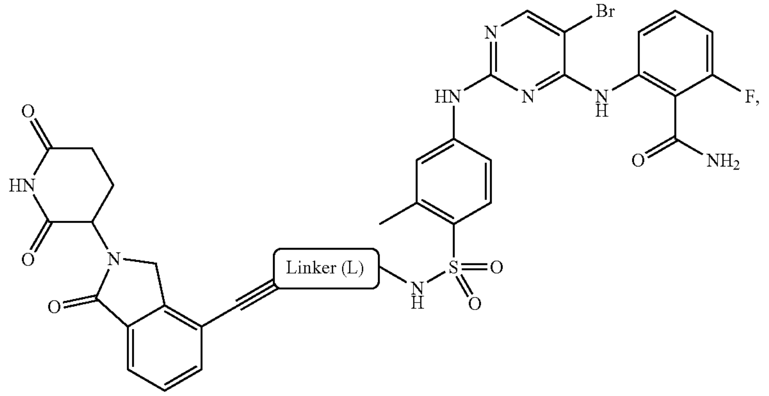

and

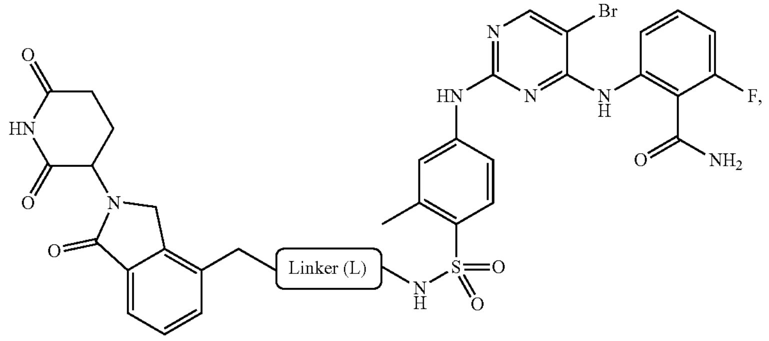

or a pharmaceutically acceptable salt or stereoisomer thereof.

Yet other degrons that bind cereblon and which may be suitable for use in the present invention are disclosed in U.S. Pat. No. 9,770,512, and U.S. Patent Application Publication Nos. 2018/0015087, 2018/0009779, 2016/0243247, 2016/0235731, 2016/0235730, and 2016/0176916, and International Patent Publications WO 2017/197055, WO 2017/197051, WO 2017/197036, WO 2017/197056 and WO 2017/197046.

In some embodiments, the E3 ubiquitin ligase that is bound by the degron is the von Hippel-Lindau (VHL) tumor suppressor. See, Iwai, et al., Proc. Nat'l. Acad. Sci. USA 96:12436-41 (1999).

In some embodiments, the degrons that bind VHL are represented by any one of the following formulas:

(D3a)
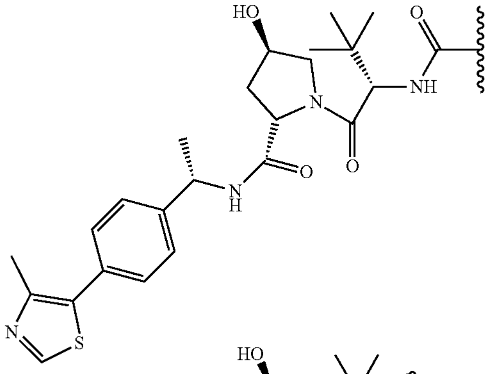
,
(D3b)
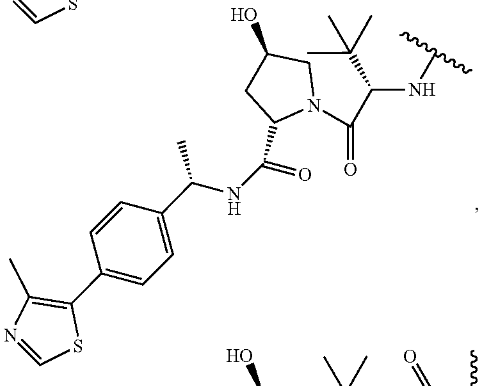
,
(D3c)
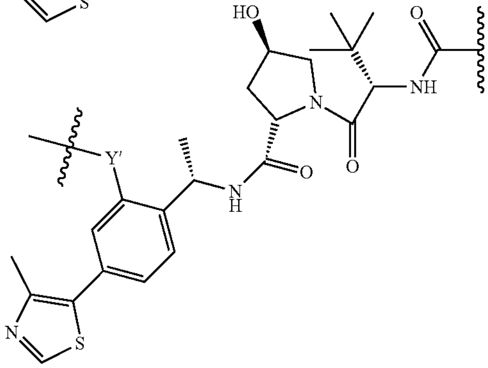
,
wherein Y' is a bond, NH, O or $CH_2$, and
(D3d)
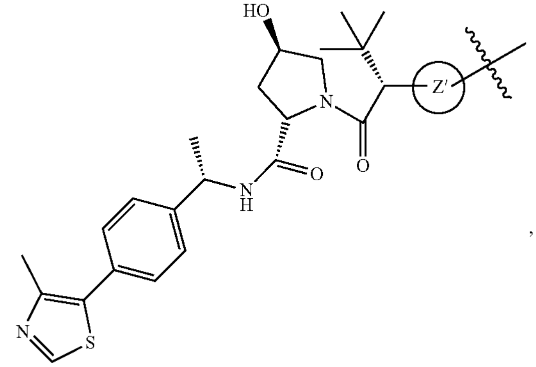
,
wherein Z' is a cyclic group, which in some embodiments is a C5-6 carbocyclic or heterocyclic group, or stereoisomer thereof. In certain embodiments, Z' is
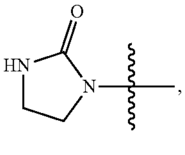
,
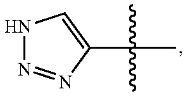
, or
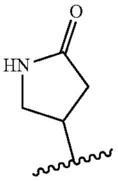
.
In some embodiments, the present invention provides a compound represented by any of the following formulas:
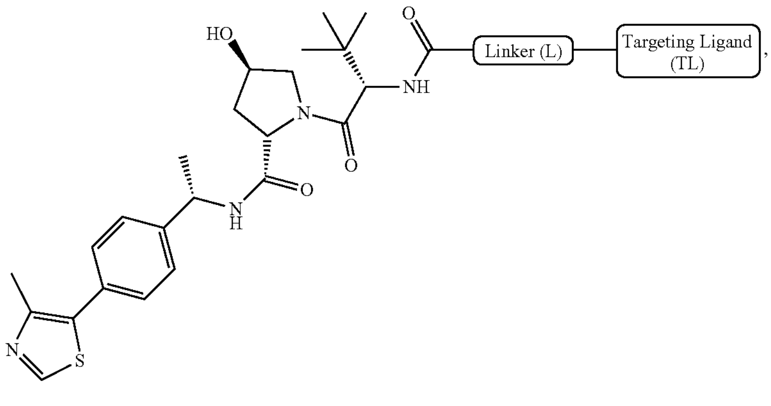
, -continued

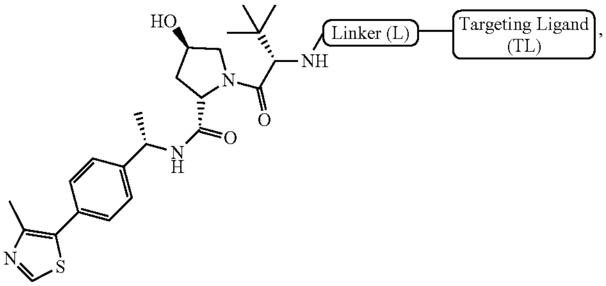

,

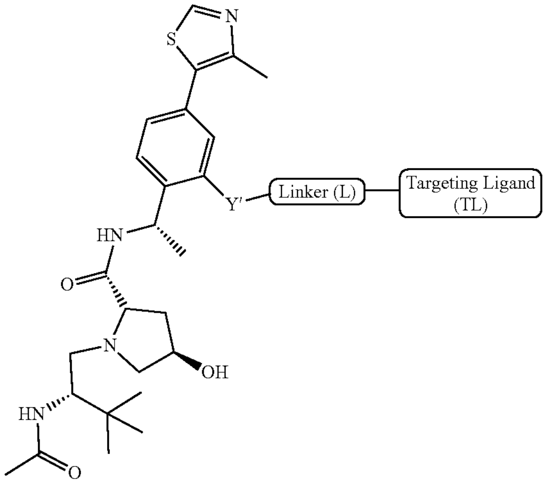

, and

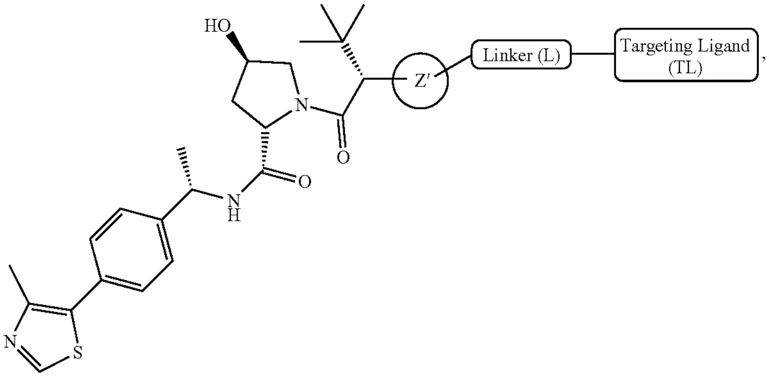

, or a pharmaceutically acceptable salt or stereoisomer thereof.

In some embodiments, the cyclic group is preferably phenyl, pyrrolyl, furanyl, thiophenyl, pyrazolyl, imidazolyl, oxazolyl, thiazolyl, pyridinyl, pyridazinyl, pyrimidinyl, benzofuranyl, benzothiophenyl, indolyl, quinolinyl, or isoquinolinyl.

Thus in some embodiments, the compounds of the present invention are represented by any one of the following formulas:

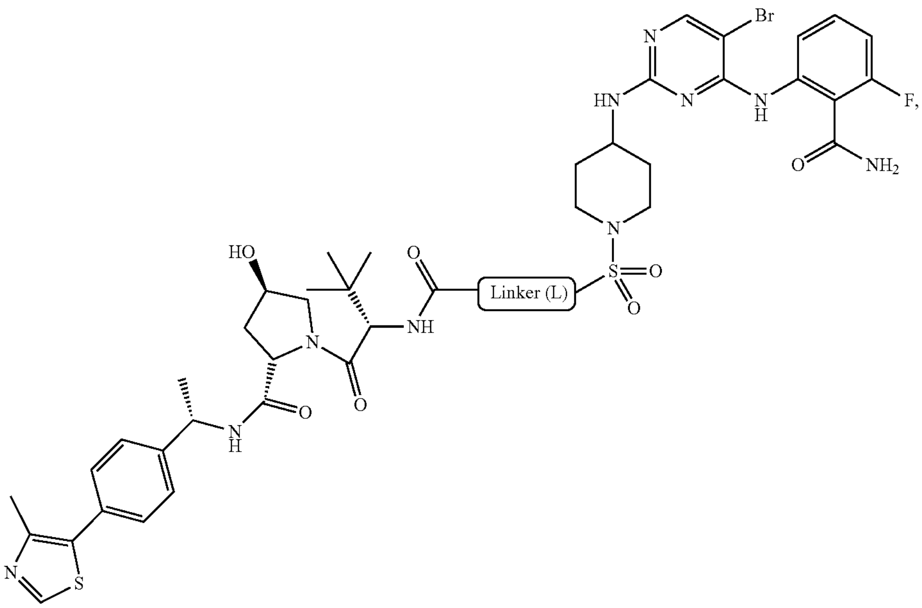

,

-continued
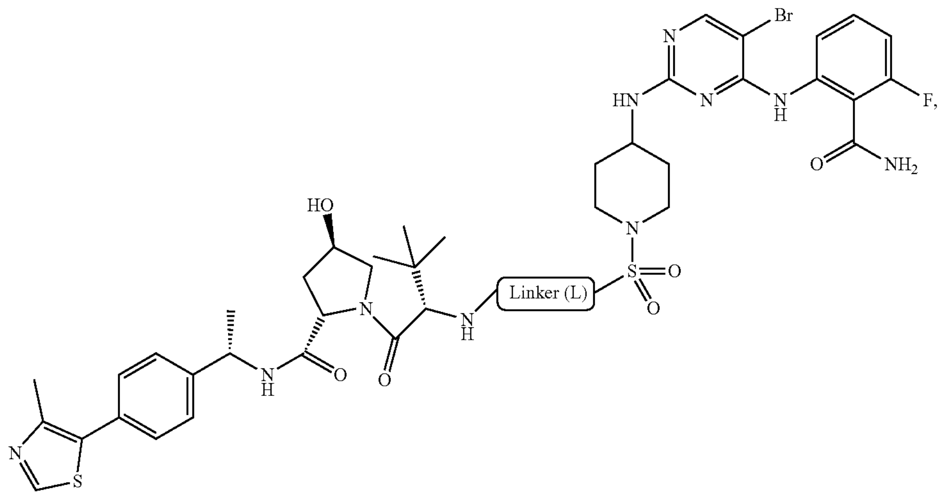
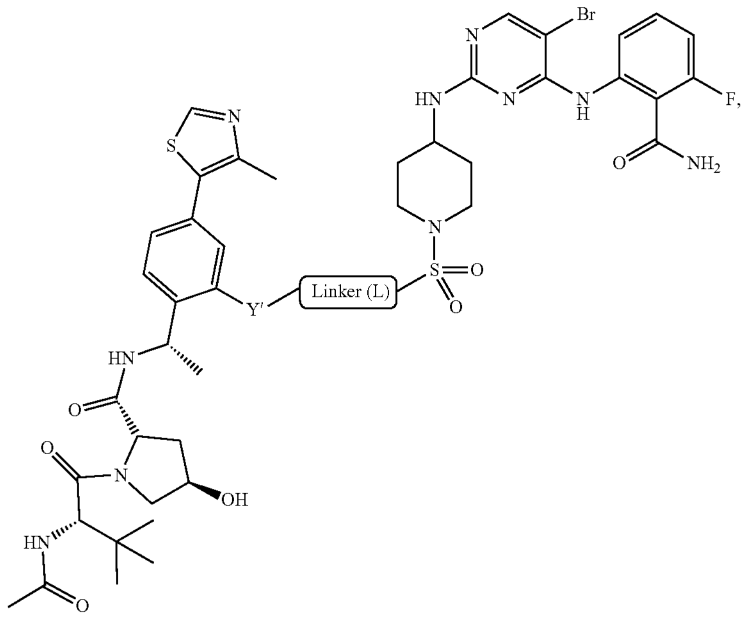
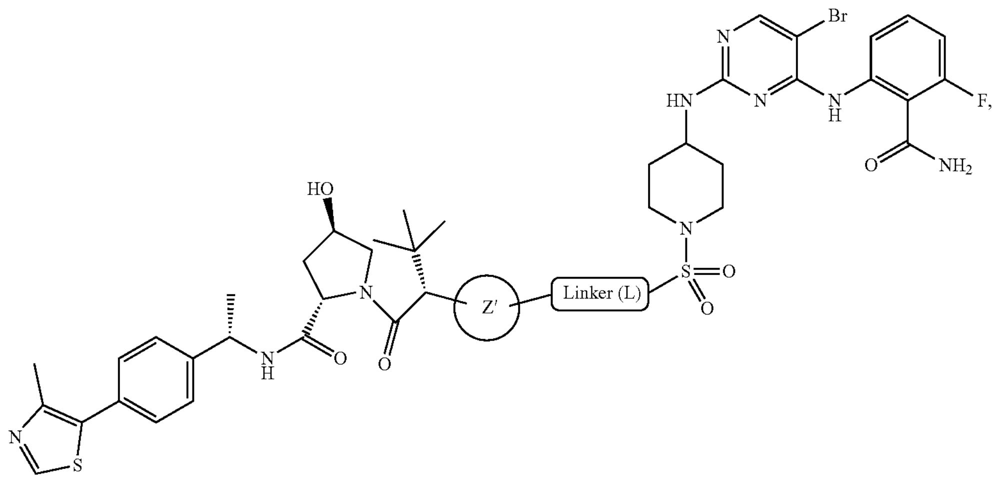

-continued
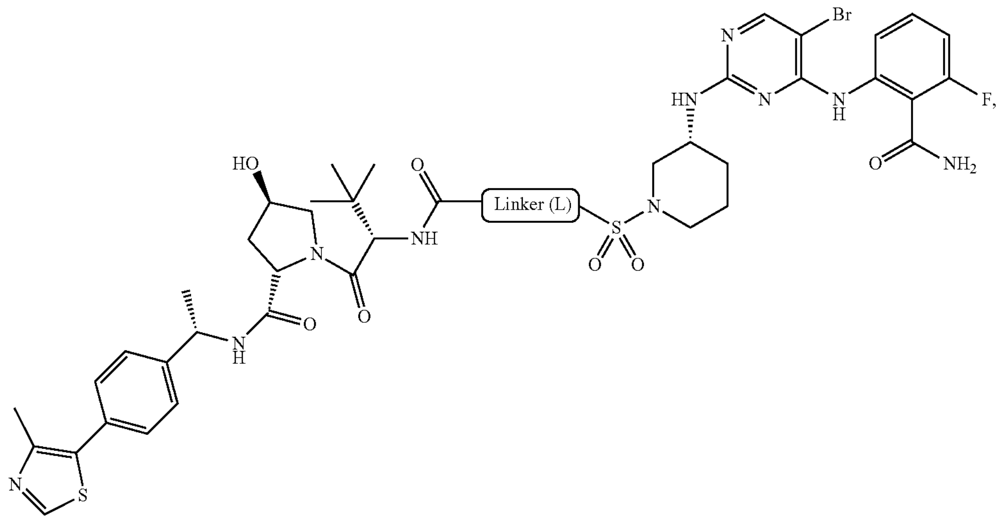
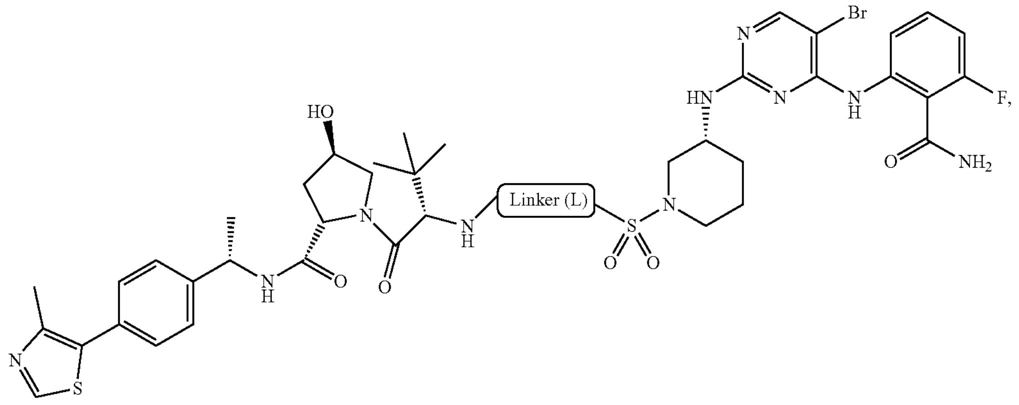
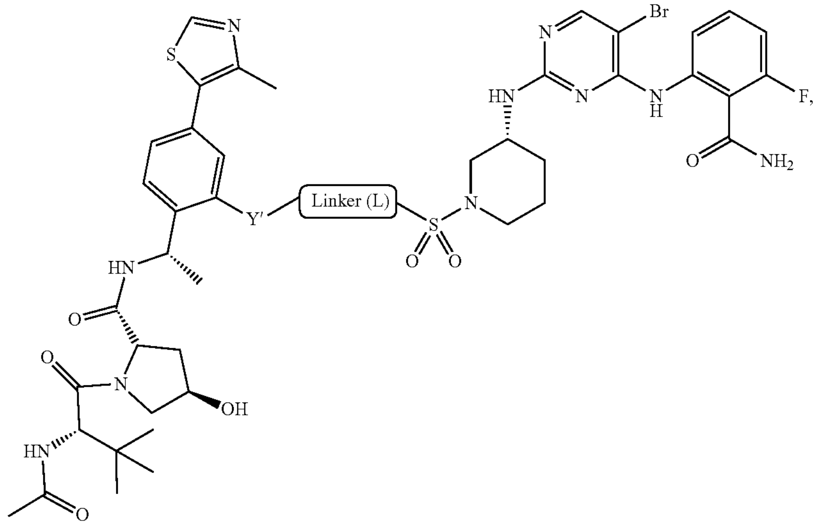

-continued
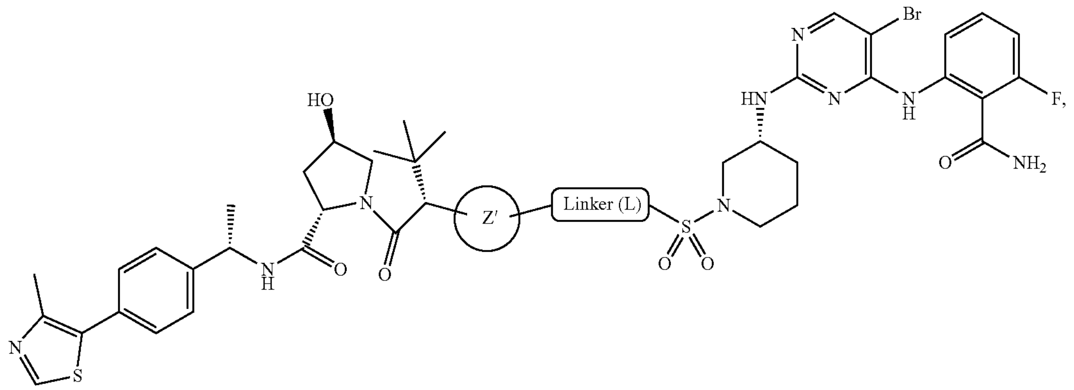
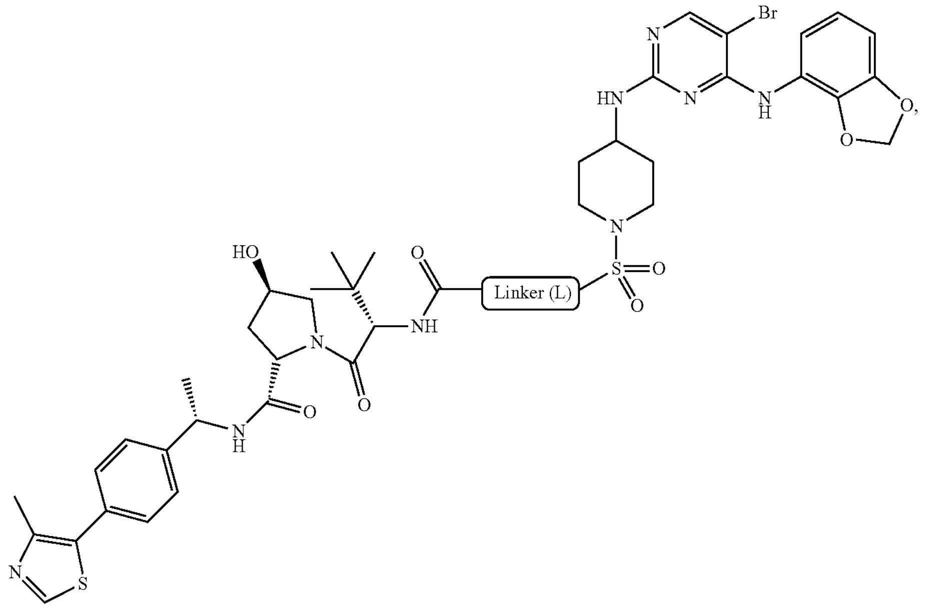
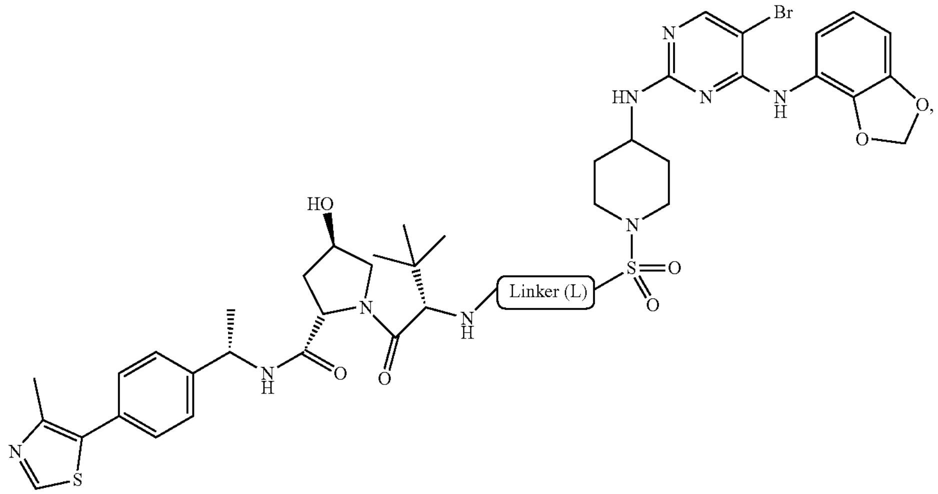

-continued
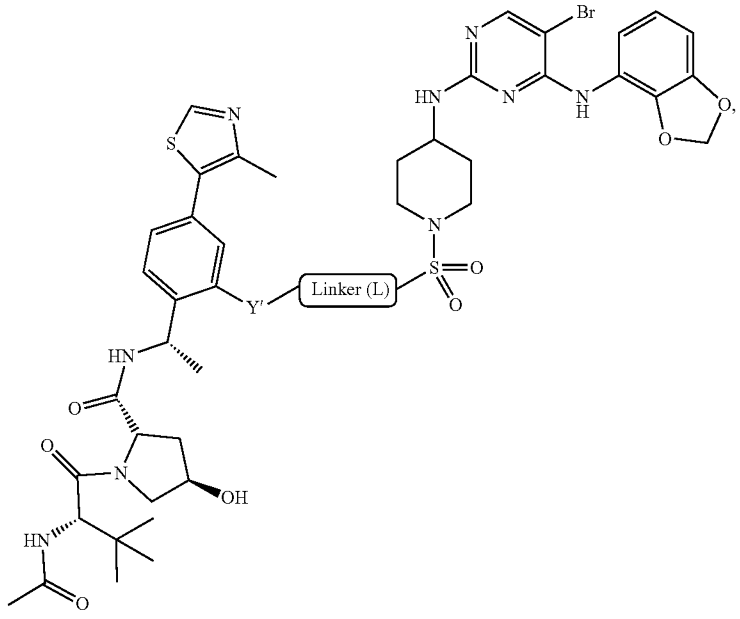
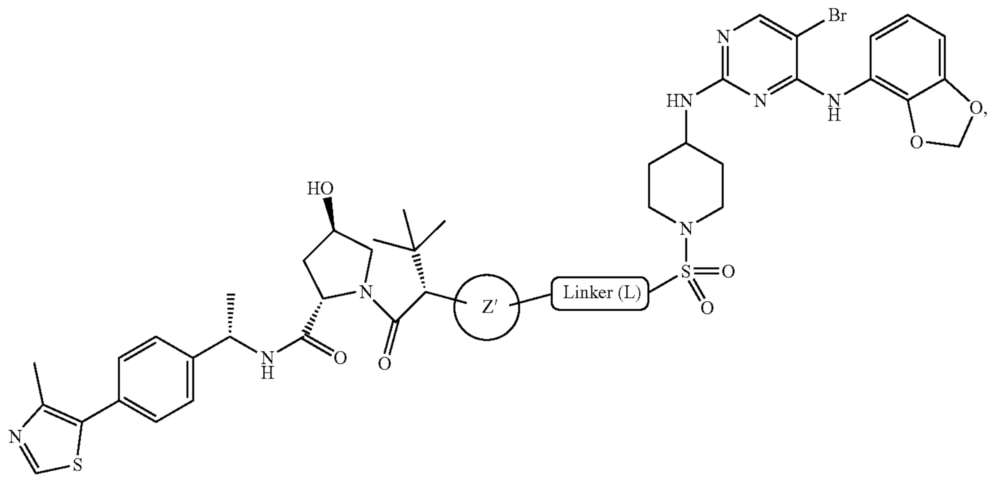
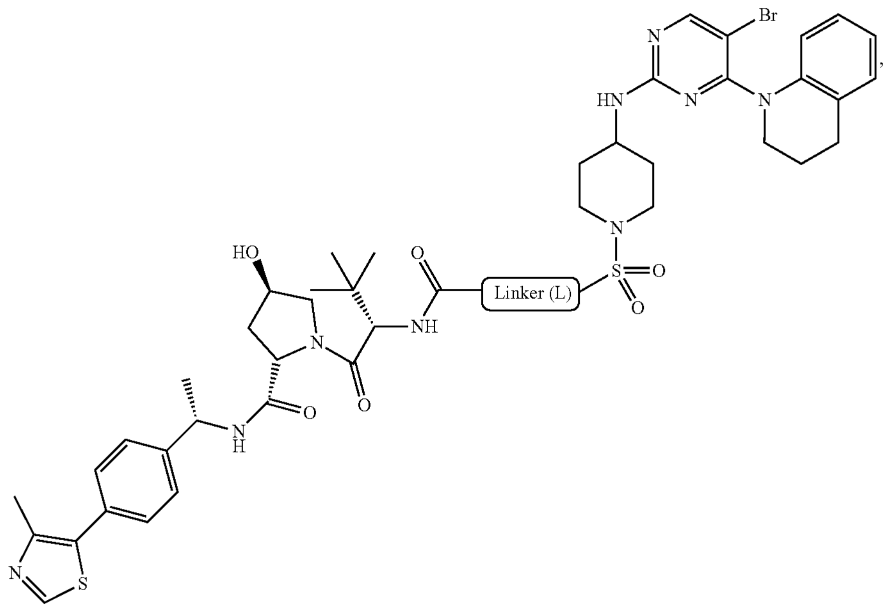

-continued
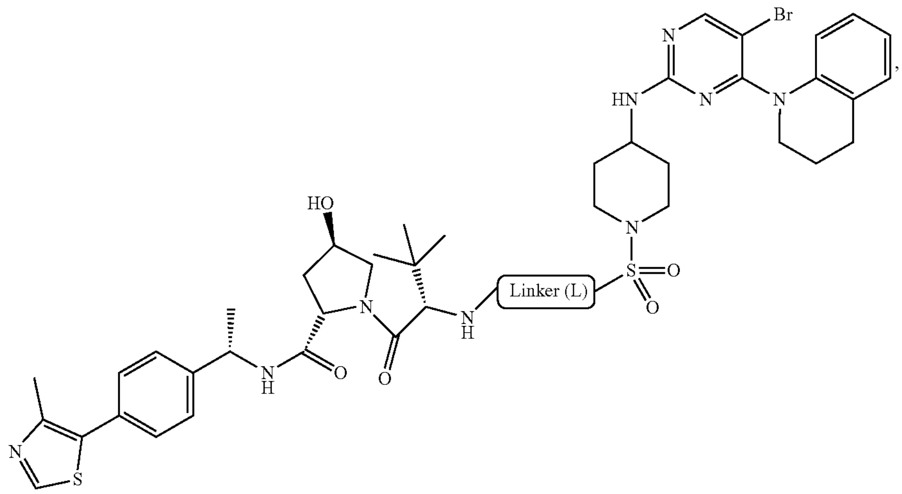
,
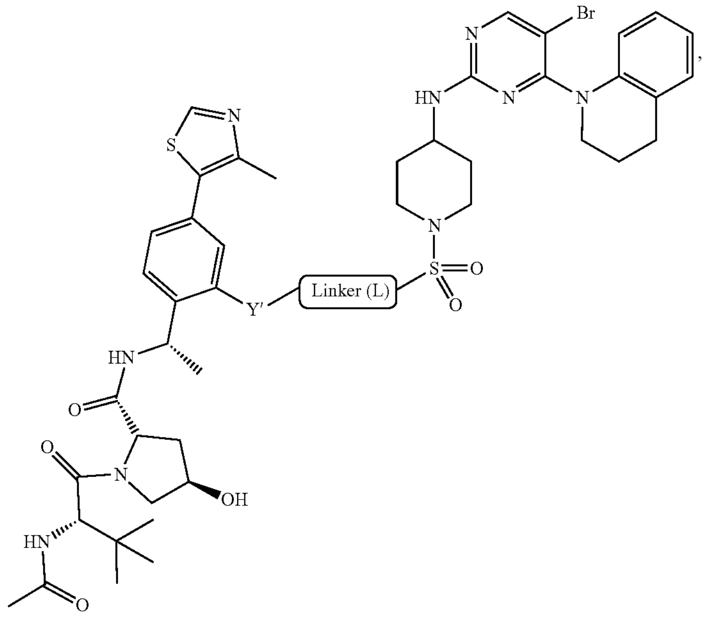
,
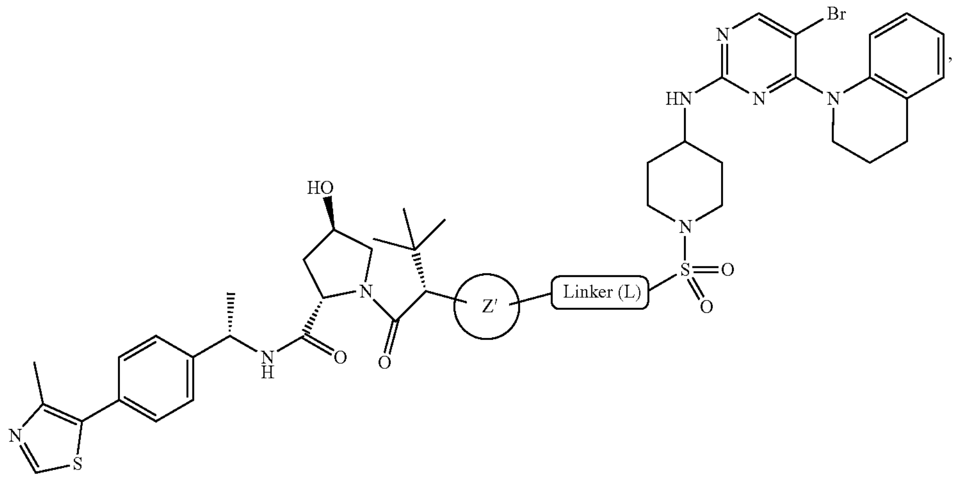
,

-continued
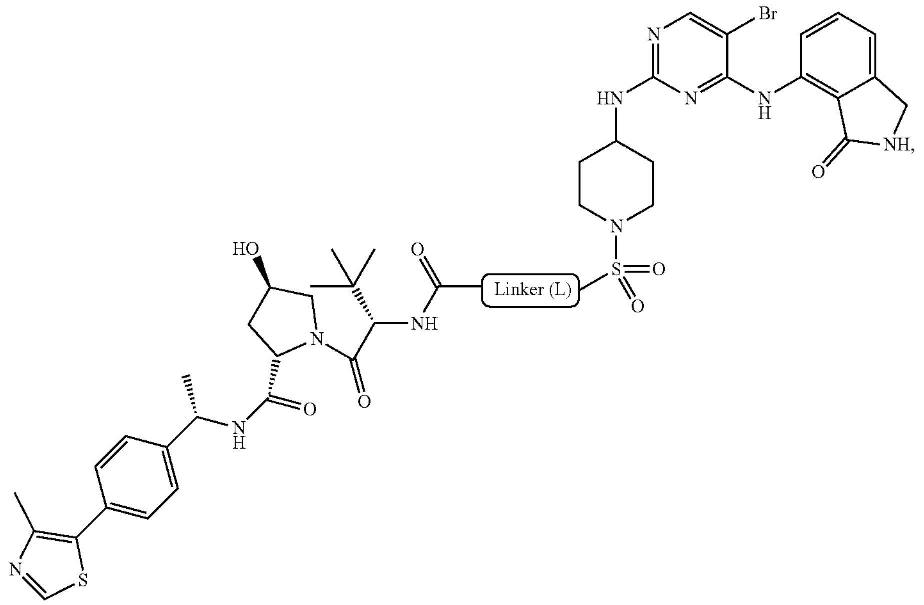
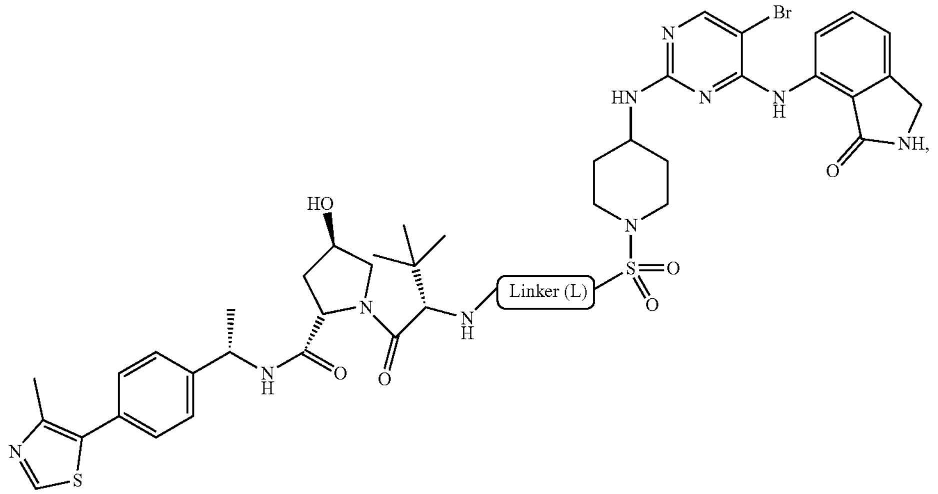
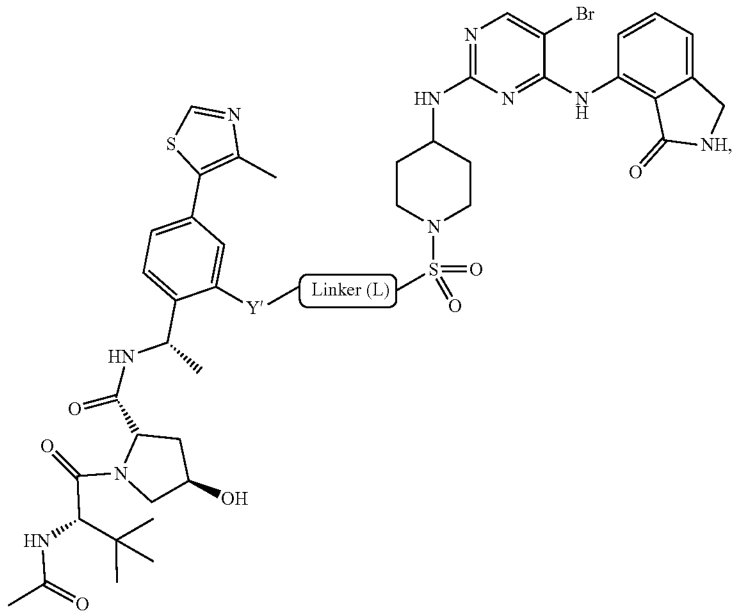

-continued
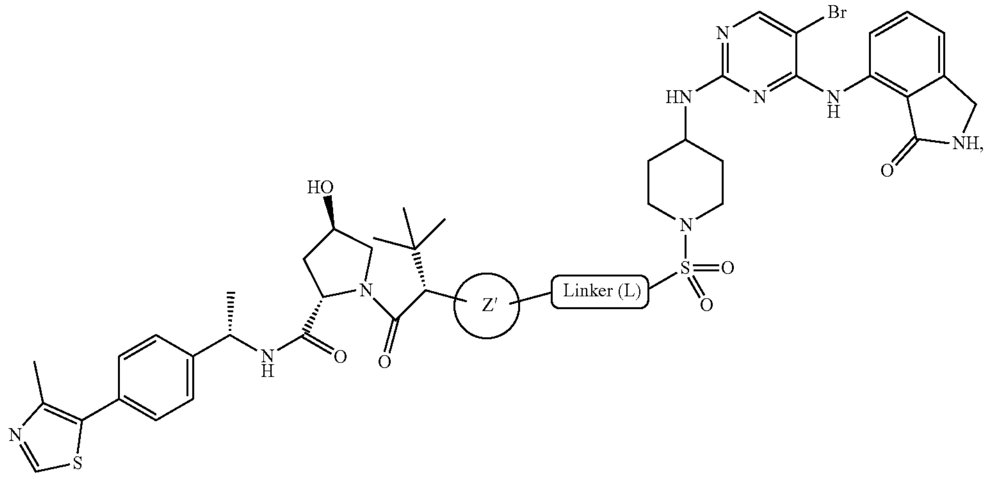
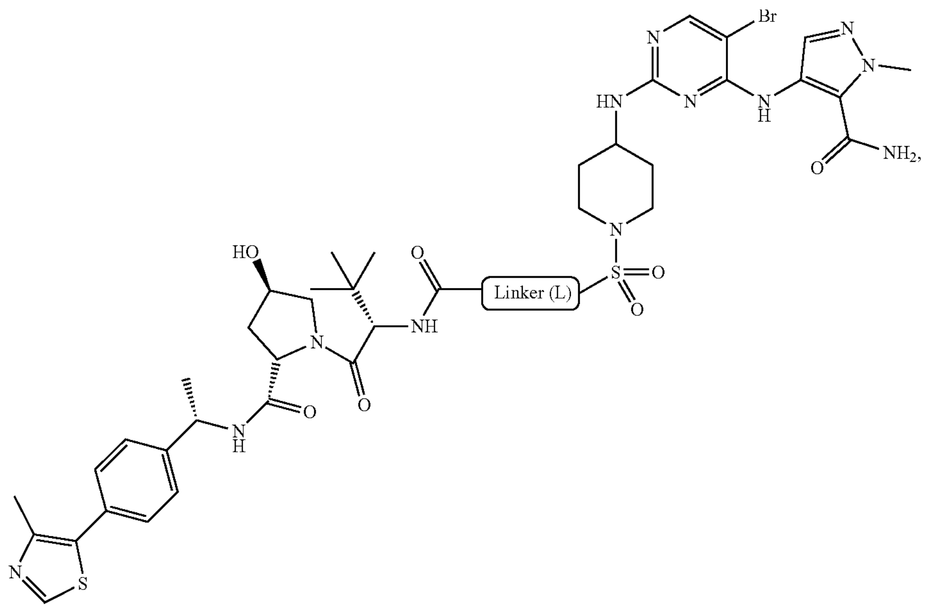
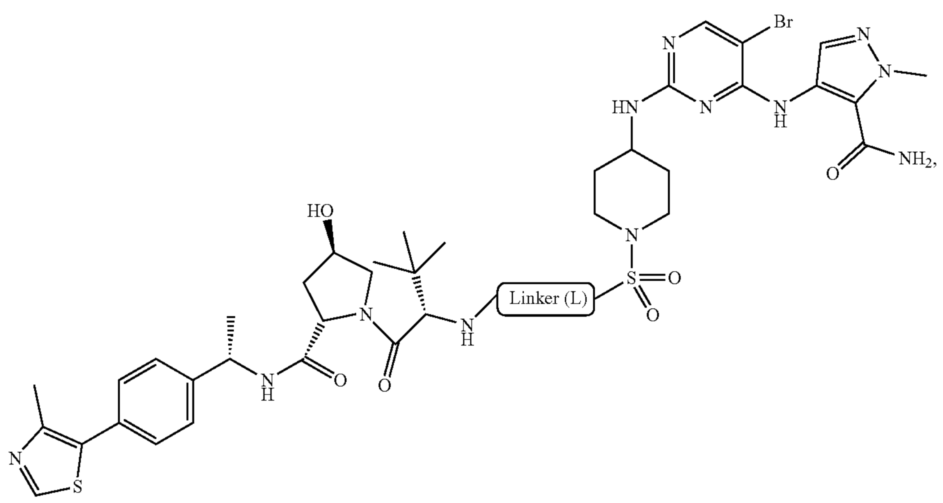

-continued
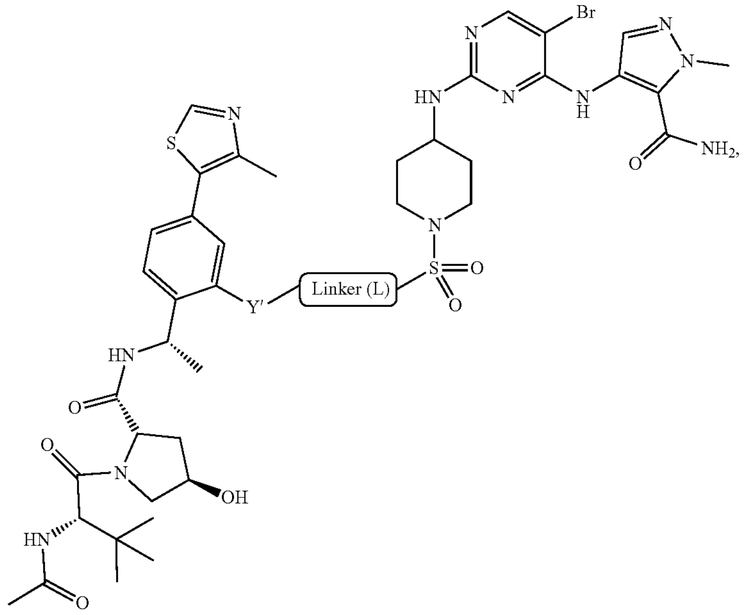
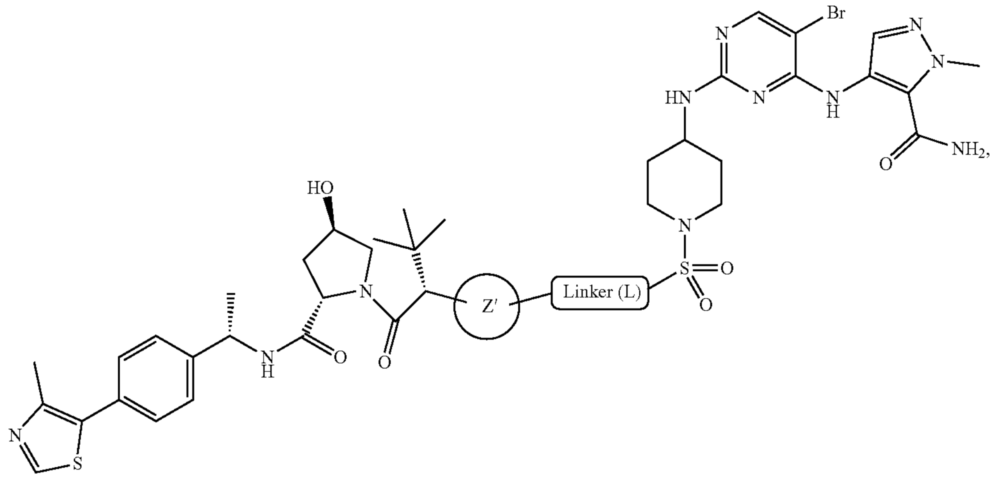
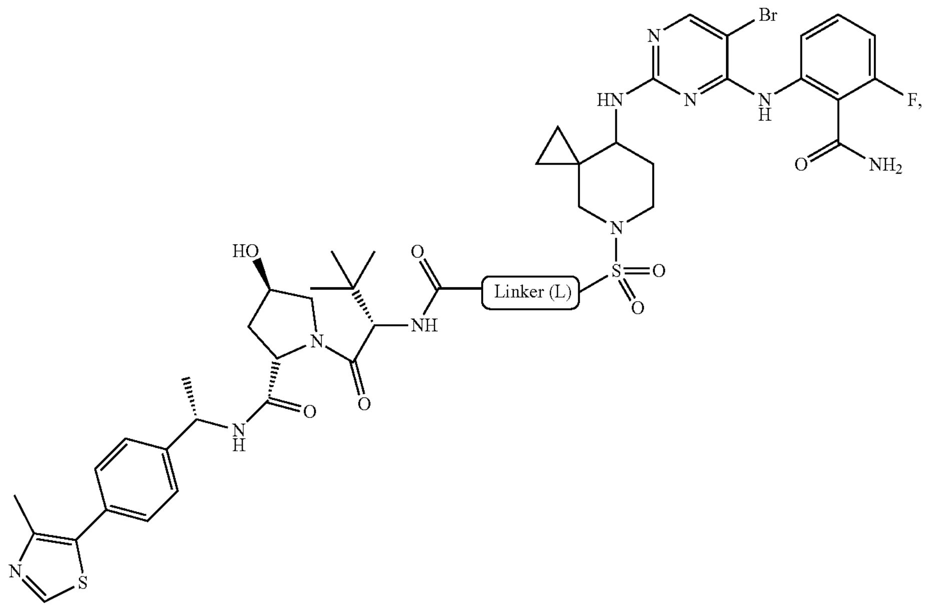

-continued
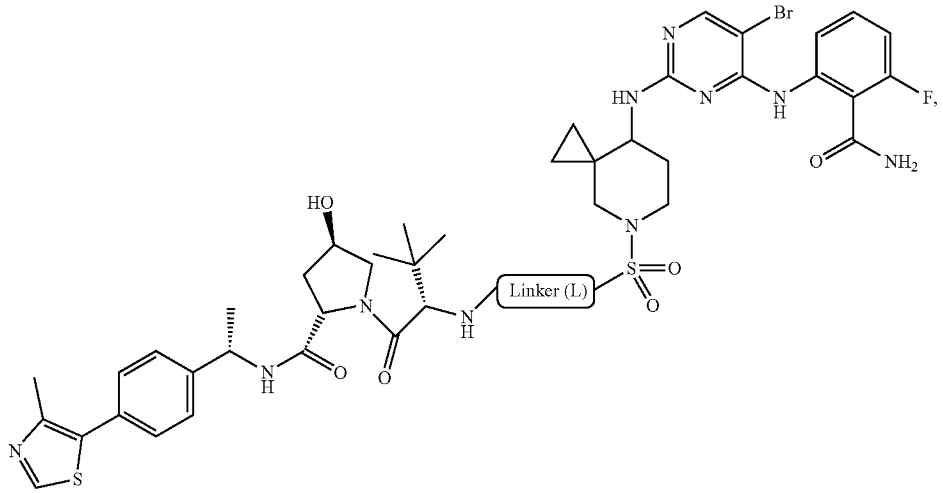
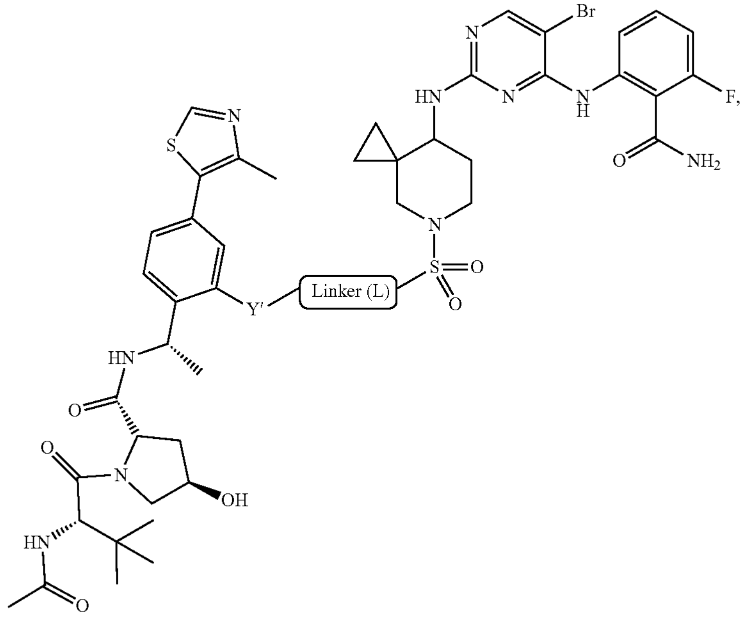
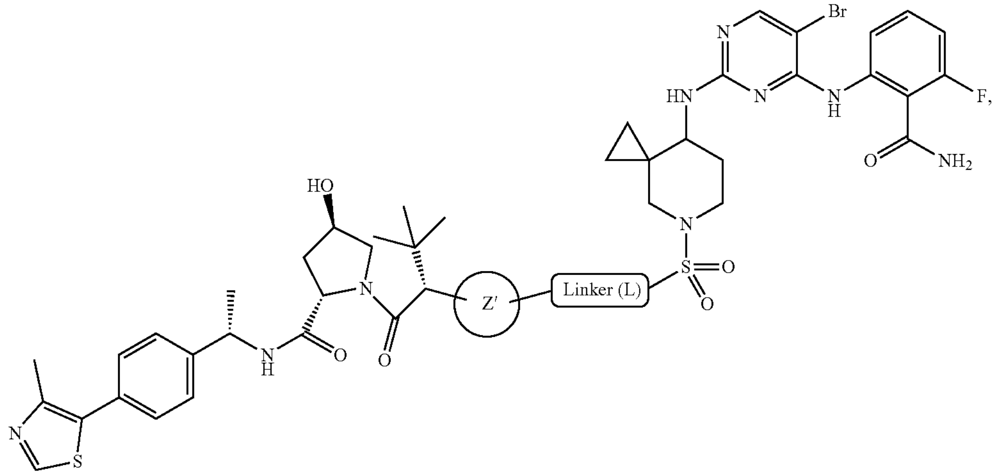

-continued
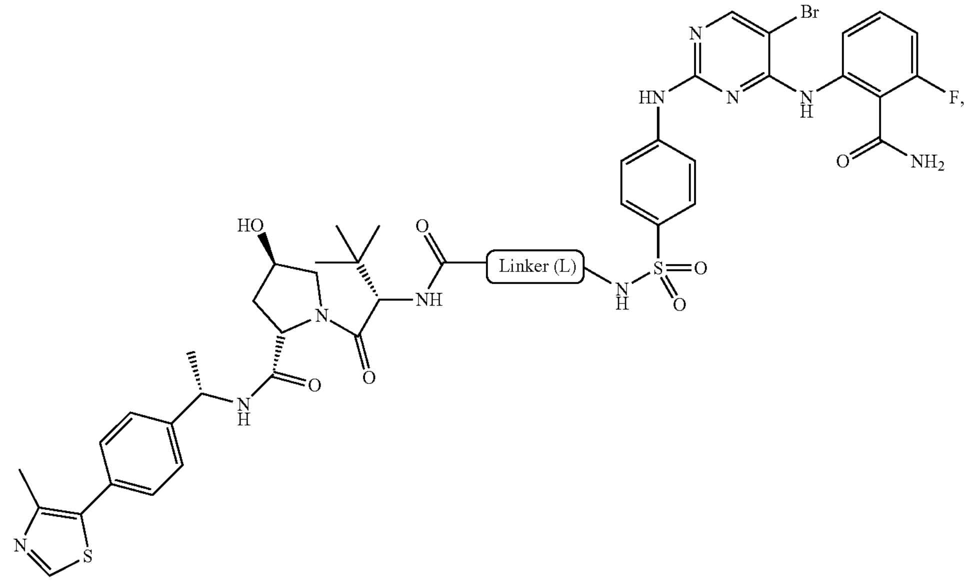
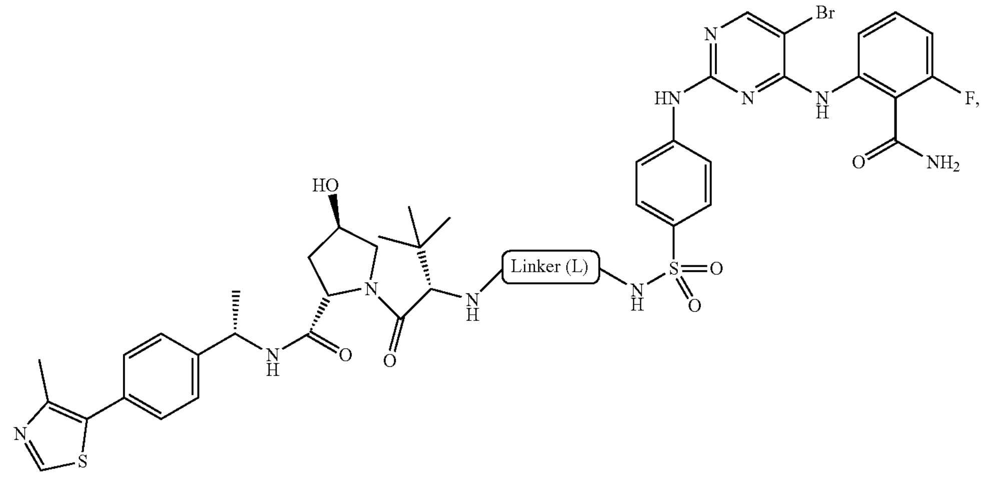
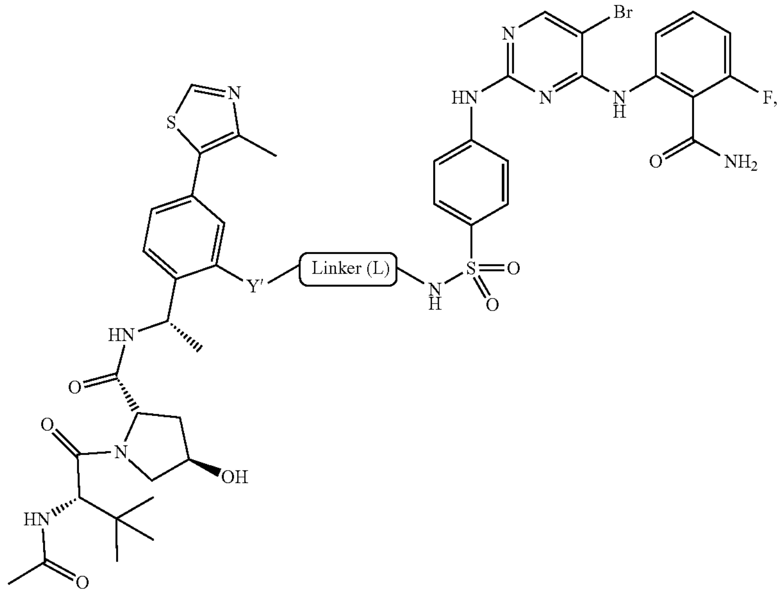

-continued
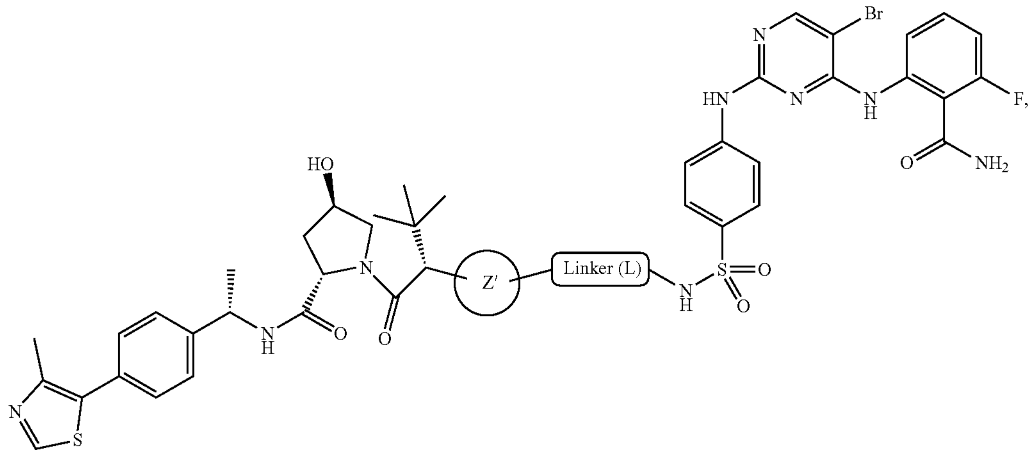
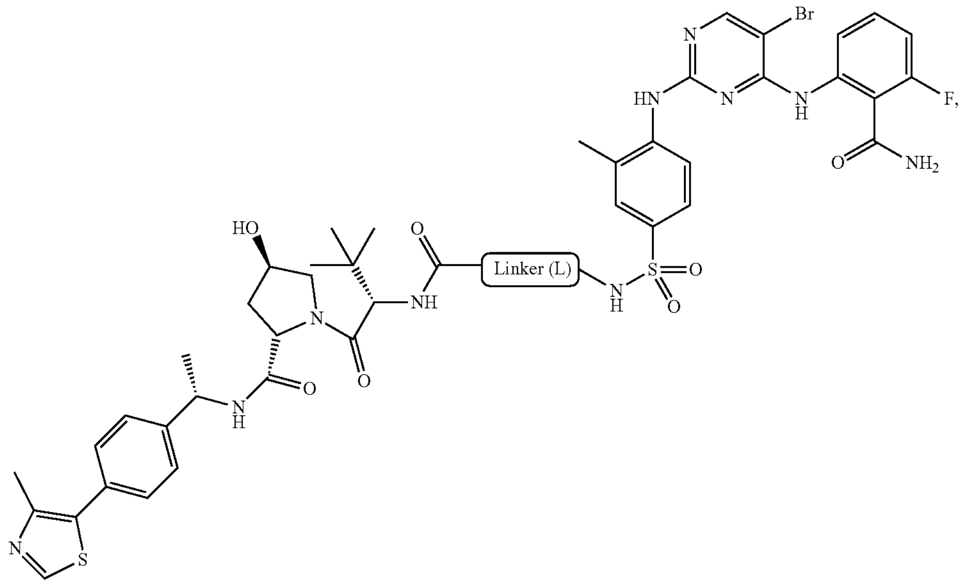
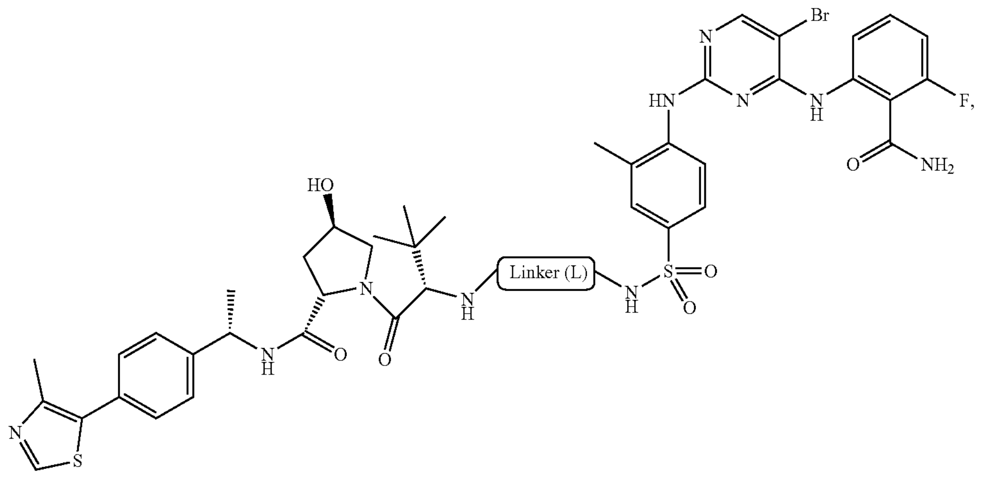

-continued
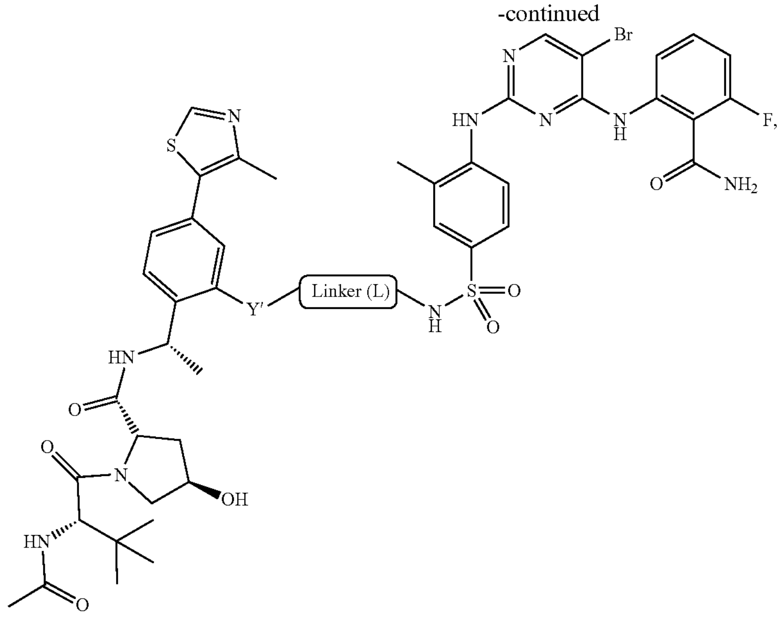
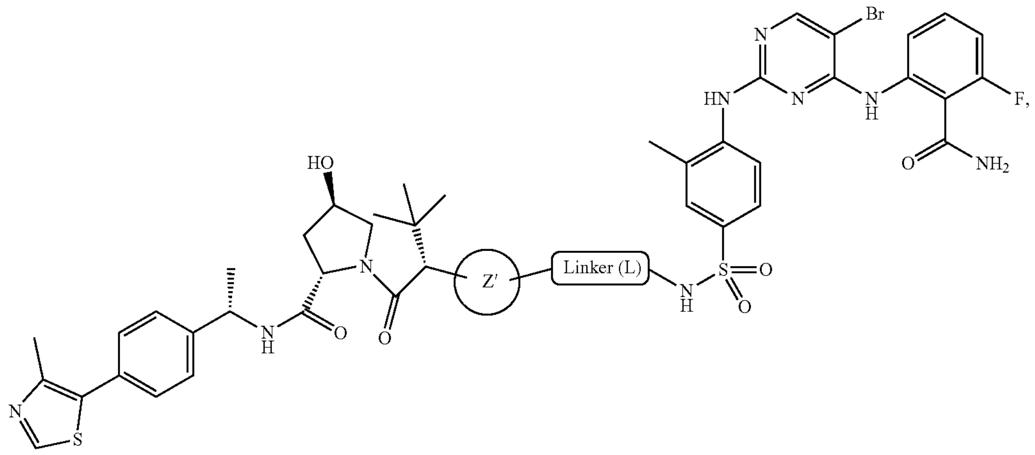
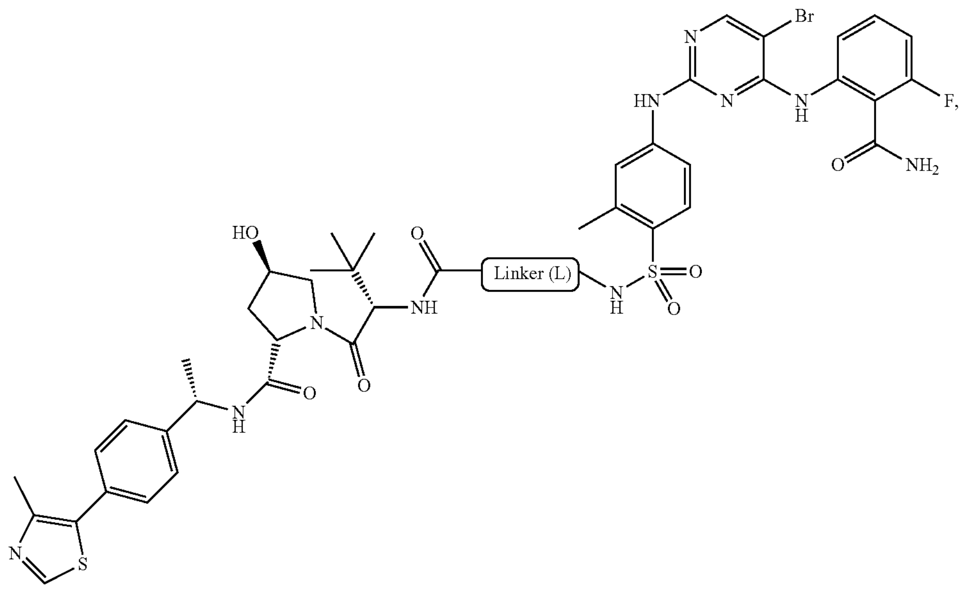

-continued

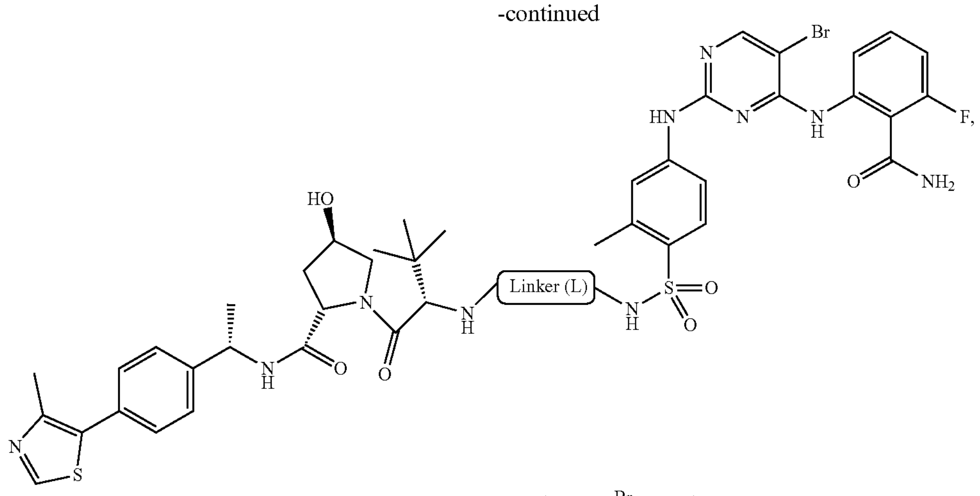

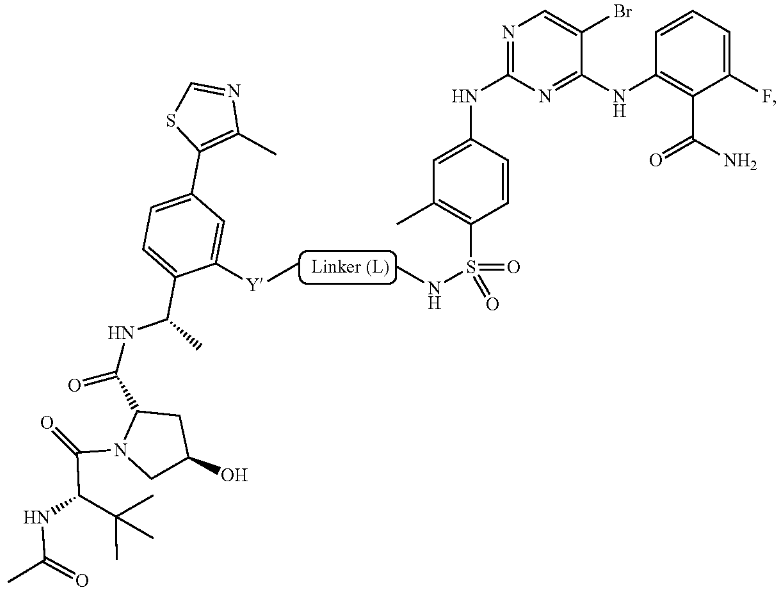

and

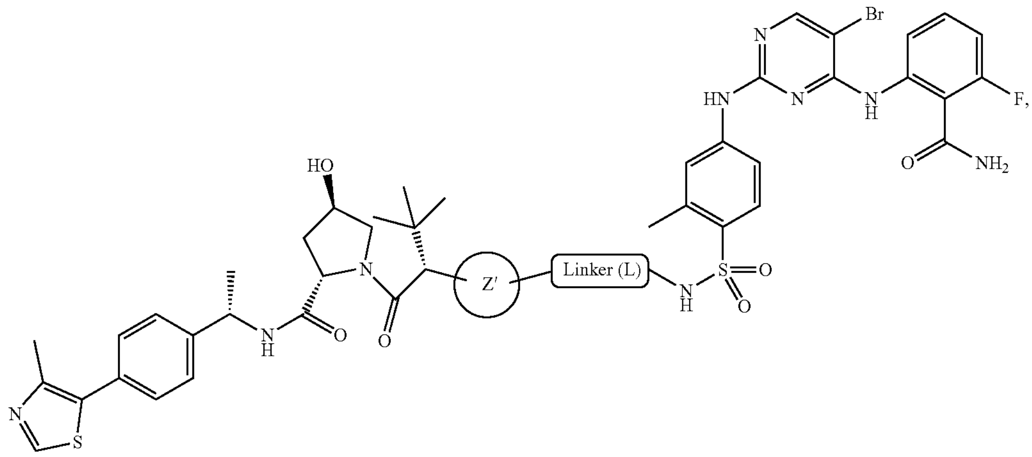

or a pharmaceutically acceptable salt or stereoisomer thereof.

Yet other degrons that bind VHL and which may be suitable for use in the present invention are disclosed in U.S. Patent Application Publication 2017/0121321 A1.

In some embodiments, the E3 ubiquitin ligase that is bound by the degron is an inhibitor of apoptosis protein (IAP). Representative examples of degrons that bind IAP and may be suitable for use in the present invention are represented by any one of the following structures:

(D4a)

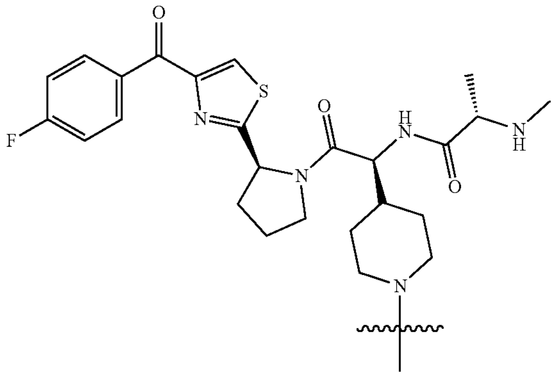

, (D4b)

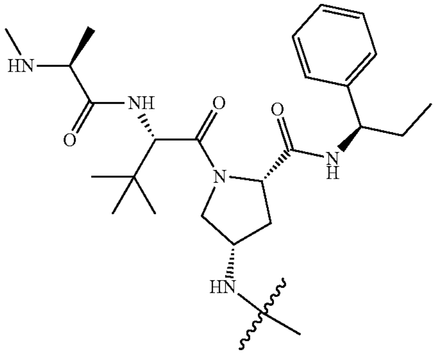

, and (D4c)

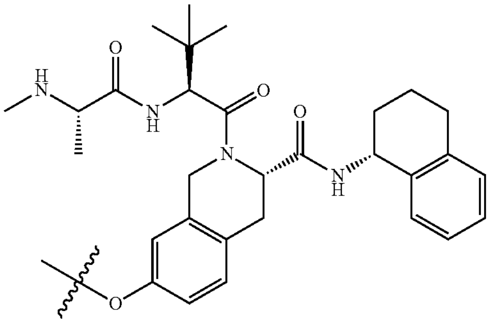

, or stereoisomer thereof.

Thus, in some embodiments, the bispecific compounds of the present invention are represented by any one of the following structures:

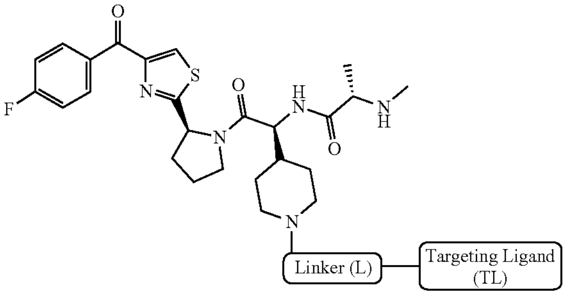

,

-continued

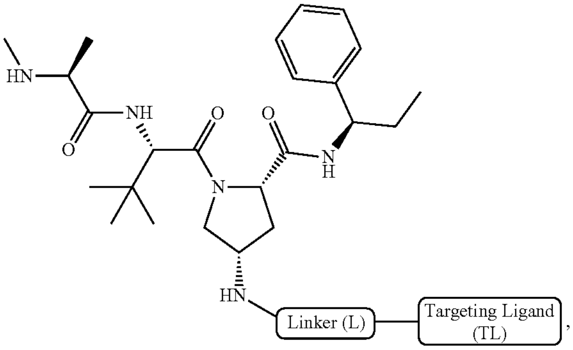

, and

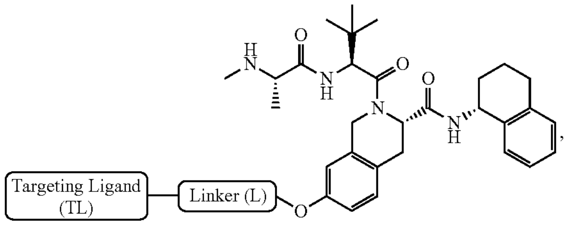

, or a pharmaceutically acceptable salt or stereoisomer thereof.

Yet other degrons that bind IAPs and which may be suitable for use as degrons in the present invention are disclosed in International Patent Application Publications WO 2008128171, WO 2008/016893, WO 2014/060768, WO 2014/060767, and WO 15092420.

In some embodiments, the E3 ubiquitin ligase that is bound by the degron is murine double minute 2 (MDM2). Representative examples of degrons that bind MDM2 and may be suitable for use in the present invention are represented by any one of the following structures:

(D5a)

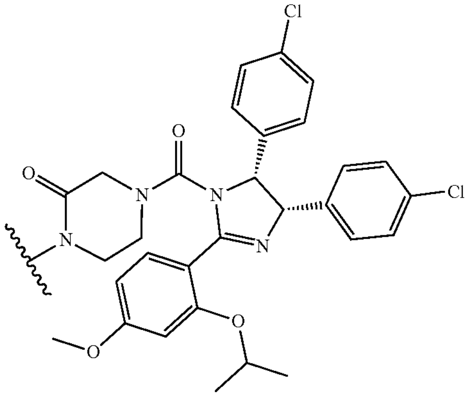

and

-continued (D5b)

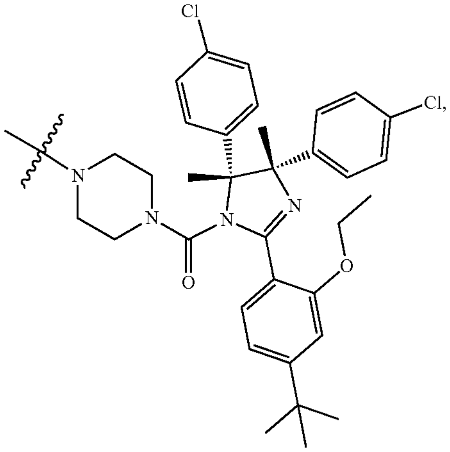

or a stereoisomer thereof.

Thus, in some embodiments, the bispecific compounds of the present invention are represented by any one of the following structures:

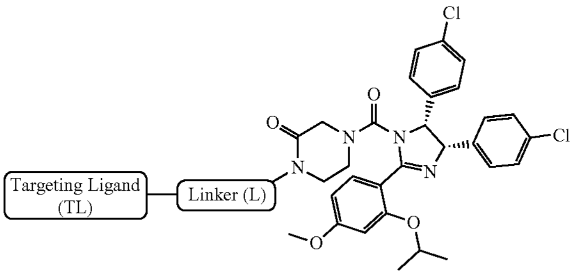

-continued and

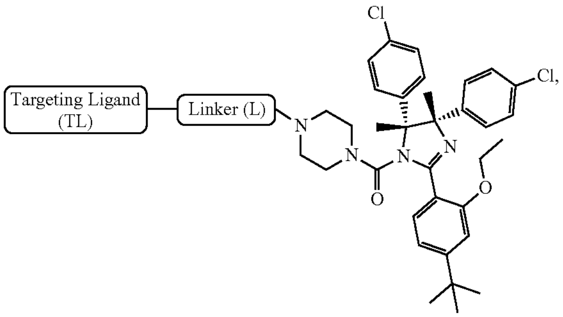

or a pharmaceutically acceptable salt or stereoisomer thereof.

Yet other degrons that bind MDM2 and which may be suitable for use as degrons in the present invention are disclosed in U.S. Pat. No. 9,993,472 B2. MDM2 is known in the art to function as an ubiquitin-E3 ligase.

Thus, in some embodiments, the compounds of this invention are represented by any structures generated by the combination of structures TL-1, L1 to L10, and the structures of the degrons described herein, including D1 to D5, or a pharmaceutically acceptable salt or stereoisomer thereof.

In some embodiments, the compounds of the present invention have the following structures:

(1)

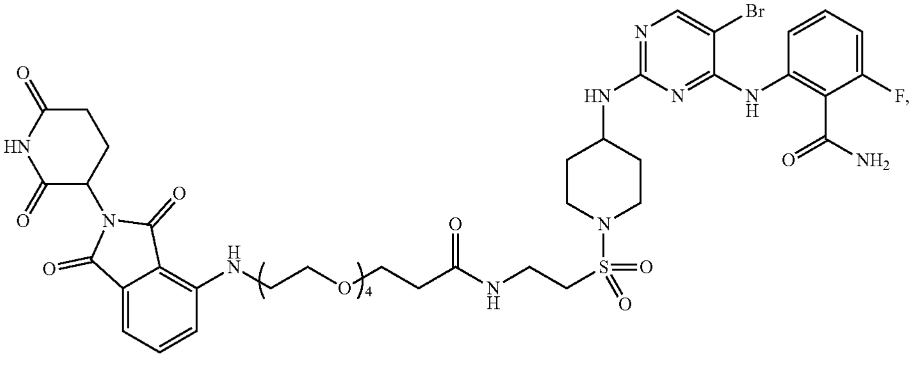

-continued
(2)
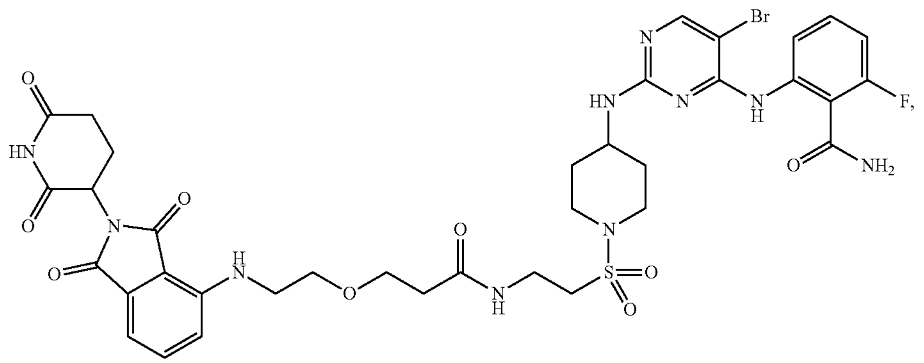
(3)
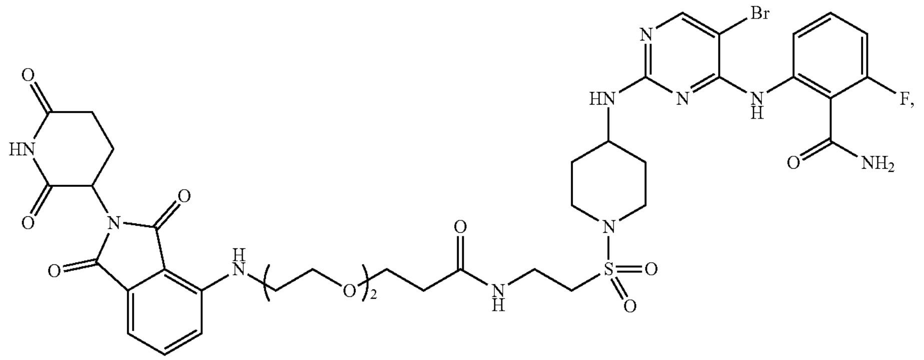
(4)
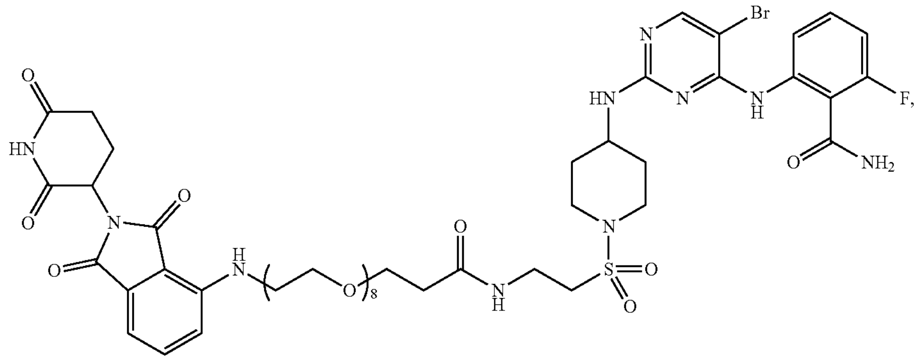
(5)
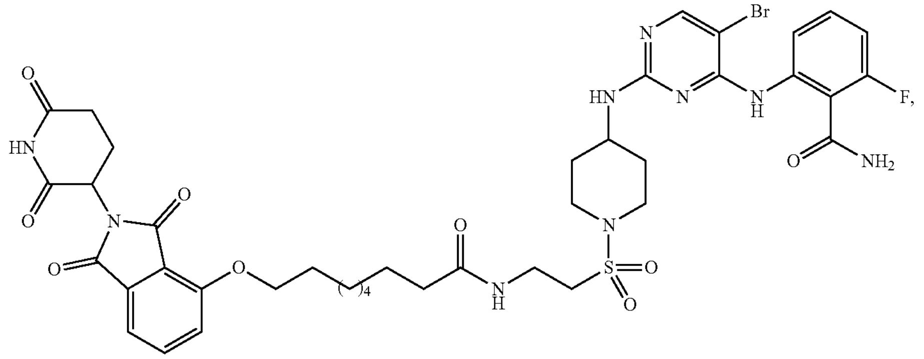

-continued
(6)
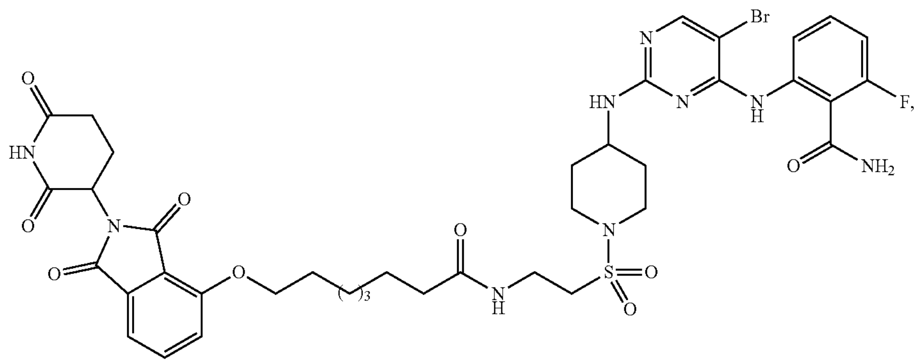
(7)
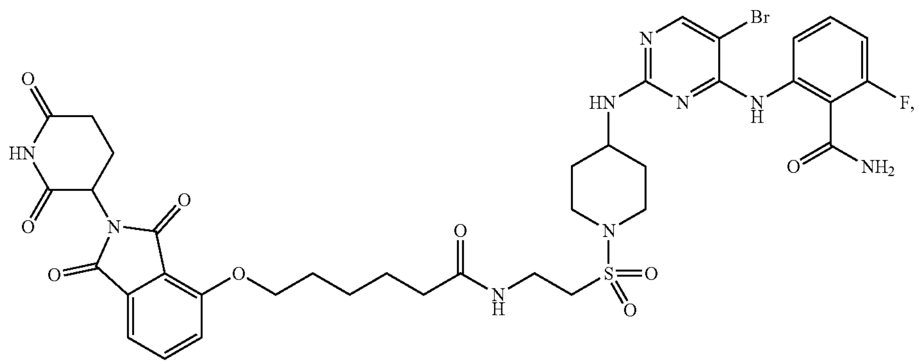
(8)
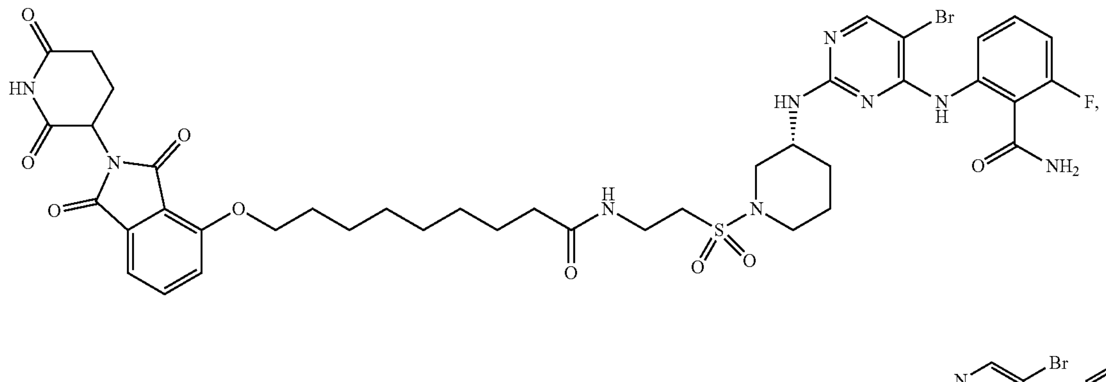
(9)
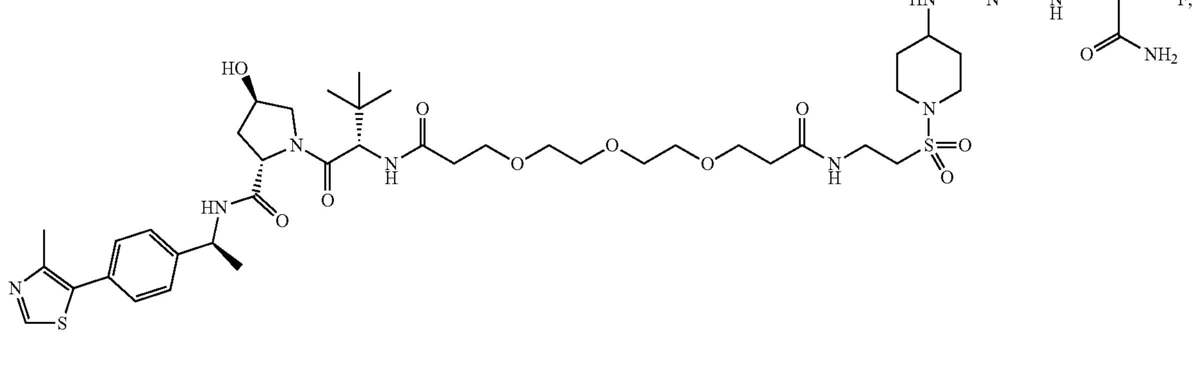

-continued
(10)
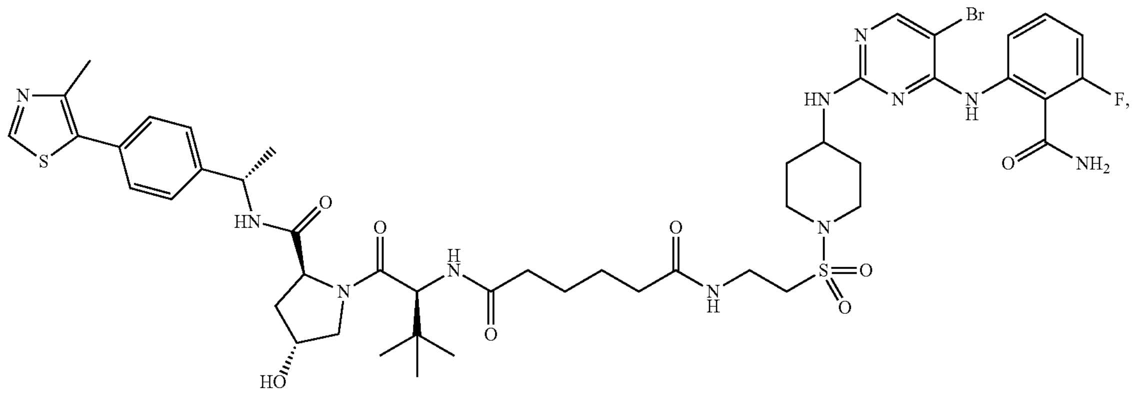
(11)
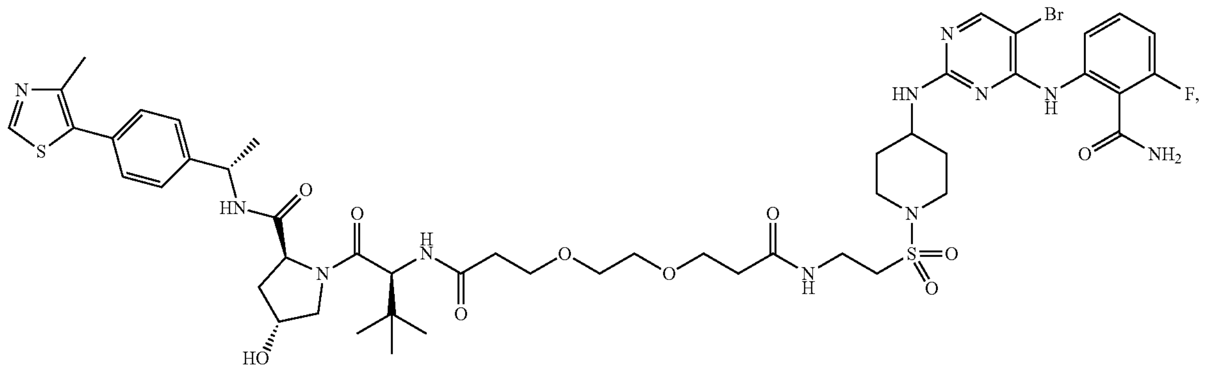
(12)
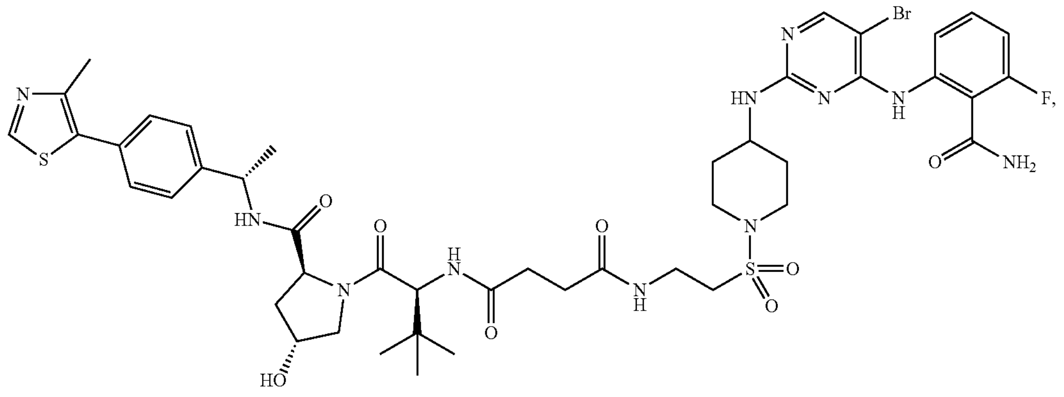
(13)
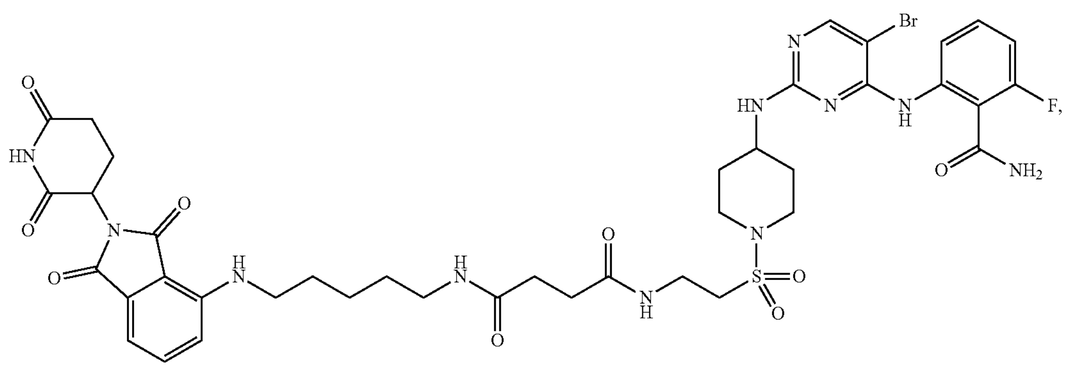

-continued
(14)
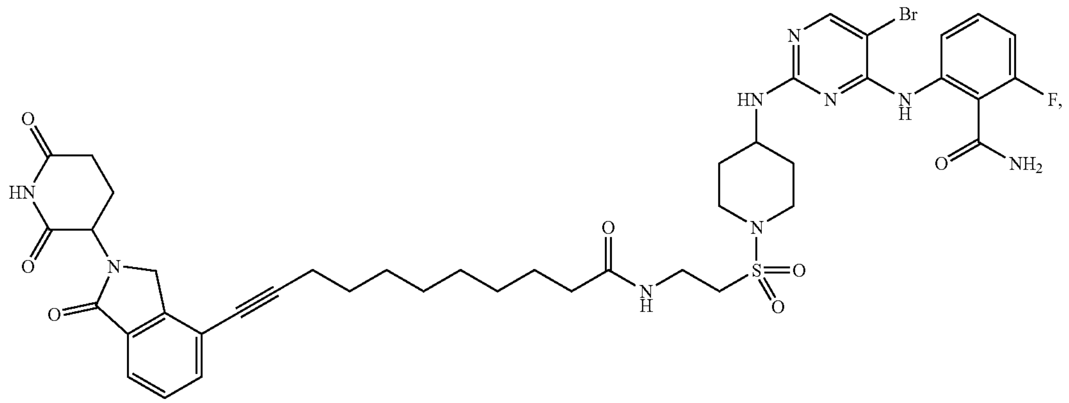
(15)
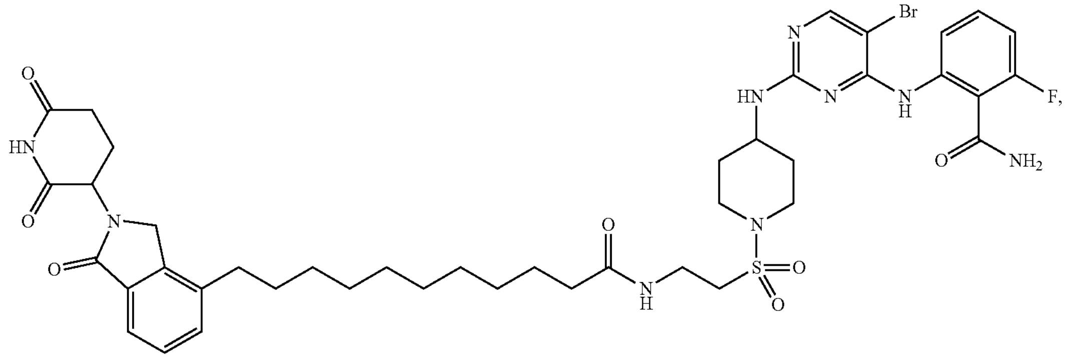
(16)
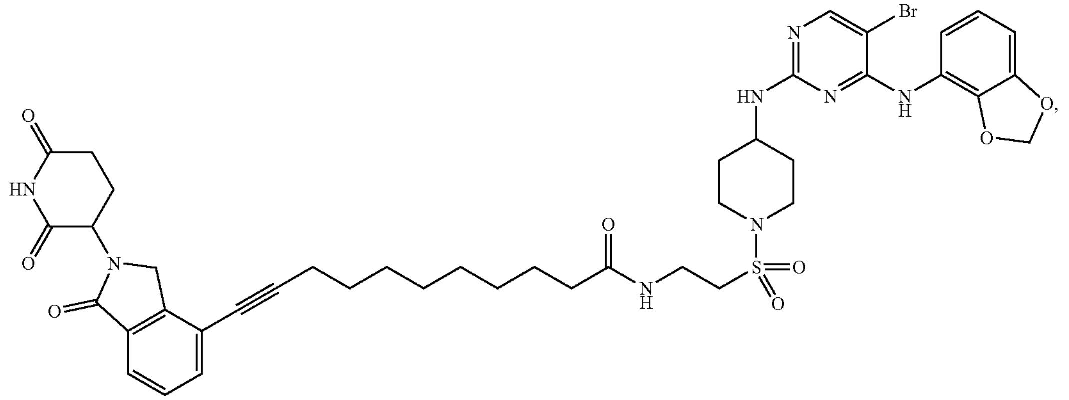
(17)
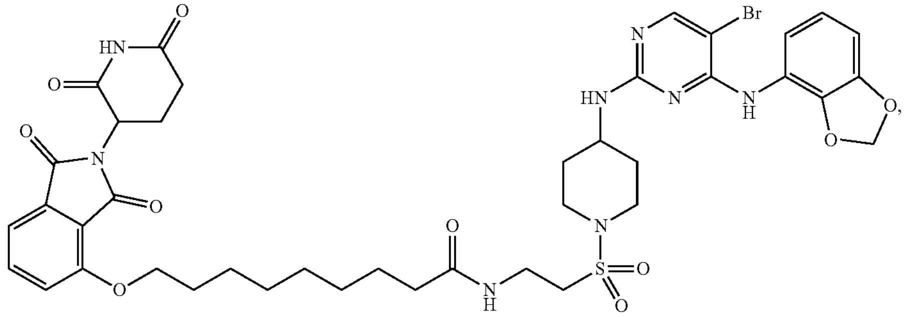

-continued
(18)
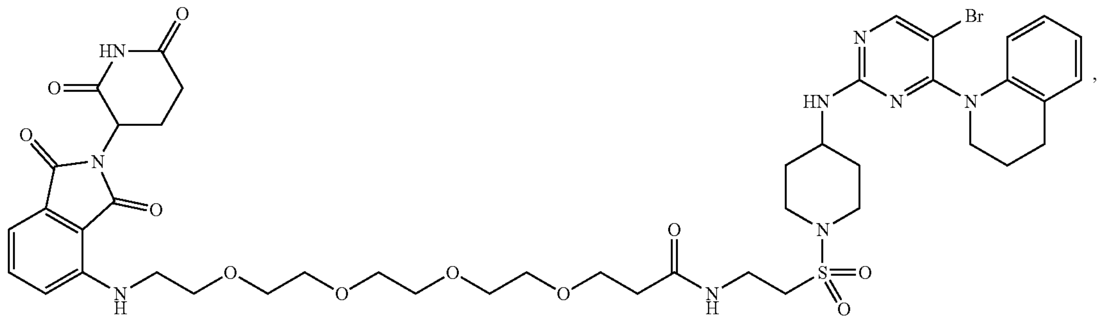
(19)
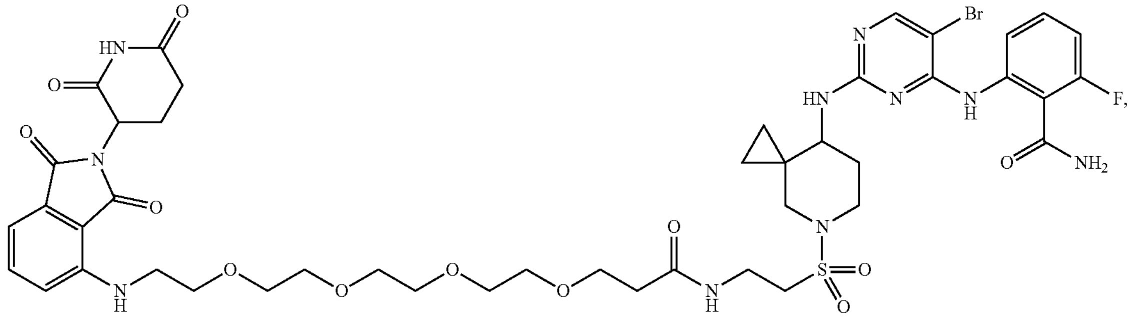
(20)
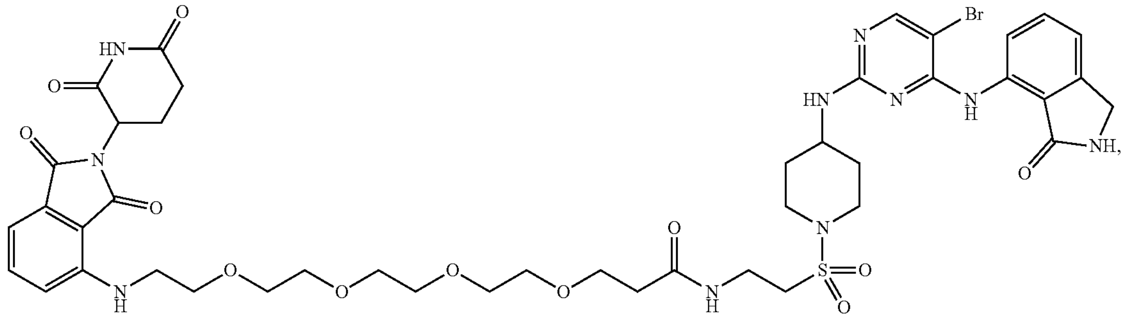
(21)
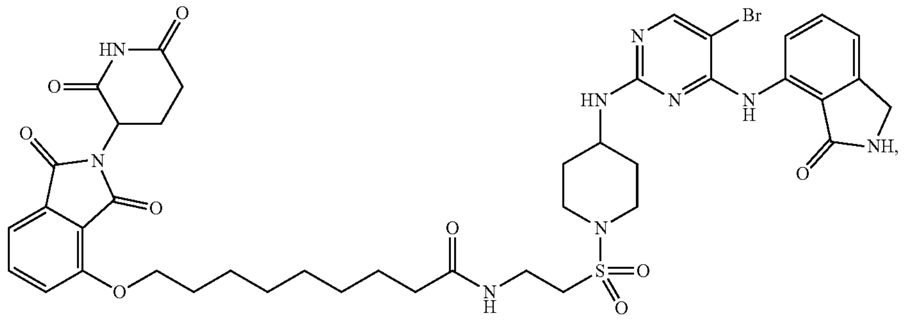
(22)
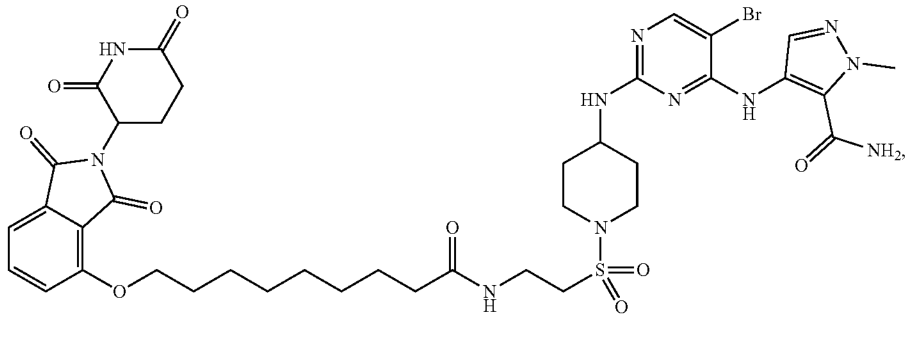

-continued
(23)
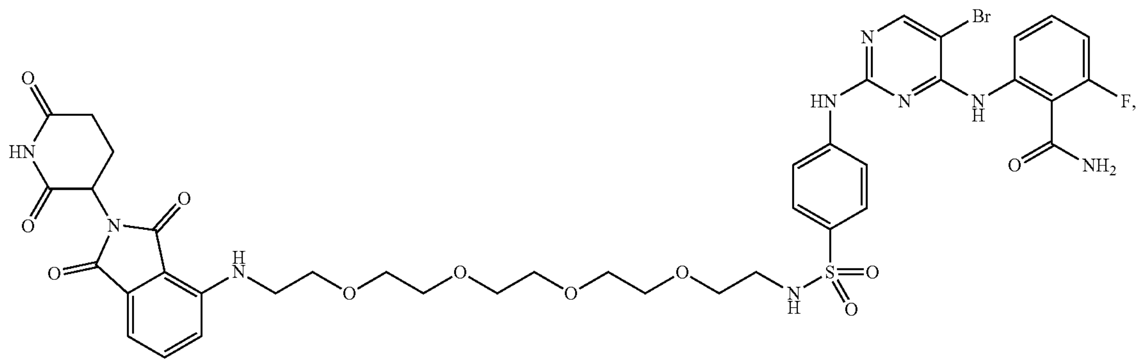
(24)
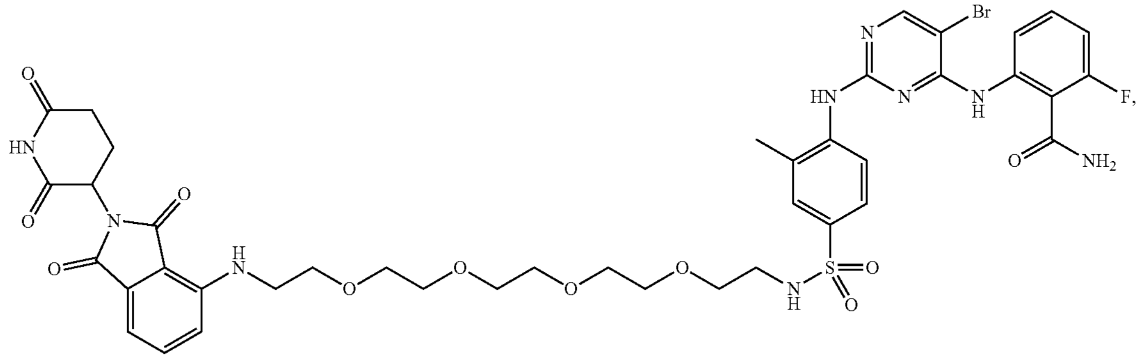
(25)
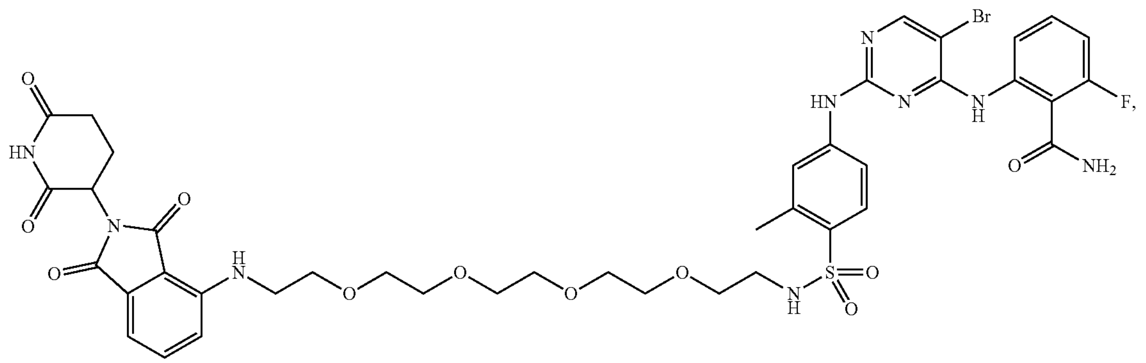
(26)
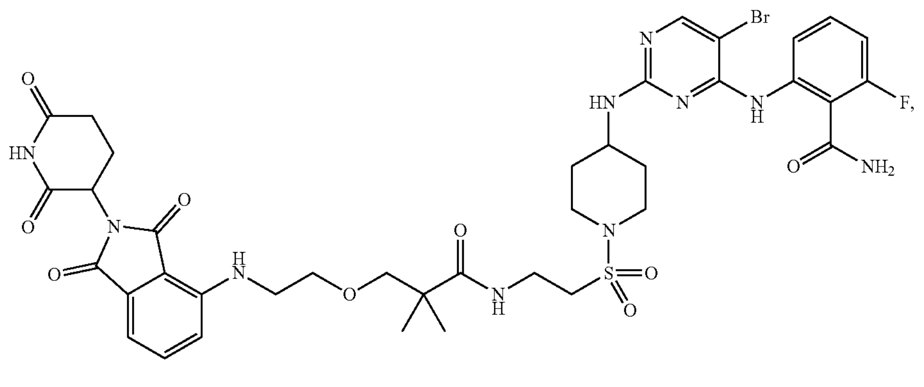

-continued
(27)
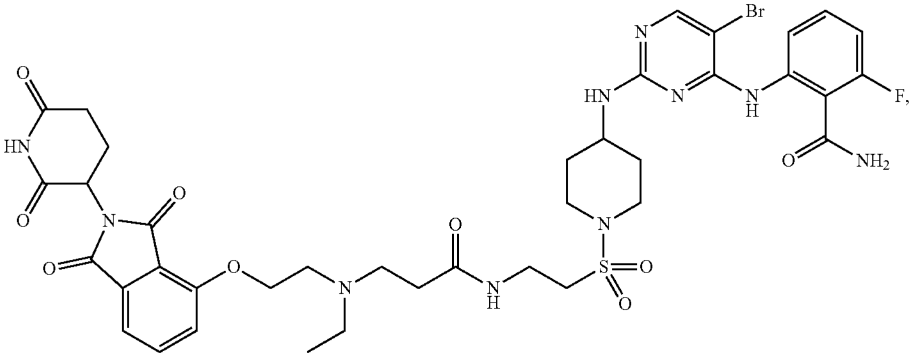
(28)
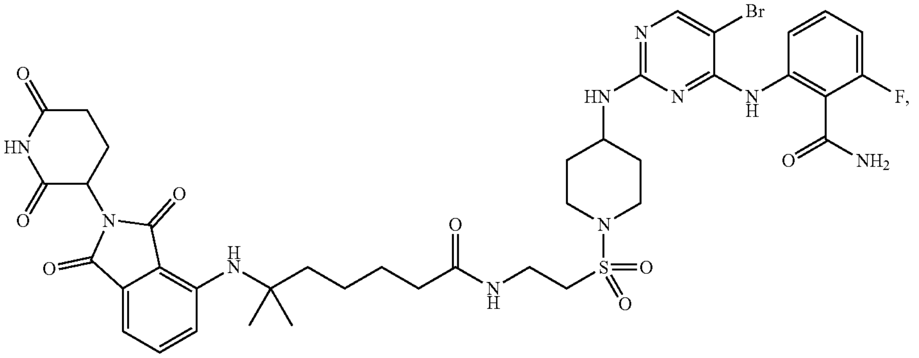
(29)
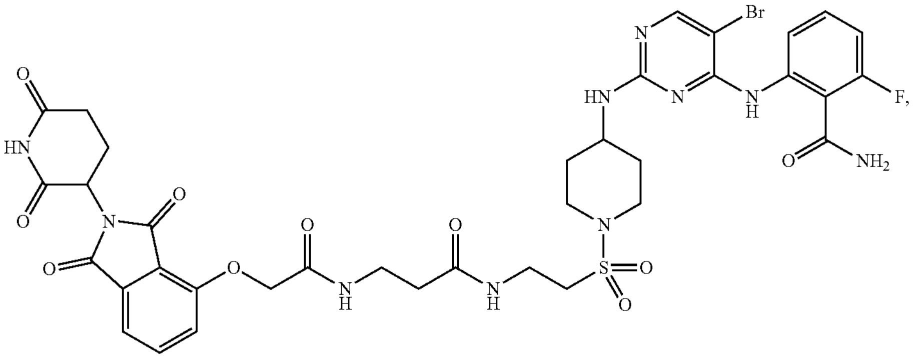
(30)
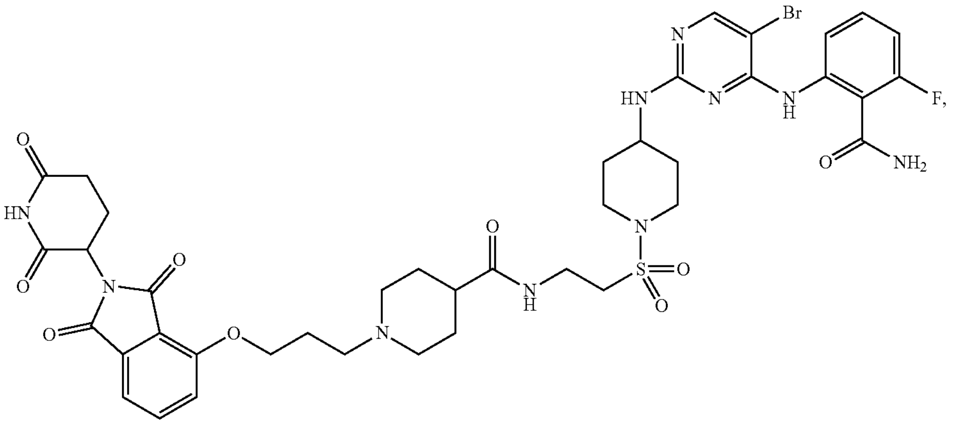

-continued
(31)
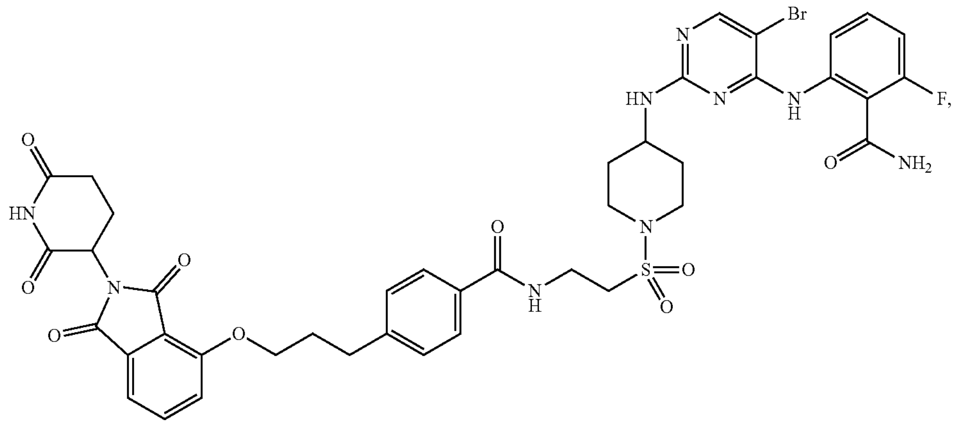
(32)
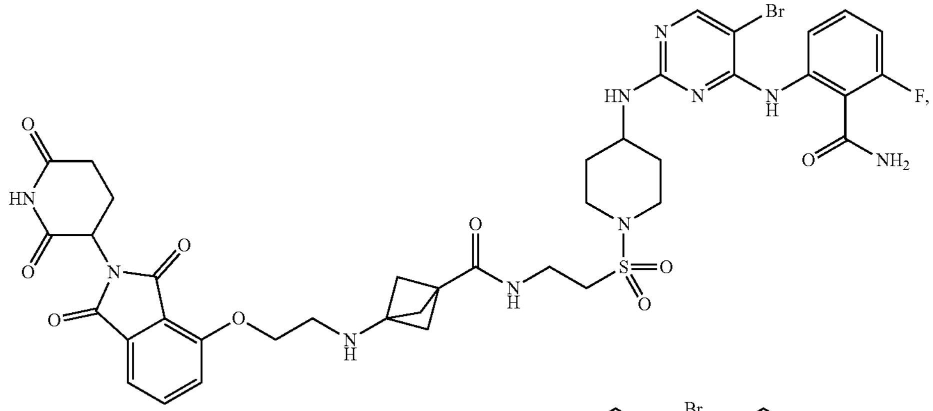
(33)
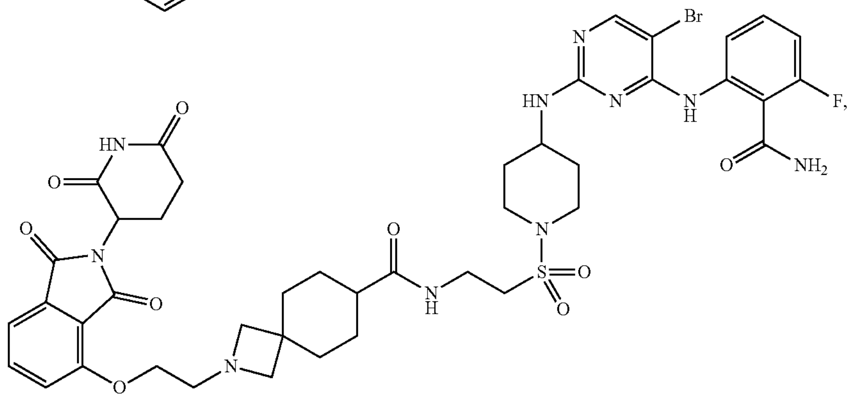
(34)
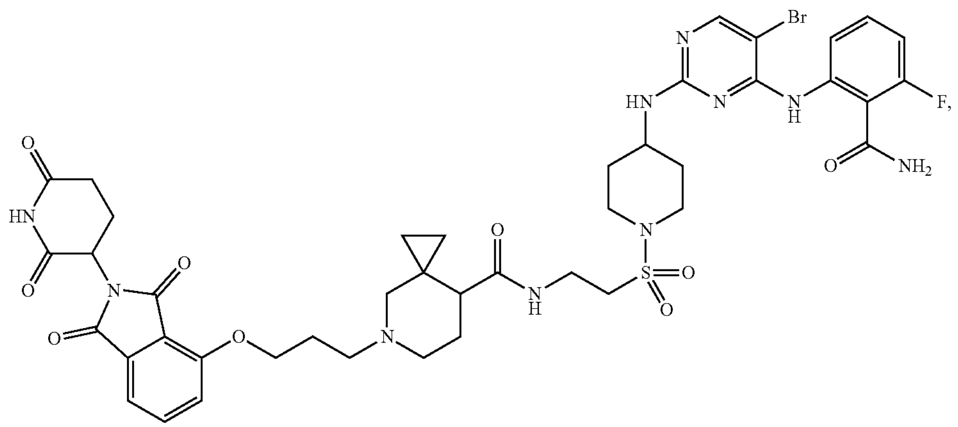

-continued
(35)
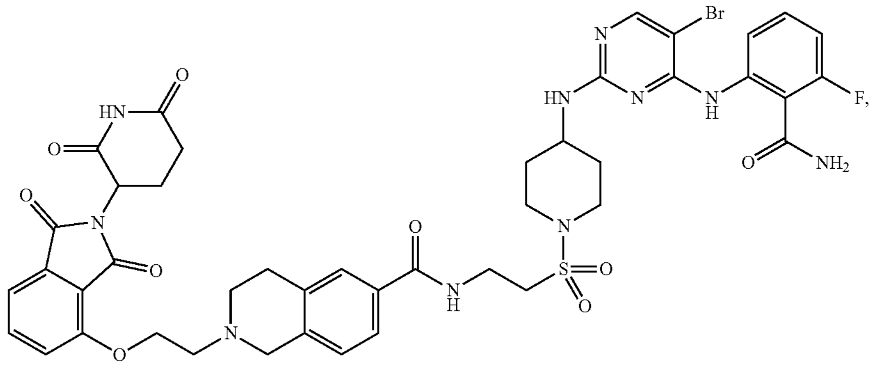
(36)
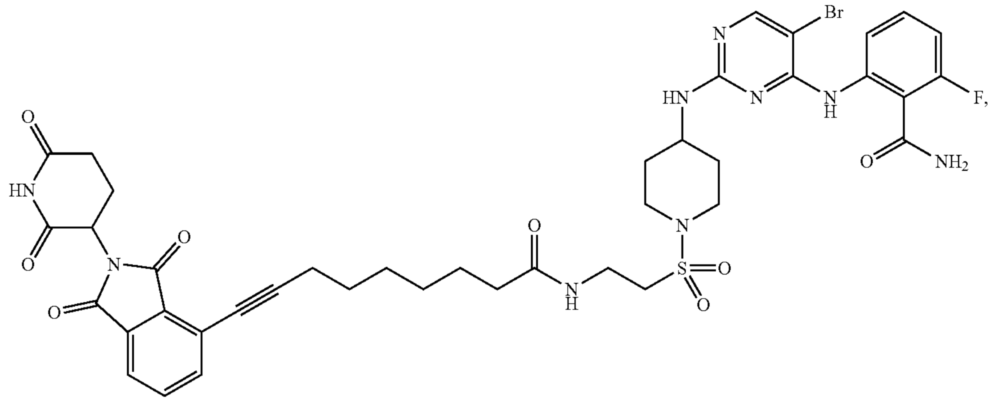
(37)
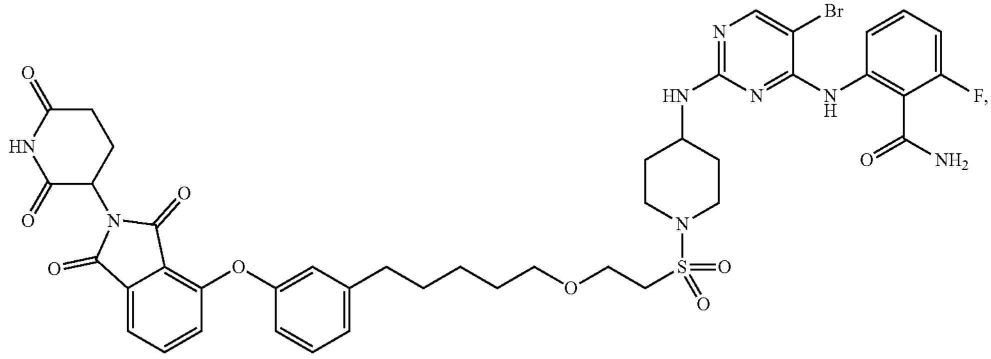
(38)
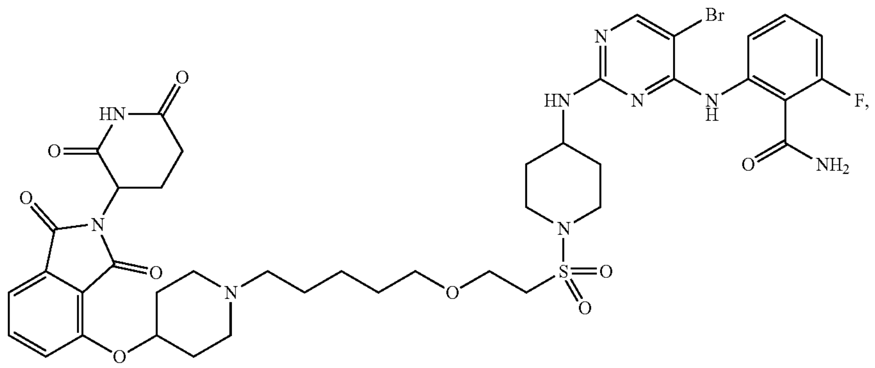

-continued
(39)
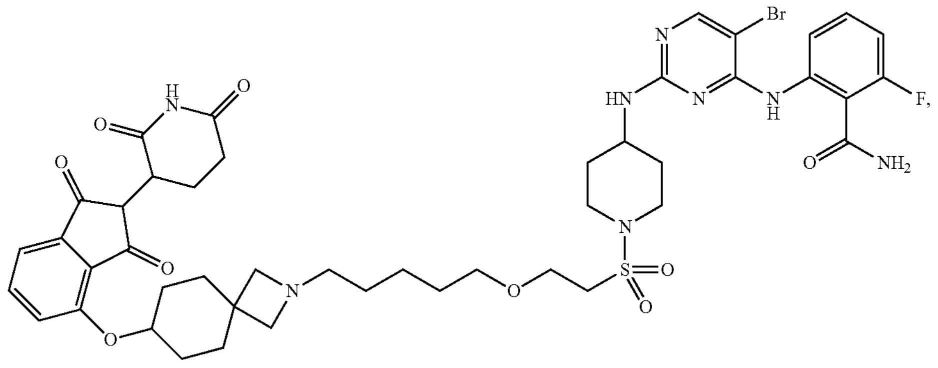
(40)
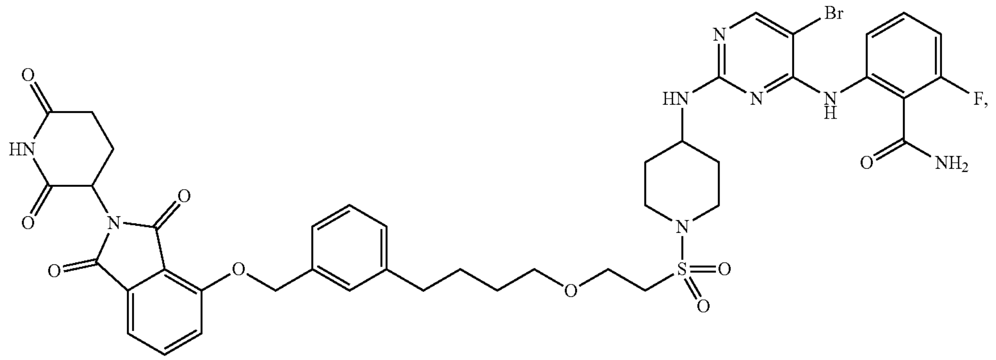
(41)
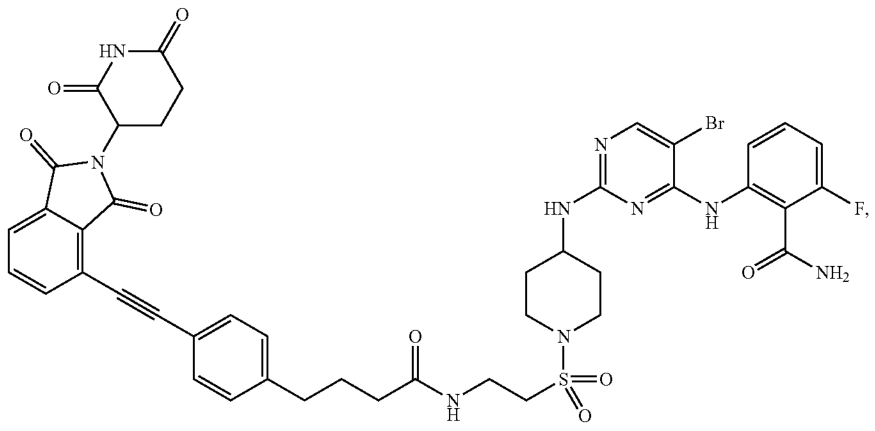
(42)
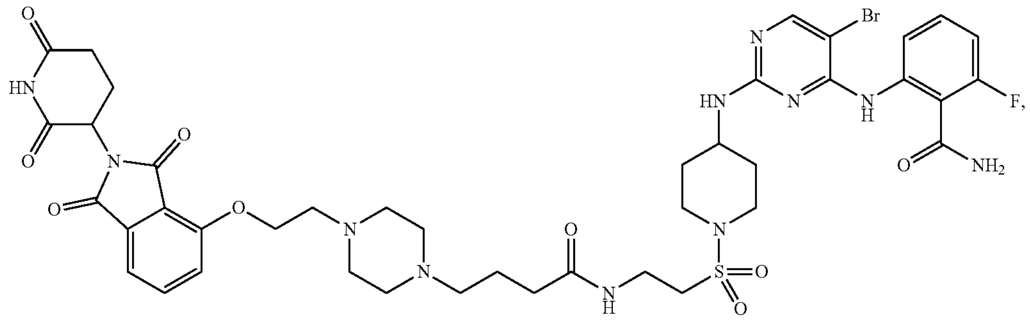

-continued
(43)
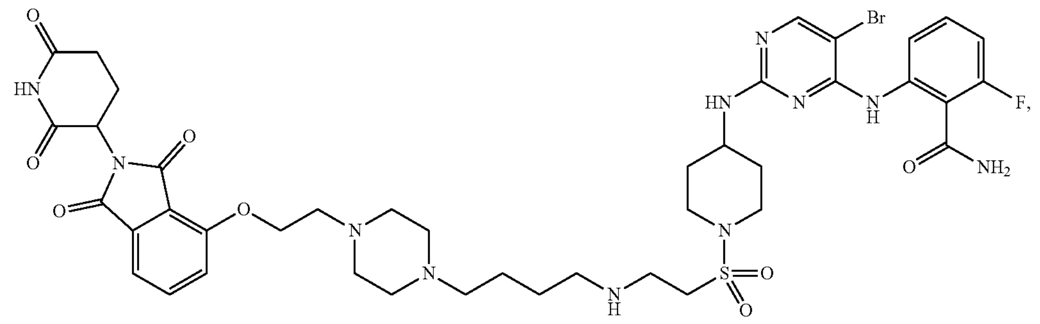
(44)
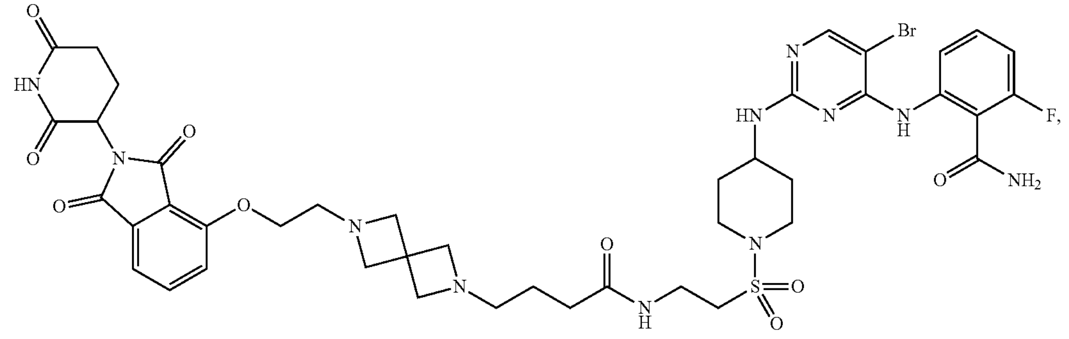
(45)
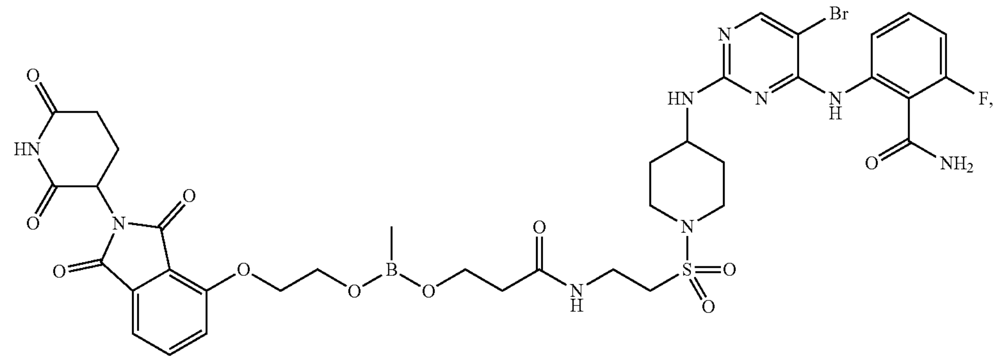
(46)
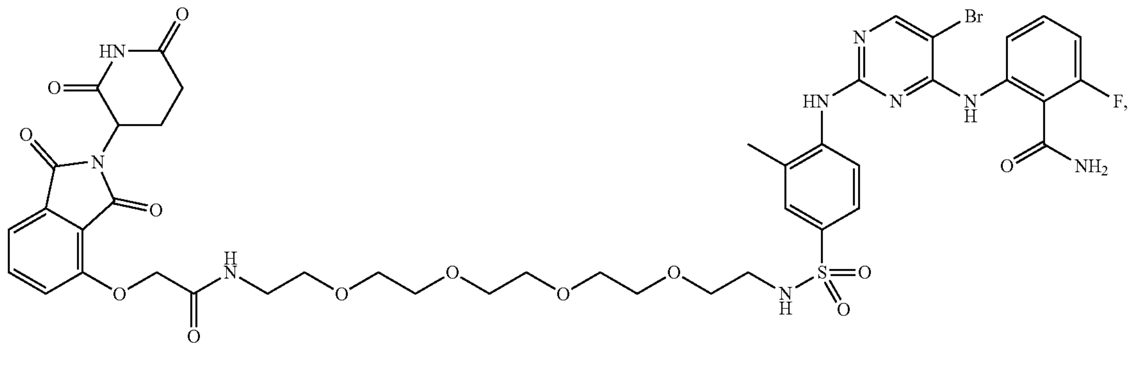

-continued (47)

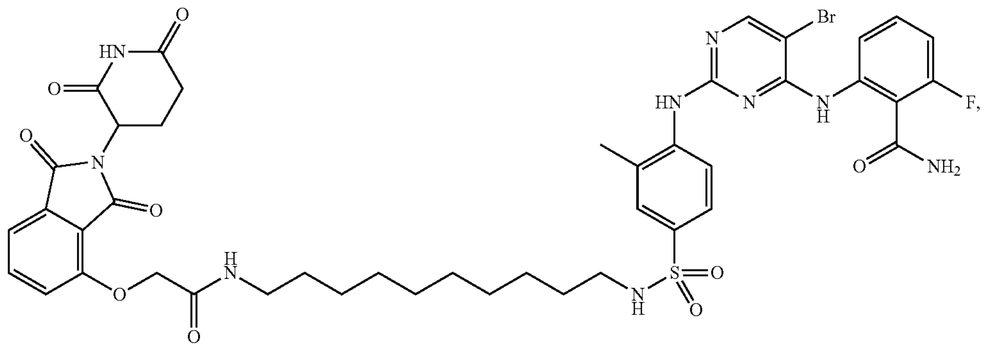

(48)

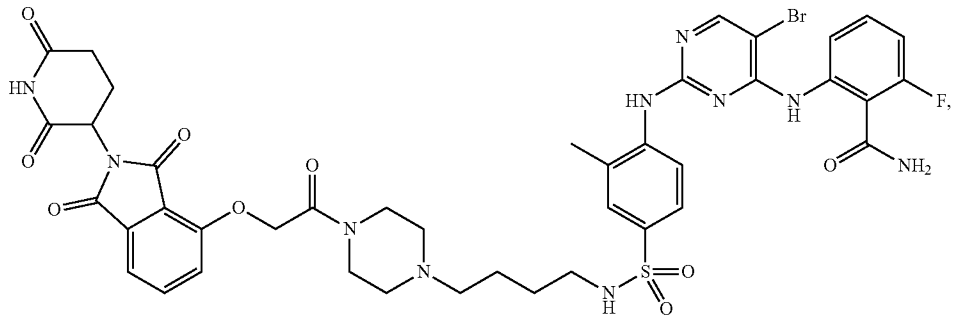

or a pharmaceutically acceptable salt or stereoisomer thereof.

Bifunctional compounds of the present invention may be in the form of a free acid or free base, or a pharmaceutically acceptable salt. As used herein, the term "pharmaceutically acceptable" refers to a material, such as a carrier or diluent, which does not abrogate the biological activity or properties of the compound, and is relatively non-toxic, i.e., the material may be administered to a subject without causing undesirable biological effects (such as dizziness or gastric upset) or interacting in a deleterious manner with any of the components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

In some embodiments, the bifunctional compound is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2H$, may afford certain therapeutic advantages resulting from greater metabolic stability, for example, increased in vivo half-life or reduced dosage requirements, and thus may be advantageous in some circumstances.

Bifunctional compounds of the present invention may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the compounds of the present invention may be made and used in the form of individual isomers and substantially free of other isomers, or in the form of a mixture of various isomers, e.g., racemic mixtures of stereoisomers.

Methods of Synthesis

In another aspect, the present invention is directed to a method for making a bifunctional compound of formula (I), or a pharmaceutically acceptable salt or stereoisomer thereof. Broadly, the inventive compounds or pharmaceutically-acceptable salts or stereoisomers thereof may be prepared by any process known to be applicable to the preparation of chemically related compounds. The compounds of the present invention will be better understood in connection with the synthetic schemes that described in various working examples and which illustrate non-limiting methods by which the compounds of the invention may be prepared.

Pharmaceutical Compositions

Another aspect of the present invention is directed to a pharmaceutical composition that includes a therapeutically effective amount of a bifunctional compound of formula (I) or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may also include one or more pharmaceutically acceptable excipients.

Broadly, bifunctional compounds of formula (I) and their pharmaceutically acceptable salts and stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intraocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the bifunctional compound may be administered relatively quickly such as in the case of a single-dose treatment and/or an acute condition.

In some embodiments, the bifunctional compounds are formulated for oral or intravenous administration (e.g., systemic intravenous injection).

Accordingly, bifunctional compounds of formula (I) may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, bifunctional compounds of formula (I) may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations for parenteral administration may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, bifunctional compounds of formula (I) may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The compositions may be formulated for buccal or sublingual administration, examples of which include tablets, lozenges and gels.

The bifunctional compounds of formula (I) may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Bifunctional compounds of formula (I) may be formulated for topical administration which as used herein, refers to administration intradermally by invention of the formulation to the epidermis. These types of compositions are typically in the form of ointments, pastes, creams, lotions, gels, solutions and sprays.

Representative examples of carriers useful in formulating bifunctional compounds for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a bifunctional compound of formula (I) or a pharmaceutically acceptable salt or a stereoisomer thereof; or a composition including a bifunctional compound of formula (I) or a pharmaceutically acceptable salt or a stereoisomer thereof, that is effective in producing the desired therapeutic response in a particular patient suffering from a disease or disorder mediated by aberrant CDK2 and CDK5. The term "therapeutically effective amount" thus includes the amount of the bifunctional compound of the invention or a pharmaceutically acceptable salt or a stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or which simply kills or inhibits the growth of diseased (e.g., cancer) cells, or reduces the amounts of CDK2 and CDK5 in diseased cells.

The total daily dosage of the bifunctional compounds and usage thereof may be decided in accordance with standard medical practice, e.g., by the attending physician using sound medical judgment. The specific therapeutically effective dose for any particular subject may depend upon a variety of factors including the disease or disorder being treated and the severity thereof (e.g., its present status); the age, body weight, general health, sex and diet of the subject; the time of administration, route of administration, and rate of excretion of the specific compound employed; the duration of the treatment; drugs used in combination or coincidental with the bifunctional compound; and like factors well known in the medical arts (see, for example, *Goodman and Gilman's, The Pharmacological Basis of Therapeutics,* 10th Edition, A. Gilman, J. Hardman and L. Limbird, eds., McGraw-Hill Press, 155-173, 2001).

Bifunctional compounds of formula (I) and their pharmaceutically acceptable salts and stereoisomers may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, or in yet other embodiments from about 10 to about 30 mg per day. In some embodiments, the total daily dosage may range from 400 mg to 600 mg. Individual dosages may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, individual dosages may be formulated to contain the desired dosage amount depending upon the number of times the compound is administered per day.

Methods of Use

In some aspects, the present invention is directed to methods of treating diseases or disorders involving aberrant (e.g., dysfunctional or dysregulated) CDK2/5 activity, that entails administration of a therapeutically effective amount of a bifunctional compound of formula (I) or a pharmaceutically acceptable salt or stereoisomer thereof, to a subject in need thereof.

The diseases or disorders may be said to be characterized or mediated by aberrant CDK2/5 activity (e.g., elevated levels of the proteins or otherwise functionally abnormal relative to a non-pathological state). A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health. In some embodiments, bifunctional compounds of the invention may be useful in the treatment of cell proliferative diseases and disorders (e.g., cancer or benign neoplasms). As used herein, the term "cell proliferative disease or disorder" refers to the conditions characterized by deregulated or abnormal cell growth, or both, including noncancerous conditions such as neoplasms, precancerous conditions, benign tumors, and cancer.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present invention may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

In some embodiments, the methods are directed to treating subjects having cancer. Broadly, the compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), cholangiocarcinoma, germ cell tumor, ovarian germ cell tumor, head and neck cancer, neuroendocrine tumors, Hodgkin's lymphoma, Ann Arbor stage III and stage IV childhood Non-Hodgkin's lymphoma, ROS1-positive refractory Non-Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, renal cell carcinoma), liver cancer, lung cancer (e.g., non-small cell lung cancer and small cell lung cancer), ALK-positive anaplastic large cell lymphoma, ALK-positive advanced malignant solid neoplasm, Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, metastatic anaplastic thyroid cancer, undifferentiated thyroid cancer, papillary thyroid cancer, pituitary tumor, plasma cell neoplasm/multiple myeloma, pleuropulmonary blastoma, prostate cancer, retinoblastoma, rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, juvenile xanthogranuloma, transitional cell cancer of the renal pelvis and ureter and other urinary organs, urethral cancer, gestational trophoblastic tumor, vaginal cancer, vulvar cancer, hepatoblastoma, rhabdoid tumor, and Wilms tumor.

Sarcomas that may be treatable with bifunctional compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue) and mesenchymous or mixed mesodermal tumor (mixed connective tissue types), and histiocytic sarcoma (immune cancer).

In some embodiments, methods of the present invention entail treatment of subjects having cell proliferative diseases or disorders of the hematological system, liver, brain, lung, colon, pancreas, prostate, skin, ovary, breast, skin (e.g., melanoma), and endometrium.

As used herein, "cell proliferative diseases or disorders of the hematological system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia.

Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, squamous cell carcinoma, and mesothelioma. Lung cancer can include "scar carcinoma", bronchioveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, a compound of the present invention may be used to treat nonmetastatic or metastatic lung cancer (e.g., NSCLC, ALK-positive NSCLC, NSCLC harboring ROS1 Rearrangement, Lung Adenocarcinoma, and Squamous Cell Lung Carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

The bifunctional compounds of formula (I) and their pharmaceutically acceptable salts and stereoisomers may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been unsuccessful, or partially successful but who have become intolerant to the particular treatment. Therapy may also be given as an adjuvant treatment, i.e., to prevent reoccurrence of cancer in patients with no currently detectable disease or after surgical removal of a tumor. Thus, in some embodiments, the compound may be administered to a patient who has received prior therapy, such as chemotherapy, radioimmunotherapy, surgical therapy, immunotherapy, radiation therapy, targeted therapy or any combination thereof.

The methods of the present invention may entail administration of a bifunctional compound of formula (I) or a pharmaceutical composition thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days) followed by a 7-day "off" period. In other embodiments, the bifunctional compound may be dosed twice a day (BID) over the course of two and a half days (for a total of 5 doses) or once a day (QD) over the course of two days (for a total of 2 doses). In other embodiments, the bifunctional compound may be dosed once a day (QD) over the course of 5 days.

Combination Therapy

Bifunctional compounds of formula (I) and their pharmaceutically acceptable salts and stereoisomers may be used in combination or concurrently with at least one other active agent, e.g., anti-cancer agent or regimen, in treating diseases and disorders. The terms "in combination" and "concurrently" in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically) to provide an increased benefit than if they were administered otherwise. For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a bifunctional compound of formula (I) in combination with one or more additional therapeutics known for use in treating the disease or condition (e.g., cancer). The dosage of the additional anticancer therapeutic may be the same or even lower than known or recommended doses. See, Hardman et al., eds., *Goodman & Gilman's The Pharmacological Basis Of Basis Of Therapeutics,* 10th ed., McGraw-Hill, New York, 2001; Physician's Desk Reference 60th ed., 2006. For example, anti-cancer agents that may be suitable for use in combination with the inventive bifunctional compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, a bifunctional compound of formula (I) and the additional (e.g., anticancer) therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more (e.g., anticancer) therapeutics may be administered within the same patient visit.

When the active components of the combination are not administered in the same pharmaceutical composition, it is understood that they can be administered in any order to a subject in need thereof. For example, a bifunctional compound of the present invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional anticancer therapeutic, to a subject in need thereof. In various aspects, the anticancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one example, the (e.g., anticancer) therapeutics are administered within the same office visit. In another example, the combination anticancer therapeutics may be administered at 1 minute to 24 hours apart.

In some embodiments involving cancer treatment, a bifunctional compound of formula (I) and the additional anti-cancer agent or therapeutic are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

Pharmaceutical Kits

The present bifunctional compounds and/or compositions containing them may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain a bifunctional compound of formula (I) or a pharmaceutical composition thereof. The kits or pharmaceutical systems of the invention may also include printed instructions for using the compounds and compositions.

These and other aspects of the present invention will be further appreciated upon consideration of the following Examples, which are intended to illustrate certain particular embodiments of the invention but are not intended to limit its scope, as defined by the claims.

EXAMPLES

These and other aspects of the present invention will be further appreciated upon consideration of the following Examples, which are intended to illustrate certain particular embodiments of the invention but are not intended to limit its scope, as defined by the claims.

Example 1: Synthesis of Intermediates

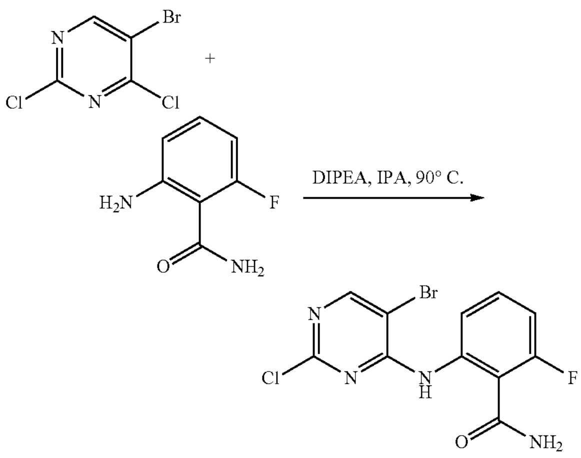

2-((5-bromo-2-chloropyrimidin-4-yl)amino)-6-fluorobenzamide

To a stirred solution of 5-bromo-2,4-dichloropyrimidine (900 mg, 3.95 mmol) and 2-amino-6-fluorobenzamide (670 mg, 4.34 mmol) in isopropyl alcohol (24.0 mL) was added N,N-diisopropylethylamine (1.37 mL, 7.90 mmol), then the mixture was heated at 90° C. for 24 hours. Precipitation occurred after cooling to room temperature. The solid was collected and dried after filtration. The title compound was obtained as an off-white powder (500 mg, 1.44 mmol, 36% yield). The product was used directly in the next step without further purification. ESI (m/z): $[M+H]^+$ 344.97, 346.97.

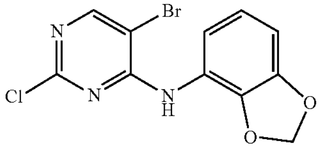 [SMILES: Clc1ncc(Br)c(Nc2cccc3c2OCO3)n1]

N-(benzo[d][1,3]dioxol-4-yl)-5-bromo-2-chloropyrimidin-4-amine

This compound was prepared following the same procedure as 2-((5-bromo-2-chloropyrimidin-4-yl)amino)-6-fluorobenzamide by using benzo[d][1,3]dioxol-4-amine in 87% yield as a white solid. ESI (m/z): $[M+H]^+$ 327.85, 329.88.

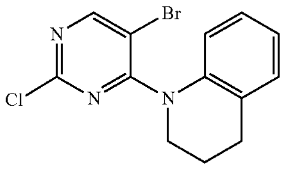 [SMILES: Clc1ncc(Br)c(N2CCCc3ccccc32)n1]

1-(5-bromo-2-chloropyrimidin-4-yl)-1,2,3,4-tetrahydroquinoline

This compound was prepared following the same procedure as 2-((5-bromo-2-chloropyrimidin-4-yl)amino)-6-fluorobenzamide by using 1,2,3,4-tetrahydroquinoline in 28% yield as a white solid. ESI (m/z): $[M+H]^+$ 323.90, 325.93.

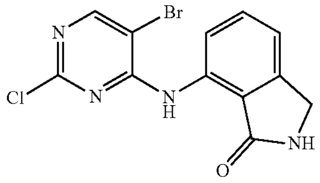 [SMILES: O=C1NCc2cccc(Nc3nc(Cl)ncc3Br)c21]

7-((5-bromo-2-chloropyrimidin-4-yl)amino)isoindolin-1-one

This compound was prepared following the same procedure as 2-((5-bromo-2-chloropyrimidin-4-yl)amino)-6-fluorobenzamide by using 7-aminoisoindolin-1-one in 35% yield as a white solid. ESI (m/z): $[M+H]^+$ 339.13, 341.11.

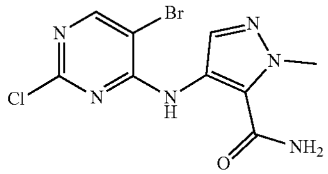 [SMILES: Cn1ncc(Nc2nc(Cl)ncc2Br)c1C(N)=O]

4-((5-bromo-2-chloropyrimidin-4-yl)amino)-1-methyl-1H-pyrazole-5-carboxamide

This compound was prepared following the same procedure as 2-((5-bromo-2-chloropyrimidin-4-yl)amino)-6-fluorobenzamide by using 4-amino-1-methyl-1H-pyrazole-5-carboxamide in 82% yield as a white solid. ESI (m/z): $[M+H]^+$ 331.12, 333.10.

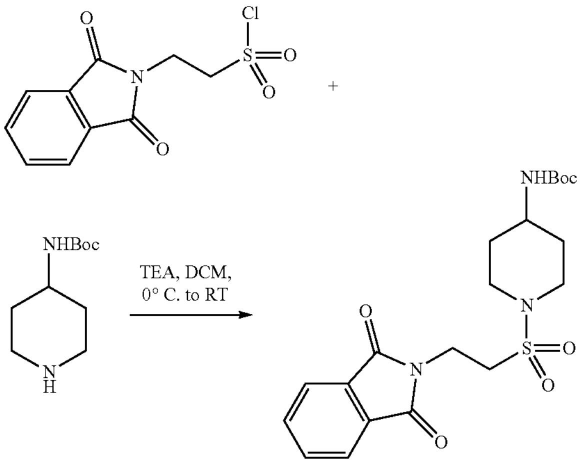

tert-Butyl (1-(2-phthalimidoethanesulfonyl)piperidin-4-yl)carbamate

To a stirred solution of tert-butyl piperidin-4-ylcarbamate (578 mg, 2.89 mmol) and triethylamine (0.80 mL, 5.78 mmol) in dichloromethane (12.0 mL) at 0° C. was added 2-phthalimidoethanesulfonyl chloride (790 mg, 2.89 mmol) in portions. The reaction mixture was gradually warmed to room temperature and stirred at room temperature for 3 hours. The reaction mixture was directly concentrated and purified via flash column chromatography (over silica) with an eluent system of 0% to 10% MeOH in dichloromethane to afford the title compound as a white solid (930 mg, 2.12 mmol, 73% yield). ESI (m/z): $[M+H-Boc]^+$338.06.

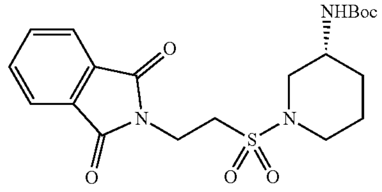 [SMILES: CC(C)(C)OC(=O)N[C@@H]1CCCN(S(=O)(=O)CCN2C(=O)c3ccccc3C2=O)C1]

tert-Butyl (R)-(1-(2-phthalimidoethanesulfonyl)piperidin-3-yl)carbamate

This compound was prepared using the same procedure as tert-butyl (1-(2-phthalimidoethanesulfonyl)piperidin-4-yl) carbamate using tert-butyl (R)-piperidin-3-ylcarbamate in 78% yield as a white solid. ESI (m/z): $[M+H-Boc]^+$338.00.

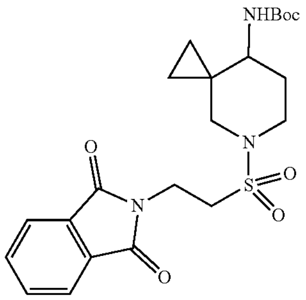 [SMILES: CC(C)(C)OC(=O)NC1CCN(S(=O)(=O)CCN2C(=O)c3ccccc3C2=O)CC12CC2]

tert-Butyl (5-((2-(1,3-dioxoisoindolin-2-yl)ethyl) sulfonyl)-5-azaspiro[2.5]octan-8-yl)carbamate This compound was prepared following the same procedure as tert-butyl (1-(2-phthalimidoethanesulfonyl)piperidin-4-yl)carbamate by using tert-butyl (5-azaspiro[2.5]octan-8-yl)carbamate in 81% yield as a white solid. ESI (m/z): $[M+H-Boc]^+$ 364.11.

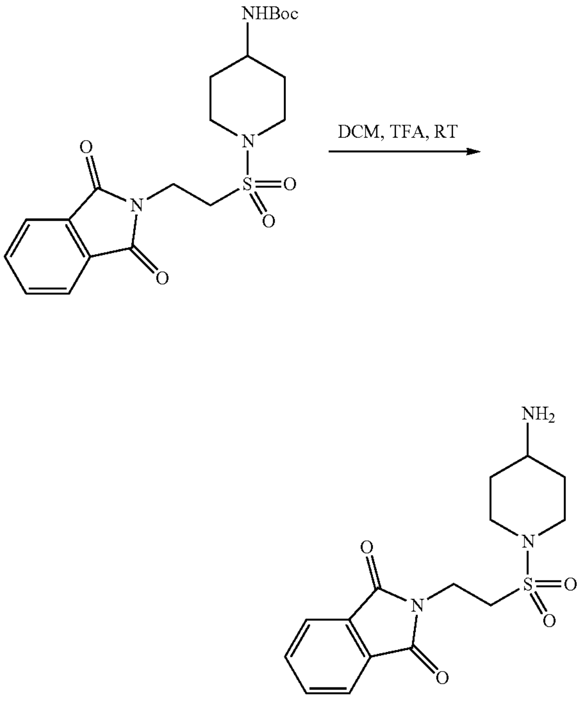

1-(2-phthalimidoethanesulfonyl)-4-aminopiperidin

To a stirred solution of tert-butyl (1-(2-phthalimidoethanesulfonyl)piperidin-4-yl)carbamate (930 mg, 2.12 mmol) in dichloromethane (4.0 mL) was added trifluoroacetic acid (0.8 mL), then the mixture was stirred at room temperature for 1.5 hours. The reaction mixture was concentrated in vacuo to afford the title compound as a white solid. The product was used directly in the next step without further purification. ESI (m/z): $[M+H]^+$ 338.06.

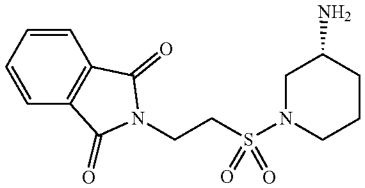 [SMILES: N[C@@H]1CCCN(S(=O)(=O)CCN2C(=O)c3ccccc3C2=O)C1]

(R)-1-(2-phthalimidoethanesulfonyl)-3-aminopiperidin

This compound was prepared using the same procedure as 1-(2-phthalimidoethanesulfonyl)-4-aminopiperidin using tert-butyl (R)-piperidin-3-ylcarbamate and isolated as a white solid. The product was used directly in the next step without further purification. ESI (m/z): $[M+H]^+$ 338.06.

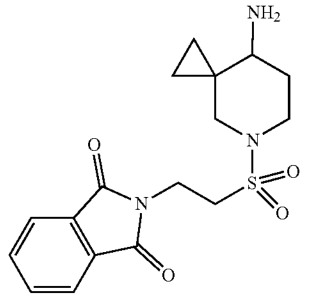 [SMILES: NC1CCN(S(=O)(=O)CCN2C(=O)c3ccccc3C2=O)CC12CC2]

2-(2-((8-amino-5-azaspiro[2.5]octan-5-yl)sulfonyl) ethyl)isoindoline-1,3-dione

This compound was prepared following the same procedure as 1-(2-phthalimidoethanesulfonyl)-4-aminopiperidin by using tert-butyl (5-((2-(1,3-dioxoisoindolin-2-yl)ethyl) sulfonyl)-5-azaspiro[2.5]octan-8-yl)carbamate and isolated as a white solid. The product was used directly in the next step without further purification. ESI (m/z): $[M+H]^+$ 364.07.

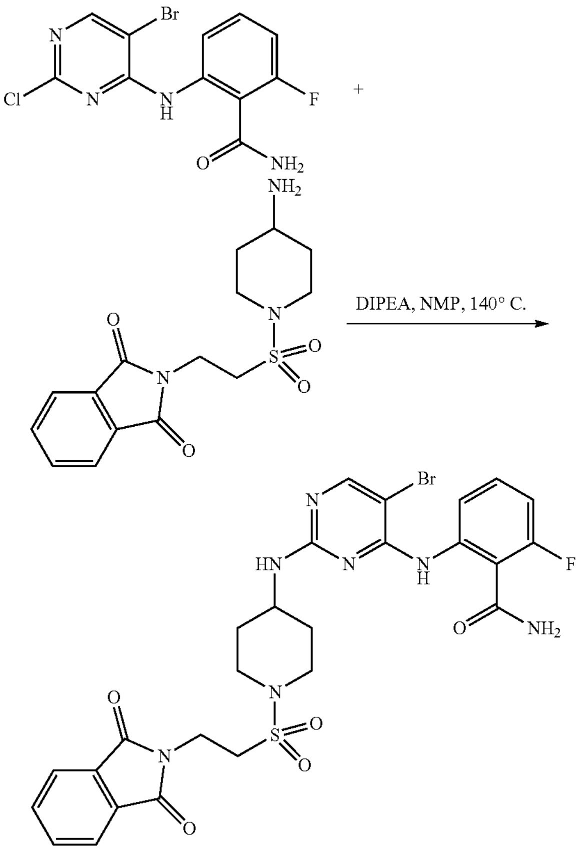

2-((5-bromo-2-((1-(2-phthalimidoethanesulfonyl) piperidin-4-yl)amino)pyrimidin-4-yl)amino)-6-fluorobenzamide To a stirred solution of 2-((5-bromo-2-chloropyrimidin-4-yl)amino)-6-fluorobenzamide (380 mg, 1.10 mmol) and 1-(2-phthalimidoethanesulfonyl)-4-aminopiperidin (371 mg, 1.10 mmol) in N-methyl-2-pyrrolidone (8.0 mL) was added diisopropylethylamine (0.95 mL, 5.50 mmol). The reaction mixture was stirred at 140° C. for 48 hours. The reaction mixture was cooled to room temperature and diluted with EtOAc (25.0 mL) and $H_2O$ (10.0 mL). The organic layer was separated, and the aqueous layer was further extracted with EtOAc (25.0 mL). The combined organics were washed with $H_2O$ (10.0 mL) and brine (10.0 mL) in sequence, dried over solid $Na_2SO_4$, and concentrated under reduced pressure. The crude mixture was purified via flash column chromatography (over silica) with an eluent system of 0% to 10% MeOH in dichloromethane to afford the title compound as an off-white solid (357 mg, 0.55 mmol, 50% yield). ESI (m/z): $[M+H]^+$ 646.15, 648.01.

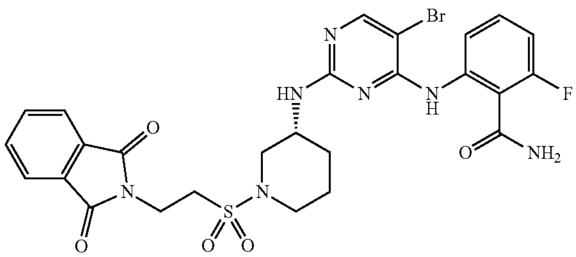 [SMILES: NC(=O)c1c(F)cccc1Nc1nc(N[C@@H]2CCCN(S(=O)(=O)CCN3C(=O)c4ccccc4C3=O)C2)ncc1Br]

(R)-2-((5-bromo-2-((1-(2-phthalimidoethanesulfonyl)piperidin-3-yl)amino)pyrimidin-4-yl)amino)-6-fluorobenzamide This compound was prepared using the same procedure as 2-((5-bromo-2-((1-(2-phthalimidoethanesulfonyl)piperidin-4-yl)amino)pyrimidin-4-yl)amino)-6-fluorobenzamide using (R)-1-(2-phthalimidoethanesulfonyl)-3-aminopiperidin in 16% yield as an off-white solid. ESI (m/z): $[M+H]^+$ 646.15, 648.07.

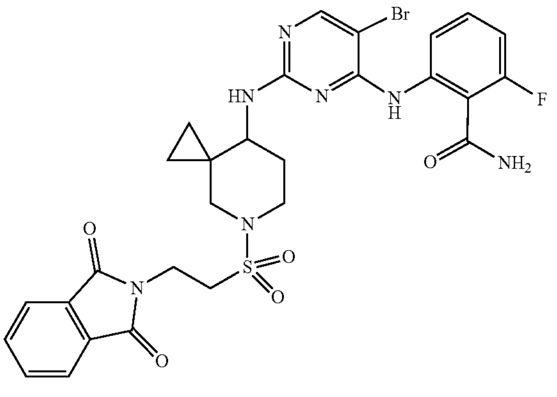 [SMILES: NC(=O)c1c(F)cccc1Nc1nc(NC2CCN(S(=O)(=O)CCN3C(=O)c4ccccc4C3=O)CC23CC3)ncc1Br]

2-((5-bromo-2-((5-((2-(1,3-dioxoisoindolin-2-yl) ethyl)sulfonyl)-5-azaspiro[2.5]octan-8-yl)amino) pyrimidin-4-yl)amino)-6-fluorobenzamide This compound was prepared following the same procedure as 2-((5-bromo-2-((1-(2-phthalimidoethanesulfonyl)piperidin-4-yl)amino)pyrimidin-4-yl)amino)-6-fluorobenzamide by using 2-(2-((8-amino-5-azaspiro[2.5]octan-5-yl) sulfonyl)ethyl)isoindoline-1,3-dione in 69% yield as an off-white solid. ESI (m/z): $[M+H]^+$ 672.17, 673.97.

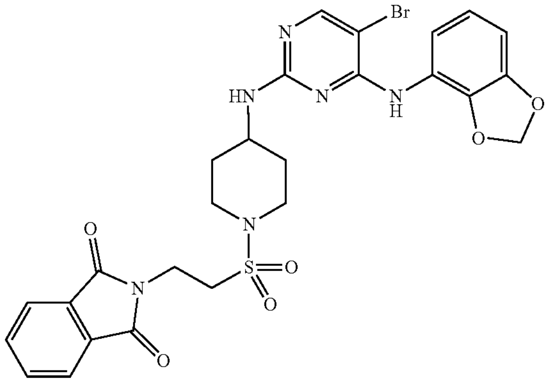 [SMILES: O=C1c2ccccc2C(=O)N1CCS(=O)(=O)N1CCC(Nc2ncc(Br)c(Nc3cccc4c3OCO4)n2)CC1]

2-(2-((4-((4-(benzo[d][1,3]dioxol-4-ylamino)-5-bromopyrimidin-2-yl)amino)piperidin-1-yl)sulfonyl)ethyl)isoindoline-1,3-dione This compound was prepared following the same procedure as 2-((5-bromo-2-((1-(2-phthalimidoethanesulfonyl)piperidin-4-yl)amino)pyrimidin-4-yl)amino)-6-fluorobenzamide by using N-(benzo[d][1,3]dioxol-4-yl)-5-bromo-2-chloropyrimidin-4-amine in 69% yield as an off-white solid. ESI (m/z): $[M+H]^+$ 629.45, 631.48.

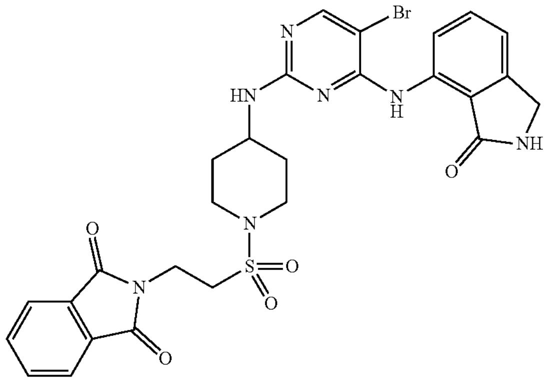

2-(2-((4-((5-bromo-4-((3-oxoisoindolin-4-yl)amino)pyrimidin-2-yl)amino)piperidin-1-yl)sulfonyl)ethyl)isoindoline-1,3-dione This compound was prepared following the same procedure as 2-((5-bromo-2-((1-(2-phthalimidoethanesulfonyl)piperidin-4-yl)amino)pyrimidin-4-yl)amino)-6-fluorobenzamide by using 7-((5-bromo-2-chloropyrimidin-4-yl)amino)isoindolin-1-one in 55% yield as an off-white solid. ESI (m/z): $[M+H]^+$ 640.18, 641.98.

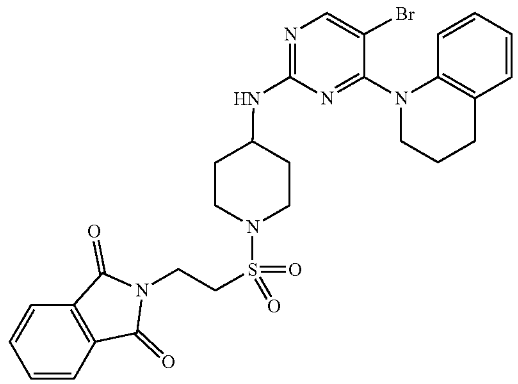 [SMILES: O=C1c2ccccc2C(=O)N1CCS(=O)(=O)N1CCC(Nc2ncc(Br)c(N3CCCc4ccccc43)n2)CC1]

2-(2-((4-((5-bromo-4-(3,4-dihydroquinolin-1(2H)-yl)pyrimidin-2-yl)amino)piperidin-1-yl)sulfonyl)ethyl)isoindoline-1,3-dione This compound was prepared following the same procedure as 2-((5-bromo-2-((1-(2-phthalimidoethanesulfonyl)piperidin-4-yl)amino)pyrimidin-4-yl)amino)-6-fluorobenzamide by using 1-(5-bromo-2-chloropyrimidin-4-yl)-1,2,3,4-tetrahydroquinoline in 98% yield as an off-white solid. ESI (m/z): $[M+H]^+$ 625.11, 626.98.

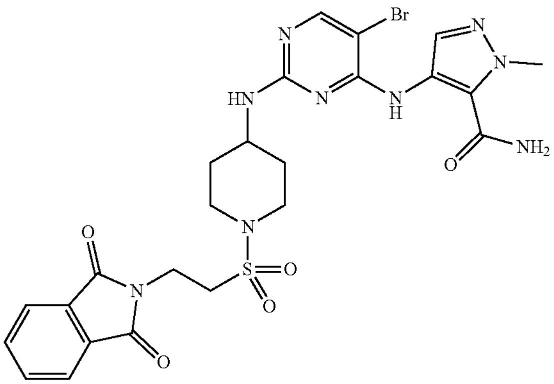 [SMILES: Cn1ncc(Nc2nc(NC3CCN(S(=O)(=O)CCN4C(=O)c5ccccc5C4=O)CC3)ncc2Br)c1C(N)=O]

4-((5-bromo-2-((1-((2-(1,3-dioxoisoindolin-2-yl)ethyl)sulfonyl)piperidin-4-yl)amino)pyrimidin-4-yl)amino)-1-methyl-1H-pyrazole-5-carboxamide This compound was prepared following the same procedure as 2-((5-bromo-2-((1-(2-phthalimidoethanesulfonyl)piperidin-4-yl)amino)pyrimidin-4-yl)amino)-6-fluorobenzamide by using 4-((5-bromo-2-chloropyrimidin-4-yl)amino)-1-methyl-1H-pyrazole-5-carboxamide in 80% yield as an off-white solid. ESI (m/z): $[M+H]^+$ 632.11, 634.03.

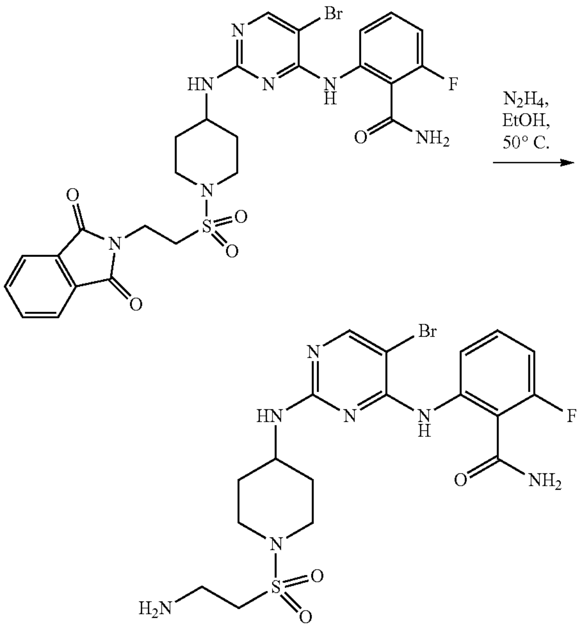

2-((2-((1-((2-aminoethyl)sulfonyl)piperidin-4-yl)amino)-5-bromopyrimidin-4-yl)amino)-6-fluorobenzamide To a solution of 2-((5-bromo-2-((1-(2-phthalimidoethanesulfonyl)piperidin-4-yl)amino)pyrimidin-4-yl)amino)-6-fluorobenzamide (58 mg, 0.089 mmol) in ethanol (1.0 mL) was added $N_2H_4$ (64% weight, 9.0 μL, 0.18 mmol). The reaction mixture was stirred at 50° C. for 30 minutes. The reaction mixture was purified directly by prep HPLC. Appropriate fractions were combined and lyophilized to afford the title compound as a white solid (25 mg, 0.048 mmol, 54% yield). ESI (m/z): $[M+H]^+$ 516.10, 518.13.

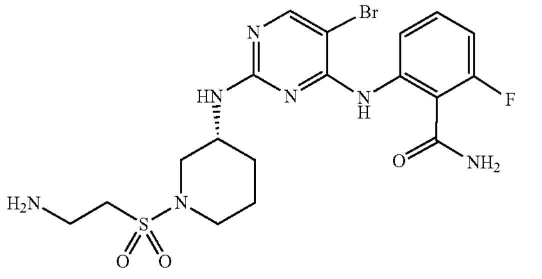 [SMILES: NCCS(=O)(=O)N1CCC[C@@H](Nc2ncc(Br)c(Nc3cccc(F)c3C(N)=O)n2)C1]

(R)-2-((2-((1-((2-aminoethyl)sulfonyl)piperidin-3-yl)amino)-5-bromopyrimidin-4-yl)amino)-6-fluorobenzamide This compound was prepared using the same procedure as 2-((2-((1-((2-aminoethyl)sulfonyl)piperidin-4-yl)amino)-5-bromopyrimidin-4-yl)amino)-6-fluorobenzamide using (R)-2-((5-bromo-2-((1-(2-phthalimidoethanesulfonyl)piperidin-3-yl)amino)pyrimidin-4-yl)amino)-6-fluorobenzamide in 96% yield as an off-white solid. ESI (m/z): $[M+H]^+$ 516.10, 518.02.

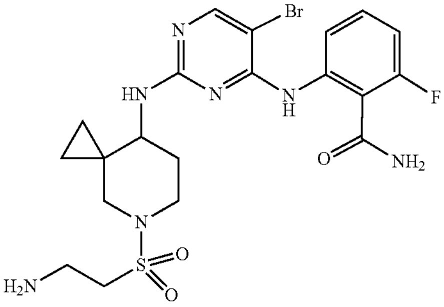 [SMILES: NCCS(=O)(=O)N1CCC(Nc2ncc(Br)c(Nc3cccc(F)c3C(N)=O)n2)C2(CC2)C1]

2-((2-((5-((2-aminoethyl)sulfonyl)-5-azaspiro[2.5]octan-8-yl)amino)-5-bromopyrimidin-4-yl)amino)-6-fluorobenzamide This compound was prepared following the same procedure as 2-((2-((1-((2-aminoethyl)sulfonyl)piperidin-4-yl)amino)-5-bromopyrimidin-4-yl)amino)-6-fluorobenzamide by using 2-((5-bromo-2-((5-((2-(1,3-dioxoisoindolin-2-yl)ethyl)sulfonyl)-5-azaspiro[2.5]octan-8-yl)amino)pyrimidin-4-yl)amino)-6-fluorobenzamide in 75% yield as an off-white solid. ESI (m/z): $[M+H]^+$ 542.07, 543.99.

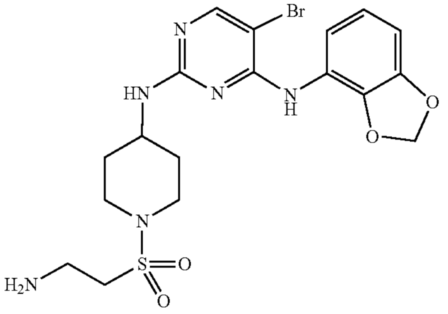 [SMILES: NCCS(=O)(=O)N1CCC(Nc2ncc(Br)c(Nc3cccc4c3OCO4)n2)CC1]

$N^2$-(1-((2-aminoethyl)sulfonyl)piperidin-4-yl)-$N^4$-(benzo[d][1,3]dioxol-4-yl)-5-bromopyrimidine-2,4-diamine This compound was prepared following the same procedure as 2-((2-((1-((2-aminoethyl)sulfonyl)piperidin-4-yl)amino)-5-bromopyrimidin-4-yl)amino)-6-fluorobenzamide by using 2-(2-((4-((4-(benzo[d][1,3]dioxol-4-ylamino)-5-bromopyrimidin-2-yl)amino)piperidin-1-yl)sulfonyl)ethyl)isoindoline-1,3-dione in 37% yield as an off-white solid. ESI (m/z): $[M+H]^+$ 499.40, 501.43.

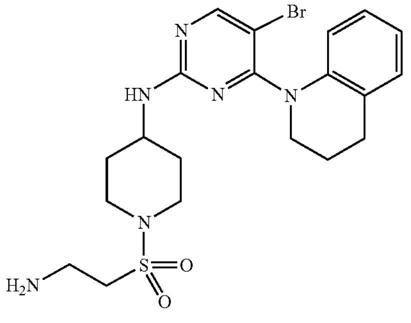 [SMILES: NCCS(=O)(=O)N1CCC(Nc2ncc(Br)c(N3CCCc4ccccc43)n2)CC1]

N-(1-((2-aminoethyl)sulfonyl)piperidin-4-yl)-5-bromo-4-(3,4-dihydroquinolin-1(2H)-yl)pyrimidin-2-amine This compound was prepared following the same procedure as 2-((2-((1-((2-aminoethyl)sulfonyl)piperidin-4-yl)amino)-5-bromopyrimidin-4-yl)amino)-6-fluorobenzamide by using 2-(2-((4-((5-bromo-4-(3,4-dihydroquinolin-1(2H)-yl)pyrimidin-2-yl)amino)piperidin-1-yl)sulfonyl)ethyl)isoindoline-1,3-dione in 30% yield as an off-white solid. ESI (m/z): $[M+H]^+$ 495.13, 497.05.

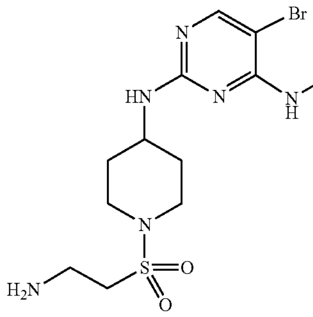

7-((2-((1-((2-aminoethyl)sulfonyl)piperidin-4-yl)amino)-5-bromopyrimidin-4-yl)amino)isoindolin-1-one This compound was prepared following the same procedure as 2-((2-((1-((2-aminoethyl)sulfonyl)piperidin-4-yl)amino)-5-bromopyrimidin-4-yl)amino)-6-fluorobenzamide by using 2-(2-((4-((5-bromo-4-((3-oxoisoindolin-4-yl)amino)pyrimidin-2-yl)amino)piperidin-1-yl)sulfonyl)ethyl)isoindoline-1,3-dione in 70% yield as an off-white solid. ESI (m/z): $[M+H]^+$ 510.14, 512.11.

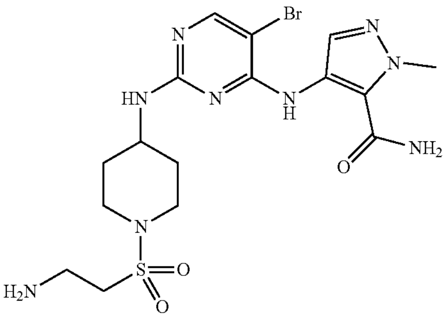 [SMILES: Cn1ncc(Nc2nc(NC3CCN(S(=O)(=O)CCN)CC3)ncc2Br)c1C(N)=O]

4-((2-((1-((2-aminoethyl)sulfonyl)piperidin-4-yl)amino)-5-bromopyrimidin-4-yl)amino)-1-methyl-1H-pyrazole-5-carboxamide This compound was prepared following the same procedure as 2-((2-((1-((2-aminoethyl)sulfonyl)piperidin-4-yl)amino)-5-bromopyrimidin-4-yl)amino)-6-fluorobenzamide by using 4-((5-bromo-2-((1-((2-(1,3-dioxoisoindolin-2-yl)ethyl)sulfonyl)piperidin-4-yl)amino)pyrimidin-4-yl)amino)-1-methyl-1H-pyrazole-5-carboxamide in 87% yield as an off-white solid. ESI (m/z): $[M+H]^+$ 502.12, 504.05.

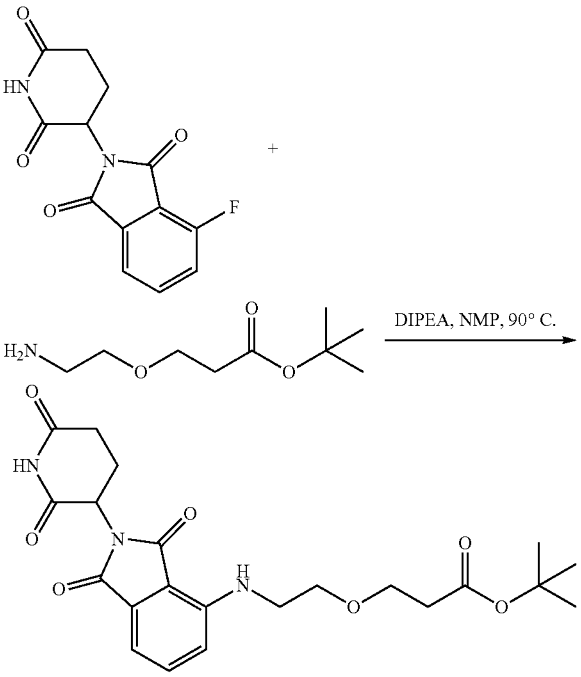

tert-Butyl 3-(2-((2-(2,6-dioxopiperidin-3-yl)-1,3-dioxoisoindolin-4-yl)amino)ethoxy)propanoate To a stirred solution of 2-(2,6-dioxopiperidin-3-yl)-4-fluoroisoindoline-1,3-dione (40 mg, 0.14 mmol) and tert-butyl 3-(2-aminoethoxy)propanoate (27 mg, 0.14 mmol) in N-methyl-2-pyrrolidone (1.0 mL) was added diisopropylethylamine (0.05 mL, 0.28 mmol). The reaction mixture was stirred at 90° C. for 15 hours. The reaction mixture was purified directly by prep HPLC and appropriate fractions were combined and lyophilized to afford the title compound as a yellow viscous oil (27.0 mg, 0.06 mmol, 42% yield). ESI (m/z): $[M+H-56]^{+\,390.10}$.

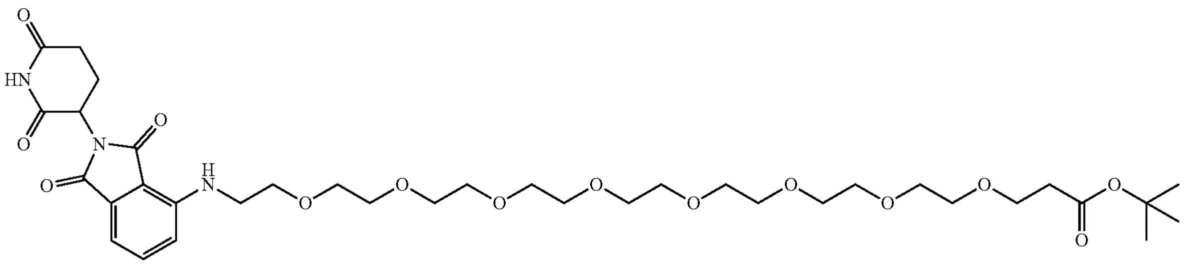 [SMILES: CC(C)(C)OC(=O)CCOCCOCCOCCOCCOCCOCCOCCOCCNc1cccc2c1C(=O)N(C1CCC(=O)NC1=O)C2=O]

tert-Butyl 1-((2-(2,6-dioxopiperidin-3-yl)-1,3-dioxoisoindolin-4-yl)amino)-3,6,9,12,15,18,21,24-octaoxaheptacosan-27-oate This compound was prepared using the same procedure as tert-butyl 3-(2-((2-(2,6-dioxopiperidin-3-yl)-1,3-dioxoisoindolin-4-yl)amino)ethoxy)propanoate using tert-butyl 1-amino-3,6,9,12,15,18,21,24-octaoxaheptacosan-27-oate in 55% yield as a yellow viscous oil. ESI (m/z): $[M+H-56]^+$ 698.27.

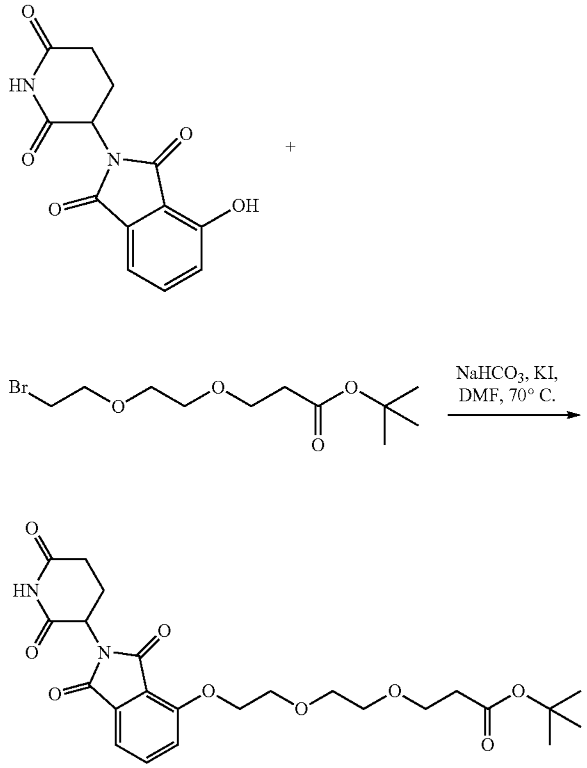

tert-Butyl 3-(2-(2-((2-(2,6-dioxopiperidin-3-yl)-1,3-dioxoisoindolin-4-yl)oxy)ethoxy)ethoxy)propanoate To a stirred solution of 2-(2,6-dioxopiperidin-3-yl)-4-hydroxyisoindoline-1,3-dione (230 mg, 0.83 mmol) and tert-butyl 3-(2-(2-bromoethoxy)ethoxy)propanoate (249 mg, 0.83 mmol) in N,N-dimethylformamide (3.0 mL) was added sodium bicarbonate (139 mg, 1.66 mmol) and potassium iodide (14 mg, 0.083 mmol). The reaction mixture was stirred at 70° C. for 18 hours. The reaction mixture was cooled to room temperature and diluted with EtOAc (15.0 mL) and $H_2O$ (10.0 mL). The organic layer was separated, and the aqueous layer was further extracted with EtOAc (15.0 mL). The combined organics were washed with $H_2O$ (10.0 mL) and brine (10.0 mL) in sequence, dried over solid $Na_2SO_4$, and concentrated under reduced pressure. The crude mixture was purified via flash column chromatography (over silica) with an eluent system of 0% to 10% MeOH in dichloromethane to afford the title compound as a yellow viscous oil (308 mg, 0.62 mmol, 75% yield). ESI (m/z): $[M+H-56]^+$ 435.15.

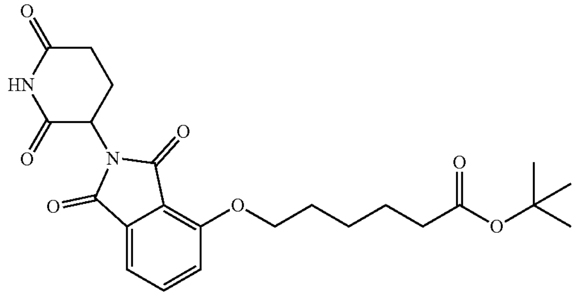 [SMILES: CC(C)(C)OC(=O)CCCCCOc1cccc2c1C(=O)N(C1CCC(=O)NC1=O)C2=O]

tert-Butyl 6-((2-(2,6-dioxopiperidin-3-yl)-1,3-dioxoisoindolin-4-yl)oxy)hexanoate This compound was prepared using the same procedure as tert-butyl 3-(2-(2-((2-(2,6-dioxopiperidin-3-yl)-1,3-dioxoisoindolin-4-yl)oxy)ethoxy)ethoxy)propanoate using tert-butyl 5-bromopentanoate in 74% yield as a yellow viscous oil. ESI (m/z): $[M+H-56]^+$ 389.27.

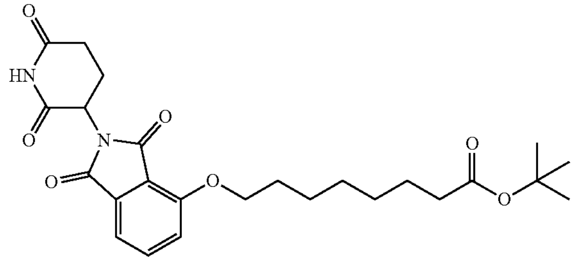 [SMILES: CC(C)(C)OC(=O)CCCCCCCOc1cccc2c1C(=O)N(C1CCC(=O)NC1=O)C2=O]

tert-Butyl 8-((2-(2,6-dioxopiperidin-3-yl)-1,3-dioxoisoindolin-4-yl)oxy)octanoate This compound was prepared using the same procedure as tert-butyl 3-(2-(2-((2-(2,6-dioxopiperidin-3-yl)-1,3-dioxoisoindolin-4-yl)oxy)ethoxy)ethoxy)propanoate using tert-butyl 7-bromoheptanoate in 70% yield as a yellow viscous oil. ESI (m/z): $[M+H-56-18]^{+\ 399.15}$.

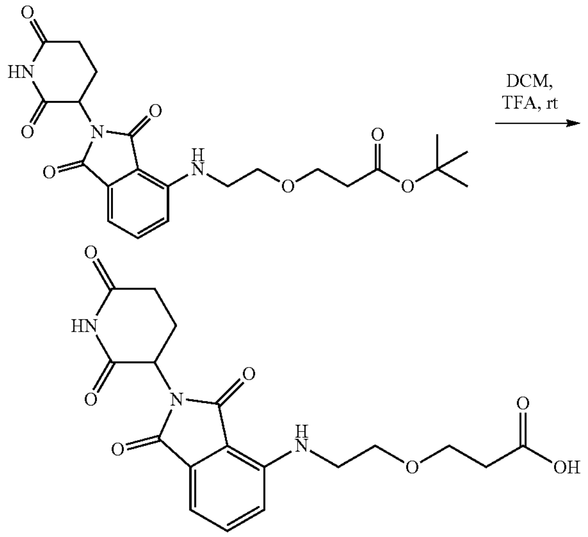

3-(2-((2-(2,6-dioxopiperidin-3-yl)-1,3-dioxoisoindolin-4-yl)amino)ethoxy)propanoic acid To a stirred solution of tert-butyl 3-(2-((2-(2,6-dioxopiperidin-3-yl)-1,3-dioxoisoindolin-4-yl)amino)ethoxy)propanoate (27 mg, 0.06 mmol) in dichloromethane (1.0 mL) was added trifluoroacetic acid (0.2 mL), then the mixture was stirred at room temperature for 1 hour. The reaction mixture was concentrated in vacuo to afford the title compound as a yellow viscous oil. The product was used directly in the next step without further purification. ESI (m/z): $[M+H]^+$ 390.10.

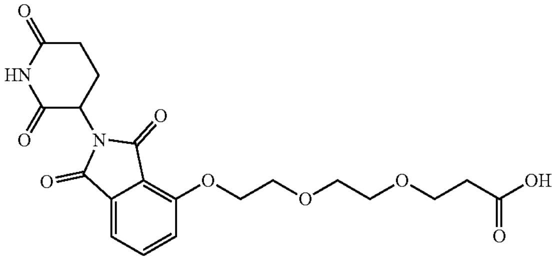

3-(2-(2-((2-(2,6-dioxopiperidin-3-yl)-1,3-dioxoisoindolin-4-yl)oxy)ethoxy)ethoxy)propanoic acid This compound was prepared using the same procedure as 3-(2-((2-(2,6-dioxopiperidin-3-yl)-1,3-dioxoisoindolin-4-yl)amino)ethoxy)propanoic acid as a yellow viscous oil. The product was used directly in the next step without further purification. ESI (m/z): $[M+H]^+$ 435.20.

1-((2-(2,6-dioxopiperidin-3-yl)-1,3-dioxoisoindolin-4-yl)amino)-3,6,9,12,15,18,21,24-octaoxaheptacosan-27-oic acid This compound was prepared using the same procedure as 3-(2-((2-(2,6-dioxopiperidin-3-yl)-1,3-dioxoisoindolin-4-yl)amino)ethoxy)propanoic acid as a yellow viscous oil. The product was used directly in the next step without further purification. ESI (m/z): $[M+H]^+$ 698.32.

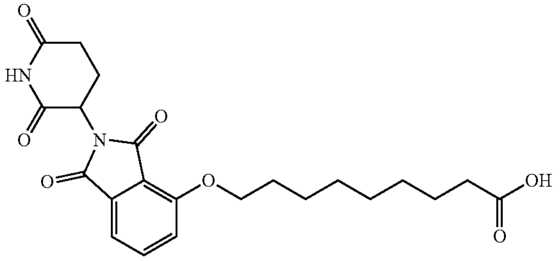 [SMILES: O=C(O)CCCCCCCCOc1cccc2c1C(=O)N(C1CCC(=O)NC1=O)C2=O]

9-((2-(2,6-dioxopiperidin-3-yl)-1,3-dioxoisoindolin-4-yl)oxy)nonanoic acid

This compound was prepared using the same procedure as 3-(2-((2-(2,6-dioxopiperidin-3-yl)-1,3-dioxoisoindolin-4-yl)amino)ethoxy)propanoic acid as a yellow viscous oil in 22% yield. ESI (m/z): $[M+H-18]^+$ 413.20.

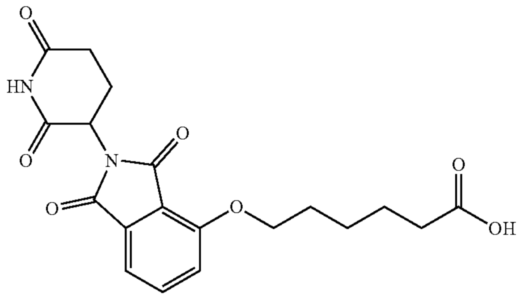 [SMILES: O=C(O)CCCCCOc1cccc2c1C(=O)N(C1CCC(=O)NC1=O)C2=O]

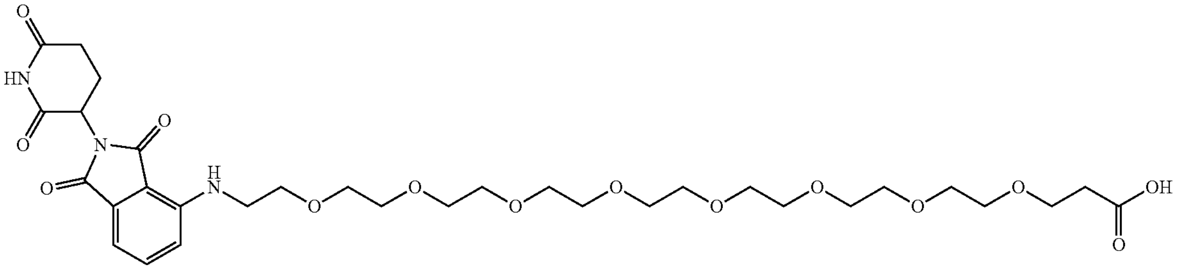

6-((2-(2,6-dioxopiperidin-3-yl)-1,3-dioxoisoindolin-4-yl)oxy)hexanoic acid

This compound was prepared using the same procedure as 3-(2-((2-(2,6-dioxopiperidin-3-yl)-1,3-dioxoisoindolin-4-yl)amino)ethoxy)propanoic acid as a yellow viscous oil. The product was used directly in the next step without further purification. ESI (m/z): [M+H]$^+$ 389.17.

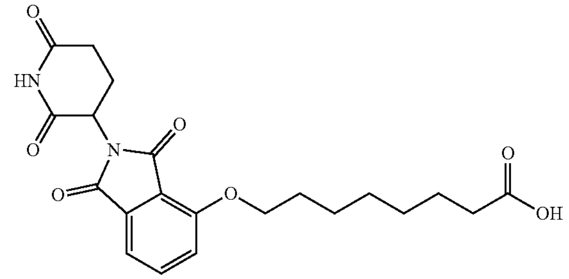 [SMILES: O=C(O)CCCCCCCOc1cccc2c1C(=O)N(C1CCC(=O)NC1=O)C2=O]

8-((2-(2,6-dioxopiperidin-3-yl)-1,3-dioxoisoindolin-4-yl)oxy)octanoic acid

This compound was prepared using the same procedure as 3-(2-((2-(2,6-dioxopiperidin-3-yl)-1,3-dioxoisoindolin-4-yl)amino)ethoxy)propanoic acid as a yellow viscous oil. The product was used directly in the next step without further purification. ESI (m/z): [M+H]$^+$ 417.27.

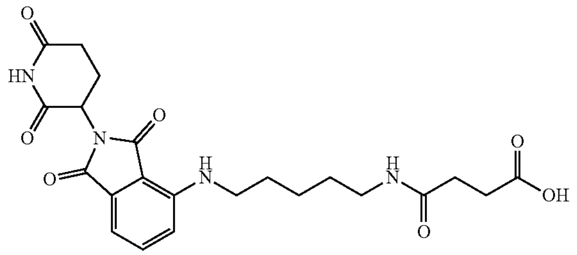 [SMILES: O=C(O)CCC(=O)NCCCCCNc1cccc2c1C(=O)N(C1CCC(=O)NC1=O)C2=O]

4-((5-((2-(2,6-dioxopiperidin-3-yl)-1,3-dioxoisoindolin-4-yl)amino)pentyl)amino)-4-oxobutanoic acid This compound was prepared following the same procedure as 3-(2-((2-(2,6-dioxopiperidin-3-yl)-1,3-dioxoisoindolin-4-yl)amino)ethoxy)propanoic acid as a yellow viscous oil. The product was used directly in the next step without further purification. ESI (m/z): [M+H]$^+$ 459.52.

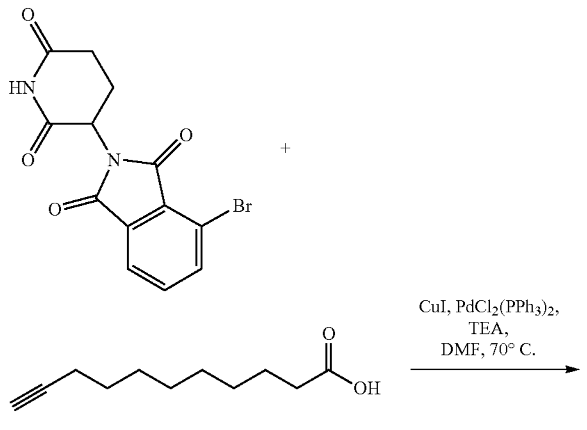

-continued

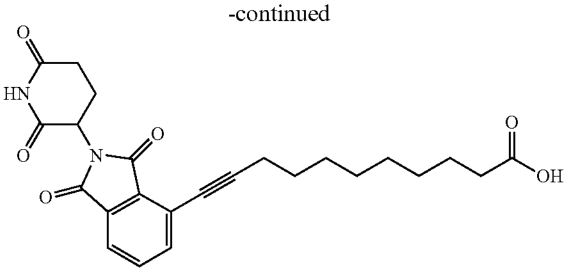

11-(2-(2,6-dioxopiperidin-3-yl)-1-oxoisoindolin-4-yl)undec-10-ynoic acid

A glass reaction tube was charged with 3-(4-bromo-1-oxoisoindolin-2-yl)piperidine-2,6-dione (80 mg, 0.24 mmol), undec-10-ynoic acid (45 mg, 0.24 mmol), CuI (5 mg, 0.024 mmol), and $PdCl_2(PPh_3)_2$ (17 mg, 0.024 mmol), sealed with a rubber septum and evacuated and filled with $N_2$ three times. Degassed dimethylformamide (2.0 mL) and triethylamine (1.0 mL) were added sequentially, and the reaction mixture was stirred at 70° C. for 18 hours. The reaction mixture was purified directly by prep HPLC and appropriate fractions were combined and lyophilized to afford the title as a white solid (40 mg, 0.094 mmol, 38% yield). ESI (m/z): [M+H]$^+$ 425.50.

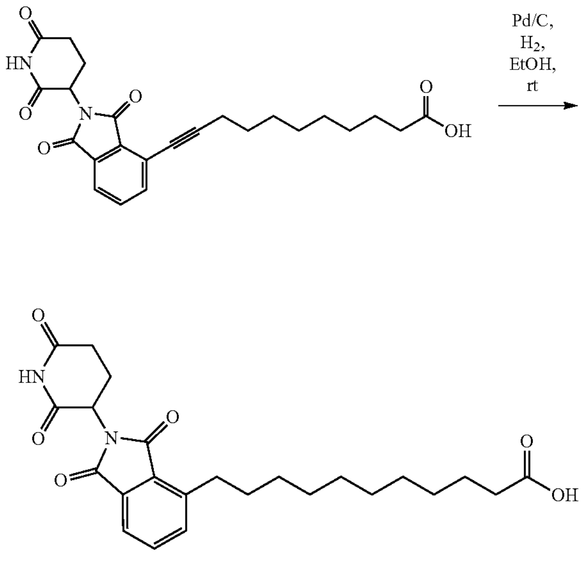

11-(2-(2,6-dioxopiperidin-3-yl)-1-oxoisoindolin-4-yl)undecanoic acid

Pd/C (5 mg, 10 wt. %) was added was added to a solution of 11-(2-(2,6-dioxopiperidin-3-yl)-1-oxoisoindolin-4-yl)undecanoic acid (30 mg, 0.076 mmol) in ethanol (3.0 mL) and the mixture was hydrogenated (1 bar $H_2$ pressure) at room temperature for 19 hours. The reaction mixture was concentrated in vacuo to afford the title compound as a white solid. The product was used directly in the next step without further purification. ESI (m/z): [M+H]$^+$ 429.56.

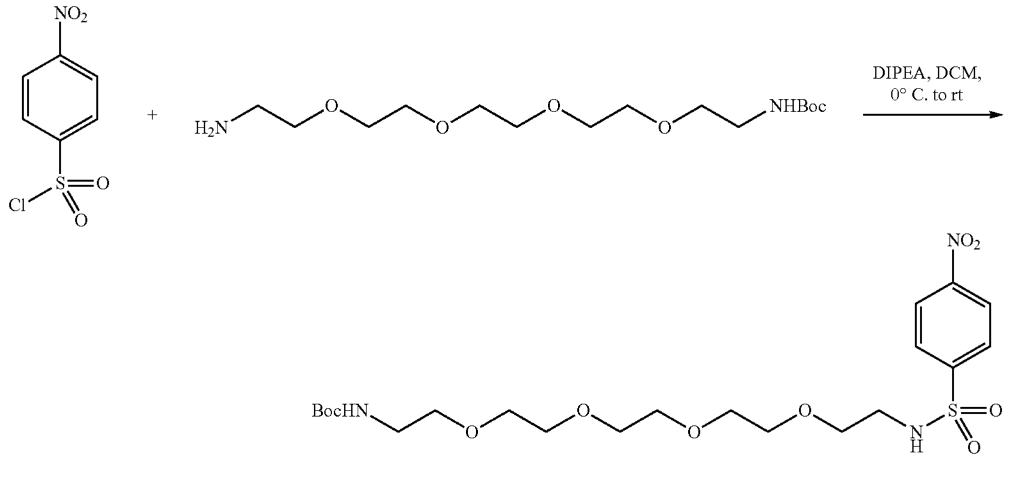

tert-Butyl (1-((4-nitrophenyl)sulfonamido)-3,6,9,13-tetraoxapentadecan-15-yl)carbamate To a stirred solution of tert-butyl (14-amino-3,6,9,12-tetraoxatetradecyl)carbamate (98 mg, 0.29 mmol) and N,N-Diisopropylethylamine (0.1 mL, 0.58 mmol) in dichloromethane (3.0 mL) at 0° C. was added 4-nitrobenzenesulfonyl chloride (65 mg, 0.29 mmol) in portions. The reaction mixture was gradually warmed to room temperature and stirred at room temperature for 3 hours. The reaction mixture was directly concentrated and purified via flash column chromatography (over silica) with an eluent system of 0% to 10% MeOH in dichloromethane to afford the title compound as a yellow viscous oil (140 mg, 0.26 mmol, 91% yield). ESI (m/z): $[M+H-Boc]^+$422.12.

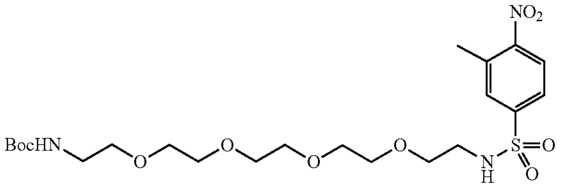 [SMILES: Cc1cc(S(=O)(=O)NCCOCCOCCOCCOCCNC(=O)OC(C)(C)C)ccc1[N+](=O)[O-]]

tert-Butyl (1-((3-methyl-4-nitrophenyl)sulfonamido)-3,6,9,13-tetraoxapentadecan-15-yl)carbamate This compound was prepared following the same procedure as tert-butyl (1-((4-nitrophenyl)sulfonamido)-3,6,9,13-tetraoxapentadecan-15-yl)carbamate in 97% yield as a yellow viscous oil. ESI (m/z): $[M+H-Boc]^+$436.12.

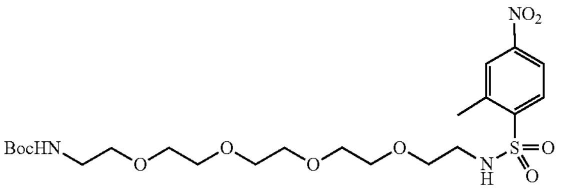 [SMILES: Cc1cc([N+](=O)[O-])ccc1S(=O)(=O)NCCOCCOCCOCCOCCNC(=O)OC(C)(C)C]

tert-Butyl (14-((2-methyl-4-nitrophenyl)sulfonamido)-3,6,9,12-tetraoxatetradecyl)carbamate This compound was prepared following the same procedure as tert-butyl (1-((4-nitrophenyl)sulfonamido)-3,6,9,13-tetraoxapentadecan-15-yl)carbamate in 98% yield as a yellow viscous oil. ESI (m/z): $[M+H-Boc]^+$436.02.

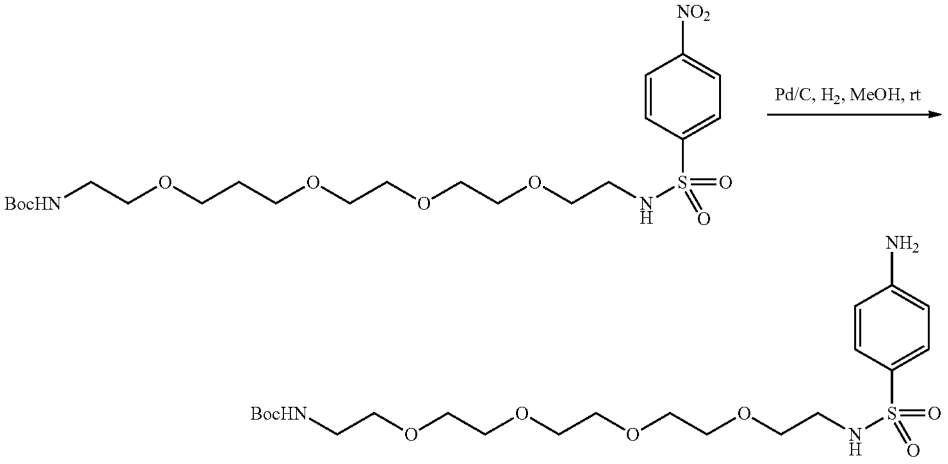

tert-Butyl (14-((4-aminophenyl)sulfonamido)-3,6,9,12-tetraoxatetradecyl)carbamate Pd/C (10 mg, 10 wt. %) was added to a solution of tert-Butyl (1-((4-nitrophenyl)sulfonamido)-3,6,9,13-tetraoxapentadecan-15-yl)carbamate (140 mg, 0.26 mmol) in methanol (3.0 mL) and the mixture was hydrogenated (1 bar $H_2$ pressure) at room temperature for 3 hours. The reaction mixture was concentrated in vacuo to afford the title compound as a yellow viscous oil. The product was used directly in the next step without further purification. ESI (m/z): $[M+H-Boc]^+$392.17.

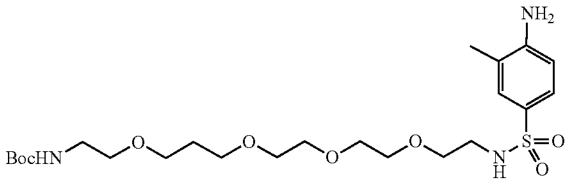 [SMILES: Cc1cc(S(=O)(=O)NCCOCCOCCOCCCOCCNC(=O)OC(C)(C)C)ccc1N]

tert-Butyl (14-((4-amino-3-methylphenyl)sulfonamido)-3,6,9,12-tetraoxatetradecyl)carbamate This compound was prepared following the same procedure as tert-butyl (14-((4-aminophenyl)sulfonamido)-3,6,9,12-tetraoxatetradecyl)carbamate as a yellow viscous oil. The product was used directly in the next step without further purification. ESI (m/z): $[M+H-Boc]^+$ 406.10.

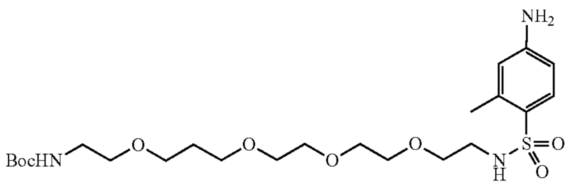 [SMILES: Cc1cc(N)ccc1S(=O)(=O)NCCOCCOCCOCCCOCCNC(=O)OC(C)(C)C]

tert-Butyl (14-((4-amino-2-methylphenyl)sulfonamido)-3,6,9,12-tetraoxatetradecyl)carbamate This compound was prepared following the same procedure as tert-butyl (14-((4-aminophenyl)sulfonamido)-3,6,9,12-tetraoxatetradecyl)carbamate as a yellow viscous oil. The product was used directly in the next step without further purification. ESI (m/z): $[M+H-Boc]^+$ 406.07.

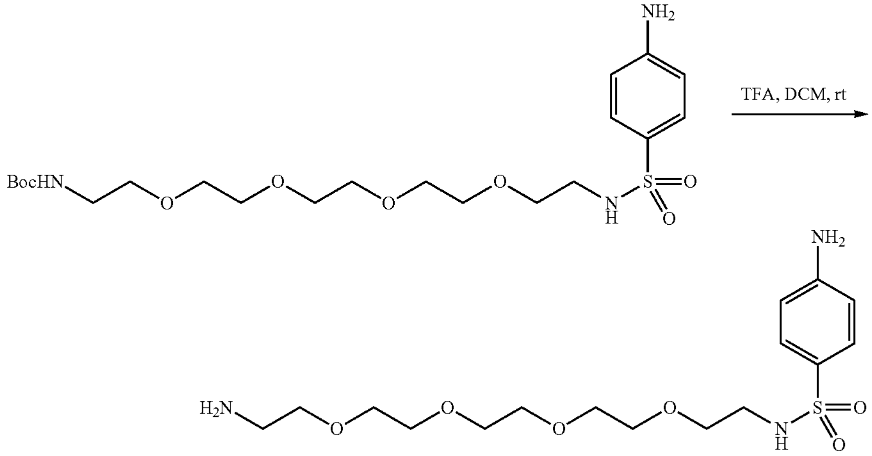

4-amino-N-(14-amino-3,6,9,12-tetraoxatetradecyl)benzenesulfonamide

To a stirred solution of tert-butyl (14-((4-aminophenyl)sulfonamido)-3,6,9,12-tetraoxatetradecyl)carbamate (130 mg, 0.26 mmol) in dichloromethane (2.0 mL) was added trifluoroacetic acid (0.5 mL) and the mixture was stirred at room temperature for 1 hour. The reaction mixture was concentrated in vacuo and purified via flash column chromatography (over silica) with an eluent system of 0% to 10% 1.75 N ammonia MeOH solution in dichloromethane to afford the title compound as a yellow viscous oil (73 mg, 0.18 mmol, 71% yield). ESI (m/z): $[M+H]^+$ 392.09.

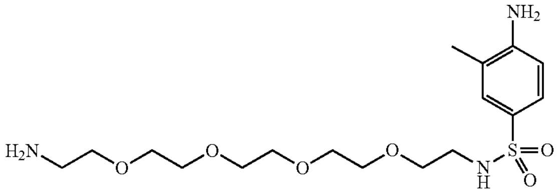 [SMILES: Cc1cc(S(=O)(=O)NCCOCCOCCOCCOCCN)ccc1N]

4-amino-N-(14-amino-3,6,9,12-tetraoxatetradecyl)-3-methylbenzenesulfonamide

This compound was prepared following the same procedure as 4-amino-N-(14-amino-3,6,9,12-tetraoxatetradecyl)benzenesulfonamide in 89% yield as a yellow viscous oil. ESI (m/z): $[M+H-Boc]^+$405.13.

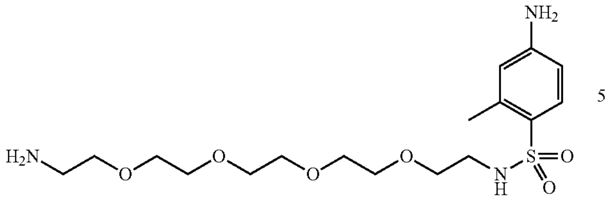

4-amino-N-(14-amino-3,6,9,12-tetraoxatetradecyl)-2-methylbenzenesulfonamide

This compound was prepared following the same procedure as 4-amino-N-(14-amino-3,6,9,12-tetraoxatetradecyl) benzenesulfonamide in 83% yield as a yellow viscous oil. ESI (m/z): [M+H−Boc]$^+$405.21

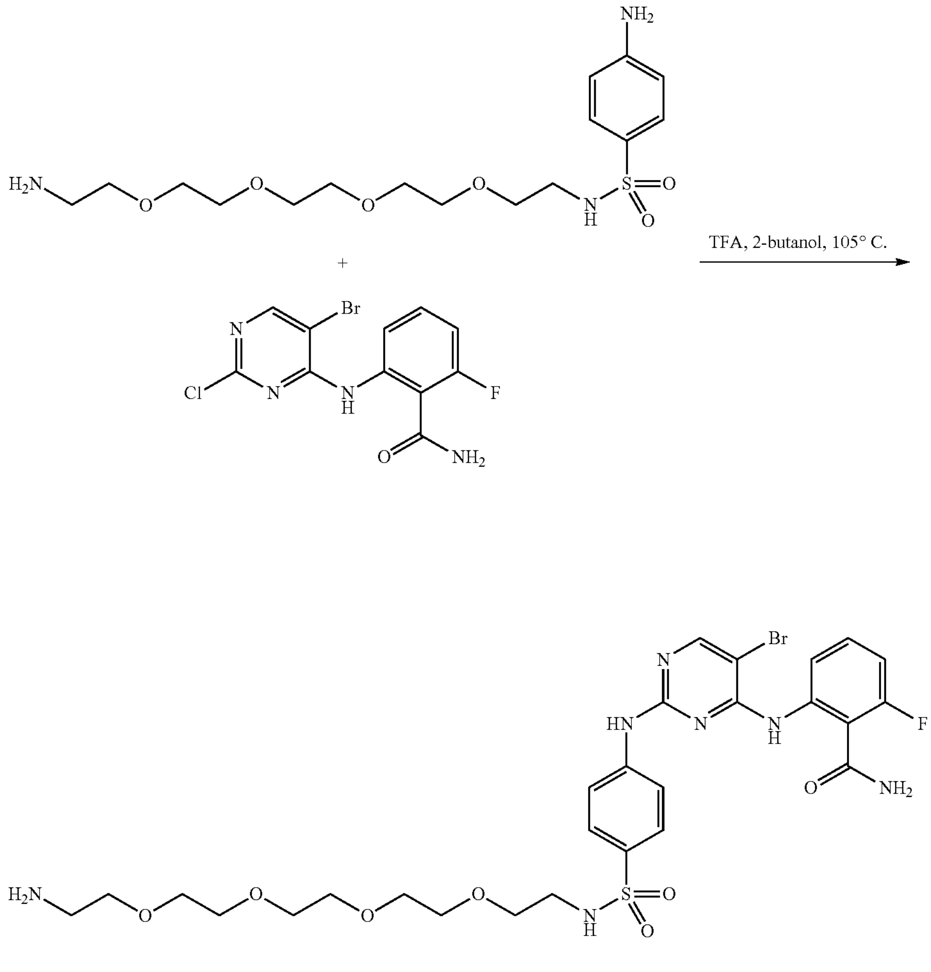 [SMILES: NCCOCCOCCOCCOCCNS(=O)(=O)c1ccc(N)cc1 ; NC(=O)c1c(F)cccc1Nc1nc(Cl)ncc1Br ; NCCOCCOCCOCCOCCNS(=O)(=O)c1ccc(Nc2ncc(Br)c(Nc3cccc(F)c3C(N)=O)n2)cc1]

2-((2-((4-(N-(14-amino-3,6,9,12-tetraoxatetradecyl) sulfamoyl)phenyl)amino)-5-bromopyrimidin-4-yl) amino)-6-fluorobenzamide To a stirred solution of 4-amino-N-(14-amino-3,6,9,12-tetraoxatetradecyl)benzenesulfonamide (20 mg, 0.051 mmol) and 2-((5-bromo-2-chloropyrimidin-4-yl)amino)-6-fluorobenzamide (18 mg, 0.051 mmol) in 2-butanol (1.0 mL) was added trifluoroacetic acid (50 μL). The reaction mixture was stirred at 105° C. for 16 hours. The reaction mixture was purified directly by prep HPLC and appropriate fractions were combined and lyophilized to afford the title compound as an off-white solid (20 mg, 0.028 mmol, 56% yield). ESI (m/z): [M+H]$^+$ 700.16, 702.25.

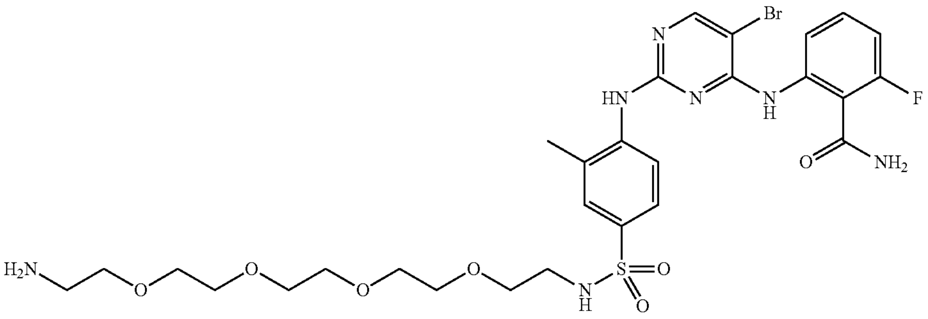 [SMILES: Cc1cc(S(=O)(=O)NCCOCCOCCOCCOCCN)ccc1Nc1ncc(Br)c(Nc2cccc(F)c2C(N)=O)n1]

2-((2-((4-(N-(14-amino-3,6,9,12-tetraoxatetradecyl) sulfamoyl)-2-methylphenyl)amino)-5-bromopyrimidin-4-yl)amino)-6-fluorobenzamide This compound was prepared following the same procedure as 2-((2-((4-(N-(14-amino-3,6,9,12-tetraoxatetradecyl) sulfamoyl)phenyl)amino)-5-bromopyrimidin-4-yl)amino)-6-fluorobenzamide in 21% yield as an off-white solid. ESI (m/z): $[M+H]^+$ 714.25, 716.23.

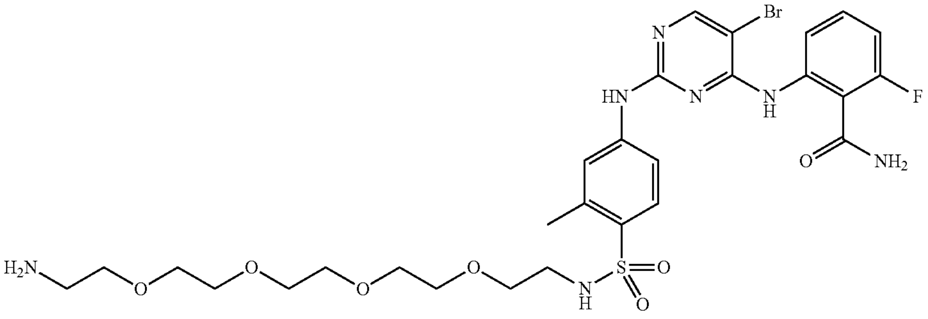 [SMILES: Cc1cc(Nc2ncc(Br)c(Nc3cccc(F)c3C(N)=O)n2)ccc1S(=O)(=O)NCCOCCOCCOCCOCCN]

2-((2-((4-(N-(14-amino-3,6,9,12-tetraoxatetradecyl) sulfamoyl)-3-methylphenyl)amino)-5-bromopyrimidin-4-yl)amino)-6-fluorobenzamide This compound was prepared following the same procedure as 2-((2-((4-(N-(14-amino-3,6,9,12-tetraoxatetradecyl) sulfamoyl)phenyl)amino)-5-bromopyrimidin-4-yl)amino)-6-fluorobenzamide in 50% yield as an off-white solid. ESI (m/z): $[M+H]^+$ 714.19, 716.25.

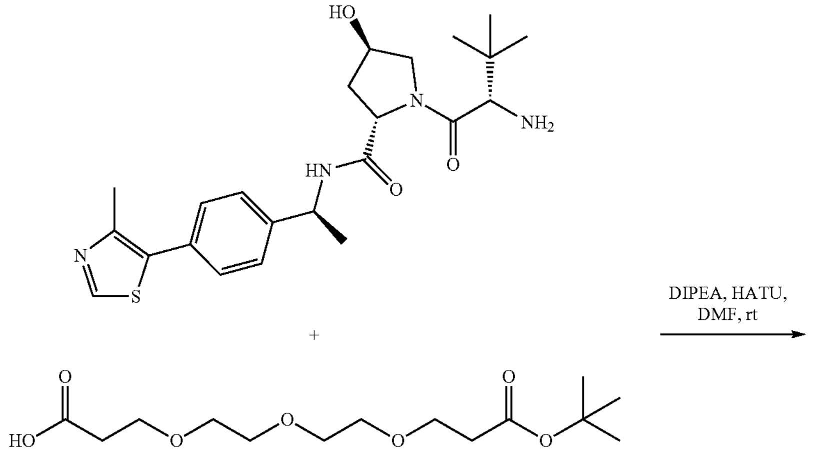

-continued

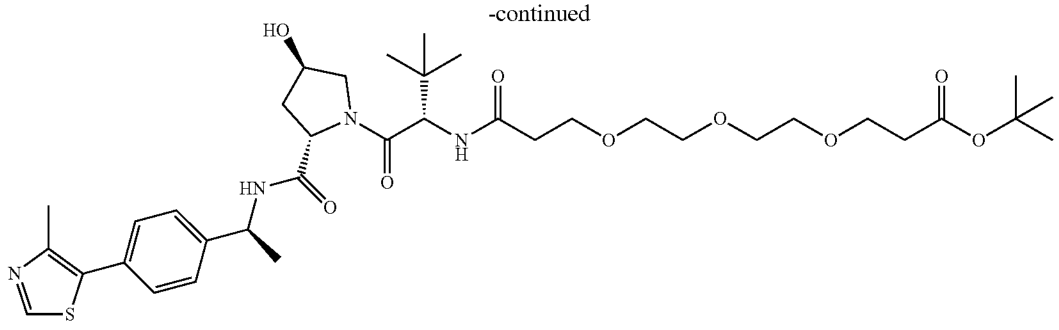

tert-Butyl (S)-15-((2S,4R)-4-hydroxy-2-(((S)-1-(4-(4-methylthiazol-5-yl)phenyl)ethyl)carbamoyl)pyrrolidine-1-carbonyl)-16,16-dimethyl-13-oxo-4,7,10-trioxa-14-azaheptadecanoate To a solution of (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (32 mg, 0.072 mmol) and 2,2-dimethyl-4-oxo-3,7,10,13-tetraoxahexadecan-16-oic acid (22 mg, 0.36 mmol) in N,N-dimethylformamide (1.0 mL) was added diisopropylethylamine (62 μL, 0.085 mmol) and HATU (54 mg, 0.144 mmol). The reaction mixture was stirred at room temperature for 10 minutes. The reaction mixture was purified directly by prep HPLC and appropriate fractions were combined and lyophilized to afford the title compound as a yellow viscous oil (40 mg, 0.054 mmol, 75% yield). ESI (m/z): $[M+H]^+$ 332.19 (fragment).

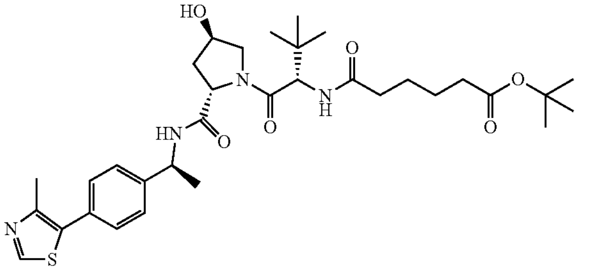 [SMILES: Cc1ncsc1-c1ccc([C@H](C)NC(=O)[C@@H]2C[C@@H](O)CN2C(=O)[C@@H](NC(=O)CCCCC(=O)OC(C)(C)C)C(C)(C)C)cc1]

tert-Butyl 6-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-6-oxohexanoate This compound was prepared using the same procedure as tert-butyl (S)-15-((2S,4R)-4-hydroxy-2-(((S)-1-(4-(4-methylthiazol-5-yl)phenyl)ethyl)carbamoyl)pyrrolidine-1-carbonyl)-16,16-dimethyl-13-oxo-4,7,10-trioxa-14-azaheptadecanoate using 6-(tert-butoxy)-6-oxohexanoic acid in 97% yield as a yellow viscous oil. ESI (m/z): $[M+H]^+$ 629.41.

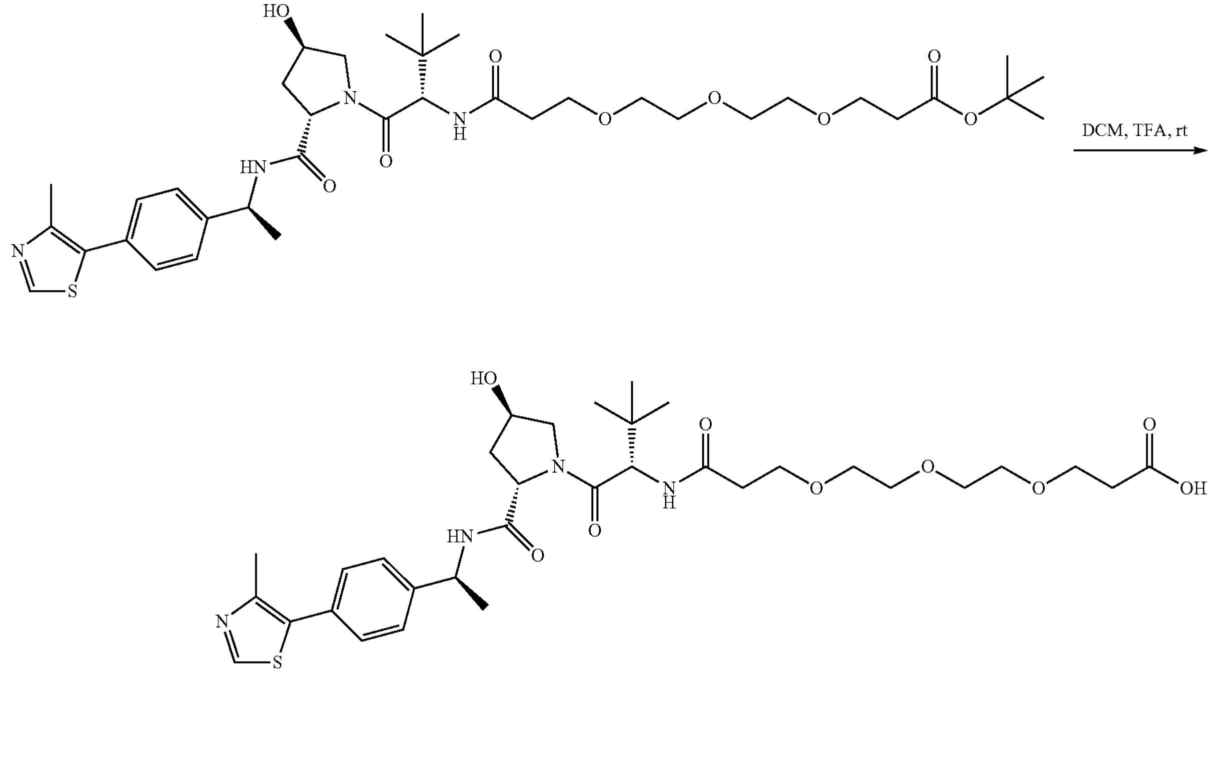 [SMILES: Cc1ncsc1-c1ccc([C@H](C)NC(=O)[C@@H]2C[C@@H](O)CN2C(=O)[C@@H](NC(=O)CCOCCOCCOCCC(=O)OC(C)(C)C)C(C)(C)C)cc1 ; Cc1ncsc1-c1ccc([C@H](C)NC(=O)[C@@H]2C[C@@H](O)CN2C(=O)[C@@H](NC(=O)CCOCCOCCOCCC(=O)O)C(C)(C)C)cc1]

(S)-15-((2S,4R)-4-hydroxy-2-(((S)-1-(4-(4-methylthiazol-5-yl)phenyl)ethyl)carbamoyl)pyrrolidine-1-carbonyl)-16,16-dimethyl-13-oxo-4,7,10-trioxa-14-azaheptadecanoic acid To a stirred solution of tert-butyl 6-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-6-oxohexanoate (20 mg, 0.027 mmol) in dichloromethane (1.0 mL) was added trifluoroacetic acid (0.2 mL), and the mixture was stirred at room temperature for 30 minutes. The reaction mixture was concentrated in vacuo to afford the title compound as a yellow viscous oil. The product was used directly in the next step without further purification. ESI (m/z): $[M+H]^+$ 677.50.

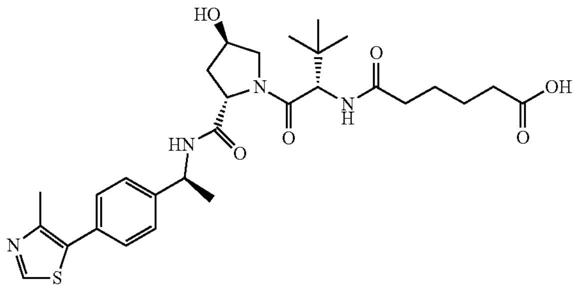 [SMILES: Cc1ncsc1-c1ccc([C@H](C)NC(=O)[C@@H]2C[C@@H](O)CN2C(=O)[C@@H](NC(=O)CCCCC(=O)O)C(C)(C)C)cc1]

6-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-6-oxohexanoic acid This compound was prepared as a yellow viscous oil using the same procedure as (S)-15-((2S,4R)-4-hydroxy-2-(((S)-1-(4-(4-methylthiazol-5-yl)phenyl)ethyl)carbamoyl)pyrrolidine-1-carbonyl)-16,16-dimethyl-13-oxo-4,7,10-trioxa-14-azaheptadecanoic acid. The product was used directly in the next step without further purification. ESI (m/z): $[M+H]^+$ 332.08 (the fragment).

Example 2: Synthesis of N-(2-((4-((5-bromo-4-((2-carbamoyl-3-fluorophenyl)amino)pyrimidin-2-yl)amino)piperidin-1-yl)sulfonyl)ethyl)-1-((2-(2,6-dioxopiperidin-3-yl)-1,3-dioxoisoindolin-4-yl)amino)-3,6,9,12-tetraoxapentadecan-15-amide (1)

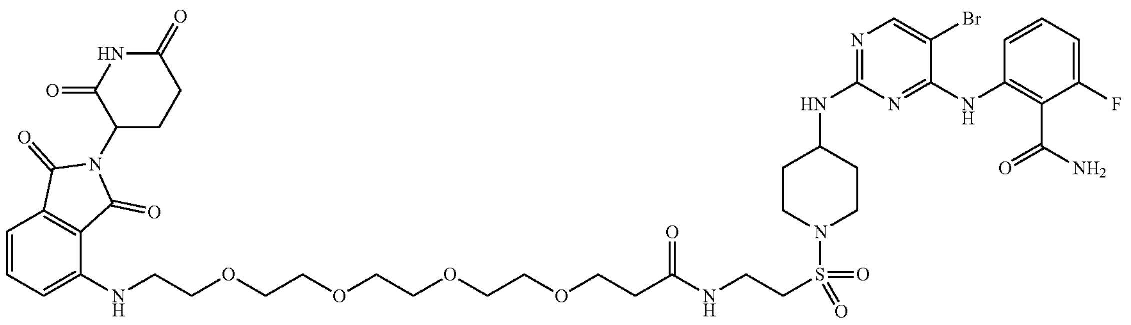 [SMILES: NC(=O)c1c(F)cccc1Nc1nc(NC2CCN(S(=O)(=O)CCNC(=O)CCOCCOCCOCCOCCNc3cccc4c3C(=O)N(C3CCC(=O)NC3=O)C4=O)CC2)ncc1Br]

Compound 1 was prepared as a yellow viscous oil using the same procedure as compound 2 in 20% yield. $^1H$ NMR (500 MHz, DMSO-$d_6$) δ 11.09 (s, 1H), 10.07 (s, 1H), 8.54-8.26 (m, 1H), 8.20-8.02 (m, 4H), 7.62-7.09 (m, 4H), 7.04 (d, J=7.0 Hz, 1H), 6.98 (t, J=10.0 Hz, 1H), 6.60 (t, J=5.5 Hz, 1H), 5.05 (dd, J=13.0, 5.5 Hz, 1H), 3.85-3.65 (m, 1H), 3.64-3.38 (m, 22H), 3.20-3.12 (m, 2H), 2.96-2.83 (m, 3H), 2.65-2.47 (m, 2H), 2.32 (t, J=6.0 Hz, 2H), 2.06-1.90 (m, 3H), 1.56-1.44 (m, 2H). ESI (m/z): $[M+H]^+$ 1019.41, 1021.39.

Example 3: Synthesis of 2-((5-bromo-2-((1-((2-(3-(2-((2-(2,6-dioxopiperidin-3-yl)-1,3-dioxoisoindolin-4-yl)amino)ethoxy)propanamido)ethyl)sulfonyl)piperidin-4-yl)amino)pyrimidin-4-yl)amino)-6-fluorobenzamide (2)

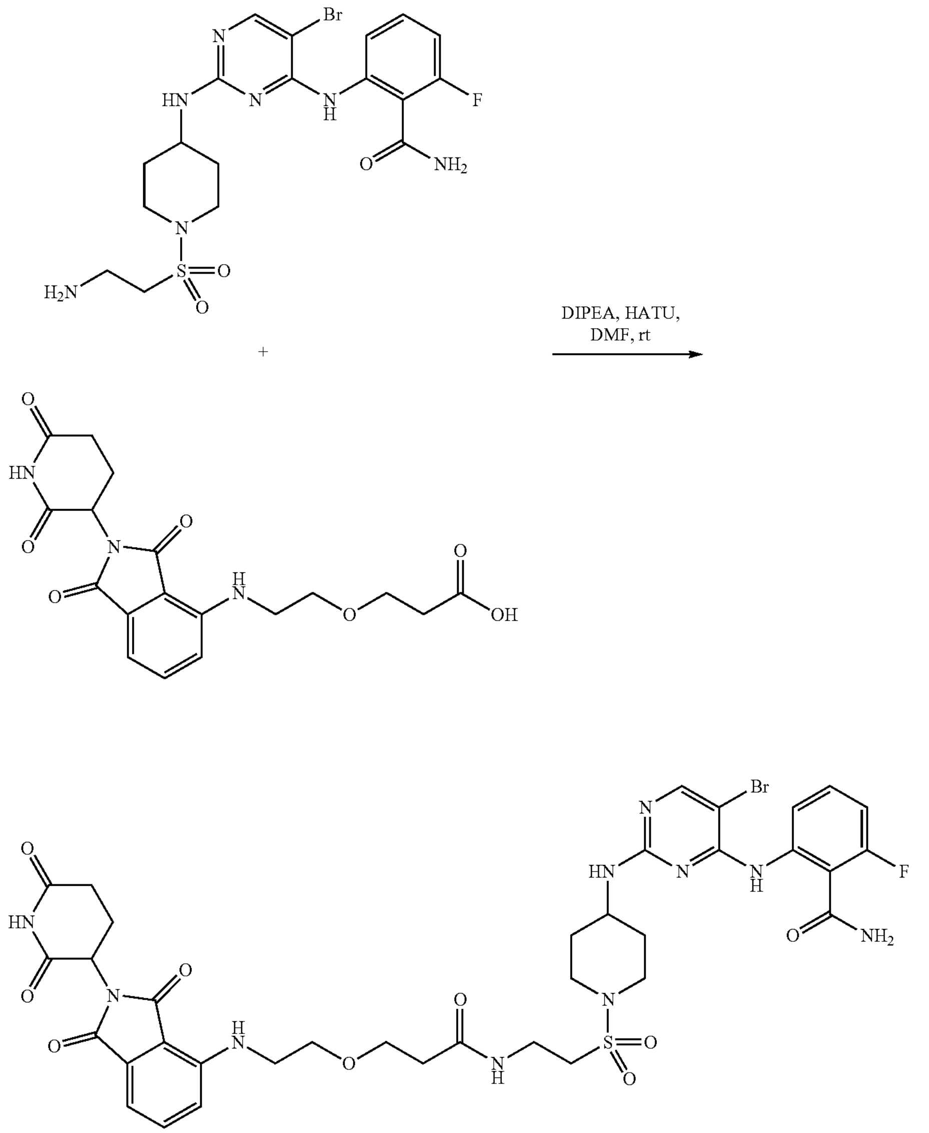 [SMILES: NCCS(=O)(=O)N1CCC(Nc2ncc(Br)c(Nc3cccc(F)c3C(N)=O)n2)CC1 ; O=C(O)CCOCCNc1cccc2c1C(=O)N(C1CCC(=O)NC1=O)C2=O ; NC(=O)c1c(F)cccc1Nc1nc(NC2CCN(S(=O)(=O)CCNC(=O)CCOCCNc3cccc4c3C(=O)N(C3CCC(=O)NC3=O)C4=O)CC2)ncc1Br]

To a solution of 2-((2-((1-((2-aminoethyl)sulfonyl)piperidin-4-yl)amino)-5-bromopyrimidin-4-yl)amino)-6-fluorobenzamide (9 mg, 0.017 mmol) and 3-(2-((2-(2,6-dioxopiperidin-3-yl)-1,3-dioxoisoindolin-4-yl)amino)ethoxy)propanoic acid (7 mg, 0.017 mmol) in N,N-dimethylformamide (1.0 mL) was added diisopropylethylamine (15 μL, 0.085 mmol) and HATU (13 mg, 0.034 mmol). The reaction mixture was stirred at room temperature for 10 minutes. The reaction mixture was purified directly by prep HPLC and appropriate fractions were combined and lyophilized to afford compound 2 as a yellow viscous oil (5.1 mg, 5.7 μmol, 33% yield). $^1$H NMR (500 MHz, DMSO-$d_6$) δ 11.09 (s, 1H), 10.10 (s, 1H), 8.52-8.24 (m, 1H), 8.20-7.92 (m, 4H), 7.60-7.10 (m, 4H), 7.03 (d, J=7.0 Hz, 1H), 6.98 (t, J=9.5 Hz, 1H), 6.57 (t, J=5.5 Hz, 1H), 5.04 (dd, J=12.5, 5.5 Hz, 1H), 3.85-3.40 (m, 11H), 3.20-3.10 (m, 2H), 2.94-2.81 (m, 3H), 2.62-2.47 (m, 2H), 2.35 (t, J=6.5 Hz, 2H), 2.06-1.89 (m, 3H), 1.55-1.42 (m, 2H). ESI (m/z): $[M+H]^+$ 887.32, 889.41.

Example 4: Synthesis of 2-((5-bromo-2-((1-((2-(3-(2-(2-((2-(2,6-dioxopiperidin-3-yl)-1,3-dioxoisoindolin-4-yl)oxy)ethoxy)ethoxy)propanamido)ethyl)sulfonyl)piperidin-4-yl)amino)pyrimidin-4-yl)amino)-6-fluorobenzamide (3)

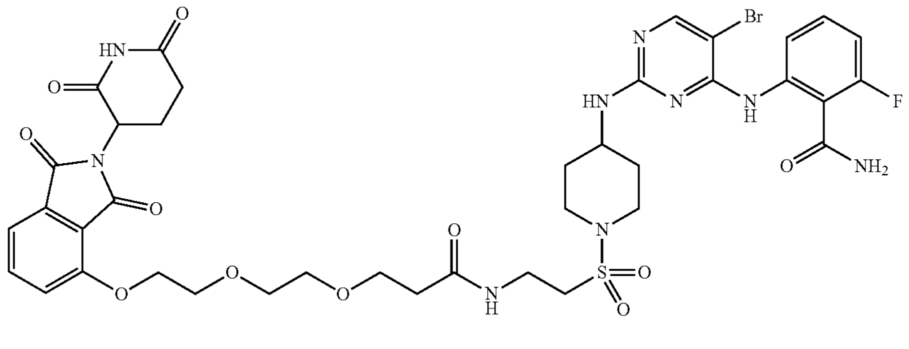 [SMILES: NC(=O)c1c(F)cccc1Nc1nc(NC2CCN(S(=O)(=O)CCNC(=O)CCOCCOCCOc3cccc4c3C(=O)N(C3CCC(=O)NC3=O)C4=O)CC2)ncc1Br]

Compound 3 was prepared as a yellow viscous oil using the same procedure as compound 2 and in 32% yield. $^1$H NMR (500 MHz, DMSO-$d_6$) δ 11.10 (s, 1H), 10.04 (s, 1H), 8.55-8.26 (m, 1H), 8.20-8.02 (m, 4H), 7.80 (dd, J=8.0, 7.5 Hz, 1H), 7.60-7.42 (m, 3H), 7.35-7.06 (m, 1H), 6.97 (t, J=9.5 Hz, 1H), 5.07 (dd, J=13.0, 5.5 Hz, 1H), 4.33 (t, J=4.0 Hz, 2H), 3.79 (t, J=5.0 Hz, 2H), 3.85-3.65 (m, 1H), 3.65-3.55 (m, 8H), 3.52-3.47 (m, 4H), 3.20-3.11 (m, 2H), 2.96-2.83 (m, 3H), 2.63-2.45 (m, 2H), 2.32 (t, J=6.0 Hz, 2H), 2.06-1.89 (m, 3H), 1.55-1.43 (m, 2H). ESI (m/z): $[M+H]^+$ 932.35, 934.10.

Example 5: Synthesis of N-(2-((4-((5-bromo-4-((2-carbamoyl-3-fluorophenyl)amino)pyrimidin-2-yl)amino)piperidin-1-yl)sulfonyl)ethyl)-1-((2-(2,6-dioxopiperidin-3-yl)-1,3-dioxoisoindolin-4-yl)amino)-3,6,9,12,15,18,21,24-octaoxaheptacosan-27-amide (4)

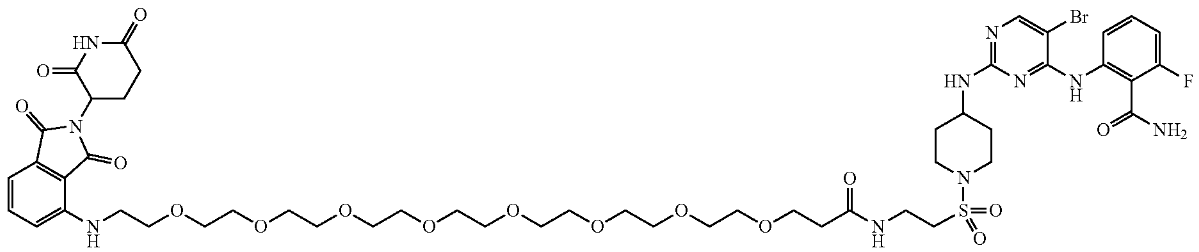 [SMILES: NC(=O)c1c(F)cccc1Nc1nc(NC2CCN(S(=O)(=O)CCNC(=O)CCOCCOCCOCCOCCOCCOCCOCCOCCNc3cccc4c3C(=O)N(C3CCC(=O)NC3=O)C4=O)CC2)ncc1Br]

Compound 4 was prepared as a yellow viscous oil using the same procedure as compound 2 in 44% yield. $^1$H NMR (500 MHz, DMSO-$d_6$) δ 11.09 (s, 1H), 11.06 (s, 1H), 8.55-8.27 (m, 1H), 8.19-8.03 (m, 4H), 7.62-7.11 (m, 4H), 7.04 (d, J=7.0 Hz, 1H), 6.98 (t, J=9.5 Hz, 1H), 6.60 (t, J=5.5 Hz, 1H), 5.05 (dd, J=13.0 5.5 Hz, 1H), 3.90-3.65 (m, 1H), 3.64-3.38 (m, 38H), 3.21-3.11 (m, 2H), 2.97-2.83 (m, 3H), 2.63-2.46 (m, 2H), 2.33 (t, J=6.5 Hz, 2H), 2.06-1.90 (m, 3H), 1.56-1.44 (m, 2H). ESI (m/z): $[M+H]^+$ 1195.46, 1197.38.

Example 6: Synthesis of 2-((5-bromo-2-((1-((2-(9-((2-(2,6-dioxopiperidin-3-yl)-1,3-dioxoisoindolin-4-yl)oxy)nonanamido)ethyl)sulfonyl)piperidin-4-yl)amino)pyrimidin-4-yl)amino)-6-fluorobenzamide (5)

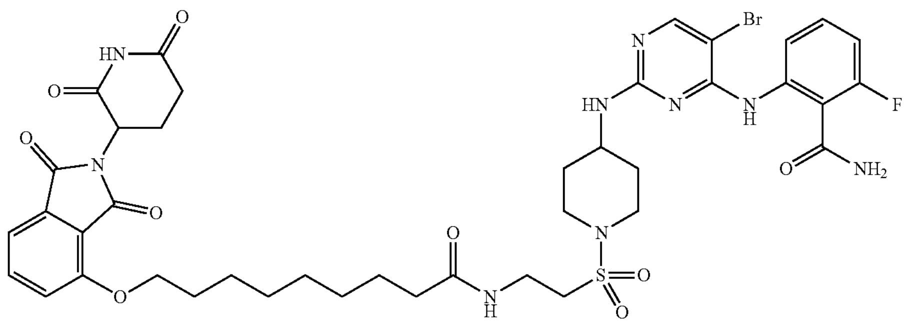 [SMILES: NC(=O)c1c(F)cccc1Nc1nc(NC2CCN(S(=O)(=O)CCNC(=O)CCCCCCCCOc3cccc4c3C(=O)N(C3CCC(=O)NC3=O)C4=O)CC2)ncc1Br]

Compound 5 was prepared as a yellow viscous oil using the same procedure as compound 2 in 21% yield. $^1$H NMR (500 MHz, DMSO-$d_6$) δ 11.10 (s, 1H), 10.40-10.10 (m, 1H), 8.52-8.22 (m, 1H), 8.22-8.06 (m, 3H), 8.04-7.96 (m, 1H), 7.79 (dd, J=8.5, 7.5 Hz, 1H), 7.70-7.20 (m, 4H), 7.01 (t, J=2.5 Hz, 1H), 5.07 (dd, J=12.5, 5.5 Hz, 1H), 4.18 (t, J=6.0 Hz, 2H), 3.85-3.65 (m, 1H), 3.64-3.54 (m, 2H), 3.44-3.36 (m, 2H), 3.20-3.10 (m, 2H), 2.96-2.82 (m, 3H), 2.63-2.45 (m, 2H), 2.10-1.99 (m, 2H), 1.99-1.89 (m, 2H), 1.78-1.69 (m, 2H), 1.56-1.38 (m, 6H), 1.36-1.20 (m, 7H). ESI (m/z): $[M+H]^+$ 928.22, 940.32.

Example 7: Synthesis of 2-((5-bromo-2-((1-((2-(8-((2-(2,6-dioxopiperidin-3-yl)-1,3-dioxoisoindolin-4-yl)oxy)octanamido)ethyl)sulfonyl)piperidin-4-yl)amino)pyrimidin-4-yl)amino)-6-fluorobenzamide (6)

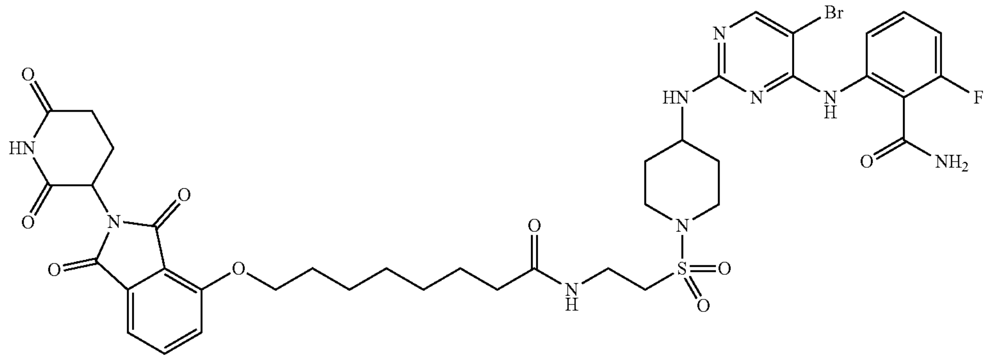 [SMILES: NC(=O)c1c(F)cccc1Nc1nc(NC2CCN(S(=O)(=O)CCNC(=O)CCCCCCCOc3cccc4c3C(=O)N(C3CCC(=O)NC3=O)C4=O)CC2)ncc1Br]

Compound 6 was prepared as a yellow viscous oil using the same procedure as compound 2 in 45% yield. $^1$H NMR (500 MHz, DMSO-$d_6$) δ 11.10 (s, 1H), 10.06 (s, 1H), 8.54-8.25 (m, 1H), 8.18-8.05 (m, 3H), 8.00 (t, J=5.5 Hz, 1H), 7.79 (dd, J=9.0, 7.5 Hz, 1H), 7.59-7.40 (m, 1H), 7.48 (d, J=8.5, 1H), 7.43 (d, J=7.5, 1H), 7.36-7.04 (m, 1H), 6.97 (t, J=9.5 Hz, 1H), 5.07 (dd, J=12.5, 5.5 Hz, 1H), 4.18 (t, J=6.5 Hz, 2H), 3.88-3.63 (m, 1H), 3.62-3.54 (m, 2H), 3.41 (dd, J=13.5, 6.0 Hz, 2H), 3.20-3.10 (m, 2H), 2.95-2.84 (m, 3H), 2.65-2.45 (m, 2H), 2.08 (t, J=7.5 Hz, 2H), 2.06-1.99 (m, 1H), 1.98-1.89 (m, 2H), 1.78-1.70 (m, 2H), 1.55-1.40 (m, 6H), 1.37-1.21 (m, 4H). ESI (m/z): $[M+H]^+$ 914.32, 916.42.

Example 8: Synthesis of 2-((5-bromo-2-((1-((2-(6-((2-(2,6-dioxopiperidin-3-yl)-1,3-dioxoisoindolin-4-yl)oxy)hexanamido)ethyl)sulfonyl)piperidin-4-yl)amino)pyrimidin-4-yl)amino)-6-fluorobenzamide (7)

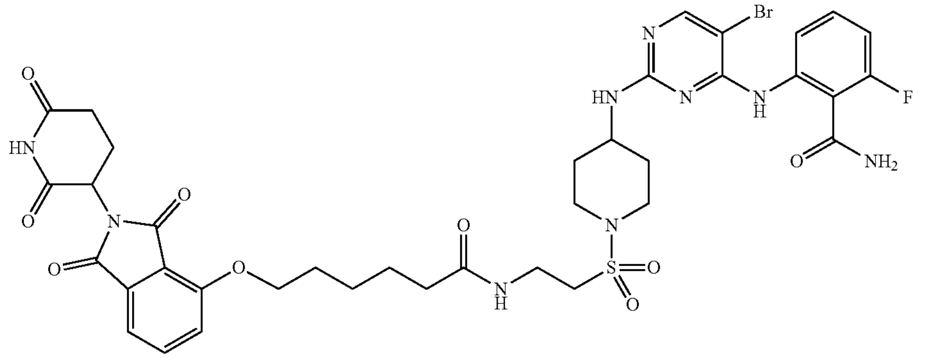 [SMILES: NC(=O)c1c(F)cccc1Nc1nc(NC2CCN(S(=O)(=O)CCNC(=O)CCCCCOc3cccc4c3C(=O)N(C3CCC(=O)NC3=O)C4=O)CC2)ncc1Br]

Compound 7 was prepared as a yellow viscous oil using the same procedure as compound 2 in 56% yield. $^{1}H$ NMR (500 MHz, DMSO-$d_6$) δ 11.10 (s, 1H), 10.34-10.09 (m, 1H), 8.50-8.00 (m, 5H), 7.80 (dd, J=8.0, 7.5 Hz, 1H), 7.68-7.24 (m, 4H), 7.01 (t, J=3.0 Hz, 1H), 5.07 (dd, J=12.5, 5.5 Hz, 1H), 4.19 (t, J=6.0 Hz, 2H), 3.85-3.65 (m, 1H), 3.62-3.55 (m, 2H), 3.41 (dd, J=13.5, 6.0 Hz, 1H), 3.21-3.12 (m, 2H), 2.95-2.82 (m, 3H), 2.65-2.45 (m, 2H), 2.11 (t, J=7.0 Hz, 2H), 2.06-1.99 (m, 1H), 1.98-1.89 (m, 2H), 1.80-1.70 (m, 2H), 1.62-1.40 (m, 6H). ESI (m/z): $[M+H]^+$ 886.22, 888.22.

Example 9: Synthesis of 2-((5-bromo-2-(((3R)-1-((2-(9-((2-(2,6-dioxopiperidin-3-yl)-1,3-dioxoisoindolin-4-yl)oxy)nonanamido)ethyl)sulfonyl)piperidin-3-yl)amino)pyrimidin-4-yl)amino)-6-fluorobenzamide (8)

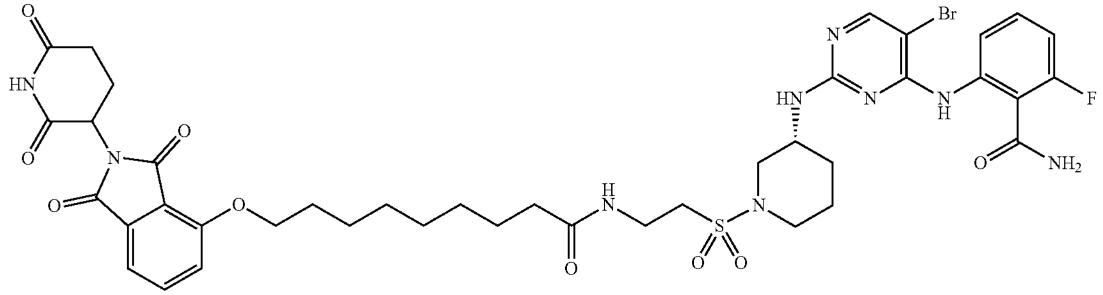 [SMILES: NC(=O)c1c(F)cccc1Nc1nc(N[C@@H]2CCCN(S(=O)(=O)CCNC(=O)CCCCCCCCOc3cccc4c3C(=O)N(C3CCC(=O)NC3=O)C4=O)C2)ncc1Br]

Compound 8 was prepared as a yellow viscous oil using the same procedure as compound 2 in 27% yield. ESI (m/z): $[M+H]^+$ 928.34, 930.37.

Example 10: Synthesis of (2S,4R)-1-((S)-19-((4-((5-bromo-4-((2-carbamoyl-3-fluorophenyl)amino)pyrimidin-2-yl)amino)piperidin-1-yl)sulfonyl)-2-(tert-butyl)-4,16-dioxo-7,10,13-trioxa-3,17-diazanonadecanoyl)-4-hydroxy-N—((S)-1-(4-(4-methylthiazol-5-yl)phenyl)ethyl)pyrrolidine-2-carboxamide (9)

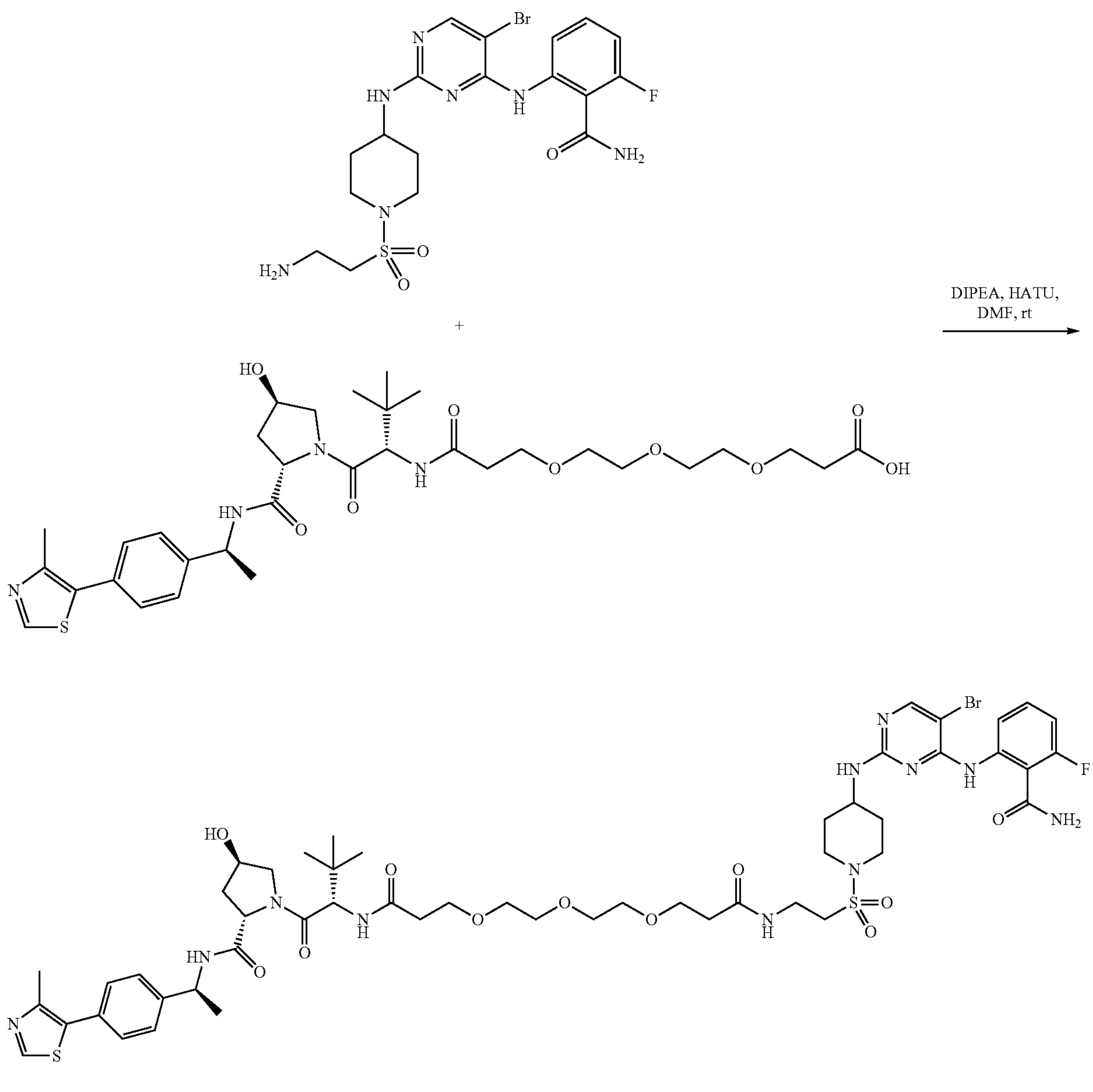

To a solution of 2-((2-((1-((2-aminoethyl)sulfonyl)piperidin-4-yl)amino)-5-bromopyrimidin-4-yl)amino)-6-fluorobenzamide (10 mg, 0.019 mmol) and (S)-15-((2S,4R)-4-hydroxy-2-(((S)-1-(4-(4-methylthiazol-5-yl)phenyl)ethyl)carbamoyl)pyrrolidine-1-carbonyl)-16,16-dimethyl-13-oxo-4,7,10-trioxa-14-azaheptadecanoic acid (19 mg, 0.029 mmol) in N,N-dimethylformamide (1.0 mL) was added diisopropylethylamine (16 μL, 0.095 mmol) and HATU (14 mg, 0.038 mmol). The reaction mixture was stirred at room temperature for 10 minutes. The reaction mixture was purified directly by prep HPLC and appropriate fractions were combined and lyophilized to afford the title compound 9 as a white solid (10.0 mg, 8.5 μmol, 43% yield). $^1$H NMR (500 MHz, DMSO-$d_6$) δ 10.60-0.24 (m, 1H), 8.99 (s, 1H), 8.37 (d, J=8.0 Hz, 1H), 8.29-8.06 (m, 5H), 7.85 (d, J=9.5 Hz, 1H), 7.68-7.41 (m, 4H), 7.40-7.36 (m, 2H), 7.16-7.00 (m, 1H), 4.95-4.85 (m, 1H), 4.52 (d, J=10.0 Hz, 1H), 4.42 (t, J=8.5 Hz, 1H), 4.30-4.25 (m, 1H), 3.80-3.68 (m, 1H), 3.64-3.55 (m, 8H), 3.52-3.39 (m, 10H), 3.20-3.13 (m, 2H), 2.90 (t, J=10.5 Hz, 2H), 2.57-2.51 (m, 1H), 2.45 (s, 3H), 2.39-2.30 (m, 3H), 2.05-1.90 (m, 3H), 1.82-1.75 (m, 1H), 1.57-1.45 (m, 2H), 1.37 (d, J=7.0 Hz, 3H), 0.93 (s, 9H). ESI (m/z): [M+H]$^+$ 1174.64, 1176.61.

Example 11: Synthesis of N[1]-(2-((4-((5-bromo-4-((2-carbamoyl-3-fluorophenyl)amino)pyrimidin-2-yl)amino)piperidin-1-yl)sulfonyl)ethyl)-N[6]—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)adipamide (10)

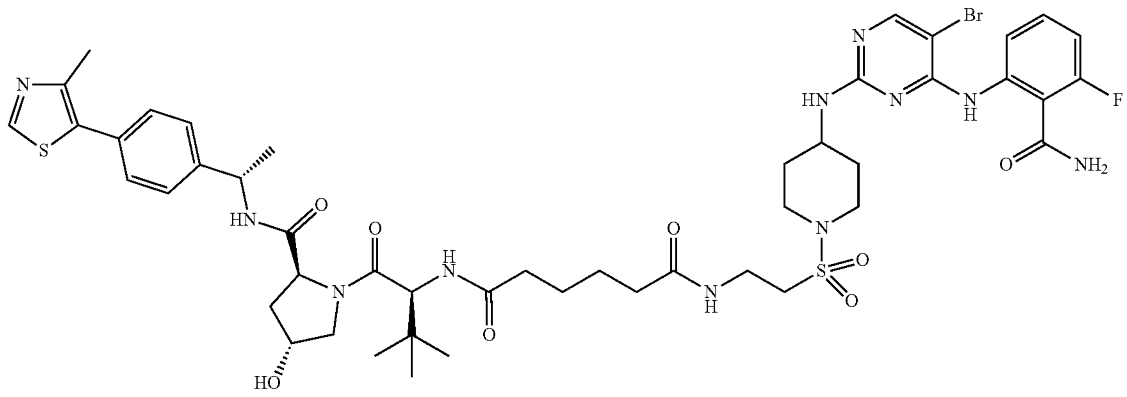 [SMILES: Cc1ncsc1-c1ccc([C@H](C)NC(=O)[C@@H]2C[C@@H](O)CN2C(=O)[C@@H](NC(=O)CCCCC(=O)NCCS(=O)(=O)N2CCC(Nc3ncc(Br)c(Nc4cccc(F)c4C(N)=O)n3)CC2)C(C)(C)C)cc1]

Compound 10 was prepared as a white solid using the same procedure as compound 9 in 17% yield. $^1$H NMR (500 MHz, DMSO-$d_6$) δ 10.05 (s, 1H), 8.98 (s, 1H), 8.54-8.28 (m, 2H), 8.17-8.06 (m, 3H), 8.00 (t, J=6.0 Hz, 1H), 7.78 (d, J=9.5 Hz, 1H), 7.60-7.08 (m, 6H), 6.98 (t, J=10.0 Hz, 1H), 5.10 (d, J=3.5 Hz, 1H), 4.96-4.88 (m, 1H), 4.51 (d, J=9.5 Hz, 1H), 4.42 (t, J=8.0 Hz, 1H), 4.30-4.25 (m, 1H), 3.86-3.65 (m, 1H), 3.63-3.55 (m, 4H), 3.44-3.38 (m, 2H), 3.19-3.11 (m, 2H), 2.92 (t, J=11.0 Hz, 2H), 2.45 (s, 3H), 2.29-2.21 (m, 1H), 2.16-2.05 (m, 3H), 2.04-1.90 (m, 3H), 1.83-1.75 (m, 1H), 1.55-1.42 (m, 6H), 1.37 (d, J=7.0 Hz, 3H), 0.93 (s, 9H). ESI (m/z): $[M+H]^+$ 1070.05, 1072.39.

Example 12: Synthesis of (2S,4R)-1-((S)-16-((4-((5-bromo-4-((2-carbamoyl-3-fluorophenyl)amino) pyrimidin-2-yl)amino)piperidin-1-yl)sulfonyl)-2-(tert-butyl)-4,13-dioxo-7,10-dioxa-3,14-diazahexadecanoyl)-4-hydroxy-N—((S)-1-(4-(4-methylthiazol-5-yl)phenyl)ethyl)pyrrolidine-2-carboxamide (11)

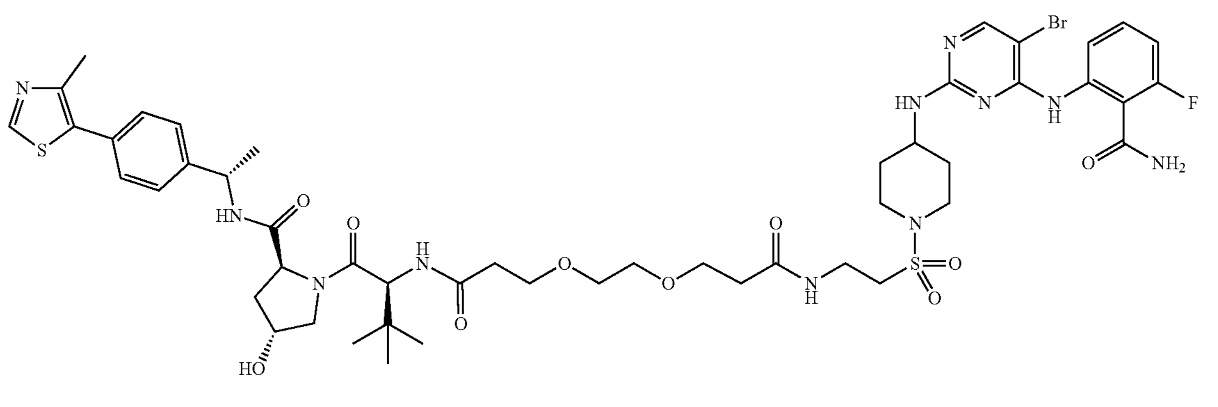 [SMILES: Cc1ncsc1-c1ccc([C@H](C)NC(=O)[C@@H]2C[C@@H](O)CN2C(=O)[C@@H](NC(=O)CCOCCOCCC(=O)NCCS(=O)(=O)N2CCC(Nc3ncc(Br)c(Nc4cccc(F)c4C(N)=O)n3)CC2)C(C)(C)C)cc1]

Compound 11 was prepared as a white solid using the same procedure as compound 9 in 18% yield. $^1$H NMR (500 MHz, DMSO-$d_6$) δ 10.06 (s, 1H), 8.98 (s, 1H), 8.55-8.28 (m, 2H), 8.20-8.04 (m, 4H), 7.85 (d, J=9.0 Hz, 1H), 7.60-7.36 (m, 5H), 7.34-7.08 (m, 1H), 6.98 (t, J=9.5 Hz, 1H), 5.10 (d, J=4.0 Hz, 1H), 4.96-4.85 (m, 1H), 4.52 (d, J=9.5 Hz, 1H), 4.42 (t, J=8.0 Hz, 1H), 4.31-4.25 (m, 1H), 3.86-3.66 (m, 1H), 3.66-3.39 (m, 14H), 3.20-3.10 (m, 2H), 2.92 (t, J=11.0 Hz, 2H), 2.58-2.50 (m, 1H), 2.45 (s, 3H), 2.39-2.30 (m, 3H), 2.05-1.90 (m, 3H), 1.82-1.75 (m, 1H), 1.55-1.44 (m, 2H), 1.37 (d, J=7.0 Hz, 3H), 0.93 (s, 9H). ESI (m/z): $[M+H]^+$ 1131.19, 1133.06.

Example 13: Synthesis of $N^1$-(2-((4-((5-bromo-4-((2-carbamoyl-3-fluorophenyl)amino)pyrimidin-2-yl)amino)piperidin-1-yl)sulfonyl)ethyl)-$N^4$—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)succinamide (12)

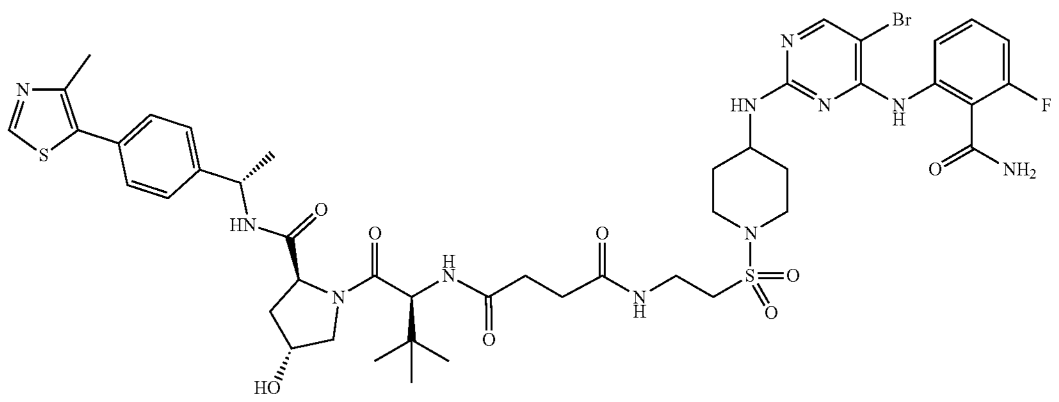 [SMILES: Cc1ncsc1-c1ccc([C@H](C)NC(=O)[C@@H]2C[C@@H](O)CN2C(=O)[C@@H](NC(=O)CCC(=O)NCCS(=O)(=O)N2CCC(Nc3ncc(Br)c(Nc4cccc(F)c4C(N)=O)n3)CC2)C(C)(C)C)cc1]

Compound 12 was prepared as a white solid using the same procedure as compound 9 in 65% yield. $^1$H NMR (500 MHz, DMSO-$d_6$) δ 10.56-10.18 (m, 1H), 8.99 (s, 1H), 8.50-8.04 (m, 6H), 7.87 (d, J=9.5 Hz, 1H), 7.83-7.36 (m, 6H), 7.15-6.99 (m, 1H), 4.97-4.86 (m, 1H), 4.47 (d, J=9.5 Hz, 1H), 4.42 (t, J=7.5 Hz, 1H), 4.31-4.25 (m, 1H), 3.84-3.67 (m, 1H), 3.66-3.54 (m, 4H), 3.44-3.37 (m, 2H), 2.91 (t, J=11.0 Hz, 2H), 2.58-2.46 (m, 1H), 2.45 (s, 3H), 2.41-2.25 (m, 3H), 2.05-1.90 (m, 3H), 1.83-1.75 (m, 1H), 1.58-1.45 (m, 2H), 1.37 (d, J=7.0 Hz, 3H), 0.93 (s, 9H). ESI (m/z): $[M+H]^+$ 1043.0, 1044.98.

Example 14: Synthesis of $N^1$-(2-((4-((5-bromo-4-((2-carbamoyl-3-fluorophenyl)amino)pyrimidin-2-yl)amino)piperidin-1-yl)sulfonyl)ethyl)-$N^4$-(5-((2-(2,6-dioxopiperidin-3-yl)-1,3-dioxoisoindolin-4-yl)amino)pentyl)succinamide (13)

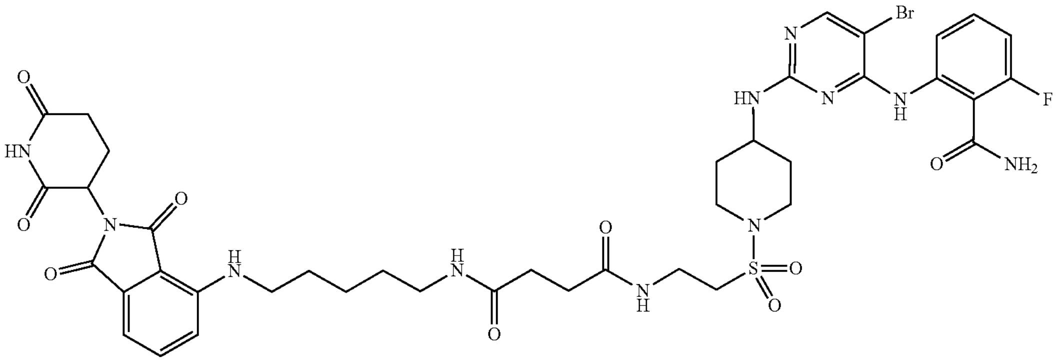 [SMILES: NC(=O)c1c(F)cccc1Nc1nc(NC2CCN(S(=O)(=O)CCNC(=O)CCC(=O)NCCCCCNc3cccc4c3C(=O)N(C3CCC(=O)NC3=O)C4=O)CC2)ncc1Br]

Compound 13 was prepared using the same procedure as compound 2 in 54% yield. $^1H$ NMR (500 MHz, DMSO-$d_6$) δ 11.08 (s, 1H), 10.40-10.10 (m, 1H), 8.52-8.02 (m, 5H), 7.80 (t, J=5.5 Hz, 1H), 7.74-7.28 (m, 3H), 7.13-6.98 (m, 3H), 6.52 (s, 1H), 5.04 (dd, J=13.0, 6.0 Hz, 1H), 3.90-3.66 (m, 1H), 3.59 (d, J=12.5 Hz, 2H), 3.40 (dd, J=13.0, 6.5 Hz, 2H), 3.31-3.24 (m, 2H), 3.18-3.12 (m, 2H), 3.03 (dd, J=12.5, 7.0 Hz, 2H), 2.96-2.83 (m, 3H), 2.64-2.52 (m, 2H), 2.36-2.26 (m, 4H), 2.08-1.90 (m, 3H), 1.61-1.46 (m, 4H), 1.46-1.38 (m, 2H), 1.37-1.28 (m, 2H). ESI (m/z): $[M+H]^+$ 956.89, 958.76.

Example 15: Synthesis of 2-((5-bromo-2-((1-((2-(11-(2-(2,6-dioxopiperidin-3-yl)-1-oxoisoindolin-4-yl)undec-10-ynamido)ethyl)sulfonyl)piperidin-4-yl)amino)pyrimidin-4-yl)amino)-6-fluorobenzamide (14)

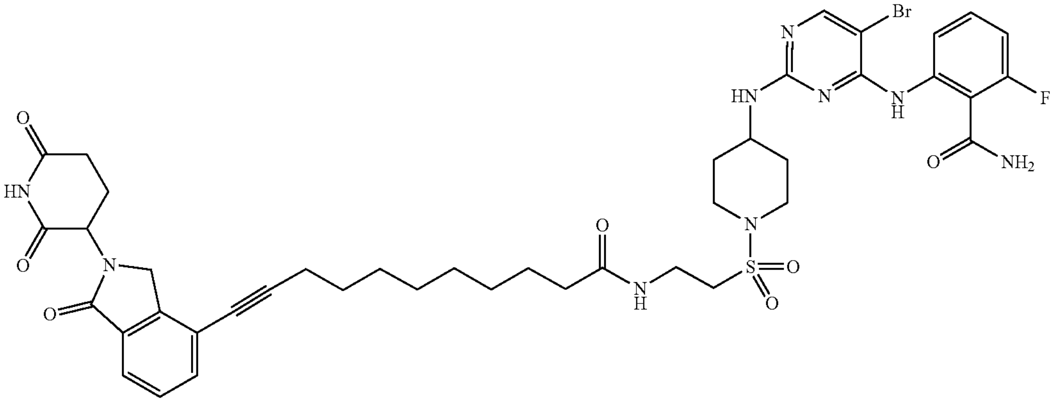 [SMILES: NC(=O)c1c(F)cccc1Nc1nc(NC2CCN(S(=O)(=O)CCNC(=O)CCCCCCCCC#Cc3cccc4c3CN(C3CCC(=O)NC3=O)C4=O)CC2)ncc1Br]

Compound 14 was prepared using the same procedure as compound 2 in 97% yield. $^1H$ NMR (500 MHz, DMSO-$d_6$) δ 10.99 (s, 1H), 10.56-10.18 (m, 1H), 8.50-8.06 (m, 4H), 8.05-7.95 (m, 1H), 7.90-7.40 (m, 5H), 7.12-7.00 (m, 1H), 5.14 (dd, J=13.0, 5.0 Hz, 1H), 4.44 (t, J=17.5 Hz, 1H), 4.30 (t, J=17.5 Hz, 1H), 3.85-3.67 (m, 1H), 3.65-3.55 (m, 2H), 3.44-3.36 (m, 2H), 3.22-3.10 (m, 2H), 2.98-2.85 (m, 3H), 2.63-2.56 (m, 1H), 2.49-2.38 (m, 3H), 2.12-1.90 (m, 5H), 1.61-1.46 (m, 6H), 1.45-1.37 (m, 2H), 1.35-1.20 (m, 6H). ESI (m/z): $[M+H]^+$ 922.87, 924.84.

Example 16: Synthesis of 2-((5-bromo-2-((1-((2-(11-(2-(2,6-dioxopiperidin-3-yl)-1-oxoisoindolin-4-yl)undecanamido)ethyl)sulfonyl)piperidin-4-yl)amino)pyrimidin-4-yl)amino)-6-fluorobenzamide (15)

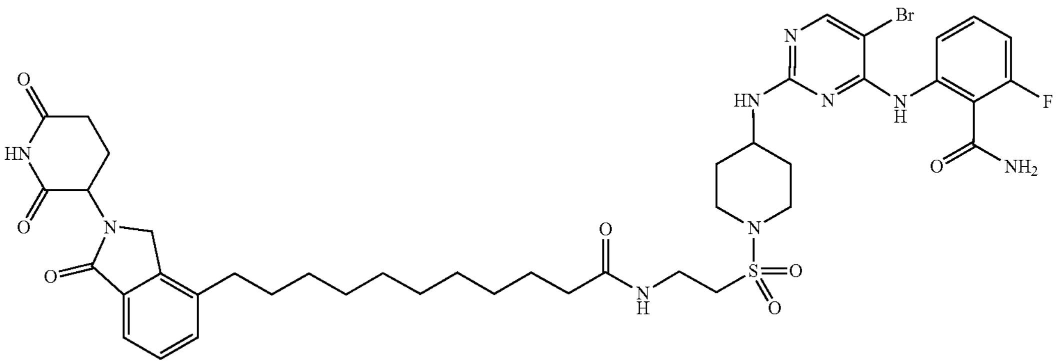 [SMILES: NC(=O)c1c(F)cccc1Nc1nc(NC2CCN(S(=O)(=O)CCNC(=O)CCCCCCCCCCc3cccc4c3CN(C3CCC(=O)NC3=O)C4=O)CC2)ncc1Br]

Compound 15 was prepared using the same procedure as compound 2 in 43% yield. $^1$H NMR (500 MHz, DMSO-$d_6$) δ 10.98 (s, 1H), 10.50-10.10 (m, 1H), 8.50-8.06 (m, 4H), 8.03-7.97 (m, 1H), 7.82-7.41 (m, 5H), 7.08-6.98 (m, 1H), 5.13 (dd, J=13.0, 5.0 Hz, 1H), 4.44 (d, J=17.0 Hz, 1H), 4.29 (d, J=17.0 Hz, 1H), 3.85-3.66 (m, 1H), 3.59 (d, J=12.0 Hz, 2H), 3.40 (dd, J=13.5 Hz, 2H), 3.20-3.10 (m, 2H), 2.97-2.86 (m, 3H), 2.66-2.57 (m, 3H), 1.63-1.43 (m, 6H), 1.34-1.16 (m, 12H). ESI (m/z): $[M+H]^+$ 926.99, 928.85.

Example 17: Synthesis of N-(2-((4-((4-(benzo[d][1,3]dioxol-4-ylamino)-5-bromopyrimidin-2-yl)amino)piperidin-1-yl)sulfonyl)ethyl)-11-(2-(2,6-dioxopiperidin-3-yl)-1-oxoisoindolin-4-yl)undec-10-ynamide (16)

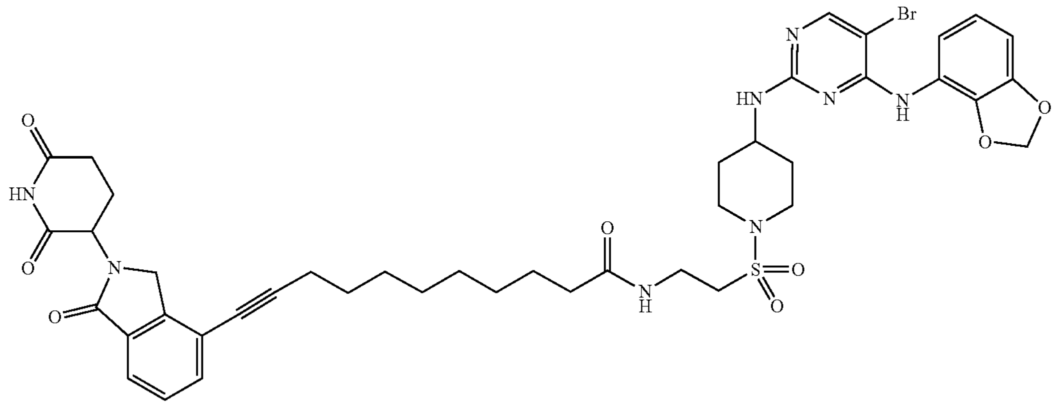 [SMILES: O=C(CCCCCCCCC#Cc1cccc2c1CN(C1CCC(=O)NC1=O)C2=O)NCCS(=O)(=O)N1CCC(Nc2ncc(Br)c(Nc3cccc4c3OCO4)n2)CC1]

Compound 16 was prepared using the same procedure as compound 2 in 43% yield. $^1$H NMR (500 MHz, DMSO-$d_6$) δ 11.00 (s, 1H), 8.75-8.15 (m, 1H), 8.07 (s, 1H), 7.97 (t, J=5.5 Hz, 1H), 7.70 (t, J=7.5 Hz, 1H), 7.62 (dd, J=7.5, 2.5 Hz, 1H), 7.51 (t, J=7.5 Hz, 1H), 7.40-6.94 (m, 2H), 6.89-6.75 (m, 2H), 6.00 (s, 2H), 5.14 (dd, J=13.0, 5.0 Hz, 1H), 4.44 (t, J=17.5 Hz, 1H), 4.44 (t, J=17.5 Hz, 1H), 3.85-3.60 (m, 1H), 3.57-3.50 (m, 2H), 3.41-3.35 (m, 2H), 3.11 (t, J=7.5 Hz, 2H), 2.96-2.56 (m, 4H), 2.49-2.41 (m, 3H), 2.10-1.98 (m, 3H), 1.89-1.80 (m, 2H), 1.60-1.53 (m, 2H), 1.52-1.36 (m, 6H), 1.33-1.20 (m, 6H). ESI (m/z): $[M+H]^+$ 926.99, 928.85.

Example 18: Synthesis of N-(2-((4-((4-(benzo[d][1,3]dioxol-4-ylamino)-5-bromopyrimidin-2-yl)amino)piperidin-1-yl)sulfonyl)ethyl)-9-((2-(2,6-dioxopiperidin-3-yl)-1,3-dioxoisoindolin-4-yl)oxy)nonanamide (17)

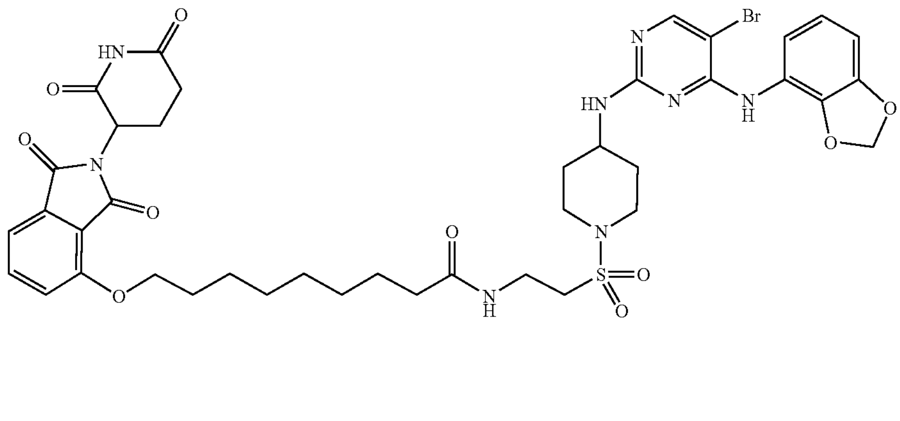 [SMILES: O=C(CCCCCCCCOc1cccc2c1C(=O)N(C1CCC(=O)NC1=O)C2=O)NCCS(=O)(=O)N1CCC(Nc2ncc(Br)c(Nc3cccc4c3OCO4)n2)CC1]

Compound 17 was prepared using the same procedure as compound 2 in 25% yield. $^1H$ NMR (500 MHz, DMSO-$d_6$) δ 11.10 (s, 1H), 9.42-9.12 (m, 1H), 8.17 (s, 1H), 7.98 (t, J=5.5 Hz, 1H), 7.90-7.70 (m, 1H), 7.80 (dd, J=9.0, 7.5 Hz, 1H), 7.50 (d, J=8.5 Hz, 1H), 7.43 (d, J=7.5 Hz, 1H), 7.02-6.96 (m, 1H), 6.91-6.77 (m, 2H), 6.01 (s, 2H), 5.07 (dd, J=13.0, 5.5 Hz, 1H), 4.19 (t, J=6.0 Hz, 2H), 4.10-3.65 (m, 1H), 3.59-3.49 (m, 2H), 3.41-3.34 (m, 2H), 3.12 (t, J=6.5 Hz, 2H), 2.93-2.83 (m, 1H), 2.73-2.63 (m, 1H), 2.62-2.55 (m, 1H), 2.54-2.45 (m, 1H), 2.09-1.98 (m, 3H), 1.89-1.79 (m, 2H), 1.78-1.70 (m, 2H), 1.53-1.37 (m, 6H), 1.36-1.20 (m, 7H). ESI (m/z): $[M+H]^+$ 911.25, 913.06.

Example 19: Synthesis of N-(2-((4-((5-bromo-4-(3,4-dihydroquinolin-1(2H)-yl)pyrimidin-2-yl)amino)piperidin-1-yl)sulfonyl)ethyl)-1-((2-(2,6-dioxopiperidin-3-yl)-1,3-dioxoisoindolin-4-yl)amino)-3,6,9,12-tetraoxapentadecan-15-amide (18)

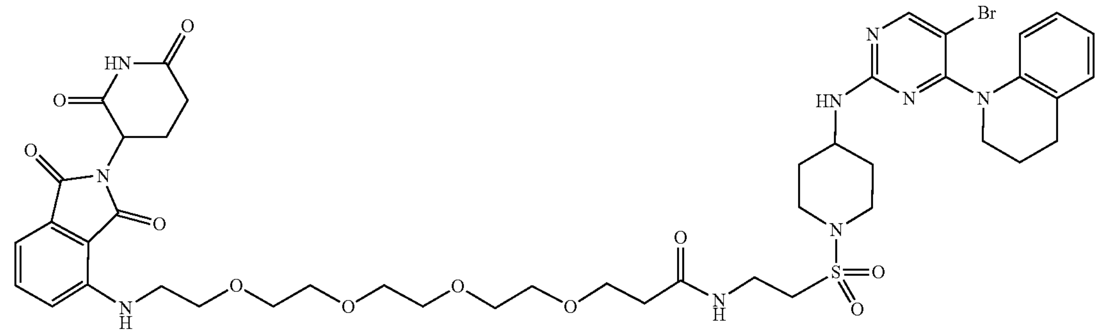 [SMILES: O=C(CCOCCOCCOCCOCCNc1cccc2c1C(=O)N(C1CCC(=O)NC1=O)C2=O)NCCS(=O)(=O)N1CCC(Nc2ncc(Br)c(N3CCCc4ccccc43)n2)CC1]

Compound 18 was prepared using the same procedure as compound 2 in 41% yield. $^1H$ NMR (500 MHz, DMSO-$d_6$) δ 11.09 (s, 1H), 8.23-8.12 (m, 1H), 8.05 (t, J=5.5 Hz, 1H), 7.58 (dd, J=8.5, 7.5 Hz, 1H), 7.34-7.20 (m, 1H), 7.14 (d, J=8.5 Hz, 1H), 7.10 (d, J=7.5 Hz, 1H), 7.04 (d, J=7.0 Hz, 1H), 7.01 (t, J=7.5 Hz, 1H), 6.87 (t, J=7.5 Hz, 1H), 6.66-6.57 (m, 1H), 5.05 (dd, J=12.5, 5.5 Hz, 1H), 3.88-3.44 (m, 23H), 3.43-3.37 (m, 2H), 3.13 (t, J=6.5 Hz, 2H), 2.95-2.83 (m, 3H), 2.74 (t, J=6.0 Hz, 2H), 2.62-2.47 (m, 2H), 2.31 (t, J=6.5 Hz, 2H), 2.06-1.98 (m, 1H), 1.96-1.87 (m, 4H), 1.55-1.44 (m, 2H). ESI (m/z): $[M+H]^+$ 998.37, 1000.28.

Example 20: Synthesis of N-(2-((8-((5-bromo-4-((2-carbamoyl-3-fluorophenyl)amino)pyrimidin-2-yl)amino)-5-azaspiro[2.5]octan-5-yl)sulfonyl)ethyl)-1-((2-(2,6-dioxopiperidin-3-yl)-1,3-dioxoisoindolin-4-yl)amino)-3,6,9,12-tetraoxapentadecan-15-amide (19)

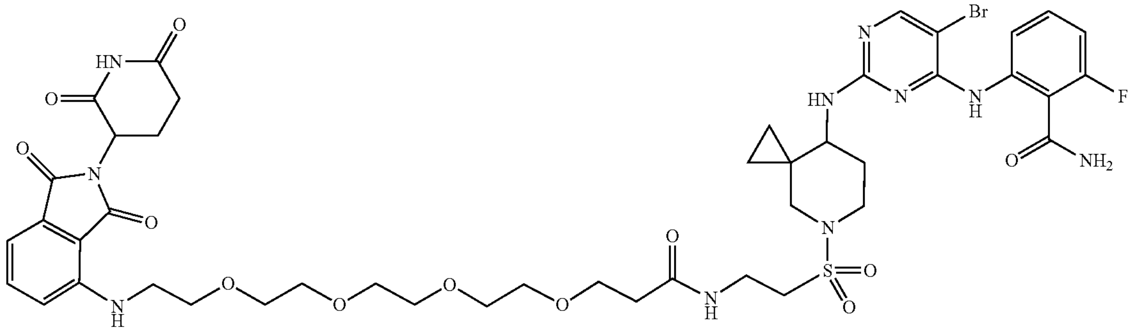 [SMILES: NC(=O)c1c(F)cccc1Nc1nc(NC2CCN(S(=O)(=O)CCNC(=O)CCOCCOCCOCCOCCNc3cccc4c3C(=O)N(C3CCC(=O)NC3=O)C4=O)CC23CC3)ncc1Br]

Compound 19 was prepared using the same procedure as compound 2 in 58% yield. $^1$H NMR (500 MHz, DMSO-$d_6$) δ 11.09 (s, 1H), 10.50-10.16 (m, 1H), 8.28-8.04 (m, 5H), 7.84-7.47 (m, 3H), 7.14 (d, J=8.0 Hz, 1H), 7.09-7.00 (m, 2H), 6.66-6.55 (m, 1H), 5.05 (dd, J=12.5, 5.5 Hz, 1H), 3.94-3.74 (m, 1H), 3.65-3.36 (m, 21H), 3.27-3.12 (m, 4H), 3.05-2.83 (m, 2H), 2.62-2.45 (m, 2H), 2.32 (t, J=6.5 Hz, 2H), 2.06-1.98 (m, 1H), 1.89-1.73 (m, 2H), 0.68-0.58 (m, 1H), 0.50-0.28 (m, 3H). ESI (m/z): $[M+H]^+$ 1045.31, 1047.34.

Example 21: Synthesis of N-(2-((4-((5-bromo-4-((3-oxoisoindolin-4-yl)amino)pyrimidin-2-yl)amino) piperidin-1-yl)sulfonyl)ethyl)-1-((2-(2,6-dioxopiperidin-3-yl)-1,3-dioxoisoindolin-4-yl)amino)-3,6,9,12-tetraoxapentadecan-15-amide (20)

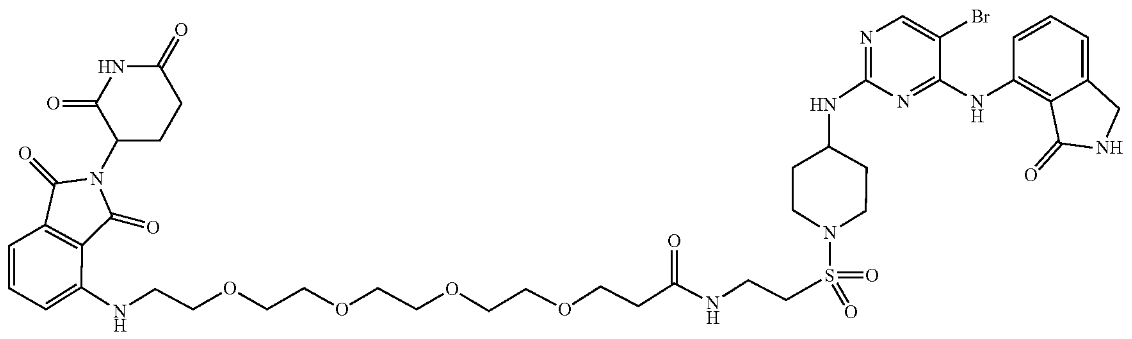 [SMILES: O=C(CCOCCOCCOCCOCCNc1cccc2c1C(=O)N(C1CCC(=O)NC1=O)C2=O)NCCS(=O)(=O)N1CCC(Nc2ncc(Br)c(Nc3cccc4c3C(=O)NC4)n2)CC1]

Compound 20 was prepared using the same procedure as compound 2 in 40% yield. $^1$H NMR (500 MHz, DMSO-$d_6$) δ 11.08 (s, 1H), 10.57 (s, 1H), 8.94-8.50 (m, 2H), 8.16 (s, 1H), 8.12-8.04 (m, 1H), 7.76-7.28 (m, 3H), 7.18 (d, J=8.0 Hz, 1H), 7.13 (d, J=8.5 Hz, 1H), 7.03 (d, J=7.0 Hz, 1H), 6.59 (t, J=5.0 Hz, 1H), 5.05 (dd, J=12.5, 5.5 Hz, 1H), 4.39 (s, 2H), 3.90-3.76 (m, 1H), 3.68-3.36 (m, 20H), 3.24-3.12 (m, 2H), 3.08-2.82 (m, 3H), 2.62-2.47 (m, 2H), 2.33 (t, J=6.5 Hz, 2H), 2.11-1.93 (m, 3H), 1.61-1.47 (m, 2H). ESI (m/z): $[M+H]^+$ 1013.33, 1015.12.

Example 22: Synthesis of N-(2-((4-((5-bromo-4-((3-oxoisoindolin-4-yl)amino)pyrimidin-2-yl)amino) piperidin-1-yl)sulfonyl)ethyl)-9-((2-(2,6-dioxopiperidin-3-yl)-1,3-dioxoisoindolin-4-yl)oxy) nonanamide (21)

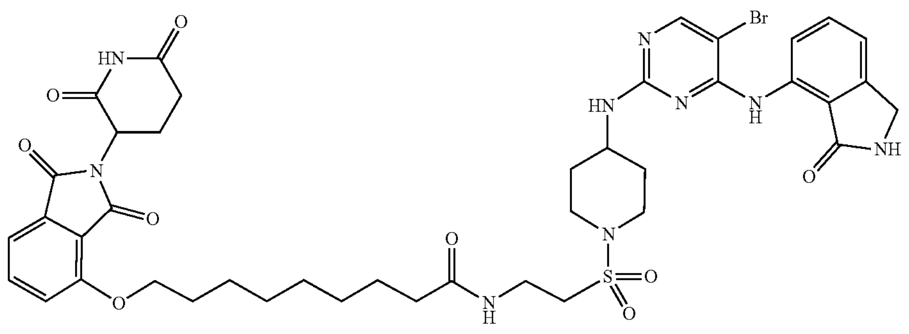 [SMILES: O=C(CCCCCCCCOc1cccc2c1C(=O)N(C1CCC(=O)NC1=O)C2=O)NCCS(=O)(=O)N1CCC(Nc2ncc(Br)c(Nc3cccc4c3C(=O)NC4)n2)CC1]

Compound 21 was prepared using the same procedure as compound 2 in 29% yield. $^1$H NMR (500 MHz, DMSO-$d_6$) δ 11.09 (s, 1H), 10.76-10.56 (m, 1H), 8.94-8.50 (m, 2H), 8.19 (s, 1H), 8.01 (s, 1H), 7.79 (t, J=7.5 Hz, 1H), 7.74-7.45 (m, 3H), 7.42 (d, J=7.5 Hz, 1H), 7.20 (t, J=5.5 Hz, 1H), 5.07 (dd, J=12.5, 5.5 Hz, 1H), 4.40 (s, 2H), 4.22-4.14 (m, 2H), 3.88-3.78 (m, 1H), 3.68-3.58 (m, 2H), 3.46-3.36 (m, 2H), 3.24-3.12 (m, 1H), 3.08-2.82 (m, 3H), 2.62-2.46 (m, 2H), 2.12-1.94 (m, 5H), 1.78-1.68 (m, 2H), 1.62-1.38 (m, 6H), 1.36-1.20 (m, 7H). ESI (m/z): $[M+H]^+$ 922.76, 924.74.

Example 23: Synthesis of 4-((5-bromo-2-((1-((2-(9-((2-(2,6-dioxopiperidin-3-yl)-1,3-dioxoisoindolin-4-yl)oxy)nonanamido)ethyl)sulfonyl)piperidin-4-yl)amino)pyrimidin-4-yl)amino)-1-methyl-1H-pyrazole-5-carboxamide (22)

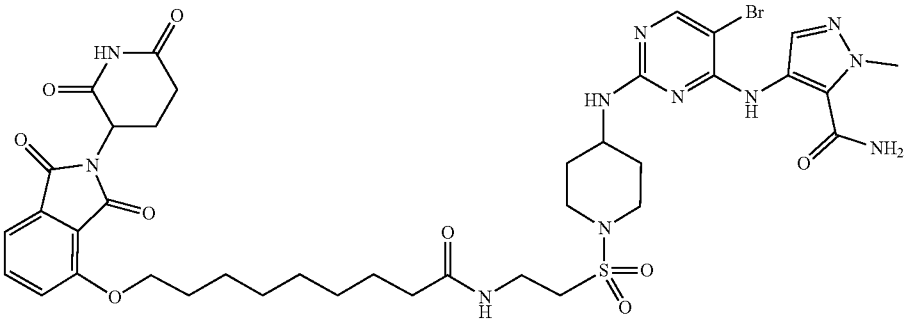 [SMILES: Cn1ncc(Nc2nc(NC3CCN(S(=O)(=O)CCNC(=O)CCCCCCCCOc4cccc5c4C(=O)N(C4CCC(=O)NC4=O)C5=O)CC3)ncc2Br)c1C(N)=O]

Compound 22 was prepared using the same procedure as compound 2 in 62% yield. $^1$H NMR (500 MHz, DMSO-$d_6$) δ 11.10 (s, 1H), 9.90-9.30 (m, 1H), 8.40-7.60 (m, 5H), 8.00 (t, J=5.5 Hz, 1H), 7.80 (t, J=7.0 Hz, 1H), 7.50 (d, J=8.5 Hz, 1H), 7.44 (d, J=7.5 Hz, 1H), 5.08 (dd, J=12.5, 5.5 Hz, 1H), 4.19 (t, J=6.0 Hz, 2H), 4.04 (s, 3H), 3.84-3.70 (m, 1H), 3.64-3.54 (m, 2H), 3.44-3.36 (m, 2H), 3.18-3.13 (m, 1H), 2.97-2.83 (m, 3H), 2.63-2.46 (m, 2H), 2.10-2.00 (m, 3H), 2.00-1.91 (m, 2H), 1.80-1.70 (m, 2H), 1.58-1.40 (m, 6H), 1.38-1.20 (m, 7H). ESI (m/z): $[M+H]^+$ 914.81, 916.78.

Example 24: Synthesis of 2-((5-bromo-2-((4-(N-(14-((2-(2,6-dioxopiperidin-3-yl)-1,3-dioxoisoindolin-4-yl)amino)-3,6,9,12-tetraoxatetradecyl)sulfamoyl)phenyl)amino)pyrimidin-4-yl)amino)-6-fluorobenzamide (23)

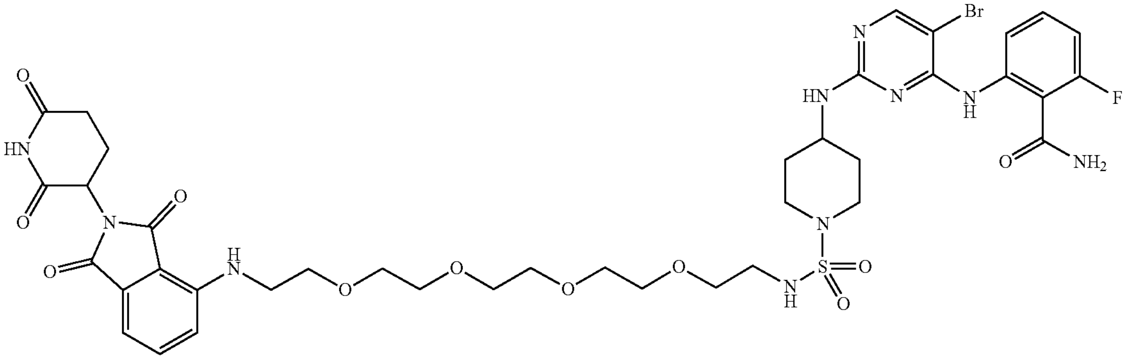 [SMILES: NC(=O)c1c(F)cccc1Nc1nc(NC2CCN(S(=O)(=O)NCCOCCOCCOCCOCCNc3cccc4c3C(=O)N(C3CCC(=O)NC3=O)C4=O)CC2)ncc1Br]

Compound 23 was prepared using the same procedure as compound 25 in 15% yield. $^1$H NMR (500 MHz, DMSO-$d_6$) δ 11.08 (s, 1H), 10.11 (s, 1H), 9.92 (s, 1H), 8.38 (s, 1H), 8.23 (d, J=8.0 Hz, 1H), 8.16 (s, 1H), 8.11 (s, 1H), 7.84 (d, J=9.0 Hz, 1H), 7.63 (d, J=9.0 Hz, 1H), 7.59-7.50 (m, 1H), 7.48 (t, J=6.0 Hz, 1H), 7.12 (d, J=8.5 Hz, 1H), 7.08 (t, J=9.0 Hz, 1H), 7.03 (d, J=7.0 Hz, 1H), 6.58 (t, J=5.5 Hz, 1H), 5.04 (dd, J=12.5, 5.5 Hz, 1H), 3.60 (t, J=5.5 Hz, 2H), 3.56-3.34 (m, 16H), 2.92-2.82 (m, 3H), 2.62-2.50 (m, 2H), 2.06-1.96 (m, 1H). ESI (m/z): $[M+H]^+$ 956.22, 958.14.

Example 25: Synthesis of 2-((5-bromo-2-((4-(N-(14-((2-(2,6-dioxopiperidin-3-yl)-1,3-dioxoisoindolin-4-yl)amino)-3,6,9,12-tetraoxatetradecyl)sulfamoyl)-2-methylphenyl)amino)pyrimidin-4-yl)amino)-6-fluorobenzamide (24)

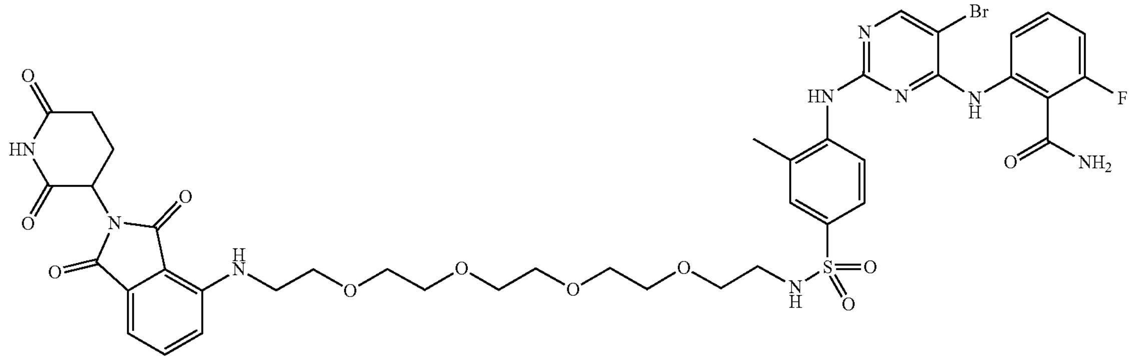 [SMILES: Cc1cc(S(=O)(=O)NCCOCCOCCOCCOCCNc2cccc3c2C(=O)N(C2CCC(=O)NC2=O)C3=O)ccc1Nc1ncc(Br)c(Nc2cccc(F)c2C(N)=O)n1]

Compound 24 was prepared using the same procedure as compound 25 in 10% yield. $^1$H NMR (500 MHz, DMSO-$d_6$) δ 11.08 (s, 1H), 10.19 (s, 1H), 9.02 (s, 1H), 8.29 (s, 1H), 8.14 (s, 1H), 8.11-8.05 (m, 2H), 7.73 (d, J=8.0 Hz, 1H), 7.63 (d, J=2.0 Hz, 1H), 7.61-7.54 (m, 3H), 7.27 (dd, J=14.0, 7.5 Hz, 1H), 7.13 (t, J=8.5 Hz, 1H), 7.04 (t, J=7.0 Hz, 1H), 6.96 (t, J=8.5 Hz, 1H), 6.59 (s, 1H), 5.05 (dd, J=12.5, 5.0 Hz, 1H), 3.60 (t, J=5.0 Hz, 2H), 3.56-3.38 (m, 16H), 2.92-2.82 (m, 3H), 2.62-2.50 (m, 2H), 2.29 (s, 3H), 2.06-1.96 (m, 1H). ESI (m/z): $[M+H]^+$ 970.89, 972.88.

Example 26: Synthesis of 2-((5-bromo-2-((4-(N-(14-((2-(2,6-dioxopiperidin-3-yl)-1,3-dioxoisoindolin-4-yl)amino)-3,6,9,12-tetraoxatetradecyl)sulfamoyl)-3-methylphenyl)amino)pyrimidin-4-yl)amino)-6-fluorobenzamide (25)

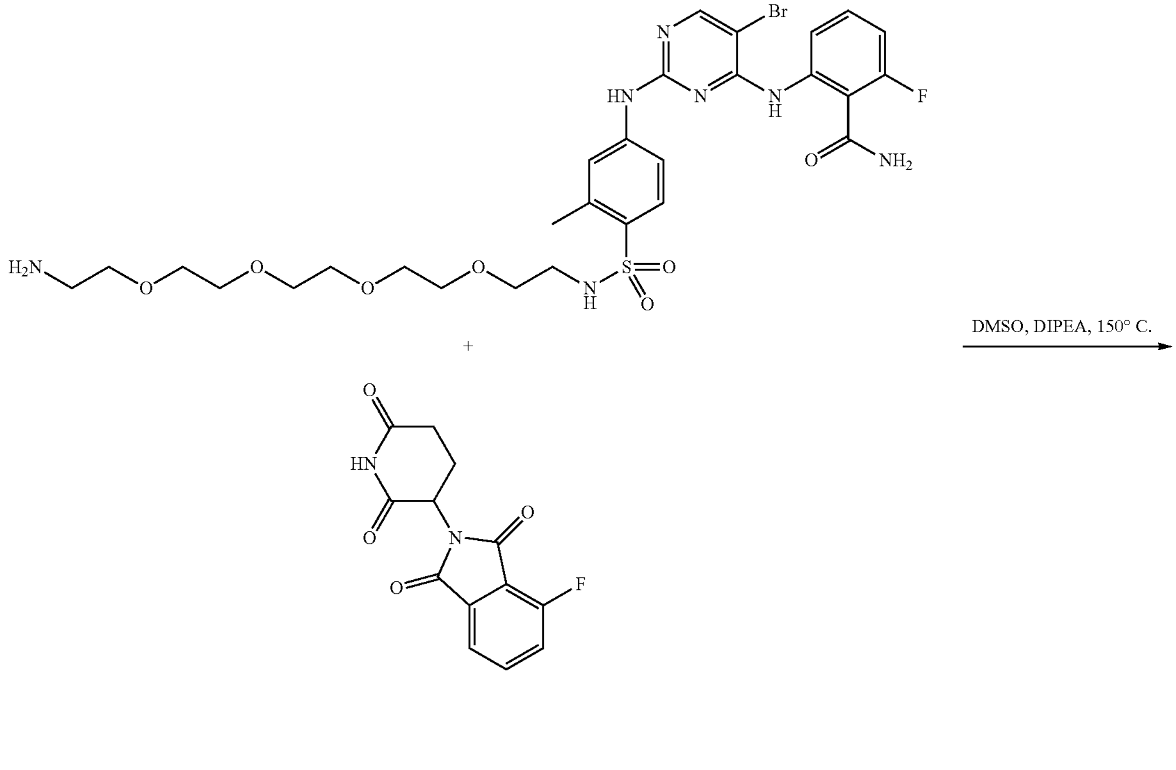

-continued

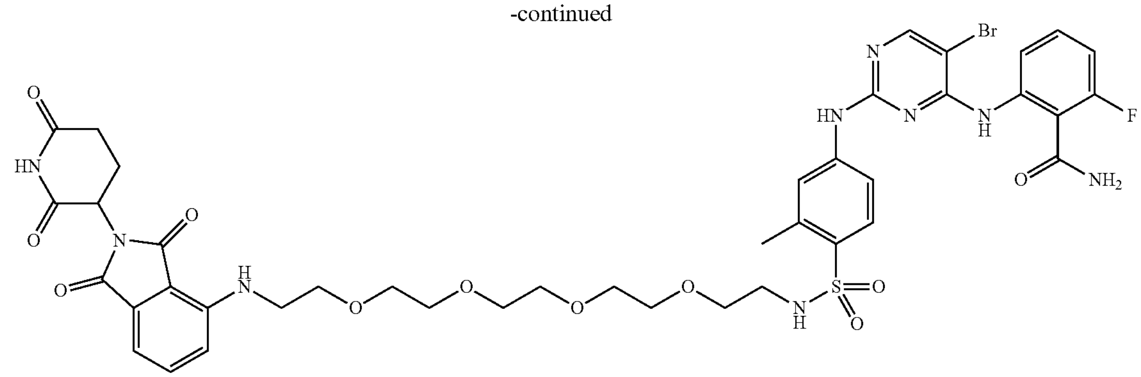

To a stirred solution of 2-((2-((4-(N-(14-amino-3,6,9,12-tetraoxatetradecyl)sulfamoyl)-3-methylphenyl)amino)-5-bromopyrimidin-4-yl)amino)-6-fluorobenzamide (11 mg, 0.015 mmol) and 2-(2,6-dioxopiperidin-3-yl)-4-fluoroisoindoline-1,3-dione (4 mg, 0.015 mmol) in dimethyl sulfoxide (1.0 mL) was added diisopropylethylamine (0.026 mL, 0.15 mmol). The reaction mixture was stirred at 150° C. for 25 minutes. The reaction mixture was purified directly by prep HPLC and appropriate fractions were combined and lyophilized to afford the title compound as a yellow viscous oil (1.5 mg, 0.0015 mmol, 10% yield). $^1$H NMR (500 MHz, DMSO-$d_6$) δ 11.08 (s, 1H), 10.13 (s, 1H), 9.83 (s, 1H), 8.37 (s, 1H), 8.23 (t, J=8.5 Hz, 1H), 8.16 (s, 1H), 8.11 (s, 1H), 7.69-7.64 (m, 2H), 7.63-7.58 (m, 1H), 7.56 (dd, J=8.5, 7.5 Hz, 1H), 7.52-7.44 (m, 2H), 7.12 (d, J=8.0 Hz, 1H), 7.08 (t, J=8.0 Hz, 1H), 7.03 (d, J=7.0 Hz, 1H), 6.58 (t, J=5.5 Hz, 1H), 5.04 (dd, J=10.0, 4.5 Hz, 1H), 3.59 (t, J=5.5 Hz, 2H), 3.55-3.34 (m, 16H), 2.92-2.83 (m, 3H), 2.62-2.50 (m, 2H), 2.46 (s, 3H), 2.06-1.96 (m, 1H). ESI (m/z): $[M+H]^+$ 970.21, 971.96.

Example 27: Synthesis of 2-((5-bromo-2-((4-(N-(1-((2-(2,6-dioxopiperidin-3-yl)-1,3-dioxoisoindolin-4-yl)oxy)-2-oxo-6,9,12,15-tetraoxa-3-azaheptadecan-17-yl)sulfamoyl)-2-methylphenyl)amino)pyrimidin-4-yl)amino)-6-fluorobenzamide (46)

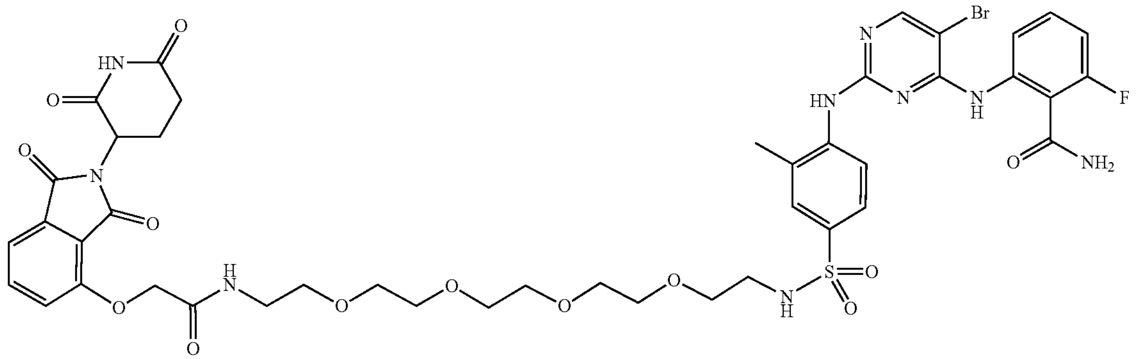 [SMILES: Cc1cc(S(=O)(=O)NCCOCCOCCOCCOCCNC(=O)COc2cccc3c2C(=O)N(C2CCC(=O)NC2=O)C3=O)ccc1Nc1ncc(Br)c(Nc2cccc(F)c2C(N)=O)n1]

Compound 46 was prepared using the same procedure as compound 2 in 30% yield. $^1$H NMR (500 MHz, DMSO-$d_6$) δ 11.11 (s, 1H), 10.21 (s, 1H), 9.04 (s, 1H), 8.29 (s, 1H), 8.14 (s, 1H), 8.10-8.05 (m, 2H), 7.99 (d, J=5.5 Hz, 1H), 7.80 (dd, J=8.0, 7.0 Hz, 1H), 7.73 (d, J=8.0 Hz, 1H), 7.64 (d, J=1.5 Hz, 1H), 7.62-7.56 (m, 2H), 7.49 (d, J=7.0 Hz, 1H), 7.39 (d, J=8.5 Hz, 1H), 7.27 (dd, J=15.0, 8.5 Hz, 1H), 6.97 (t, J=10.0 Hz, 1H), 5.11 (dd, J=12.5, 5.0 Hz, 1H), 4.78 (s, 2H), 3.51-3.42 (m, 14H), 3.40 (t, J=6.0 Hz, 2H), 3.33-3.28 (m, 2H), 2.94-2.84 (m, 3H), 2.65-2.50 (m, 2H), 2.29 (s, 3H), 2.08-1.97 (m, 1H). ESI (m/z): $[M+H]^+$ 1028.23, 1030.22; found, 1028.89, 1030.81.

Example 28: Synthesis of 2-((5-bromo-2-((4-(N-(10-(2-((2-(2,6-dioxopiperidin-3-yl)-1,3-dioxoisoindolin-4-yl)oxy)acetamido)decyl)sulfamoyl)-2-methylphenyl)amino)pyrimidin-4-yl)amino)-6-fluorobenzamide (47)

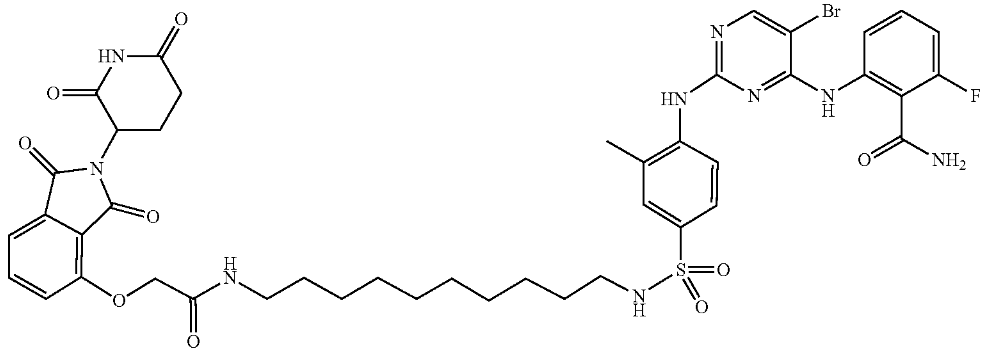 [SMILES: Cc1cc(S(=O)(=O)NCCCCCCCCCCNC(=O)COc2cccc3c2C(=O)N(C2CCC(=O)NC2=O)C3=O)ccc1Nc1ncc(Br)c(Nc2cccc(F)c2C(N)=O)n1]

Compound 47 was prepared using the same procedure as compound 2 in 32% yield. $^{1}$H NMR (500 MHz, DMSO-$d_6$) δ 11.11 (s, 1H), 10.21 (s, 1H), 9.00 (s, 1H), 8.29 (s, 1H), 8.14 (s, 1H), 8.11 (d, J=8.5 Hz, 1H), 8.07 (s, 1H), 7.90 (t, J=6.0 Hz, 1H), 7.80 (dd, J=8.5, 7.0 Hz, 1H), 7.73 (d, J=8.5 Hz, 1H), 7.62 (d, J=2.0 Hz, 1H), 7.57 (dd, J=8.0, 2.0 Hz, 1H), 7.49 (d, J=7.0 Hz, 1H), 7.44 (t, J=6.0 Hz, 1H), 7.38 (d, J=8.5 Hz, 1H), 7.30-7.23 (m, 1H), 6.95 (t, J=9.5 Hz, 1H), 5.11 (dd, J=12.5, 5.5 Hz, 1H), 4.76 (s, 2H), 3.15-3.07 (m, 2H), 2.94-2.83 (m, 1H), 2.75-2.66 (m, 2H), 2.64-2.50 (m, 2H), 2.29 (s, 3H), 2.08-1.98 (m, 1H), 1.44-1.30 (m, 4H), 1.27-1.07 (m, 12H). ESI (m/z): $[M+H]^+$ 964.25, 966.24; found, 964.80, 964.71.

Example 29: Synthesis of 2-((5-bromo-2-((4-(N-(4-(4-(2-((2-(2,6-dioxopiperidin-3-yl)-1,3-dioxoisoindolin-4-yl)oxy)acetyl)piperazin-1-yl)butyl)sulfamoyl)-2-methylphenyl)amino)pyrimidin-4-yl)amino)-6-fluorobenzamide (48)

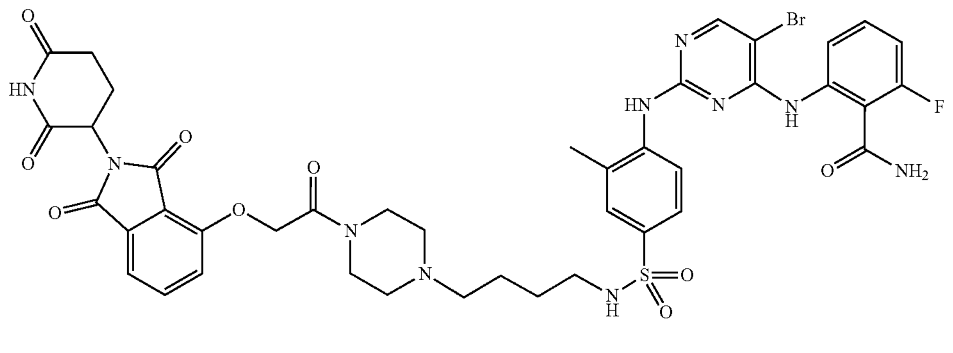 [SMILES: Cc1cc(S(=O)(=O)NCCCCN2CCN(C(=O)COc3cccc4c3C(=O)N(C3CCC(=O)NC3=O)C4=O)CC2)ccc1Nc1ncc(Br)c(Nc2cccc(F)c2C(N)=O)n1]

Compound 48 was prepared using the same procedure as compound 2 in 11% yield. $^{1}$H NMR (500 MHz, DMSO-$d_6$) δ 11.10 (s, 1H), 10.19 (s, 1H), 9.01 (s, 1H), 8.29 (s, 1H), 8.15 (s, 1H), 8.11 (d, J=9.0 Hz, 1H), 8.07 (s, 1H), 7.79-7.72 (m, 2H), 7.63 (d, J=2.0 Hz, 1H), 7.58 (dd, J=8.5, 2.0 Hz, 1H), 7.51 (t, J=5.5 Hz, 1H), 7.44 (d, J=7.0 Hz, 1H), 7.33-7.24 (m, 2H), 6.97 (t, J=9.5 Hz, 1H), 5.15 (s, 2H), 5.10 (dd, J=13.0, 5.5 Hz, 1H), 3.44-3.37 (m, 4H), 2.94-2.84 (m, 1H), 2.79-2.71 (m, 2H), 2.64-2.50 (m, 2H), 2.40-2.18 (m, 6H), 2.30 (s, 3H), 2.07-1.99 (m, 1H), 1.45-1.35 (m, 4H). ESI (m/z): $[M+H]^+$ 949.21, 951.21; found, 949.73, 951.76.

Example 30: The CDK2 and CDK5 $IC_{50}$ Values of Compounds 1-25 and 46-48

CDK2 and CDK5 $IC_{50}$ data were attained through the use of Invitrogen™ commercial assays. The method for CDK2 (assay ID: 315, kinase|Z'-LYTE™|CDK2/Cyclin A|Km app) used a 10-point titration. The method for CDK5 (assay ID: 318, kinase|Z'-LYTE™|CDK5/p25|Km app) used a 10-point titration. All the bifunctional compounds showed potent biochemical inhibition on both CDK2/5 enzymes.

TABLE 1

| Compound No. | CDK2 $IC_{50}$ (nM) | CDK5 $IC_{50}$ (nM) |
|---|---|---|
| 1 | 6.4 | 8.1 |
| 2 | 5.1 | 3.8 |
| 3 | 4.9 | 4.8 |
| 4 | 7.3 | 8.4 |
| 5 | 28.7 | 16.1 |
| 6 | 17.1 | 11.8 |
| 7 | 20.5 | 13.7 |
| 8 | 347.0 | 241.0 |
| 9 | 7.5 | 4.1 |
| 10 | 9.1 | 4.3 |
| 11 | 6.8 | 4.8 |
| 12 | 5.3 | 3.7 |
| 13 | 3.8 | 4.3 |
| 14 | 57.2 | 31.2 |
| 15 | 50.0 | 18.2 |
| 16 | >370 | 4370 |
| 17 | 253 | 924 |
| 18 | 23.7 | 27.4 |
| 19 | 116 | 71.3 |
| 20 | 4.7 | 5.8 |
| 21 | 10.5 | 7.6 |
| 22 | 5.7 | 5.7 |
| 23 | 10.9 | 7.0 |
| 24 | 6.5 | 6.8 |
| 25 | 8.1 | 7.1 |
| 46 | 1.7 | 1.4 |
| 47 | 19.4 | 18.2 |
| 48 | 2.0 | 2.9 |

Example 31: Knockdown of CDKs in Jurkat Cells

Figure 1B:
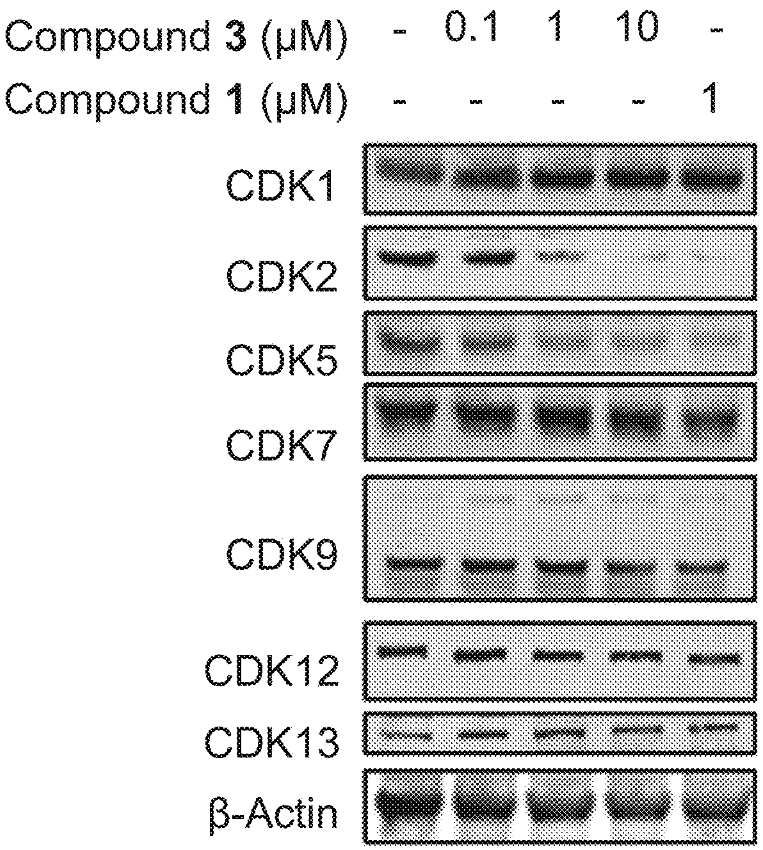
Figure 1C:
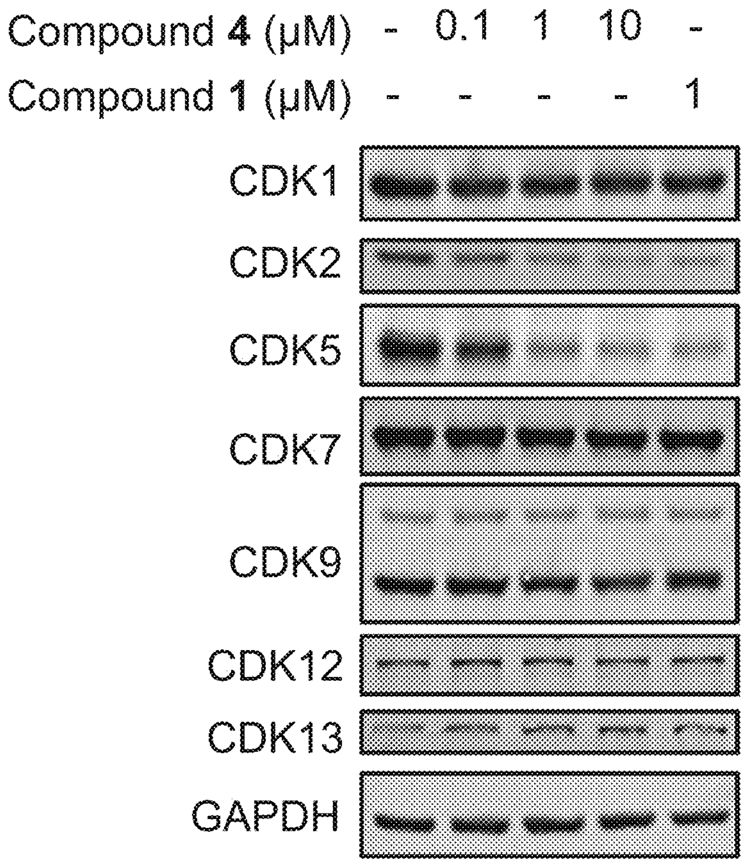
Figure 2A:
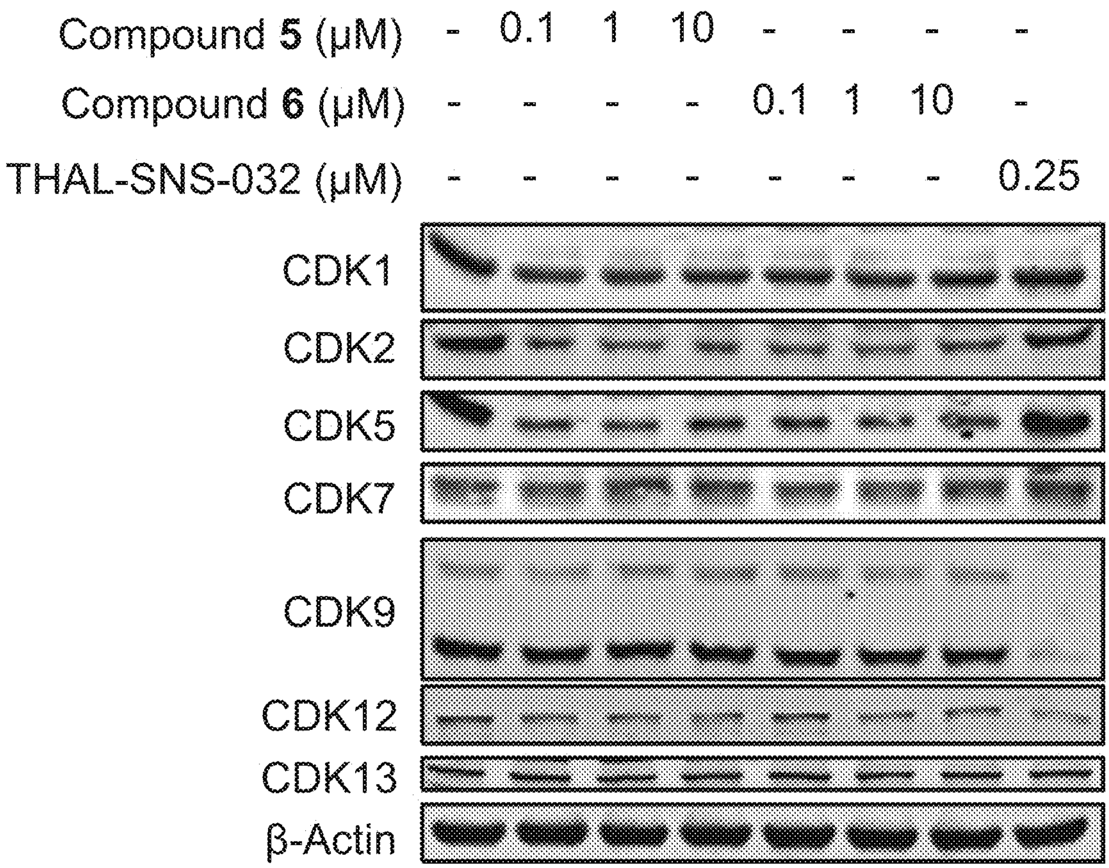
FIG. 2A and FIG. 2B are immunoblots that show the selective knockdown of CDK2/5 in Jurkat cells after 6 hours at various concentrations for inventive compounds 5-7 and THAL-SNS-032.
Figure 2B:
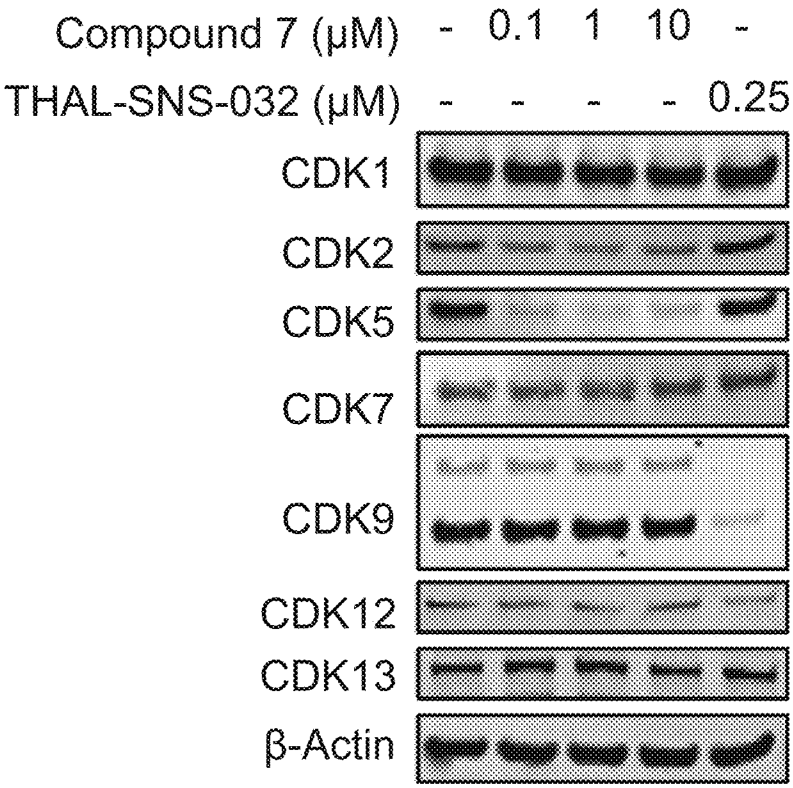
Figure 3:
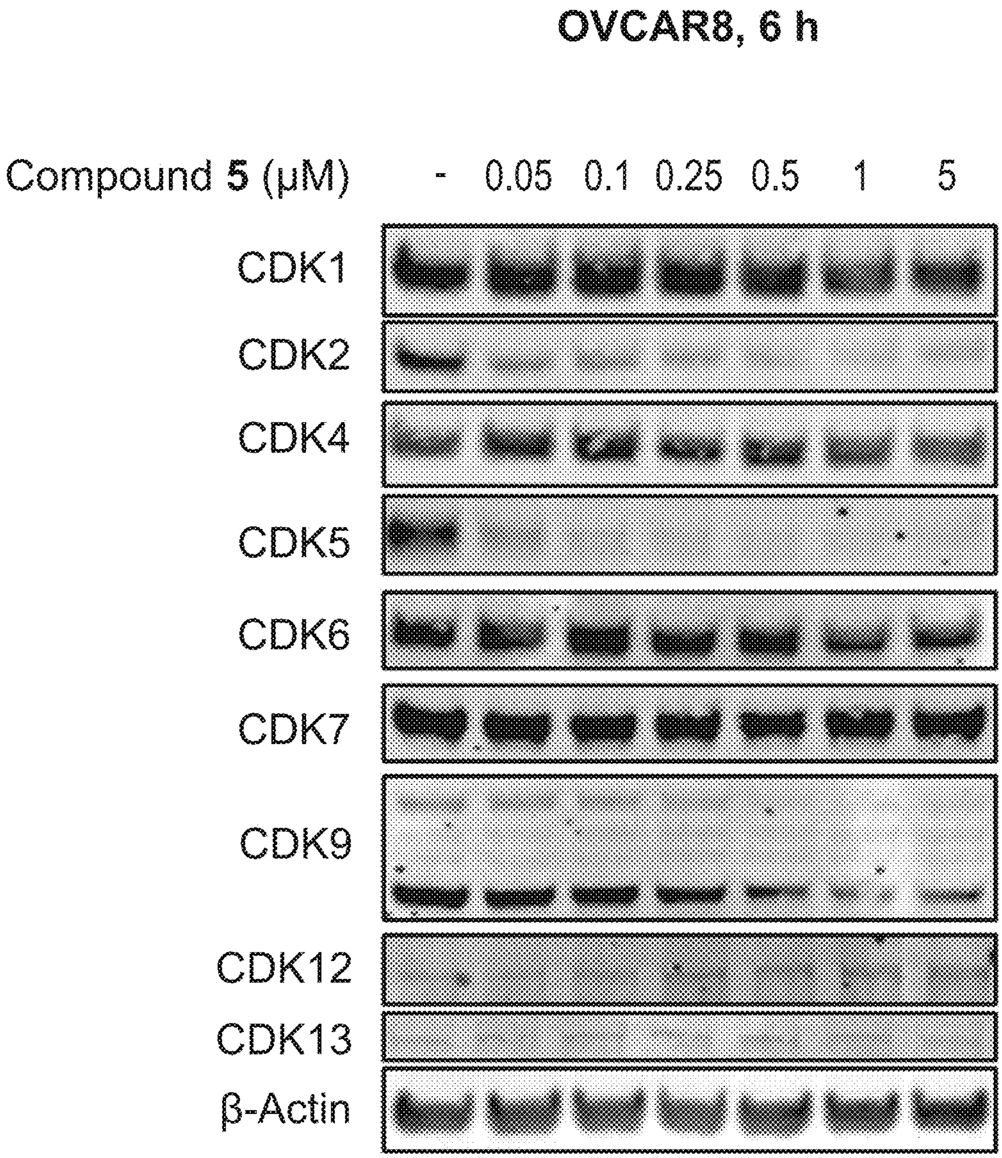
FIG. 3 is an immunoblot that shows the selective knockdown of CDK2/5 in OVCAR8 cells after 6 hours at various concentrations of inventive compound 5.

Jurkat acute T cell leukemia cells were treated with 0, 0.1 μM, 1 μM, and 10 μM of compounds 1-7 or 0.25 μM THAL-SNS-032 (a known CDK9 degrader, as a positive control for CDK9 degradation) for 6 hours, and then lysed and immunoblotted with antibodies to CDK1, CDK2, CDK5, CDK7, CDK9, CDK12, CDK13 and R-Actin (FIG. 1A-FIG. 2B). The results indicated that compounds 1-7 induced the degradation of CDK2 and CDK5 after 6 hours at the indicated concentrations. THAL-SNS-032 induced CDK9 degradation as expected.

All patent publications and non-patent publications are indicative of the level of skill of those skilled in the art to which this invention pertains. All these publications (including any specific portions thereof that are referenced) are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A bifunctional compound having a structure represented by formula:

(I)

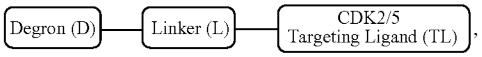

wherein the CDK2/5 targeting ligand is represented by the formula (TL-1):

(TL-1)

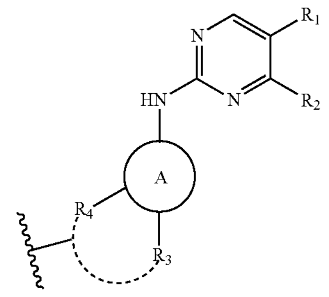

wherein:

$R_1$ represents Br or $CF_3$;

$R_2$ represents $OR_5$, $NHR_5$,

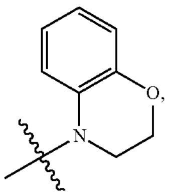

or

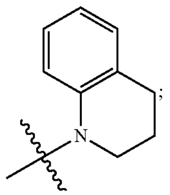

;

$R_5$ represents

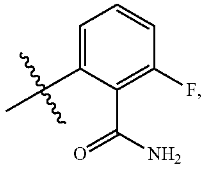

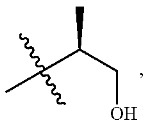

,

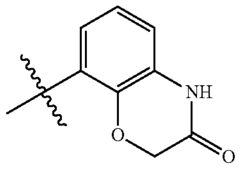

,

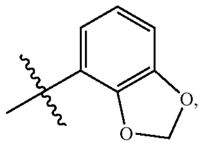

-continued

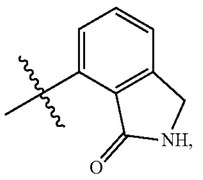 or 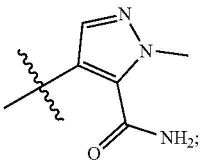

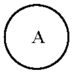

represents optionally substituted cyclopentyl, optionally substituted cyclohexyl, optionally substituted phenyl, optionally substituted pyridinyl, optionally substituted pyrrolidinyl, or optionally substituted piperidinyl;

$R_3$ represents

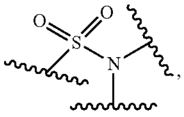, 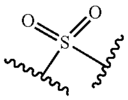,

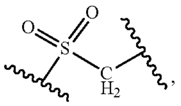, or 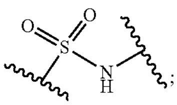;

$R_4$ represents H, C(O), or

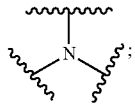;

provided that when $R_3$ represents

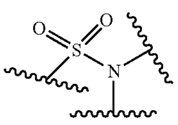 or 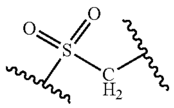

and $R_4$ represents C(O) or

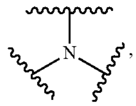, $R_3$ and $R_4$ together with the atoms to which they are bound form a 5-membered cyclic sulfonamide, the degron is represented by formula D1 or D2:

(D1)

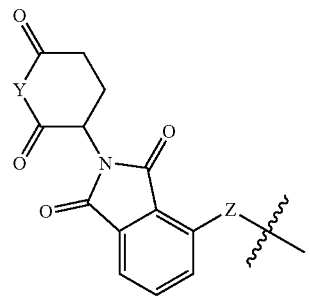

or (D2)

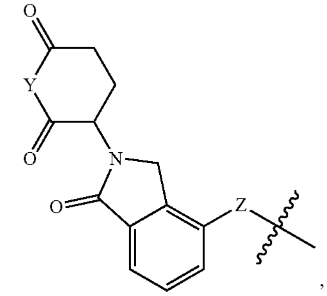, wherein

Y is NH or NMe; and

Z is $CH_2$, NH, O, or C≡, and the linker is an alkylene chain which may be interrupted by, and/or terminate at either or both termini in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —$S(O)_2$—, —OS(O)—, —S(O)O—, —S(O)—, —$OS(O)_2$—, —$S(O)_2O$—, —$N(R')S(O)_2$—, —$S(O)_2N(R')$—, —N(R')S(O)—, —S(O)N(R')—, —$N(R')S(O)_2N(R')$—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different, or the linker is a polyethylene glycol chain which may terminate at either or both termini in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —$S(O)_2$—, —OS(O)—, —S(O)O—, —S(O)—, —$OS(O)_2$—, —$S(O)_2O$—, —$N(R')S(O)_2$—, —$S(O)_2N(R')$—, —N(R')S(O)—, —S(O)N(R'), —$N(R')S(O)_2N(R')$—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different, or a pharmaceutically acceptable salt or stereoisomer thereof.

2. The bifunctional compound of claim 1, which is represented by the formula (I-1a):

(I-1a)

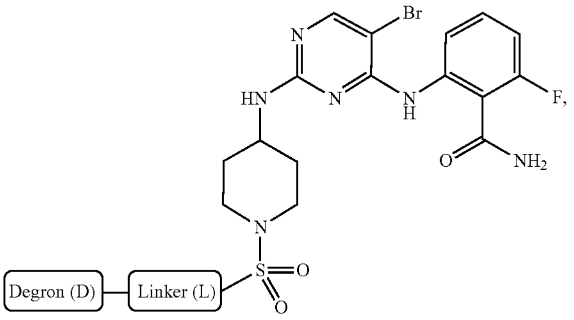

or a pharmaceutically acceptable salt or stereoisomer thereof.

3. The bifunctional compound of claim 1, which is represented by the formula (I-1b):

(I-1b)

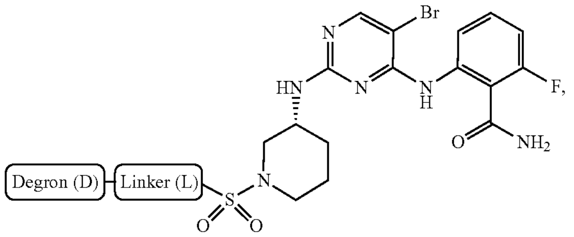

or a pharmaceutically acceptable salt or stereoisomer thereof.

4. The bifunctional compound of claim 1, which is represented by formula (I-1c):

(I-1c)

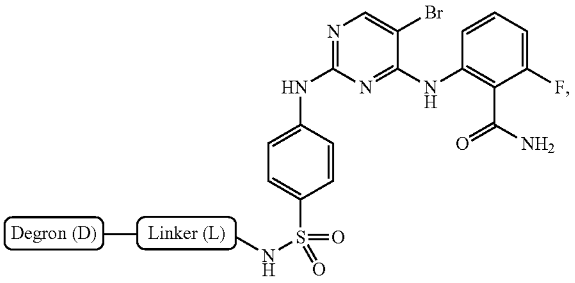

or a pharmaceutically acceptable salt or stereoisomer thereof.

5. The bifunctional compound of claim 1, which is represented by formula (I-1l):

(I-1l)

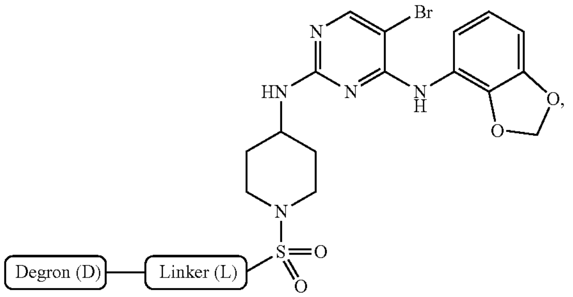

or a pharmaceutically acceptable salt or stereoisomer thereof.

6. The bifunctional compound of claim 1, which is represented by formula (I-1m):

(I-1m)

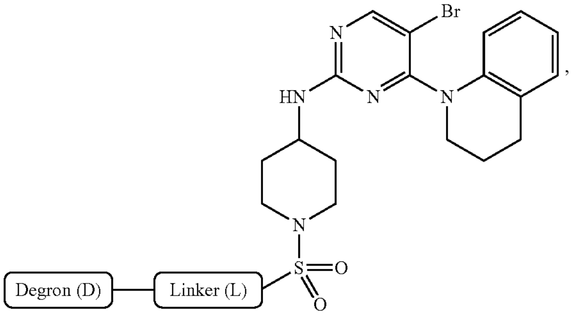

or a pharmaceutically acceptable salt or stereoisomer thereof.

7. The bifunctional compound of claim 1, which is represented by formula (I-1n):

(I-1n)

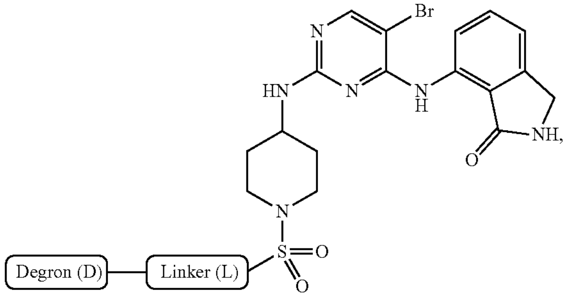

or a pharmaceutically acceptable salt or stereoisomer thereof.

8. The bifunctional compound of claim 1, which is represented by formula (I-1o):

(I-1o)

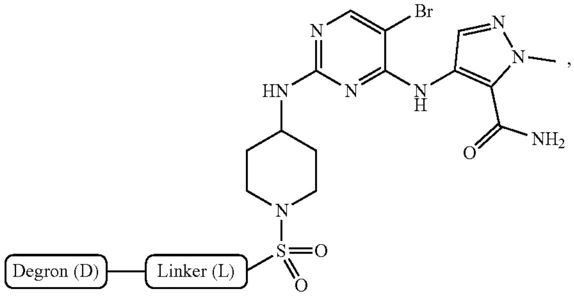

or a pharmaceutically acceptable salt or stereoisomer thereof.

9. The bifunctional compound of claim 1, which is represented by formula (I-1p):

(I-1p)

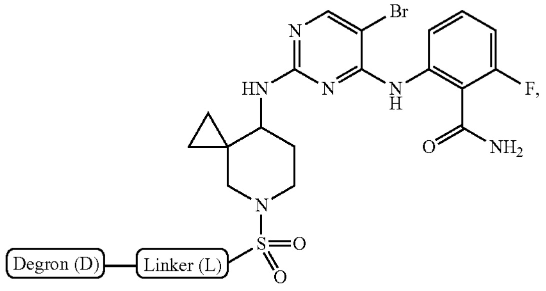

or a pharmaceutically acceptable salt or stereoisomer thereof.

10. The bifunctional compound of claim 1, which is represented by formula (I-1q):

(I-1q)

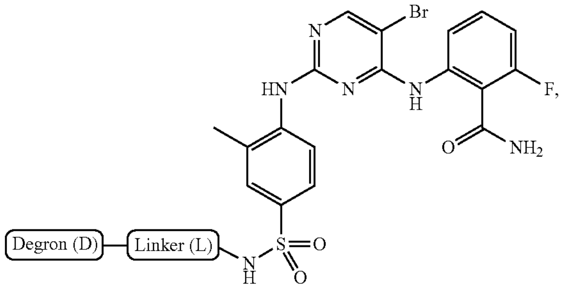

or a pharmaceutically acceptable salt or stereoisomer thereof.

11. The bifunctional compound of claim 1, which is represented by formula (I-1r):

(I-1r)

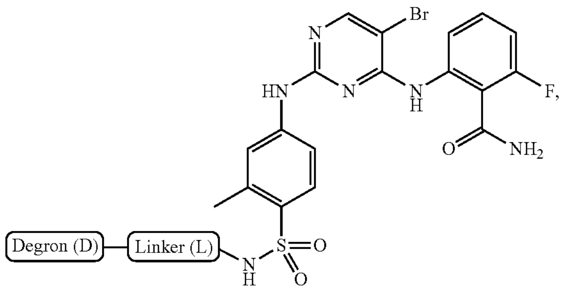

or a pharmaceutically acceptable salt or stereoisomer thereof.

12. The bifunctional compound of claim 1, wherein the linker is an alkylene chain which may be interrupted by, and/or terminate at either or both termini in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, $—S(O)_2—$, —OS(O)—, —S(O)O—, —S(O)—, $—OS(O)_2—$, $—S(O)_2O—$, $—N(R')S(O)_2—$, $—S(O)_2N(R')—$, —N(R')S(O)—, —S(O)N(R')—, $—N(R')S(O)_2N(R')—$, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different.

13. The bifunctional compound of claim 12, wherein the linker is an alkylene chain having 1-10 alkylene units and terminating in

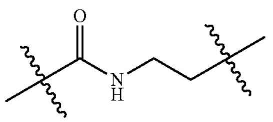,
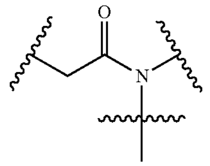,
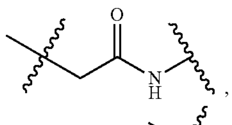,
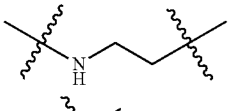, or
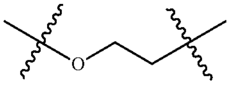.

14. The bifunctional compound of claim 1, wherein the linker is a polyethylene glycol chain which may terminate at either or both termini in at least one of —S—, —N(R')—, —C≡C—, —C(O)—, —C(O)O—, —OC(O)—, —OC(O)O—, —C(NOR')—, —C(O)N(R'), —C(O)N(R')C(O)—, —C(O)N(R')C(O)N(R')—, —N(R')C(O)—, —N(R')C(O)N (R')—, —N(R')C(O)O—, —OC(O)N(R')—, —C(NR')—, —N(R')C(NR')—, —C(NR')N(R')—, —N(R')C(NR')N(R')—, —OB(Me)O—, —$S(O)_2$—, —OS(O)—, —S(O)O—, —S(O)—, —$OS(O)_2$—, —$S(O)_2O$—, —N(R')$S(O)_2$—, —$S(O)_2N$(R')—, —N(R')S(O)—, —S(O)N(R'), —N(R')$S(O)_2N$(R'), —N(R')S(O)N(R'), $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different.

15. The bifunctional compound of claim 14, wherein the linker is a polyethylene glycol linker having 2-8 PEG units and terminating in

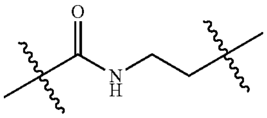
,
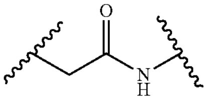
,
or
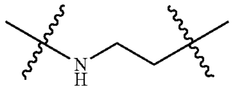
.

16. The bifunctional compound of claim 1, which is represented by any one of the following formulas:

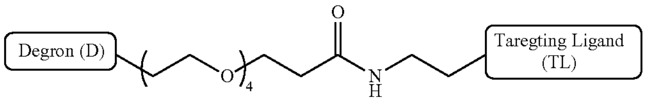
,
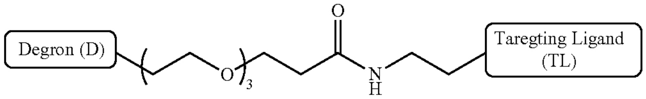
,
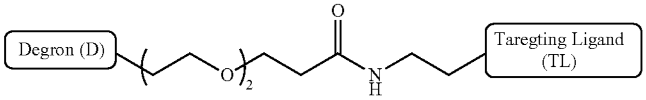
,
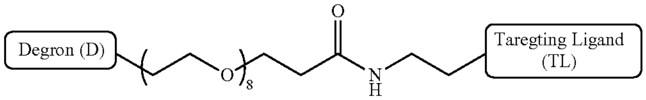
,
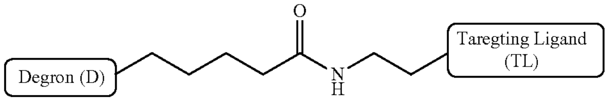
,
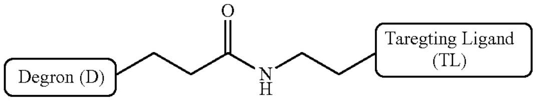
,
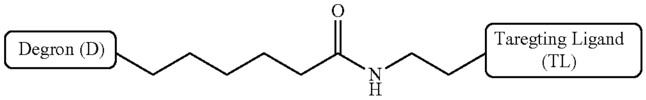
,
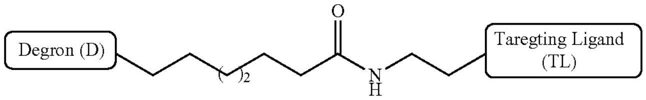
,
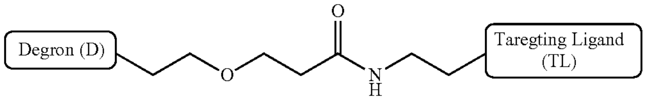
,
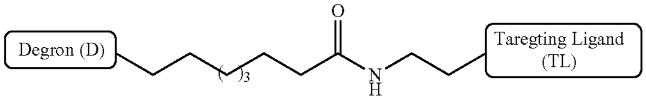
,
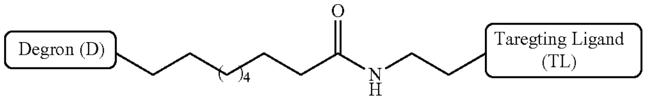
,
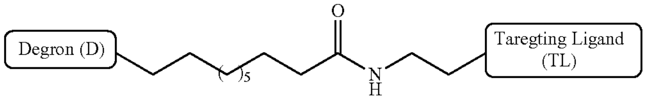
,
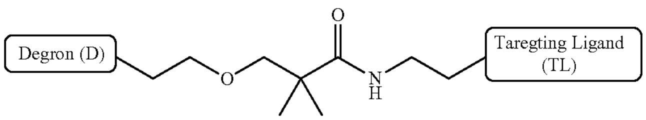
,
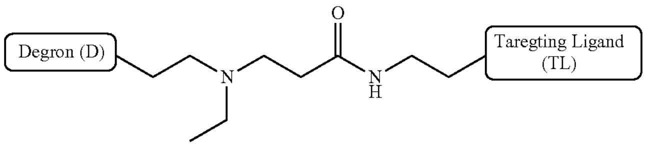
, -continued
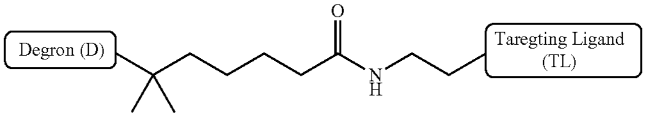
,
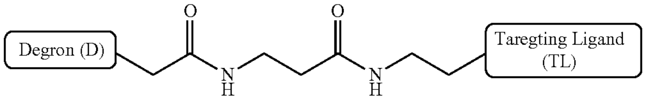
,
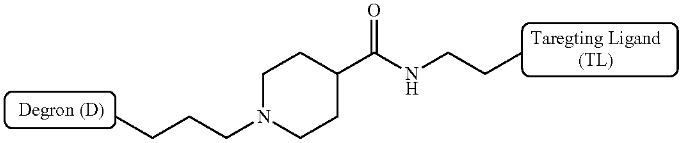
,
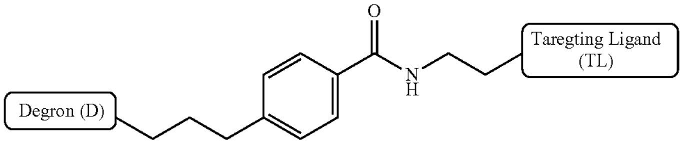
,
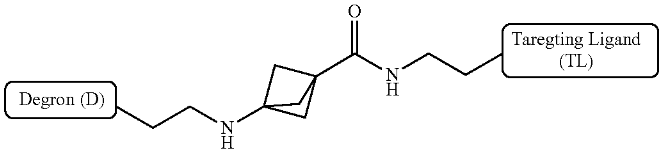
,
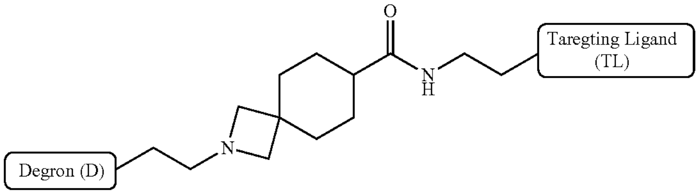
,
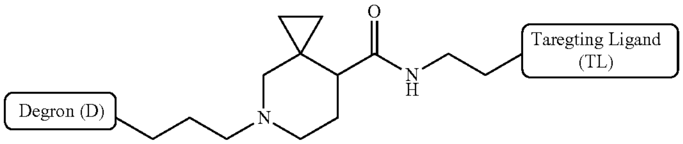
,
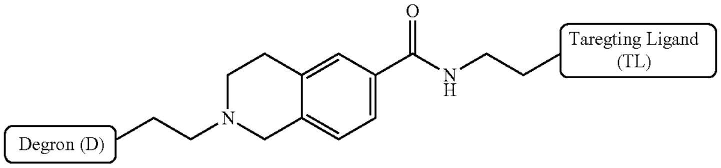
,
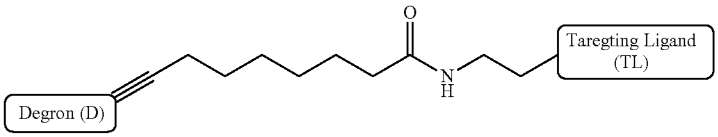
,
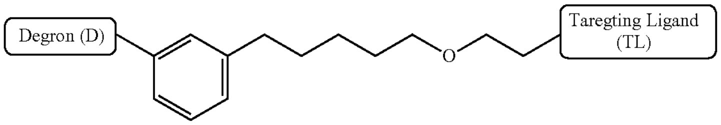
,
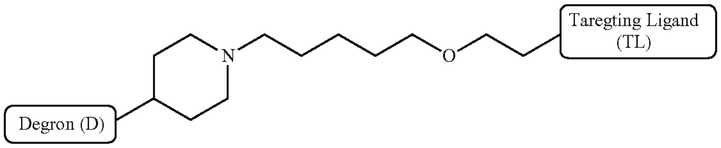
,
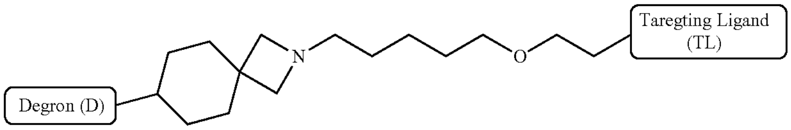
, -continued
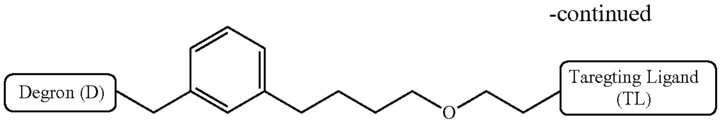
,
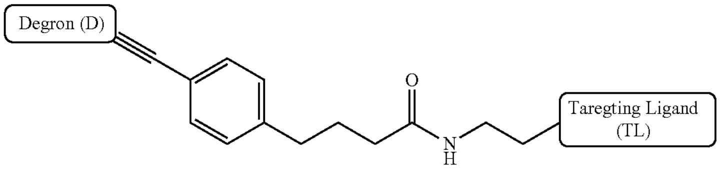
,
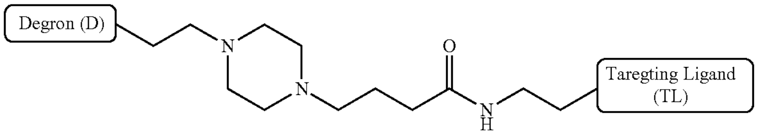
,
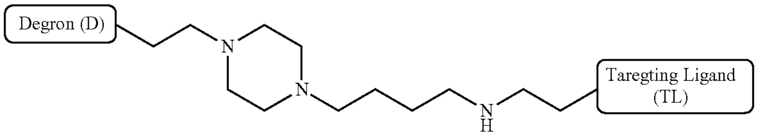
,
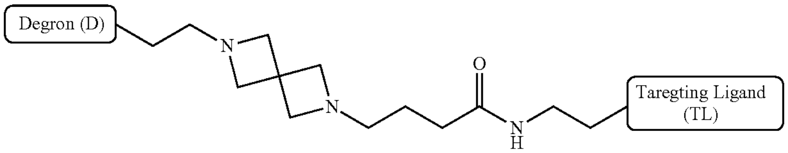
,
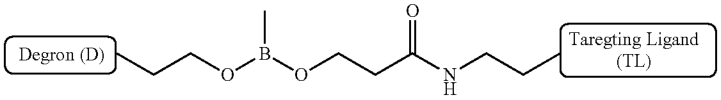
,
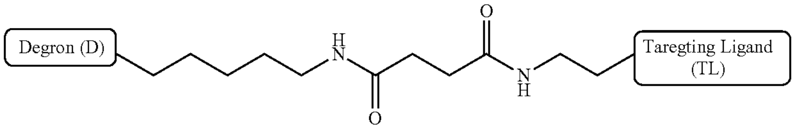
,
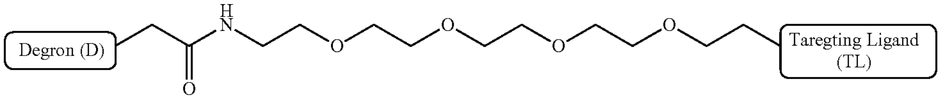
,
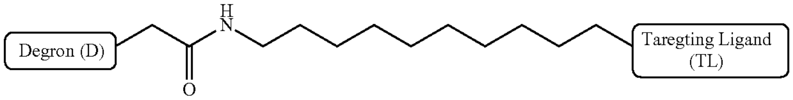
, or
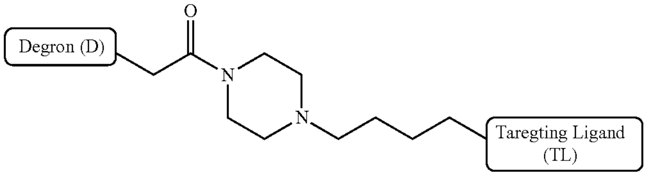
,
or a pharmaceutically acceptable salt or stereoisomer thereof.
17. The bifunctional compound of claim 1, which is represented by any one of the following formulas:

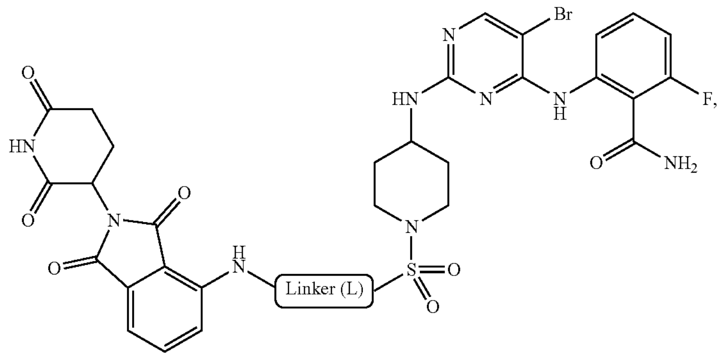
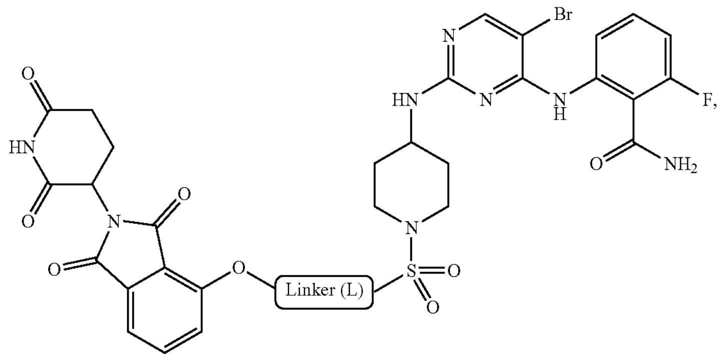
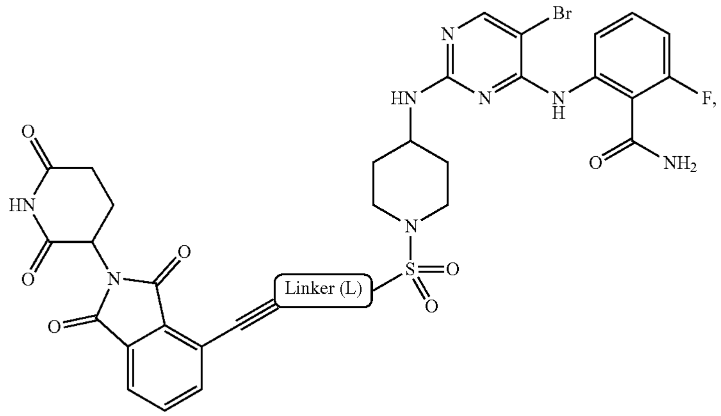
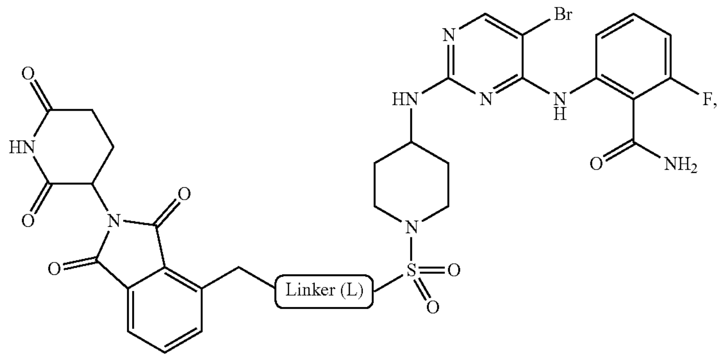

-continued
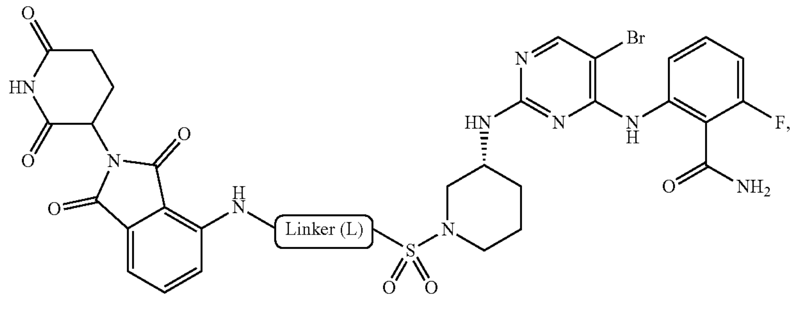
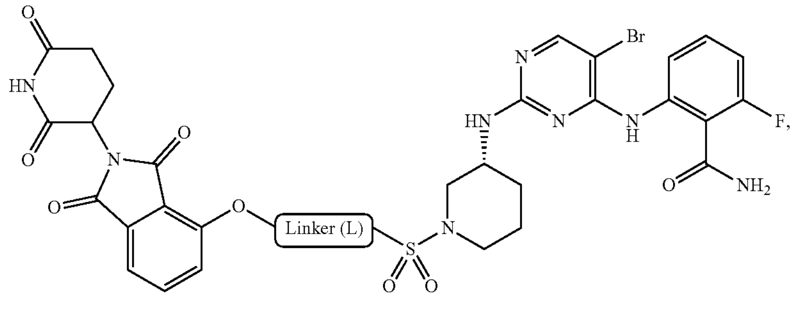
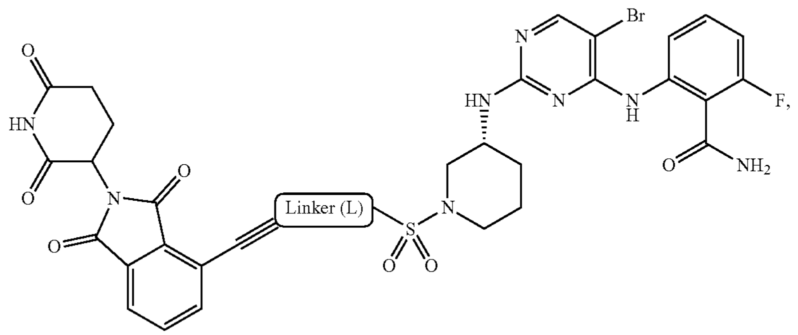
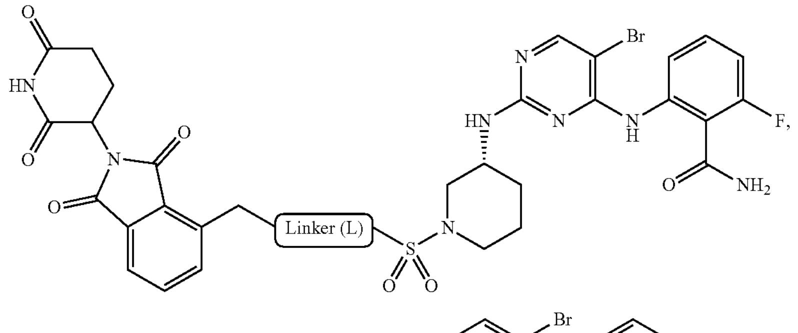
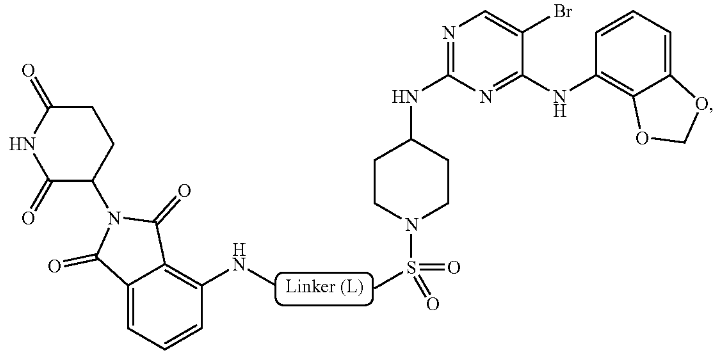

-continued
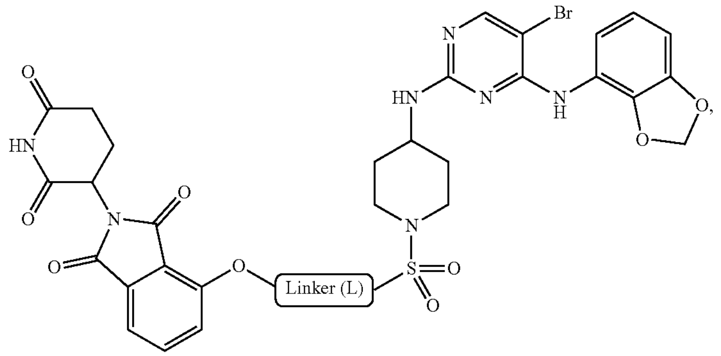
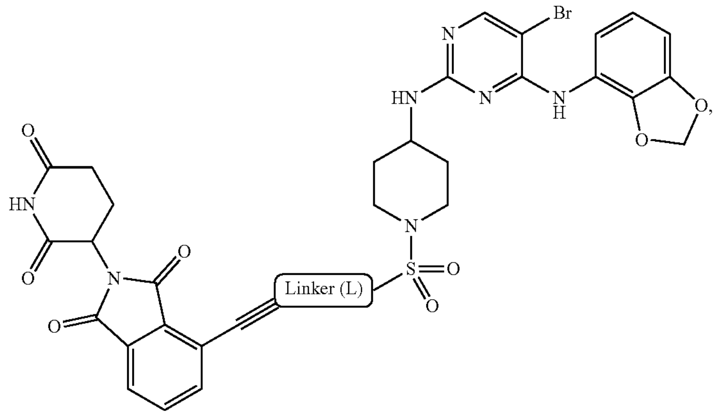
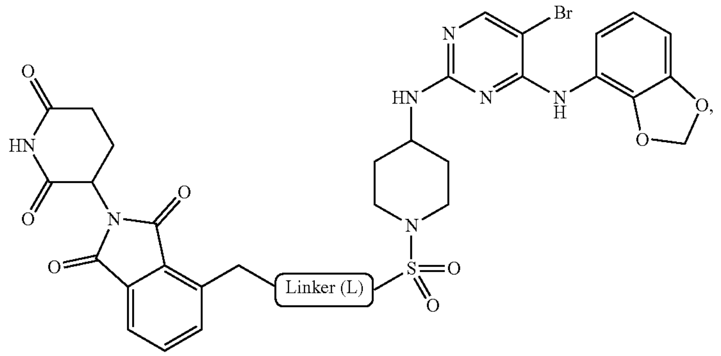
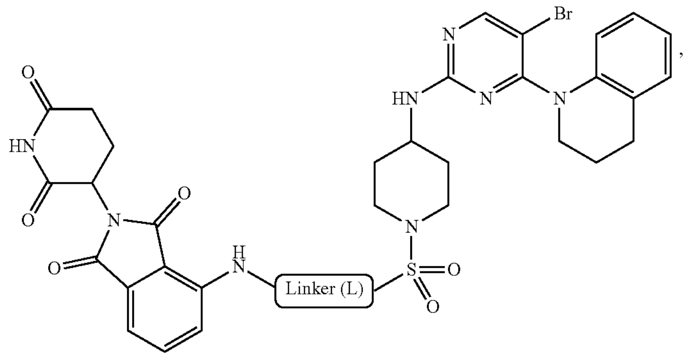

-continued
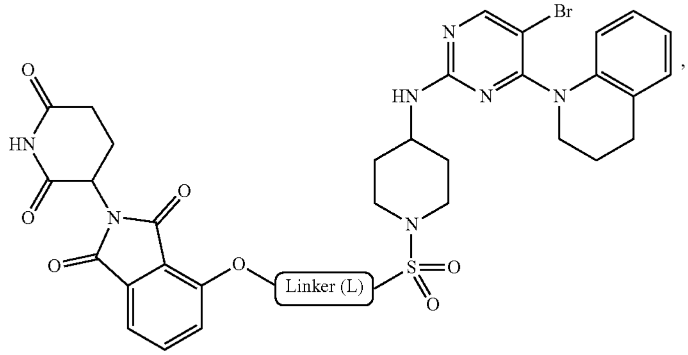
,
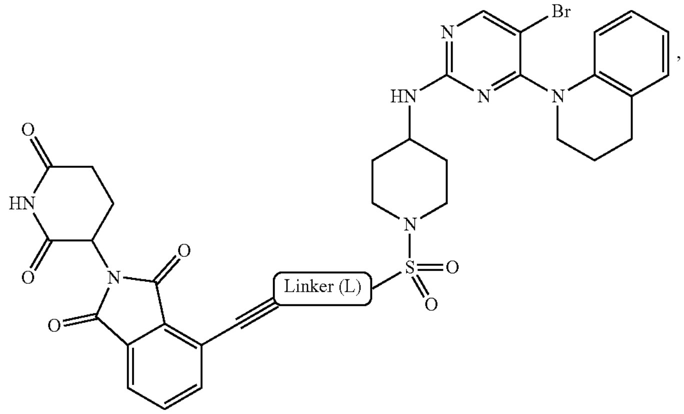
,
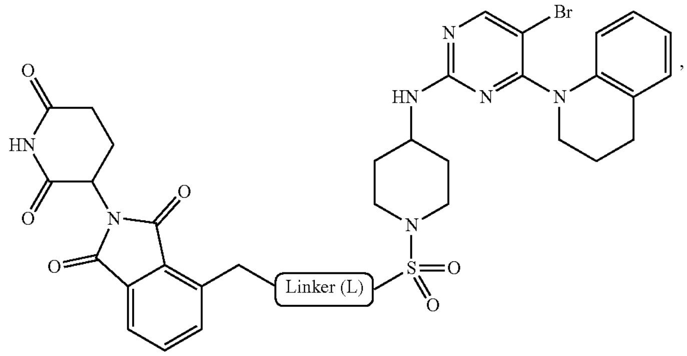
,
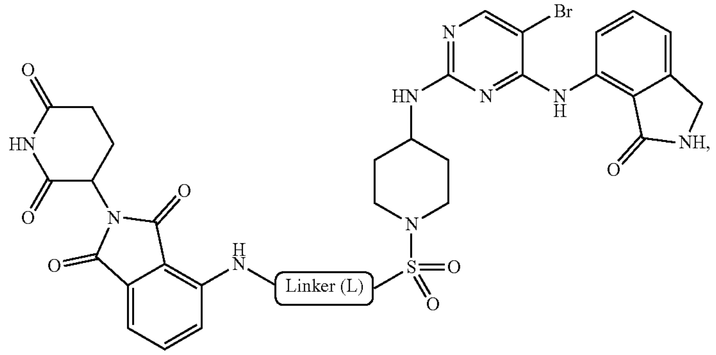
,

-continued
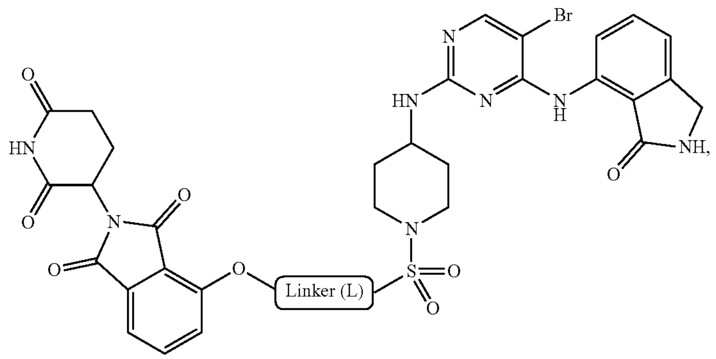
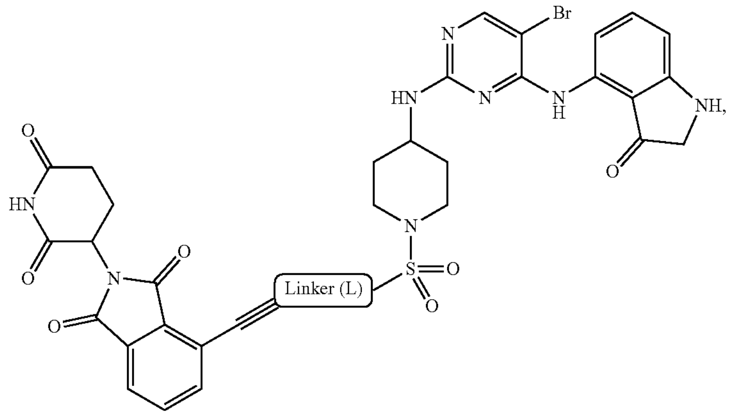
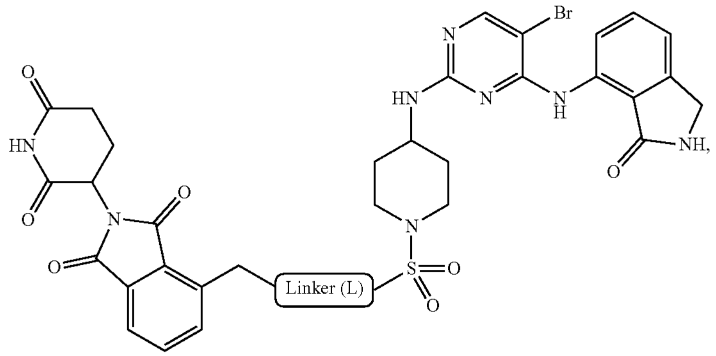
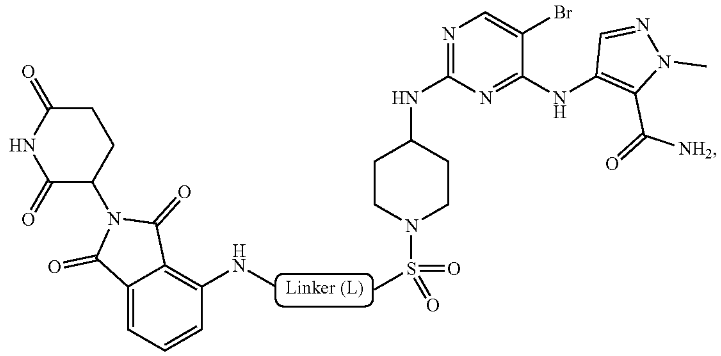

-continued
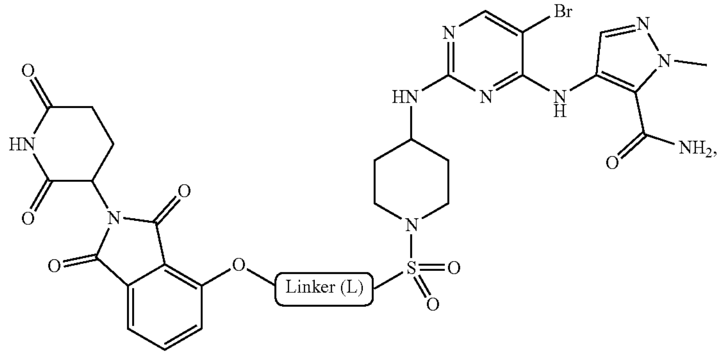
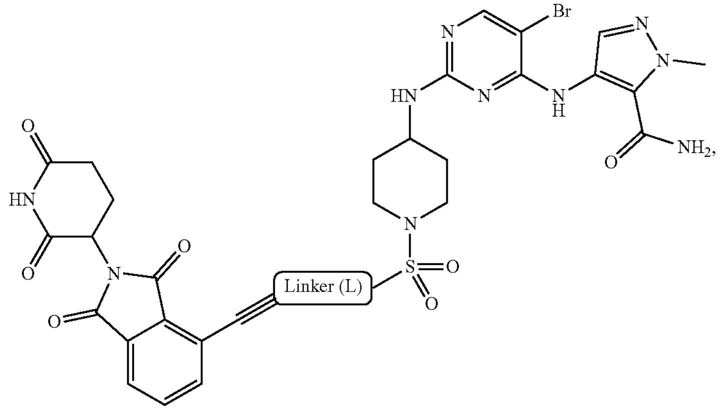
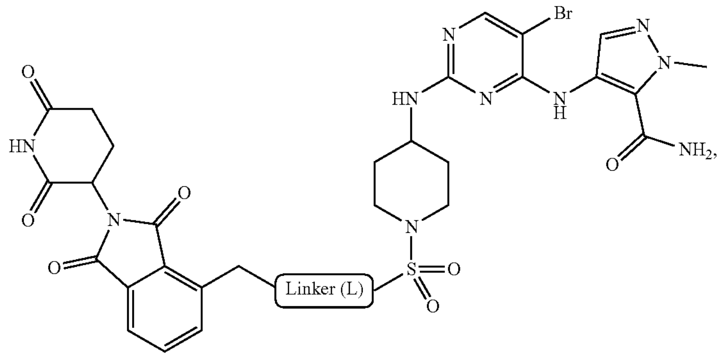
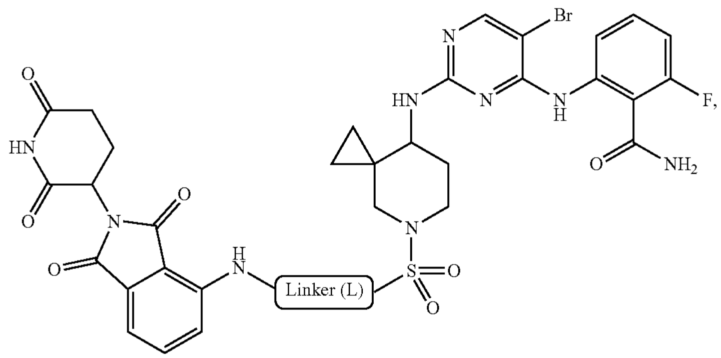

-continued
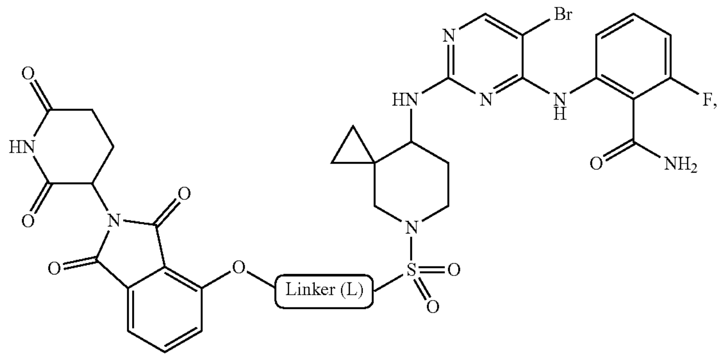
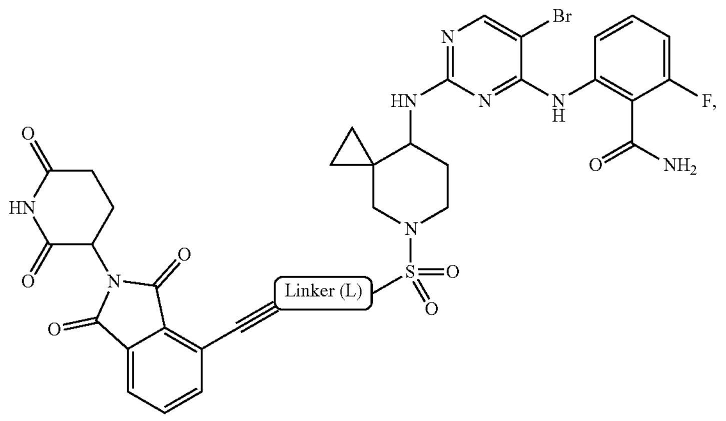
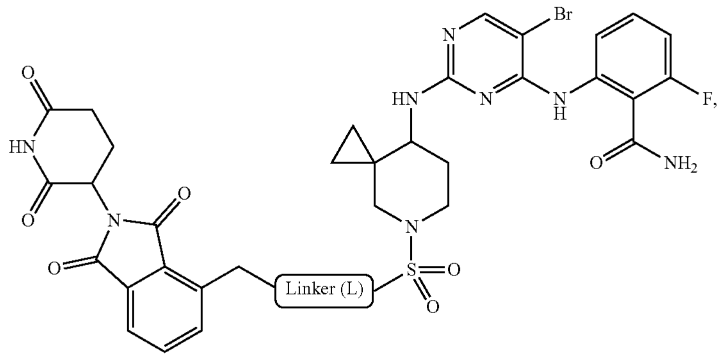
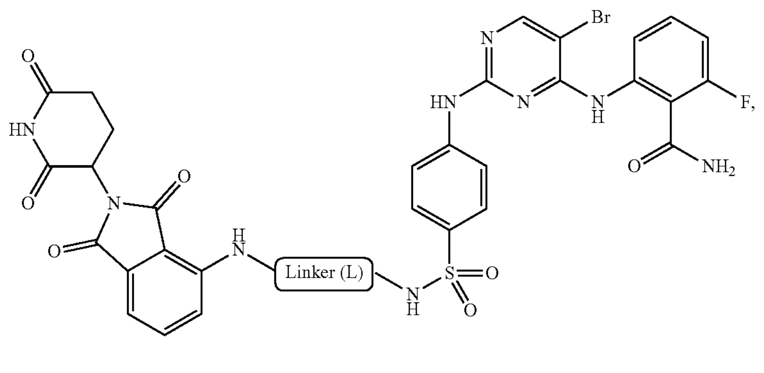

-continued
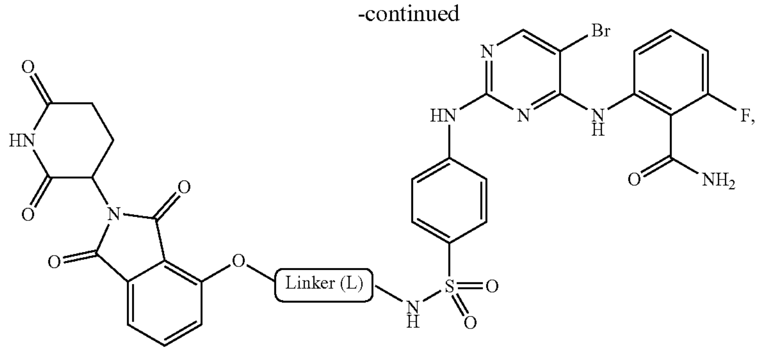
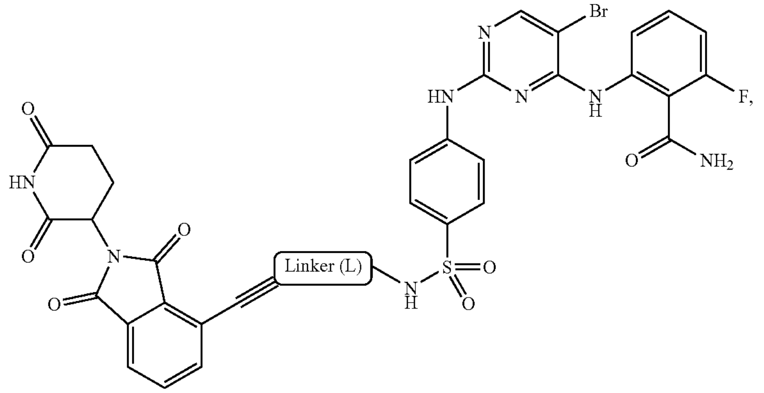
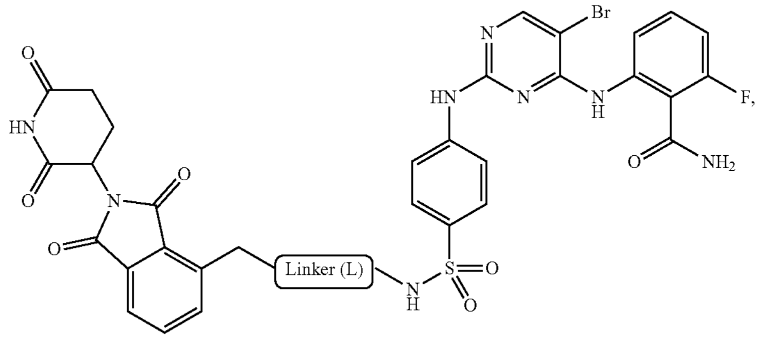
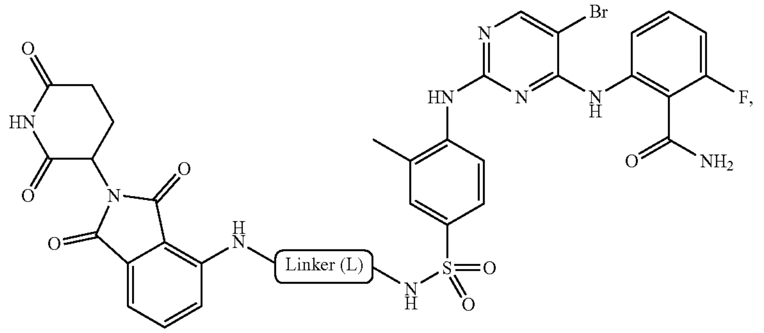
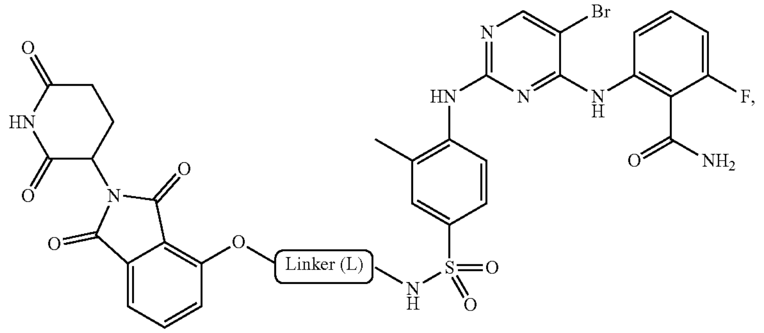

-continued
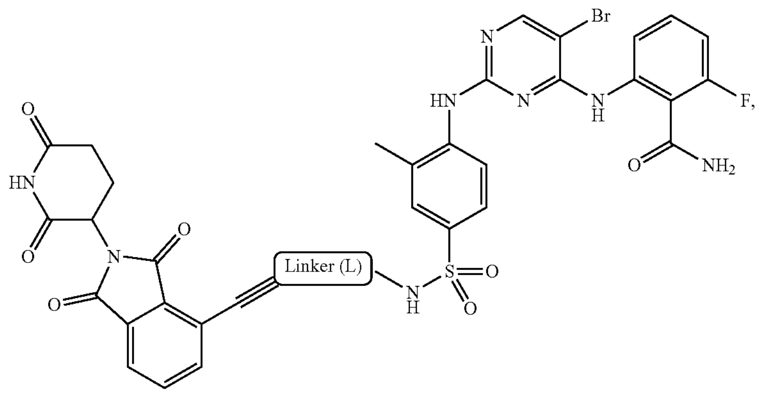
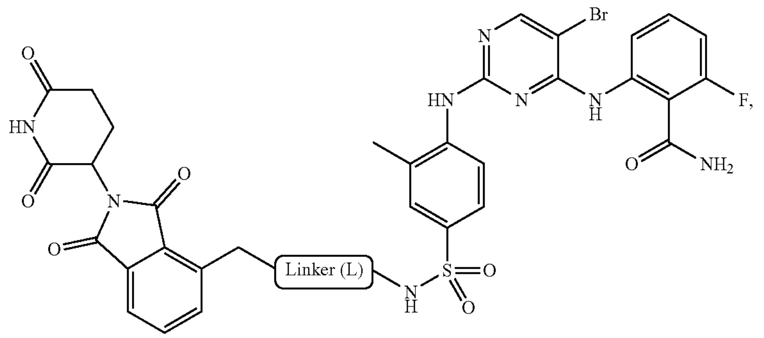
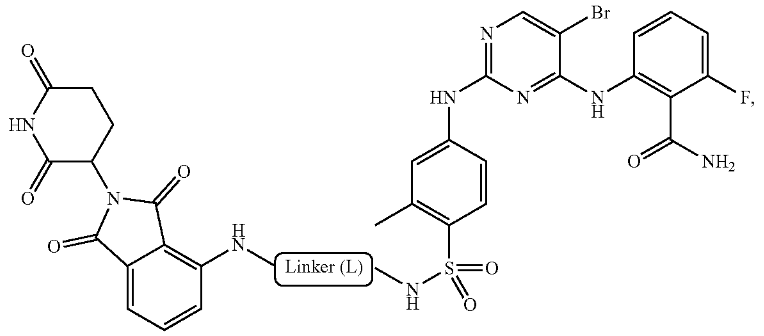
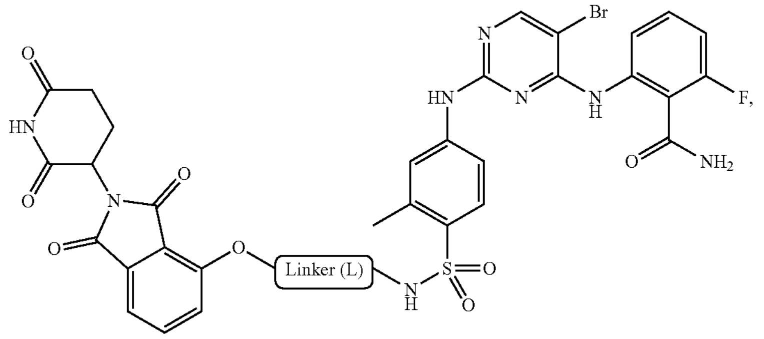

-continued
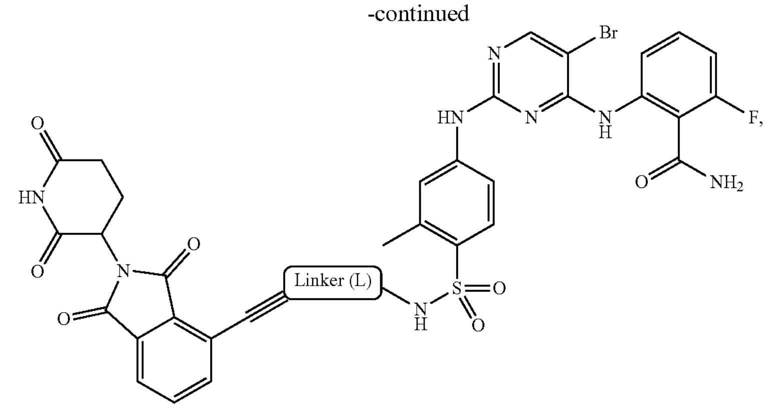
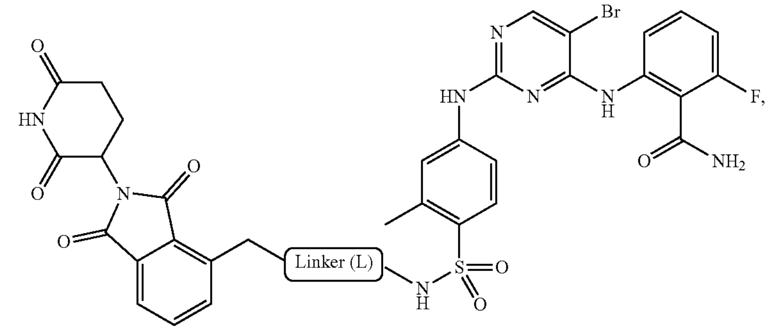
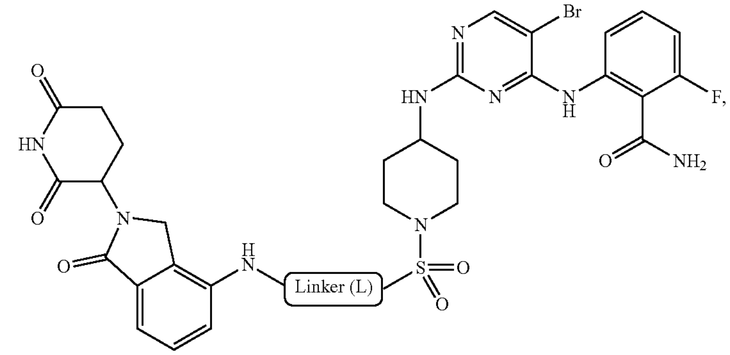
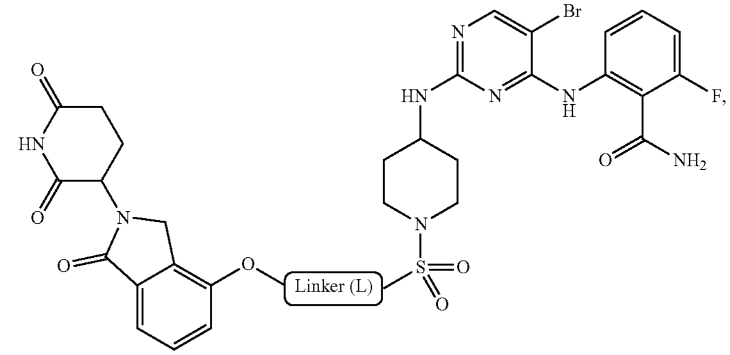

-continued
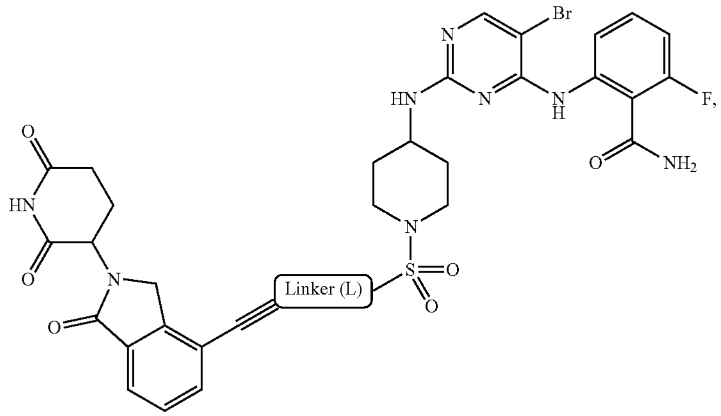
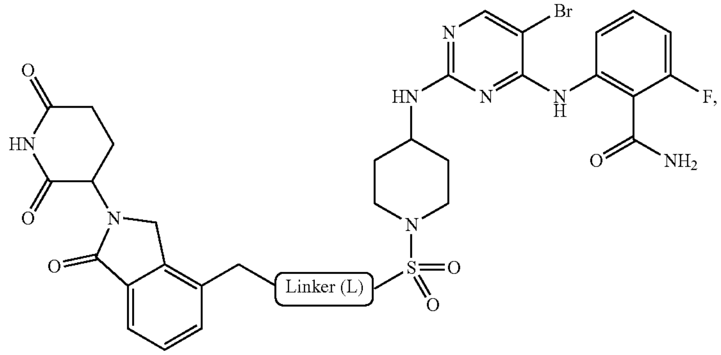
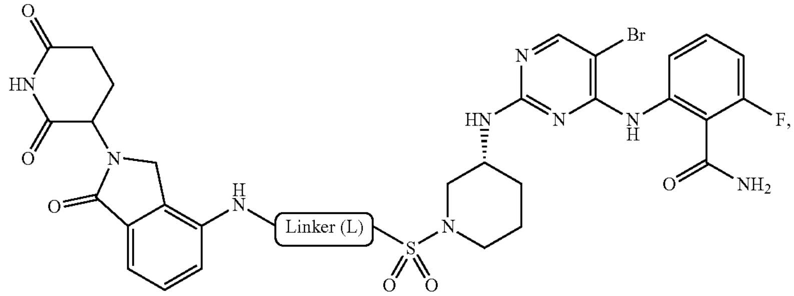
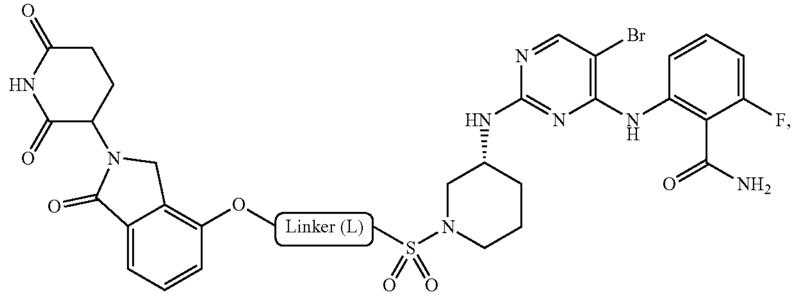
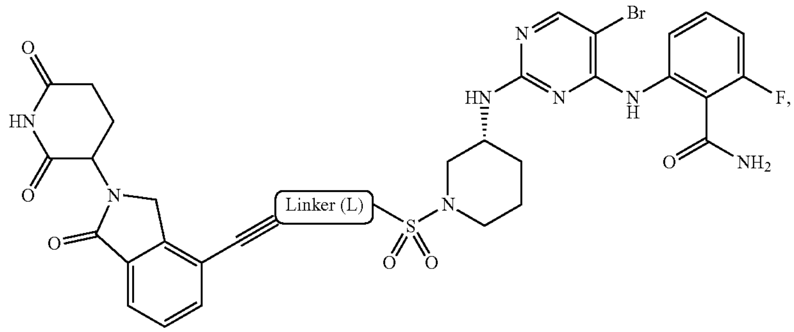

-continued
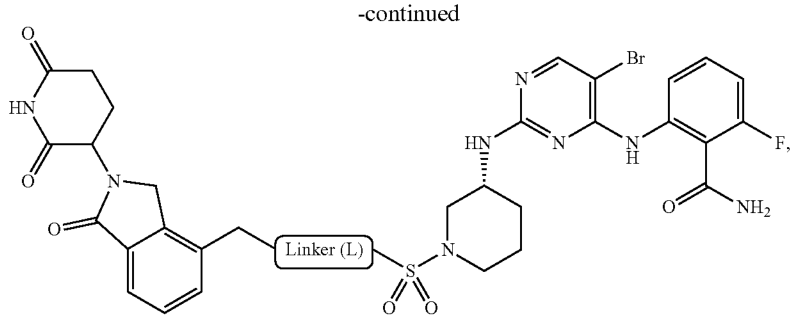
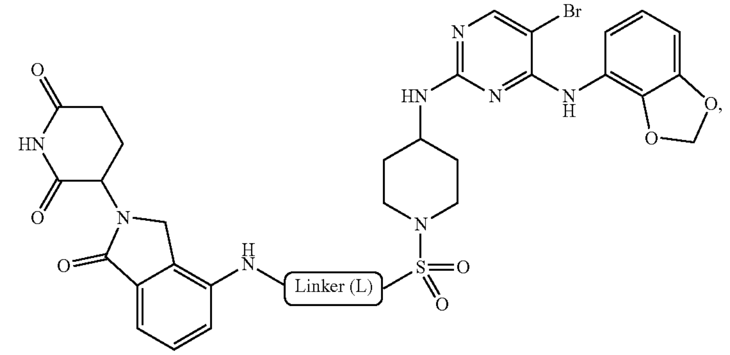
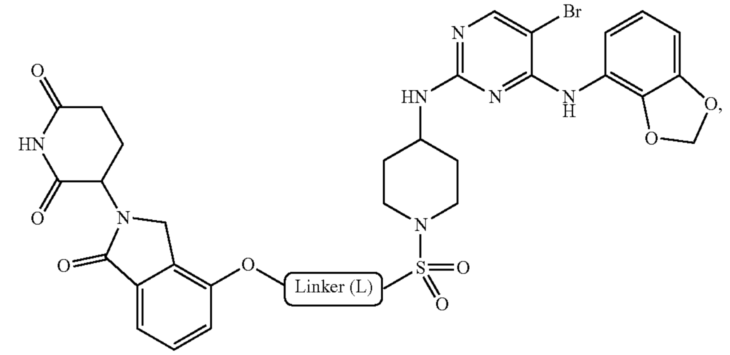
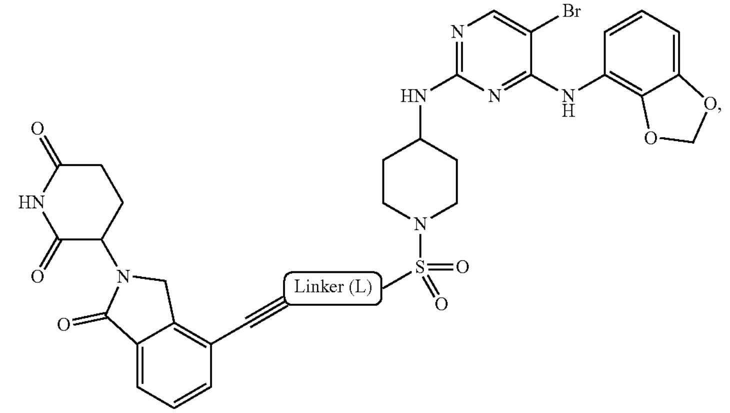

-continued
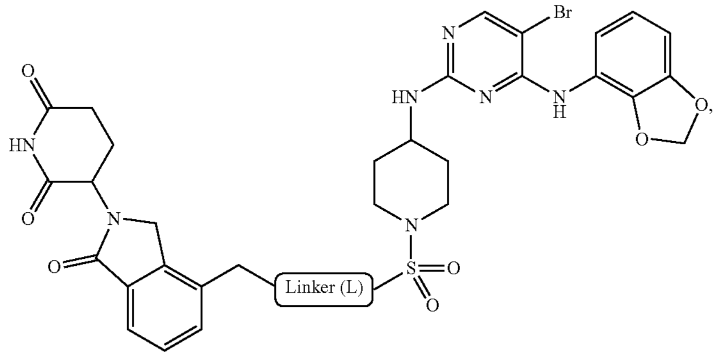
,
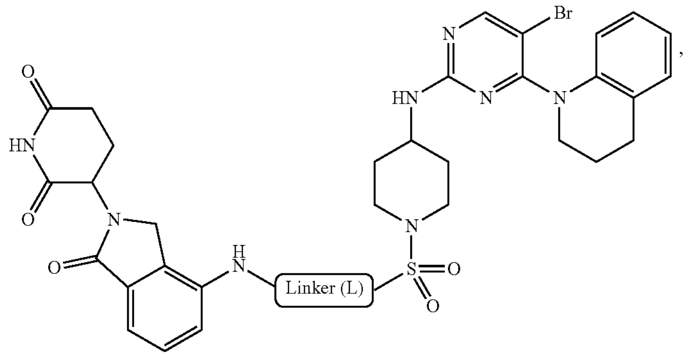
,
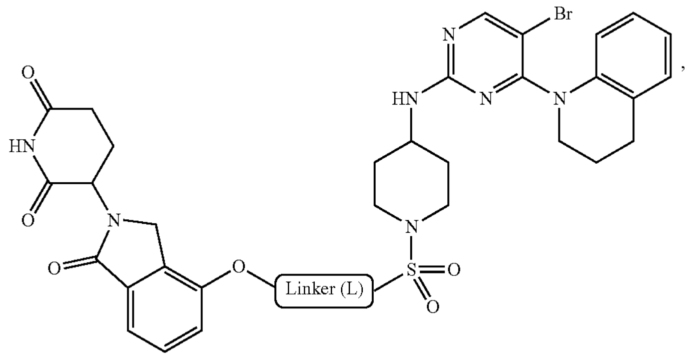
,
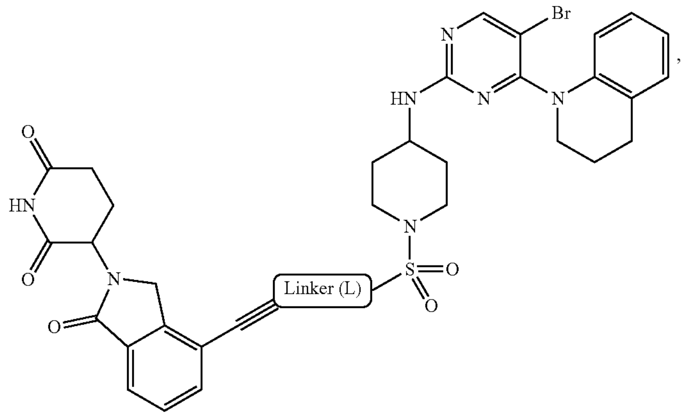
,

-continued
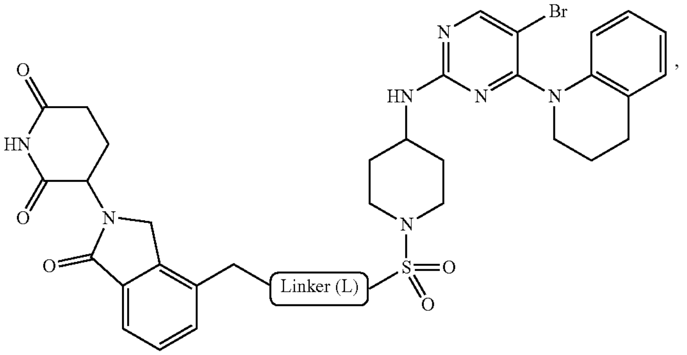
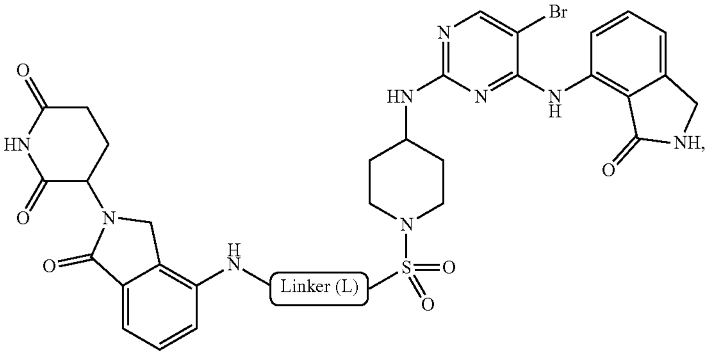
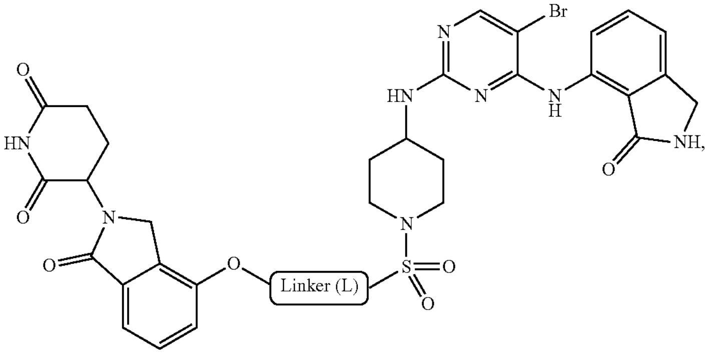
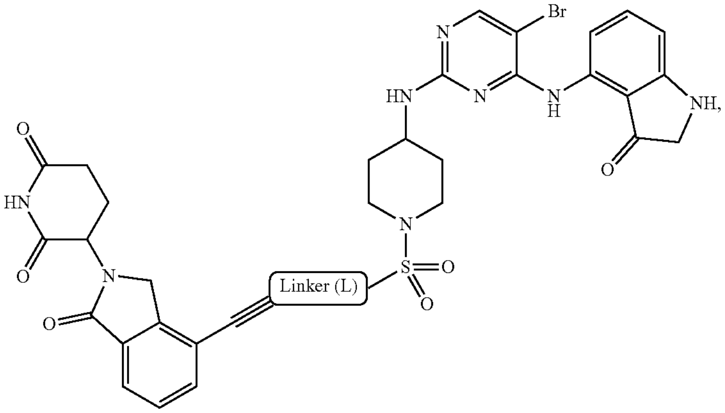

-continued
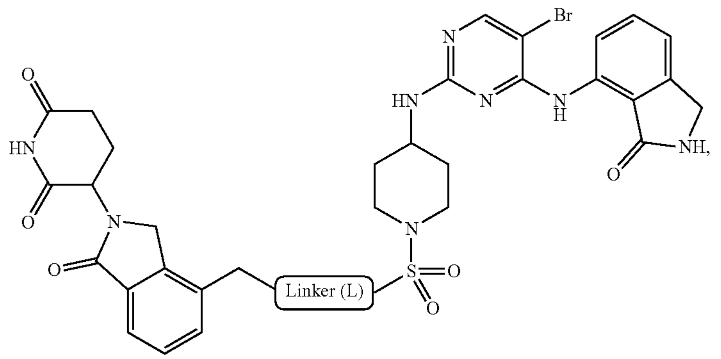
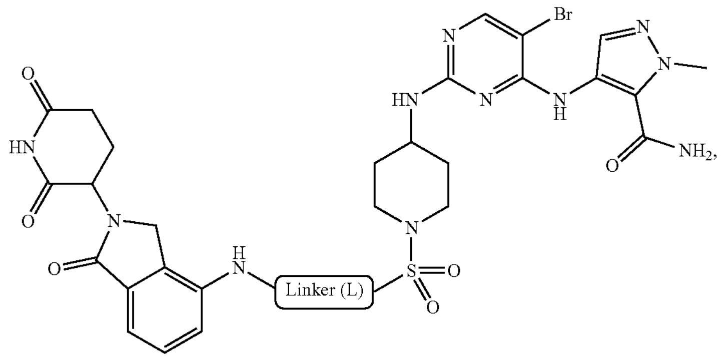
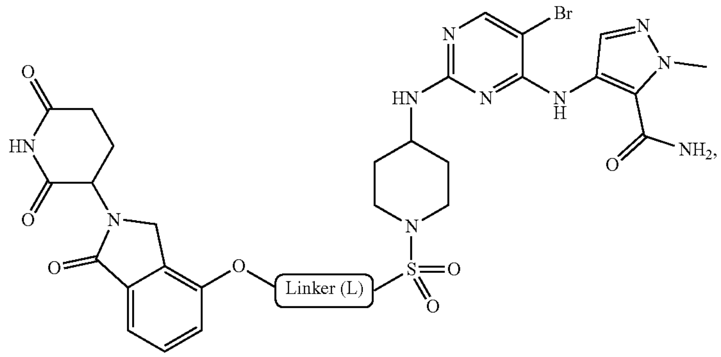
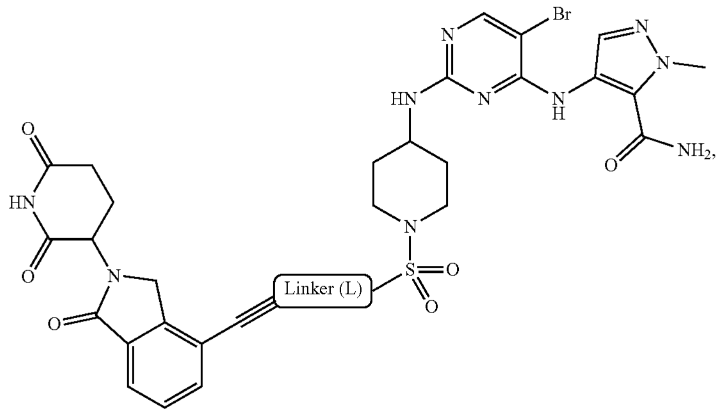

-continued
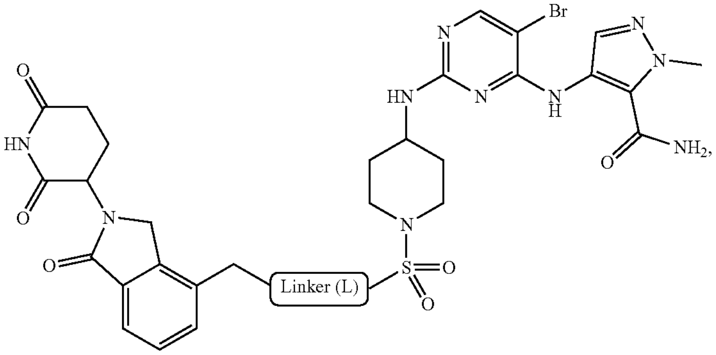
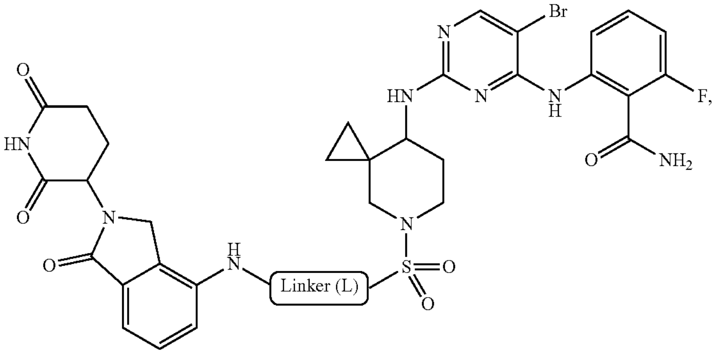
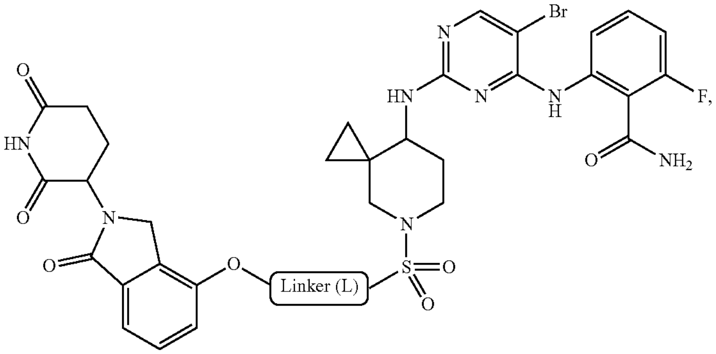
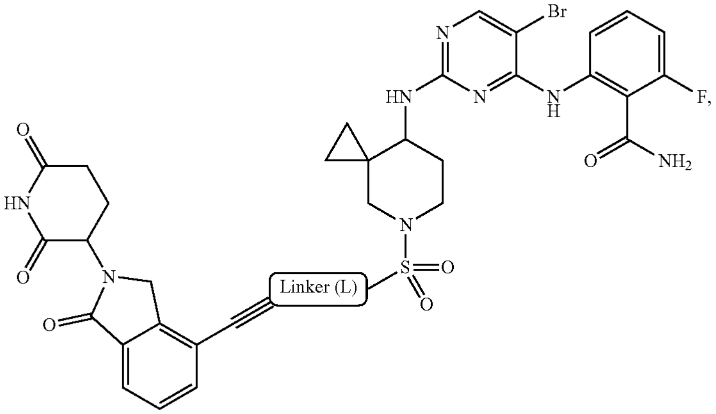

-continued
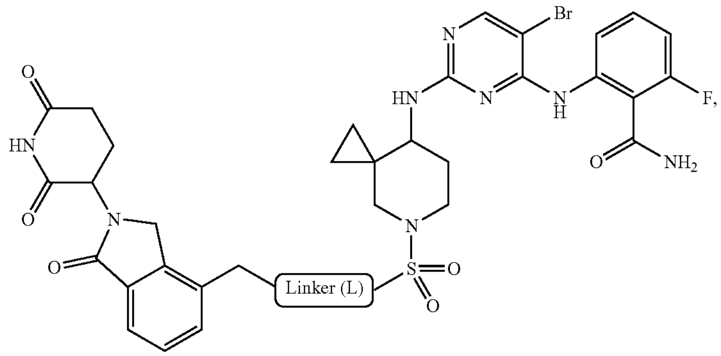
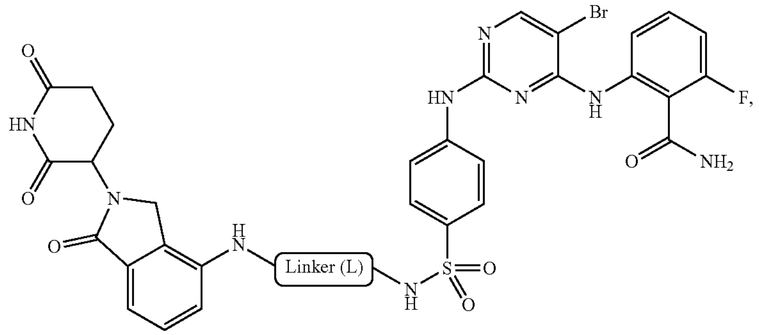
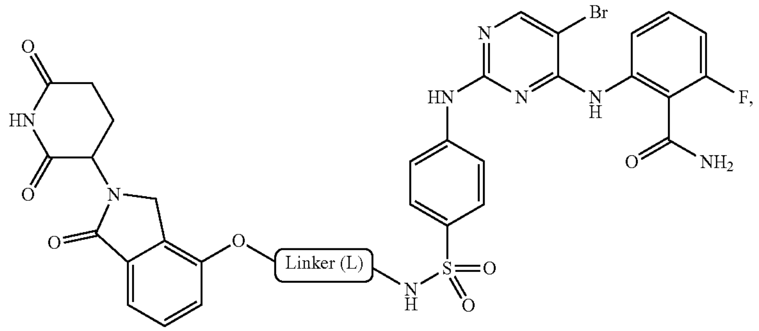
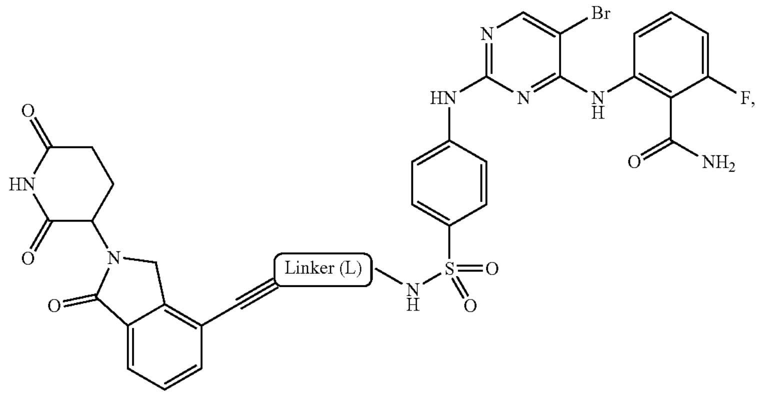

-continued
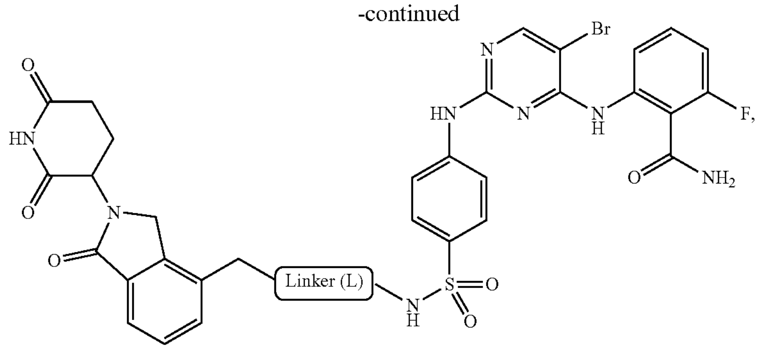
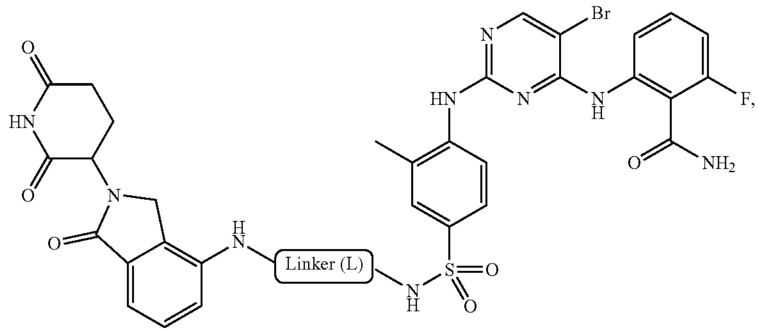
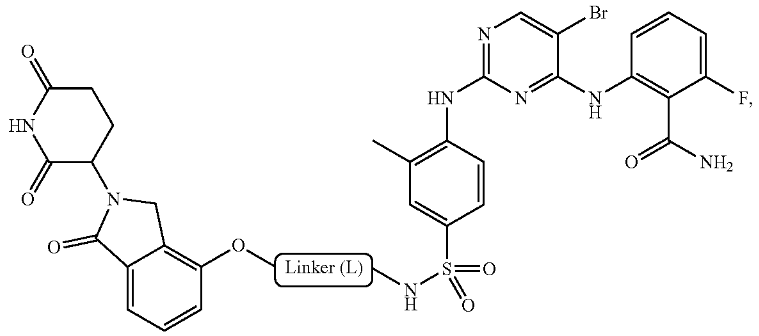
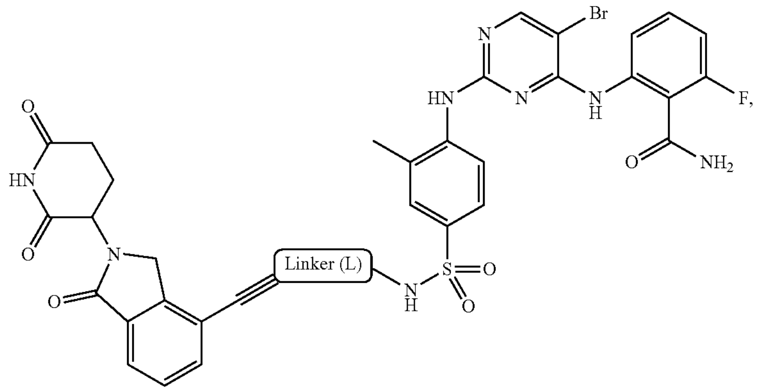
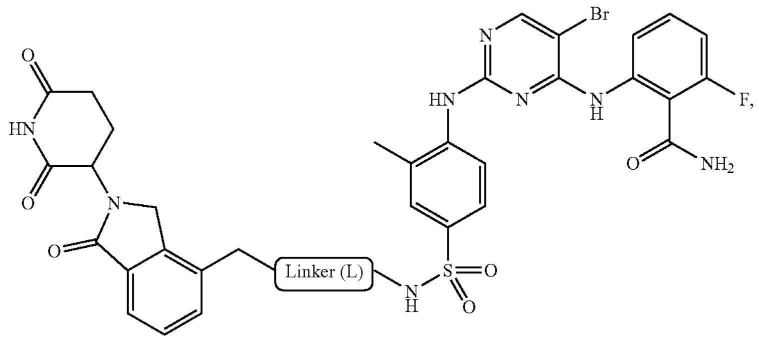

-continued
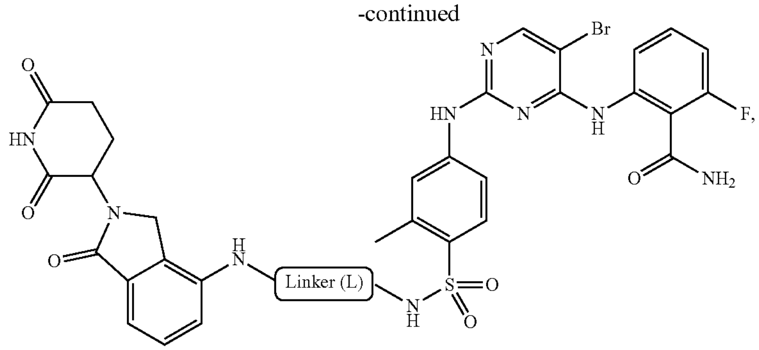
,
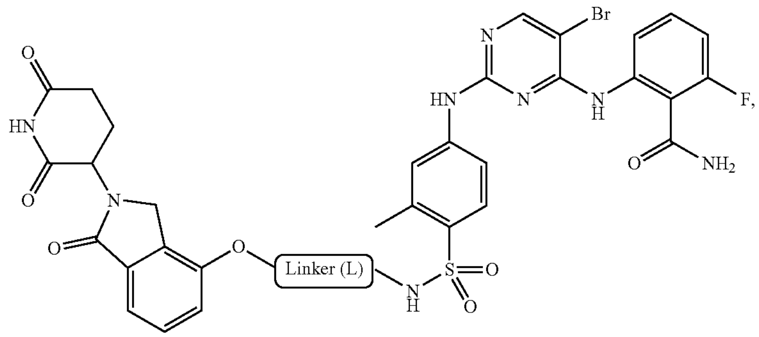
,
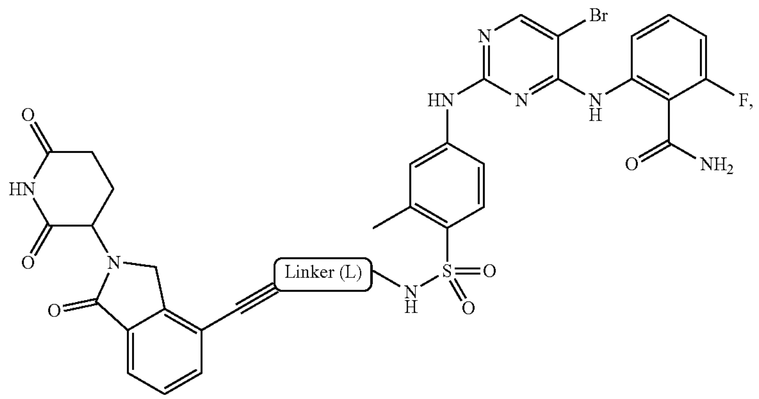
, and
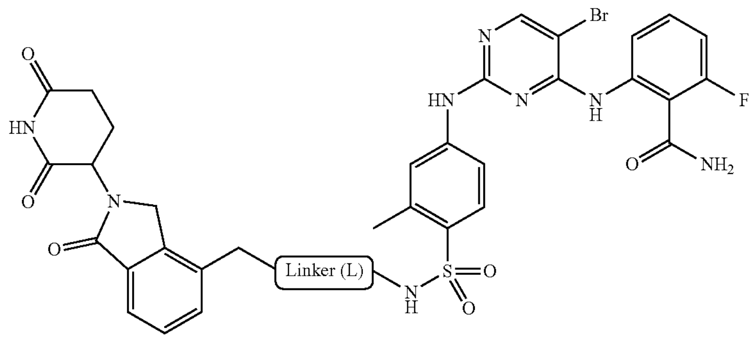

or a pharmaceutically acceptable salt or stereoisomer thereof.

18. A bifunctional compound having a structure represented by formula:

(I)

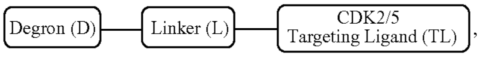

wherein the CDK2/5 targeting ligand is represented by the formula (TL-1):

(TL-1)

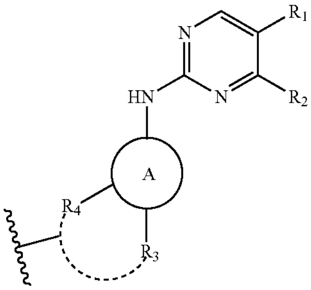

wherein:

$R_1$ represents Br or $CF_3$;

$R_2$ represents $OR_5$, $NHR_5$,

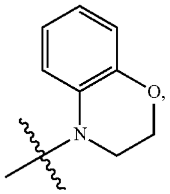

or

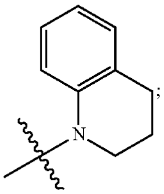

$R_5$ represents

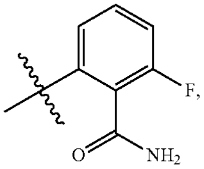

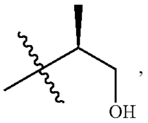

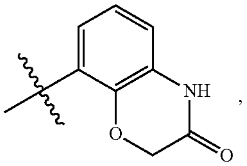

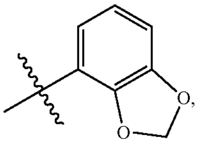

-continued

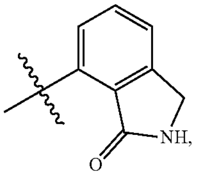

or

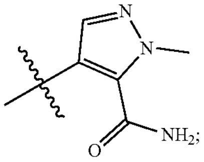

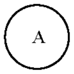

represents optionally substituted cyclopentyl, optionally substituted cyclohexyl, optionally substituted phenyl, optionally substituted pyridinyl, optionally substituted pyrrolidinyl, or optionally substituted piperidinyl;

$R_3$ represents

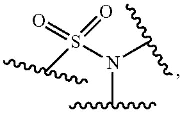

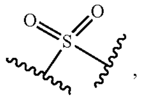

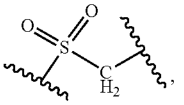

or

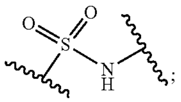

$R_4$ represents H, C(O), or

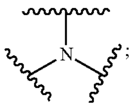 [SMILES: *N(*)*]

provided that when $R_3$ represents

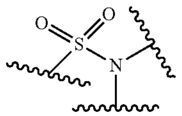

or

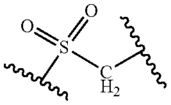

and $R_4$ represents C(O) or

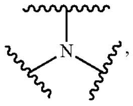

$R_3$ and $R_4$ together with the atoms to which they are bound form a 5-membered cyclic sulfonamide, wherein the degron is represented by any one of the structures:

(D3a)

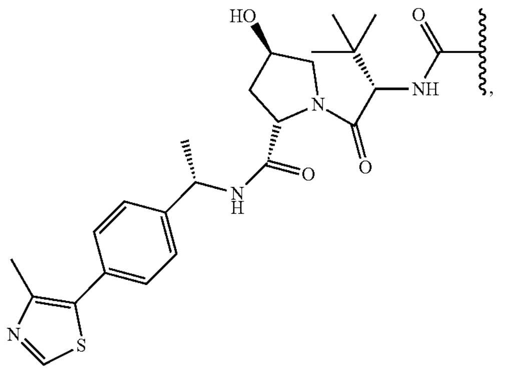

(D3b)

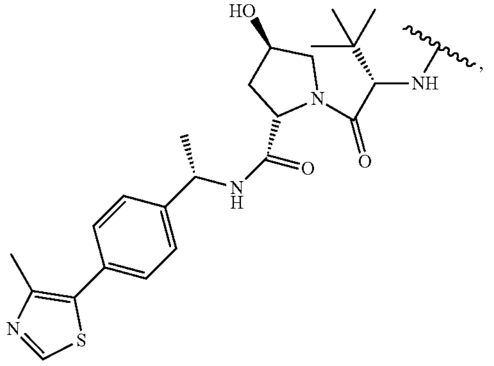

(D3c)

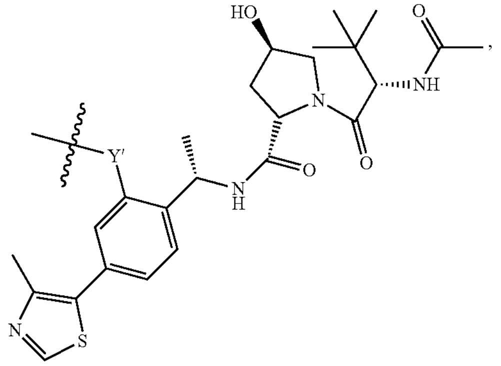

wherein Y' is a bond, NH, O or $CH_2$; or (D3d)

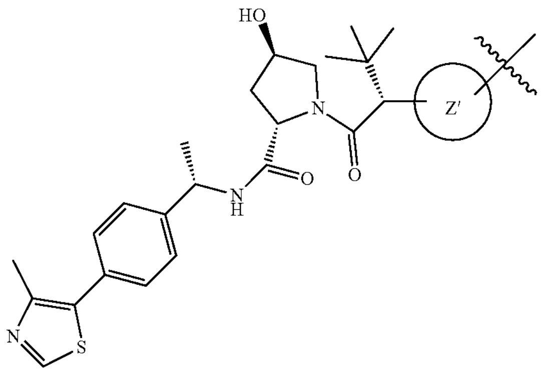

, wherein Z' is a cyclic group; or stereoisomer thereof, and the linker is an alkylene chain which may be interrupted by, and/or terminate at either or both termini in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —$S(O)_2$—, —OS(O)—, —S(O)O—, —S(O)—, —$OS(O)_2$—, —$S(O)_2O$—, —$N(R')S(O)_2$—, —$S(O)_2N(R')$—, —N(R')S(O)—, —S(O)N(R')—, —$N(R')S(O)_2N(R')$—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different, or the linker is a polyethylene glycol chain which may terminate at either or both termini in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —$S(O)_2$—, —OS(O)—, —S(O)O—, —S(O)—, —$OS(O)_2$—, —$S(O)_2O$—, —$N(R')S(O)_2$—, —$S(O)_2N(R')$—, —N(R')S(O)—, —S(O)N(R')—, —$N(R')S(O)_2N(R')$—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different, or a pharmaceutically acceptable salt or stereoisomer thereof.

19. The bifunctional compound of claim 18, which is represented by any one of the following formulas:

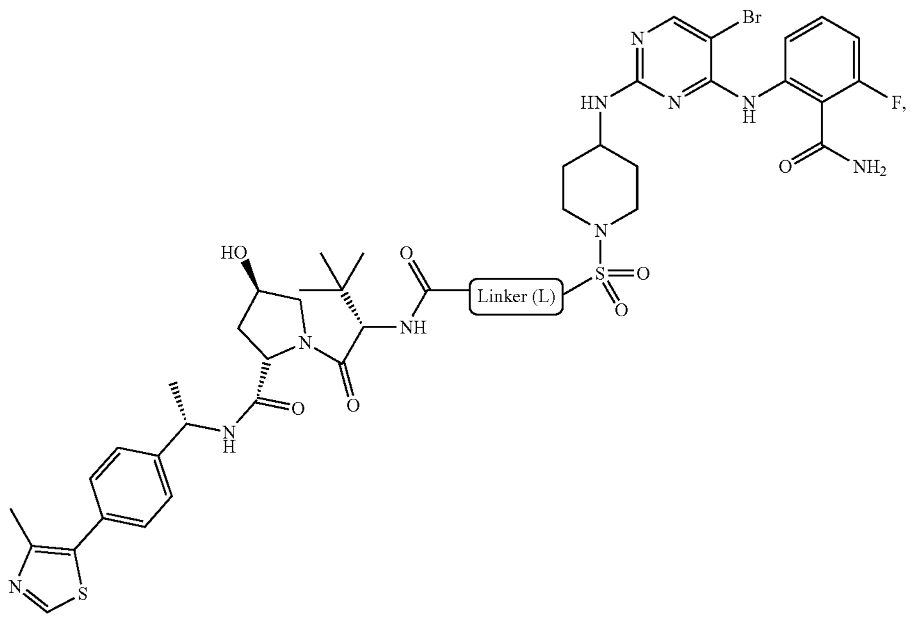
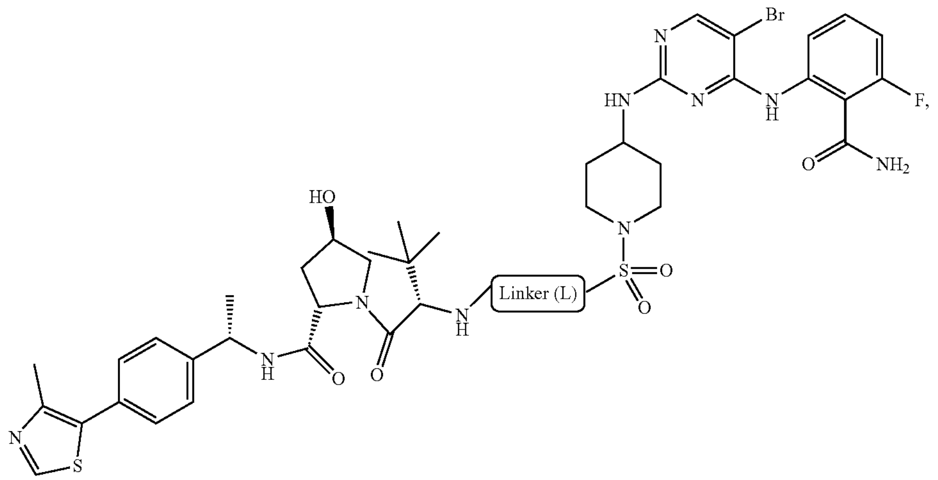
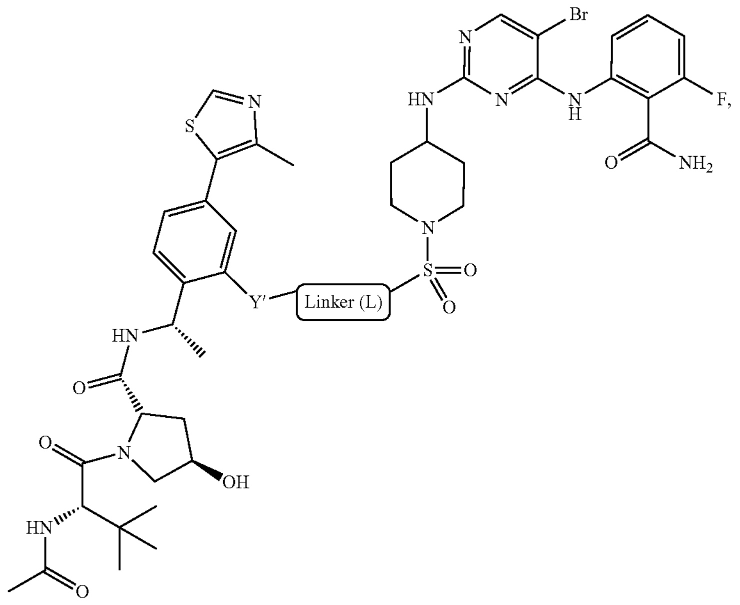

-continued
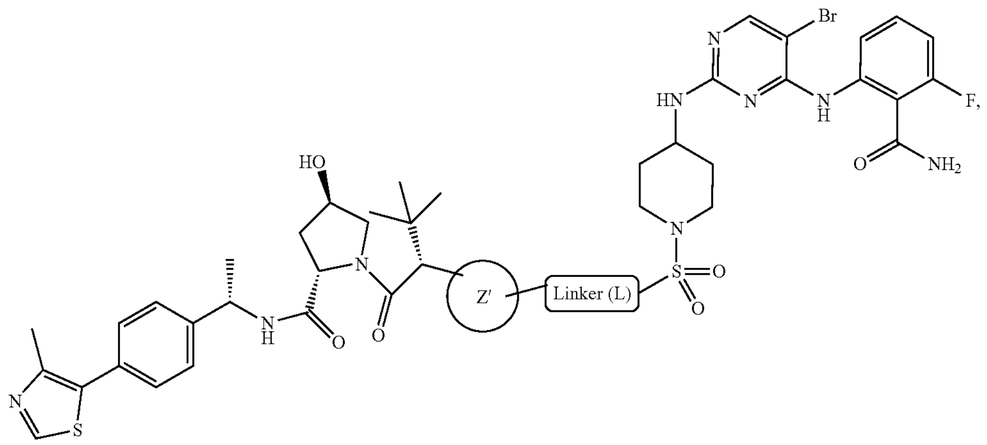
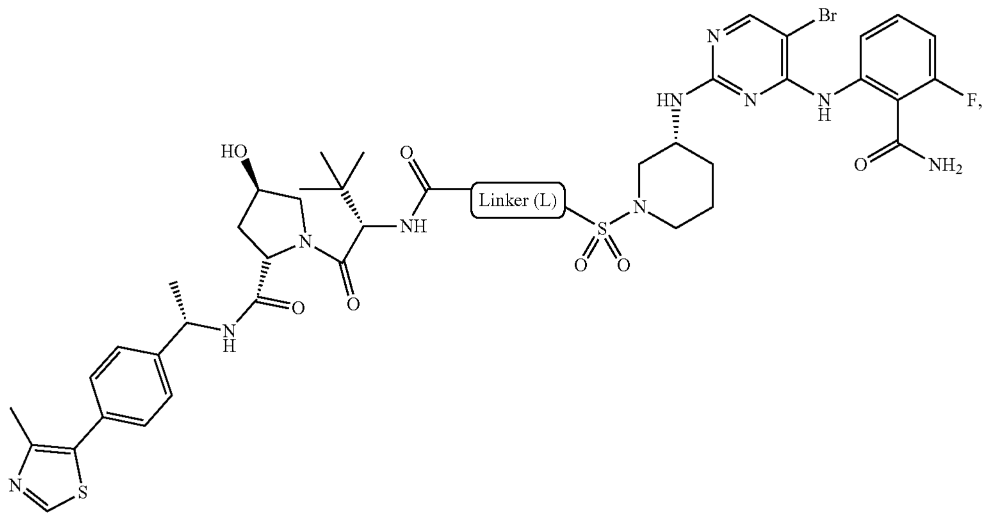
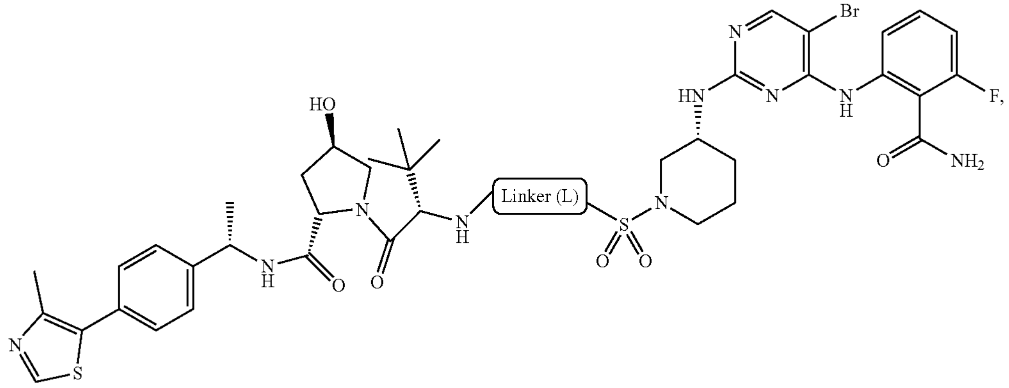

-continued
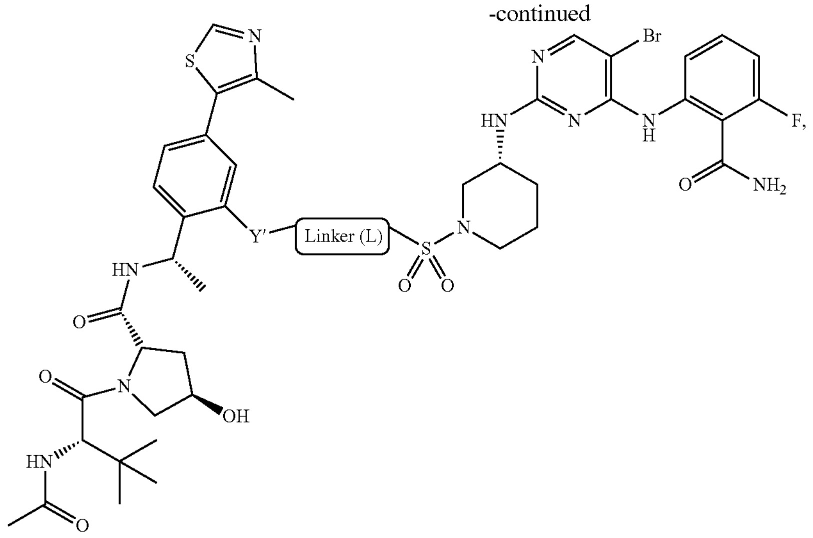
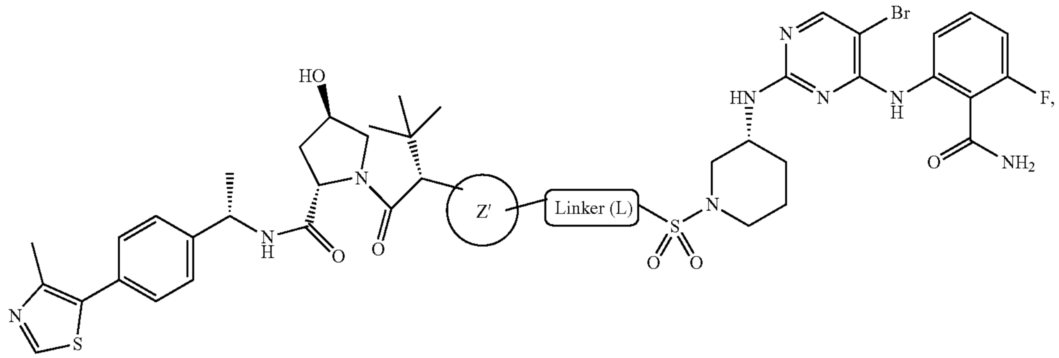
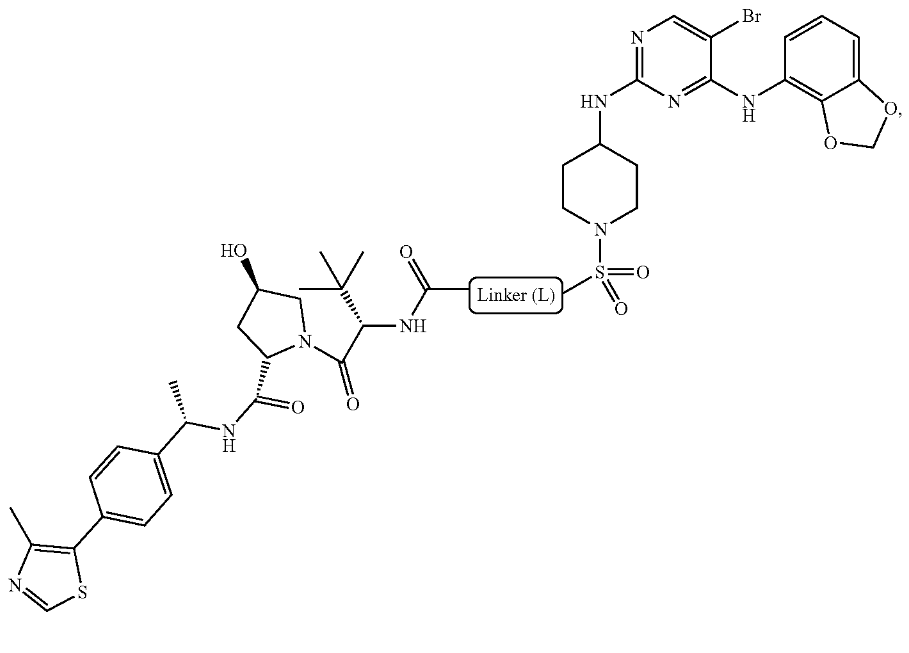

-continued
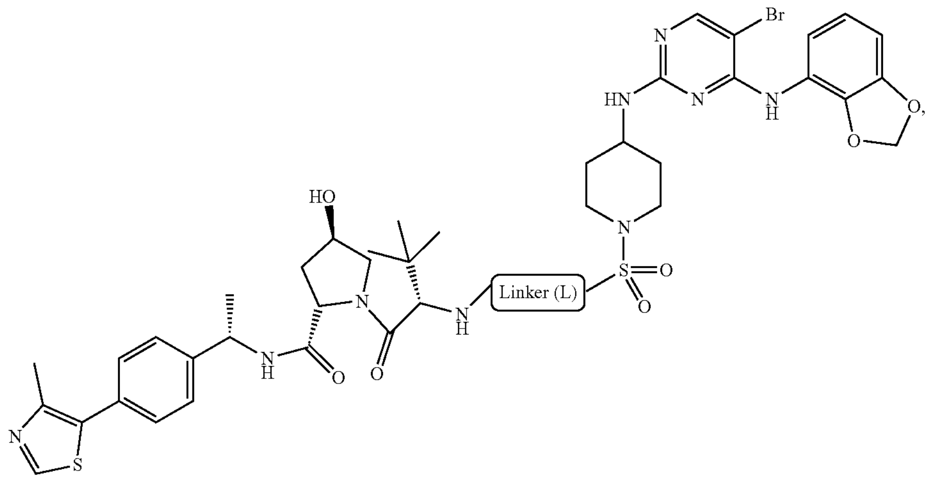
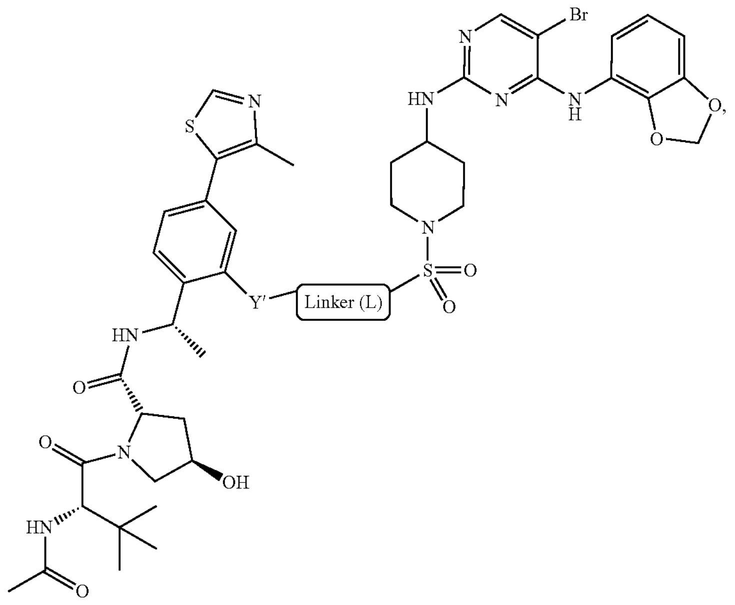
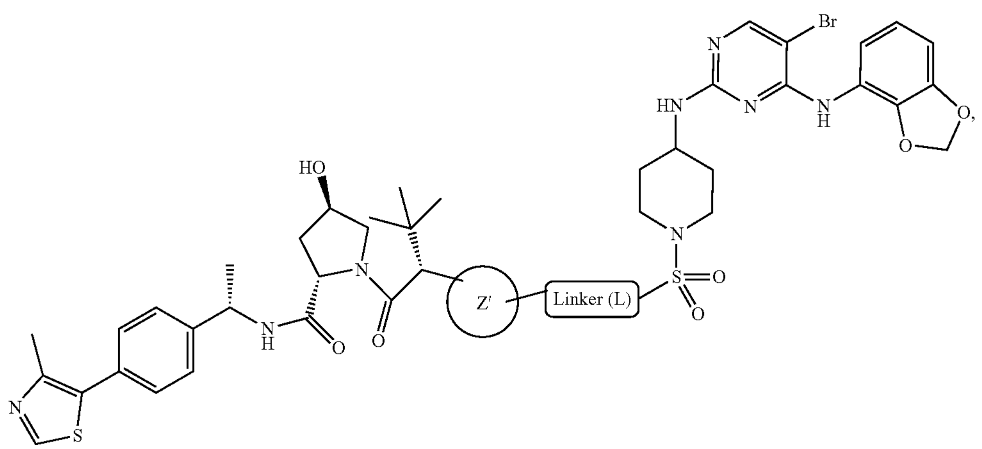

-continued
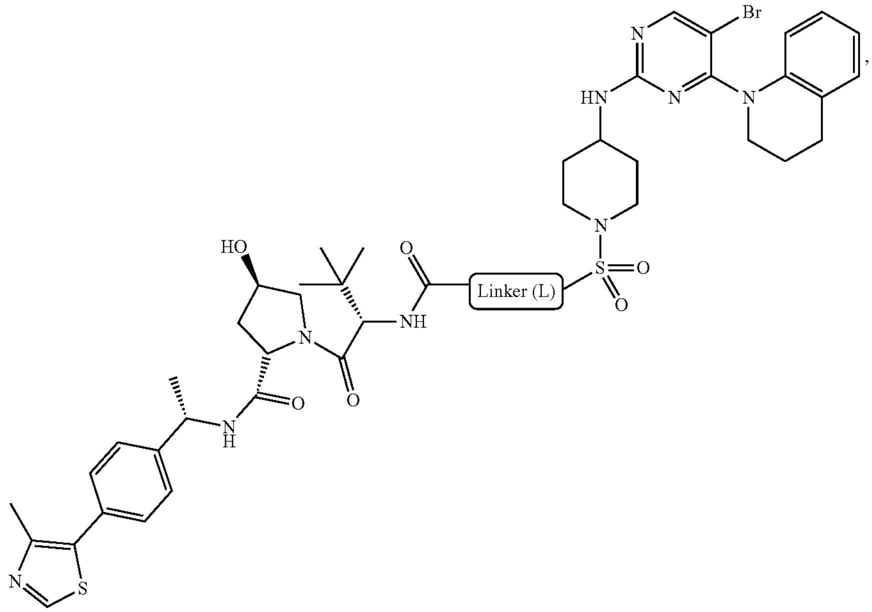
,
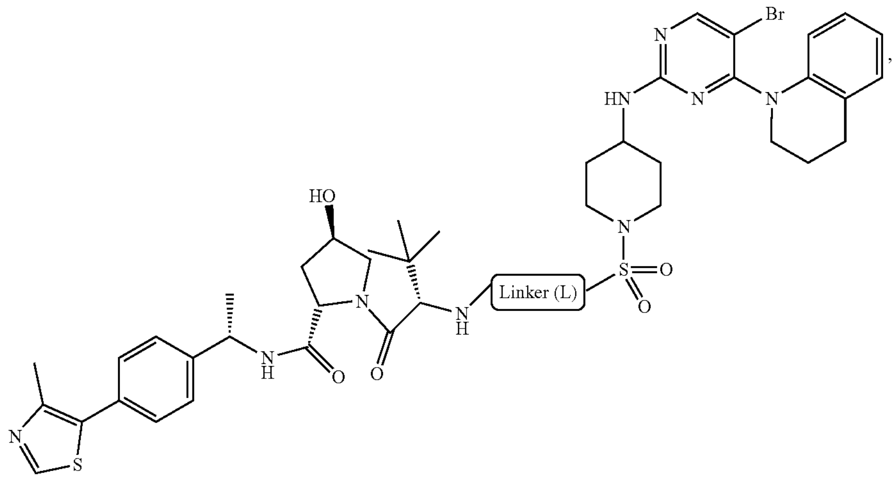
,
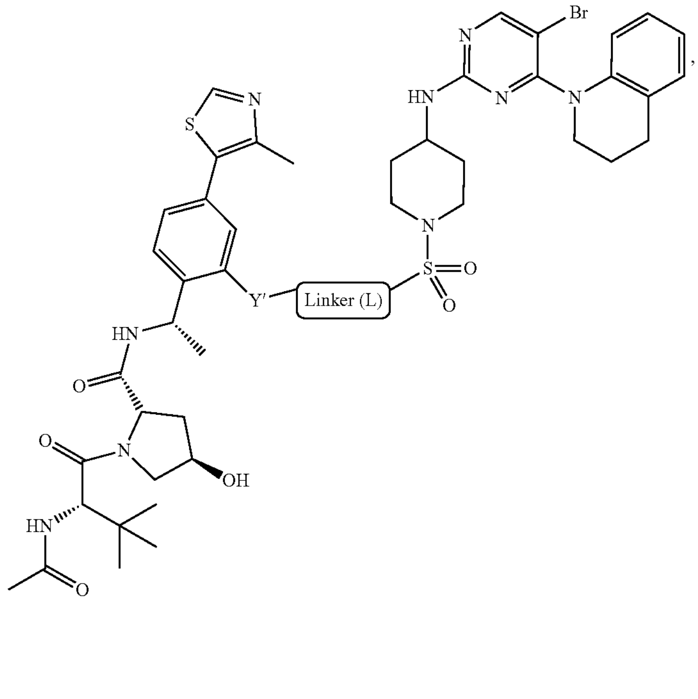
,

-continued
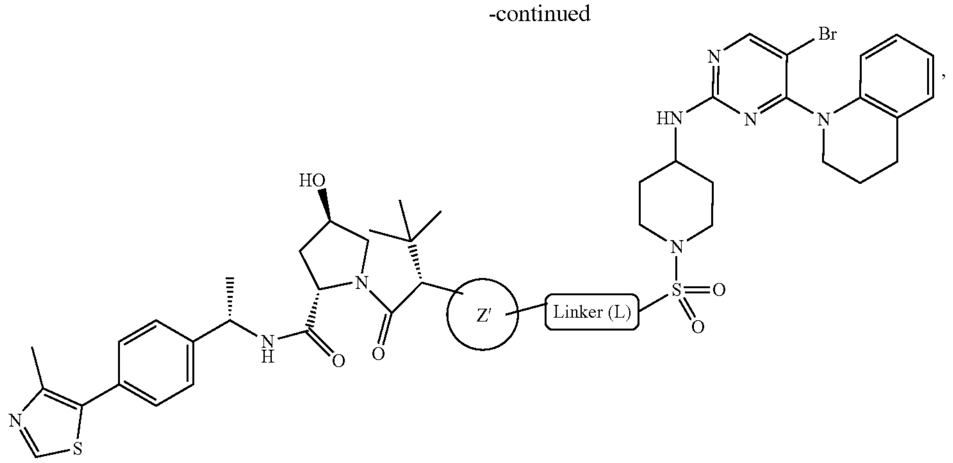
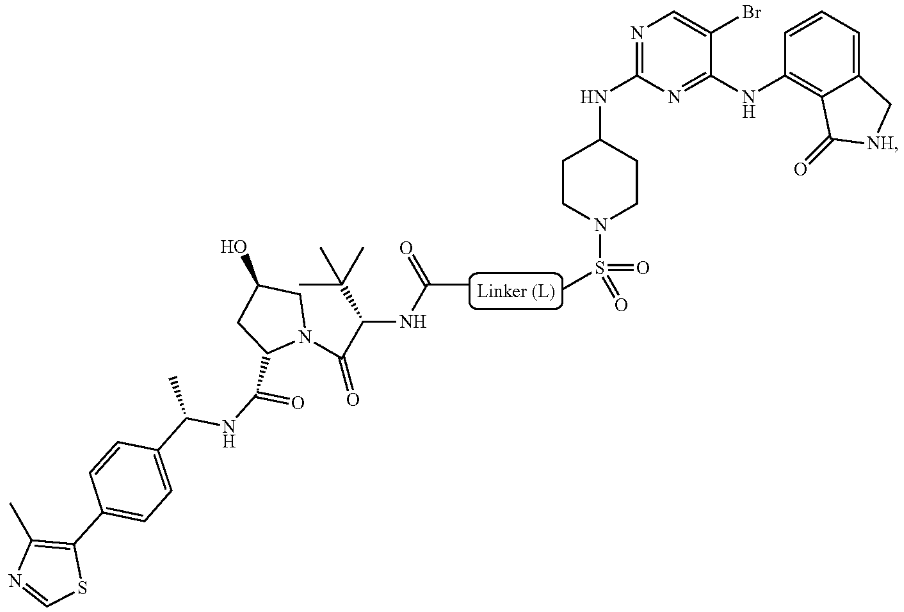
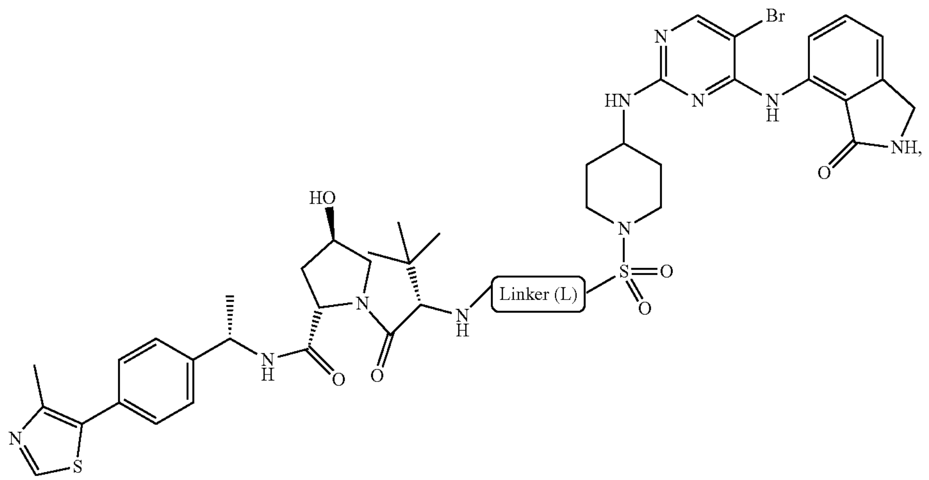

-continued
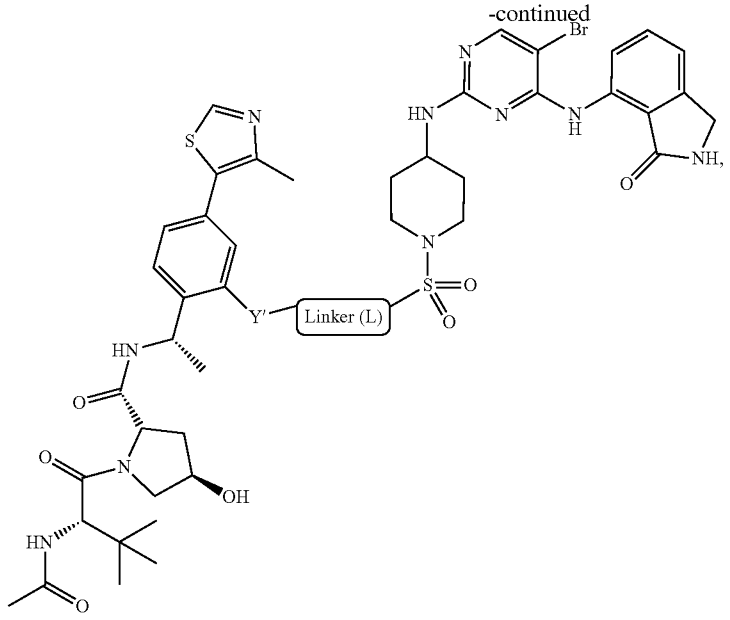
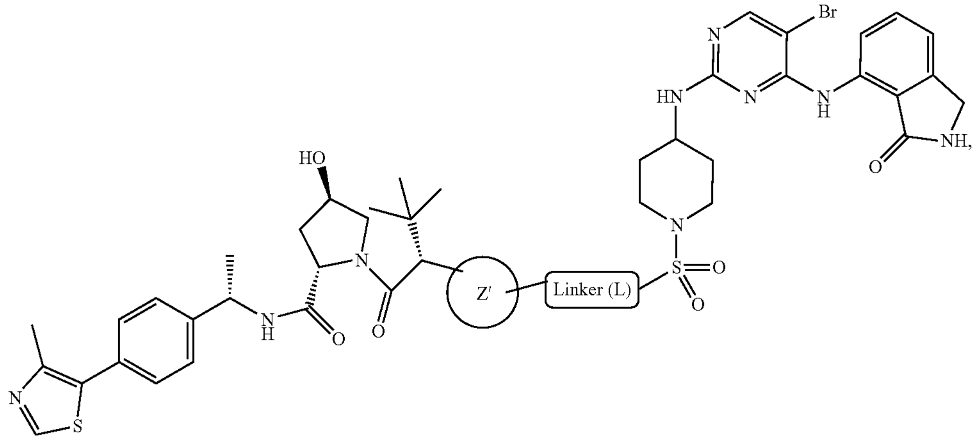
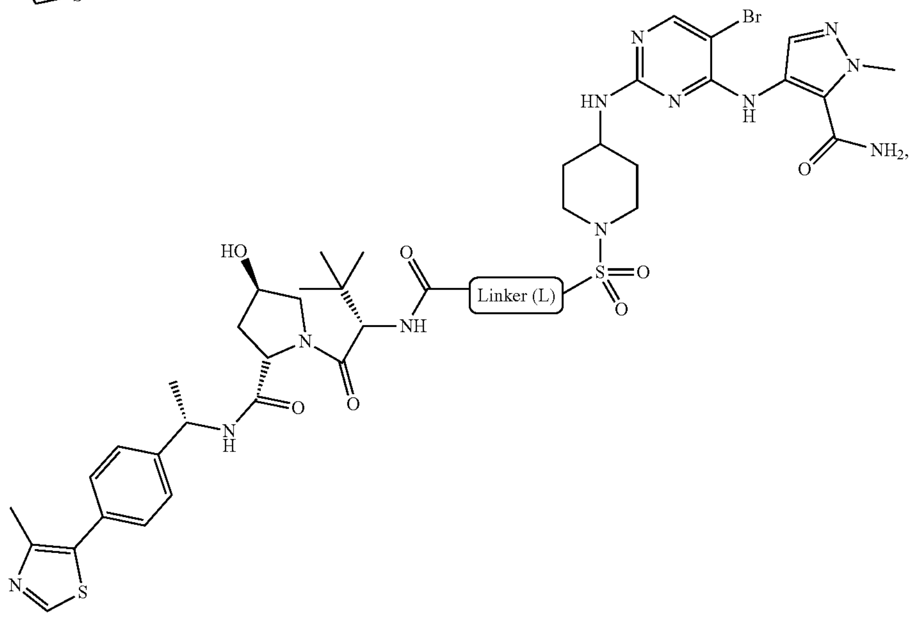

-continued
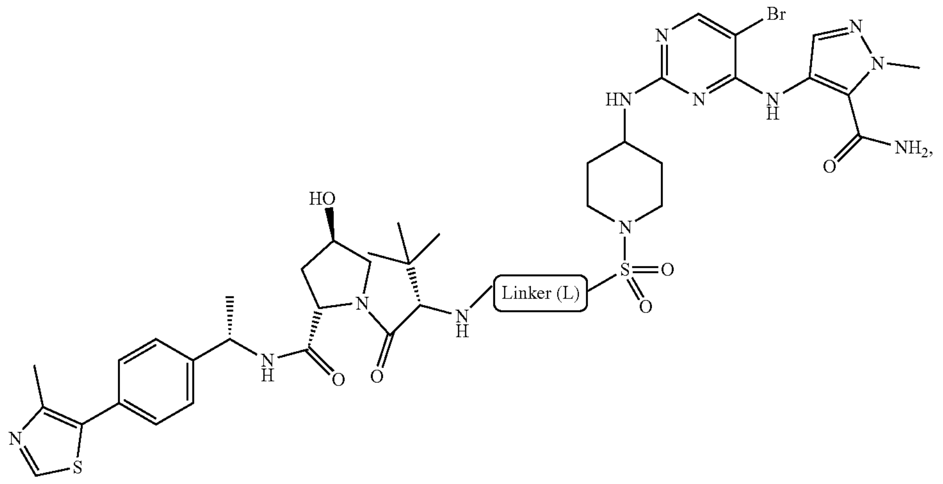
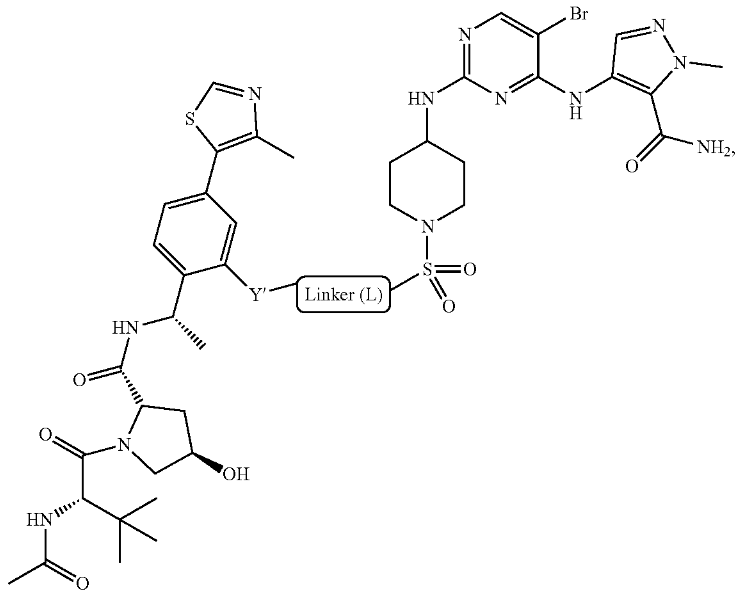
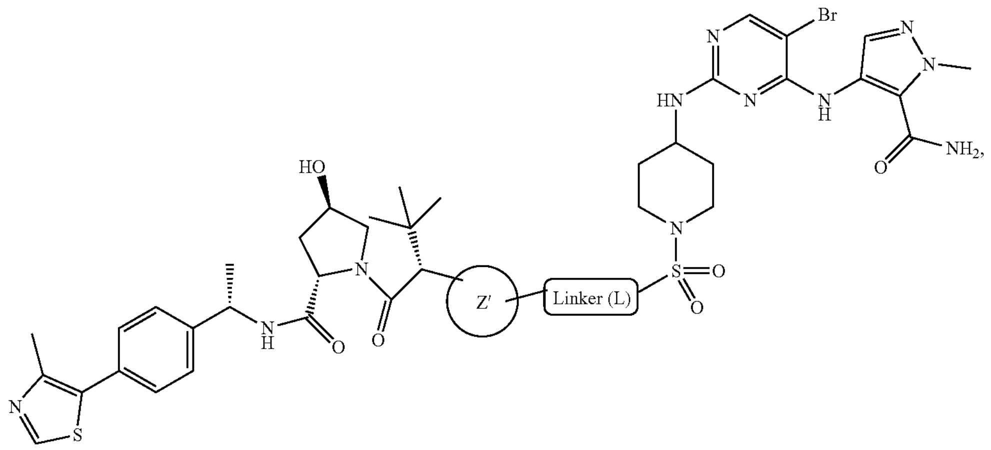

-continued
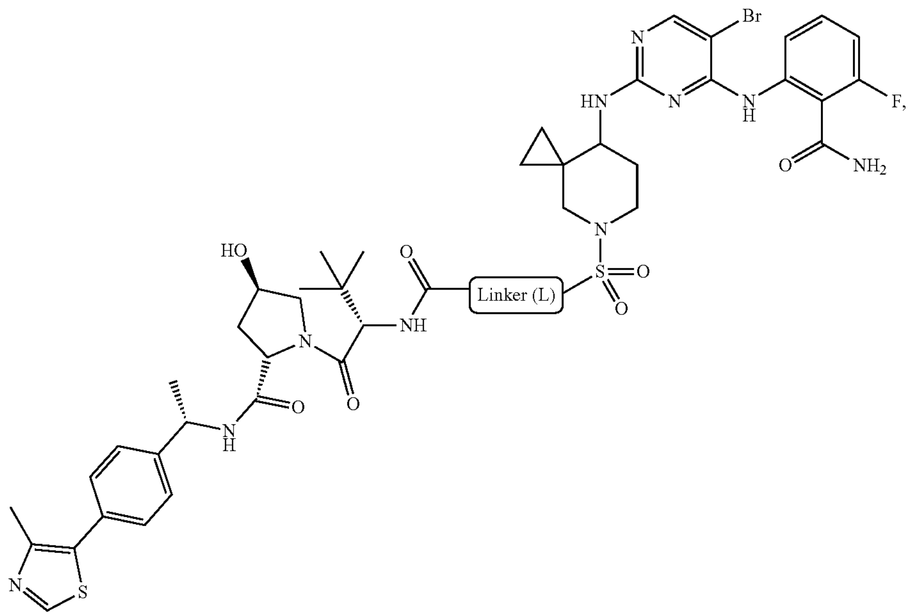
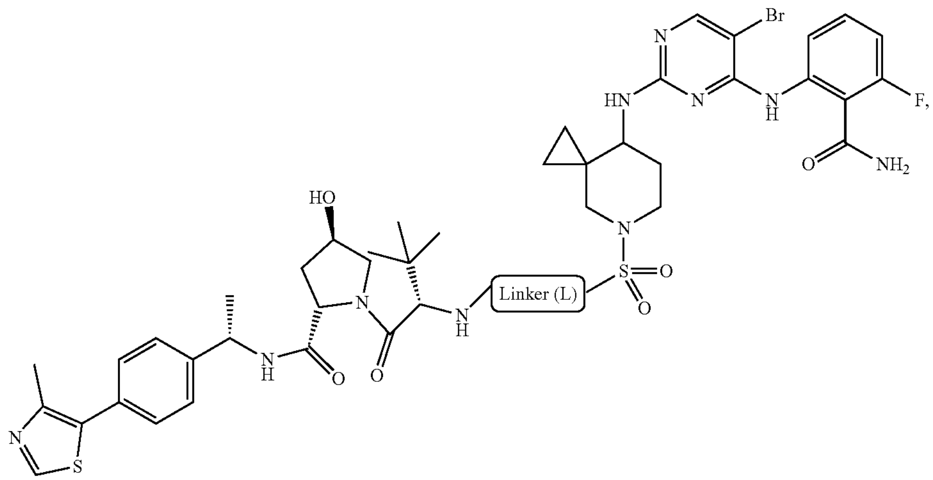
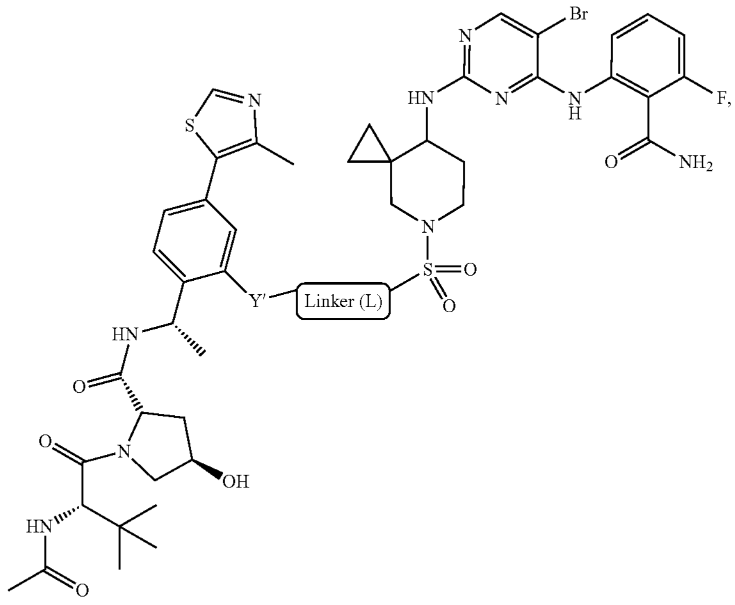

-continued
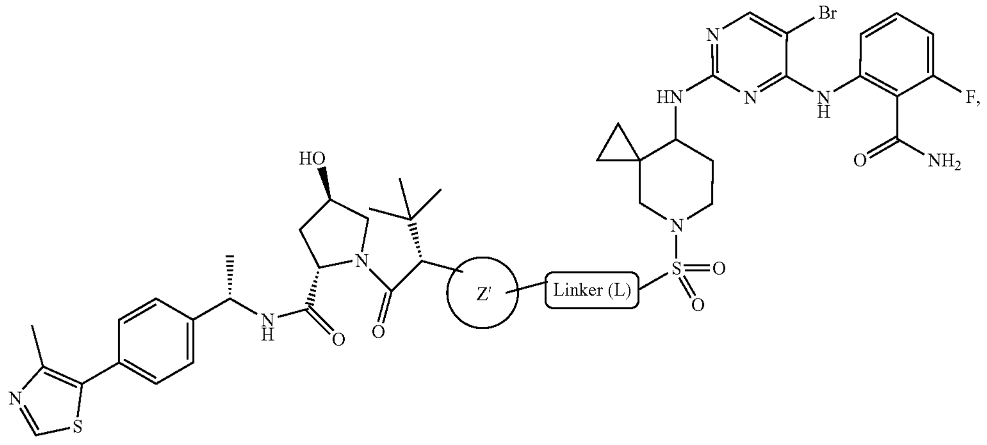
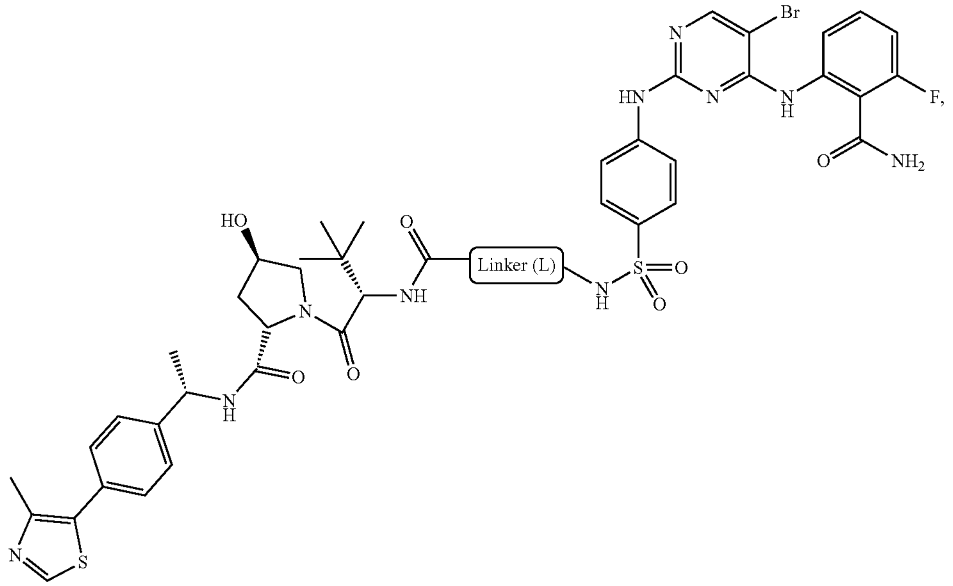
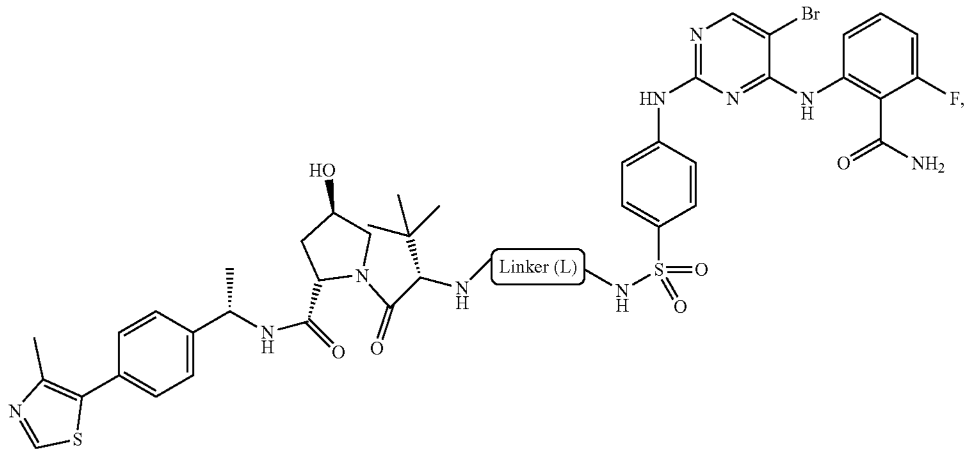

-continued
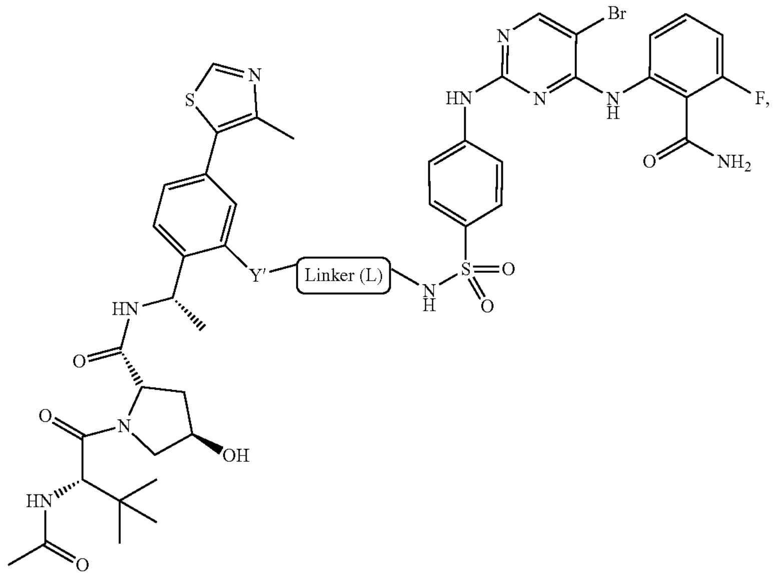
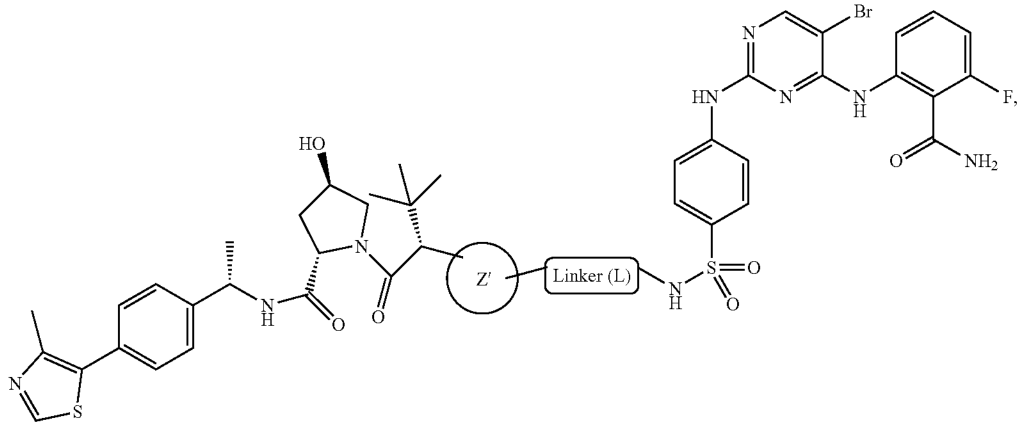
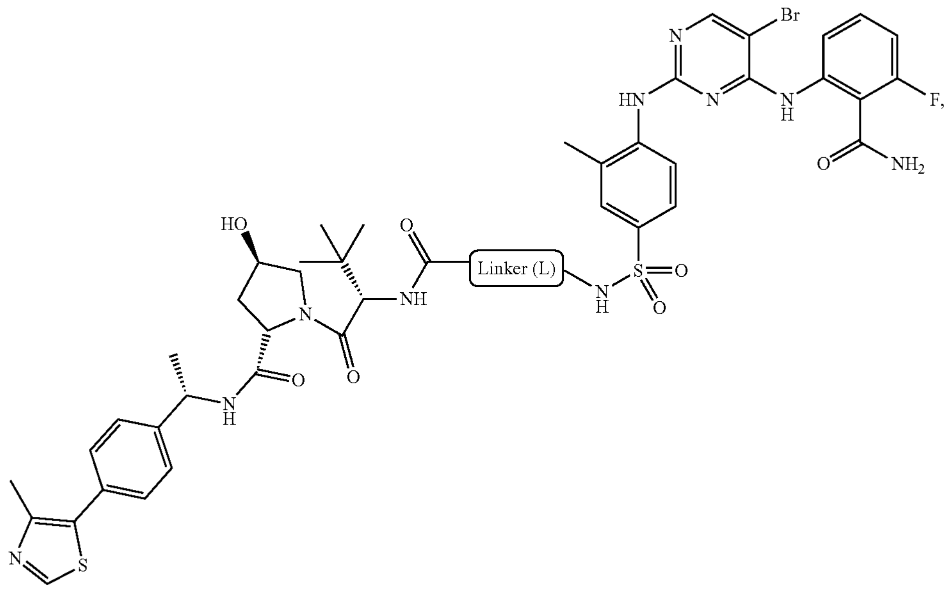

-continued
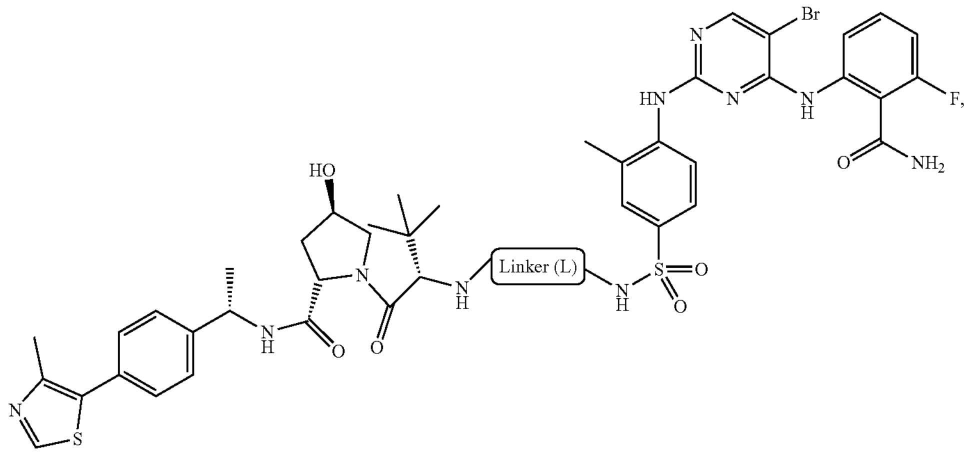
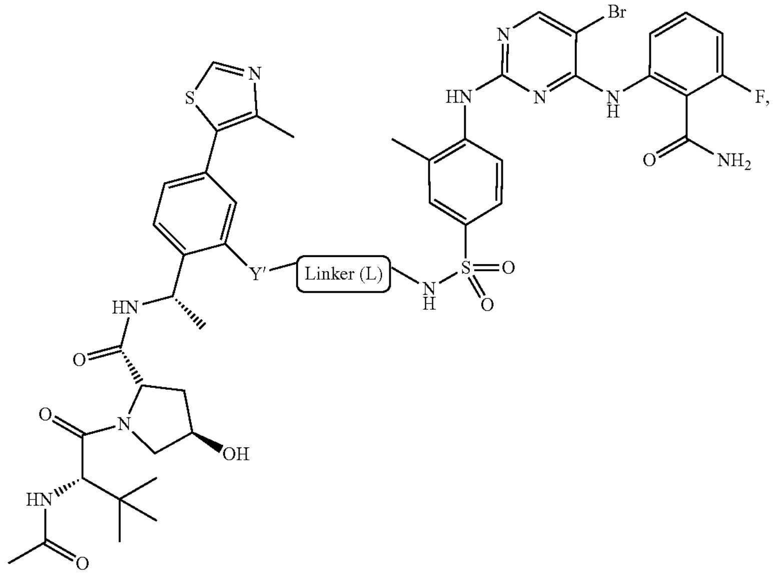
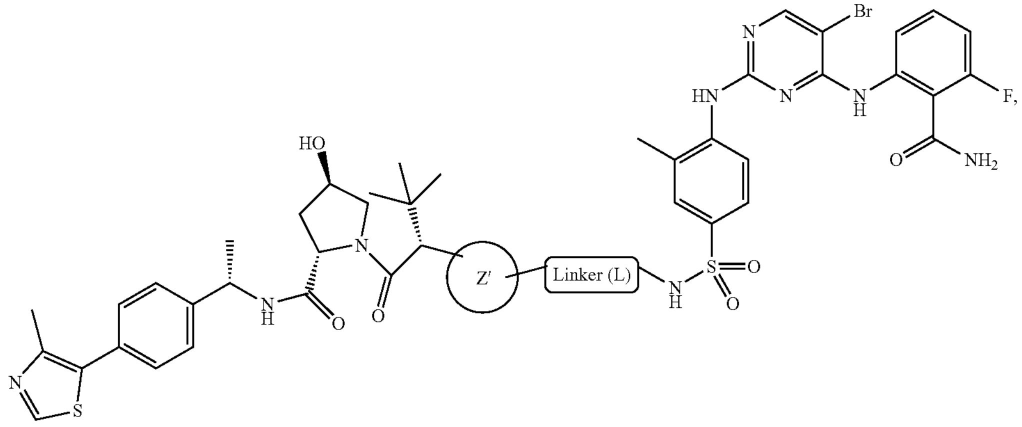

-continued
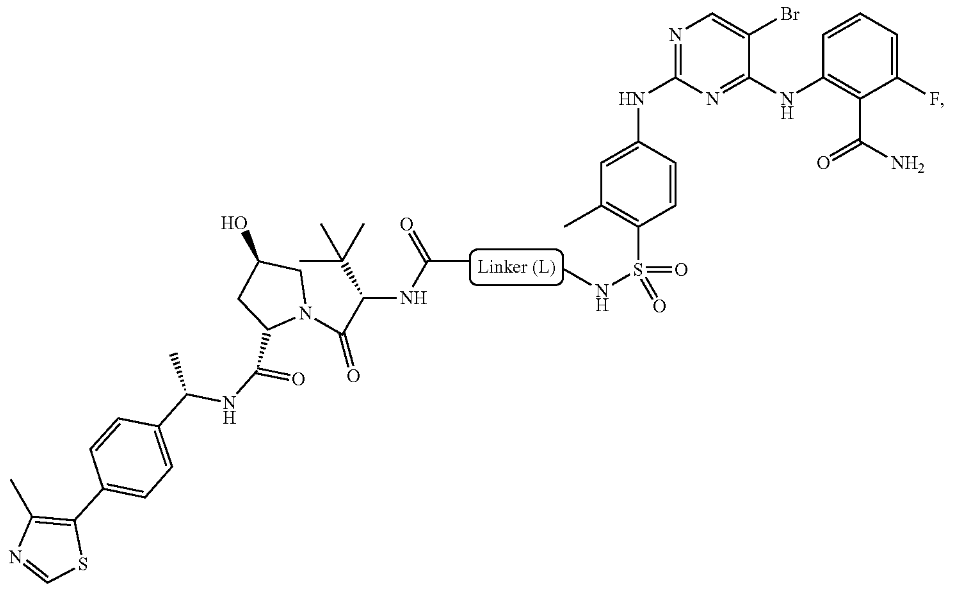
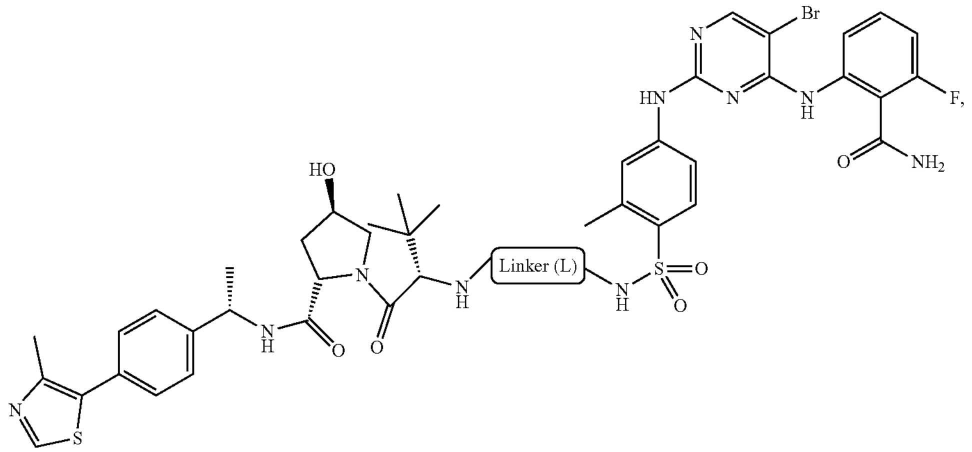
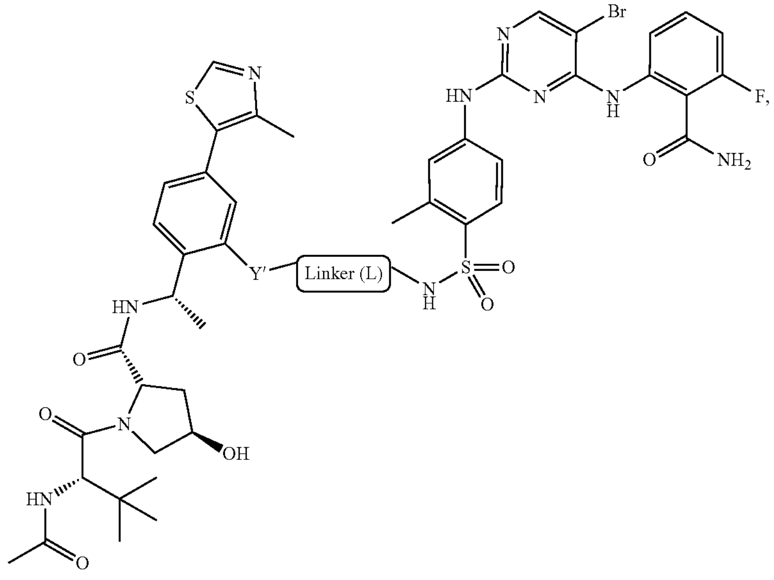
and

-continued
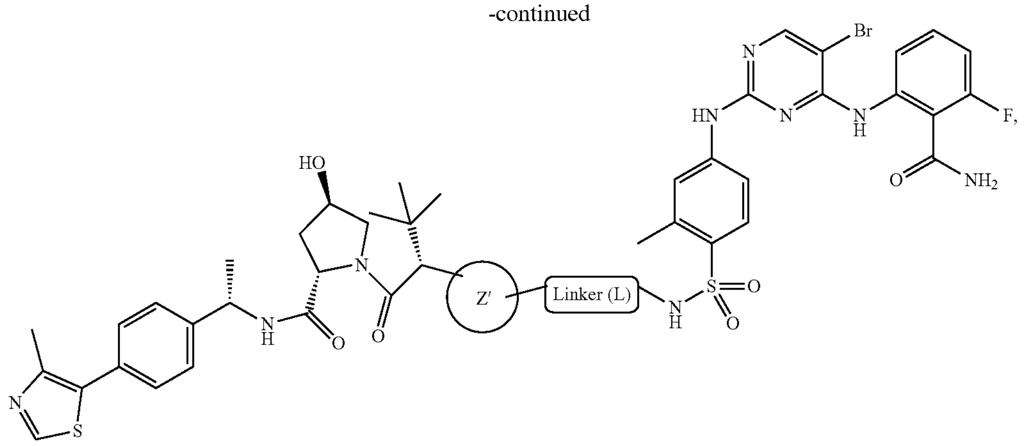
or a pharmaceutically acceptable salt or stereoisomer thereof.
20. The bifunctional compound of claim 18, which is:
(9)
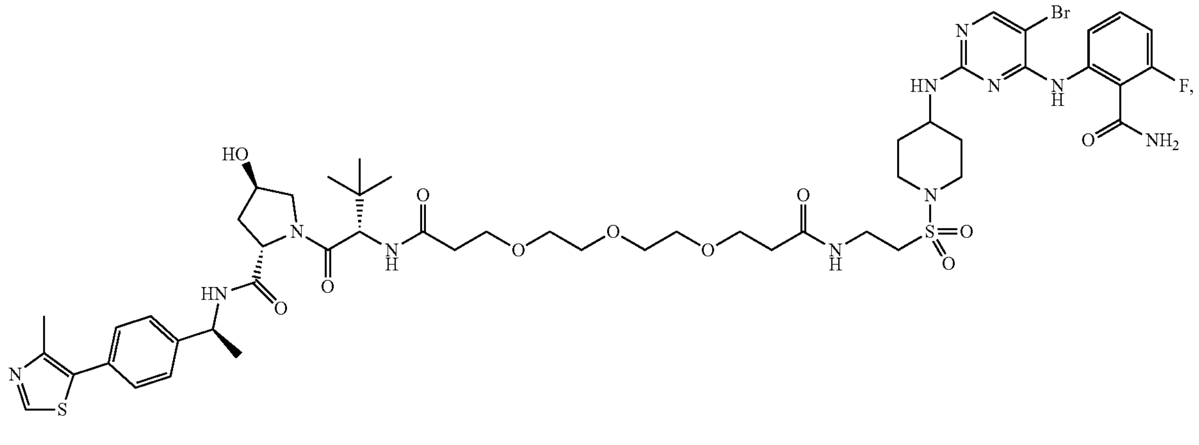
(10)
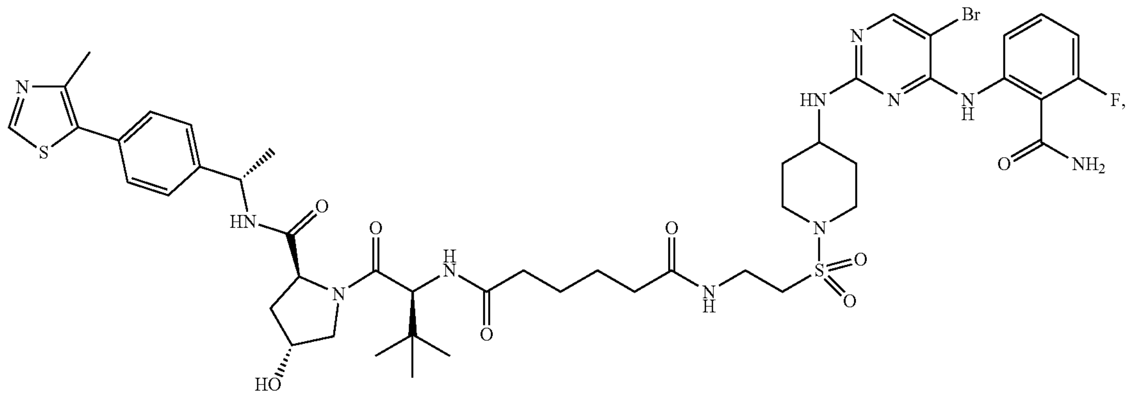

-continued (11)

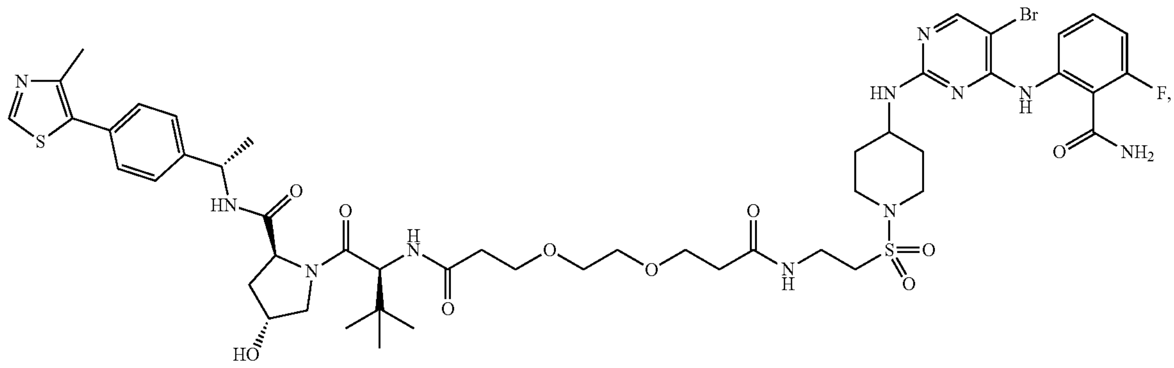

F, or (12)

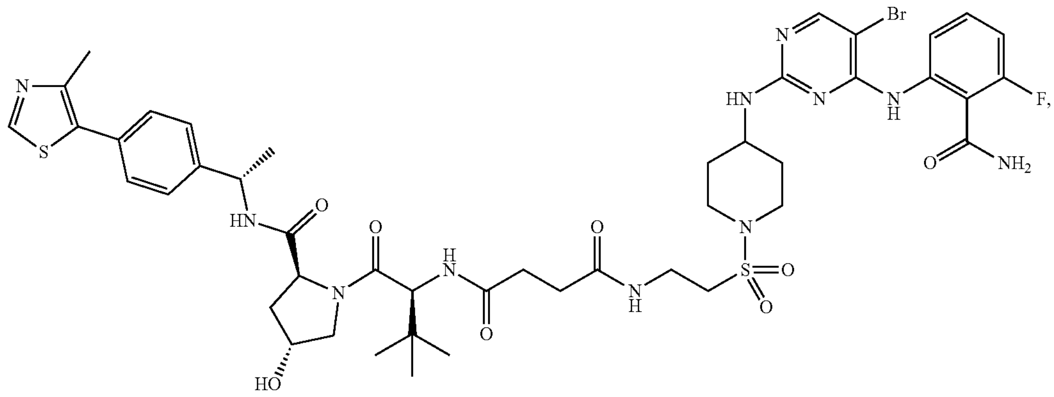

F, or a pharmaceutically acceptable salt, or stereoisomer thereof.

21. A pharmaceutical composition, comprising a therapeutically effective amount of the bifunctional compound of claim 18, or pharmaceutically acceptable salt or stereoisomer thereof, and a pharmaceutically acceptable carrier.

22. A method of treating cancer, comprising administering to a subject in need thereof a therapeutically effective amount of the bifunctional compound of claim 18, or a pharmaceutically acceptable salt or stereoisomer thereof, wherein the cancer is ovarian cancer or T-cell leukemia.

23. The bifunctional compound of claim 1, which is:

(1)

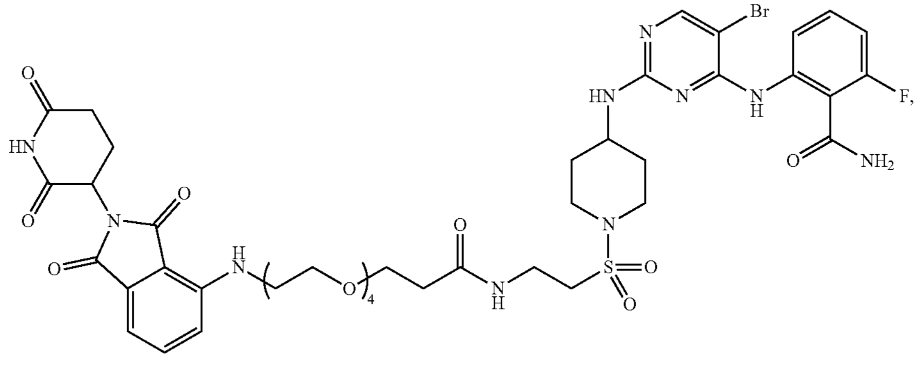

F,

-continued
(2)
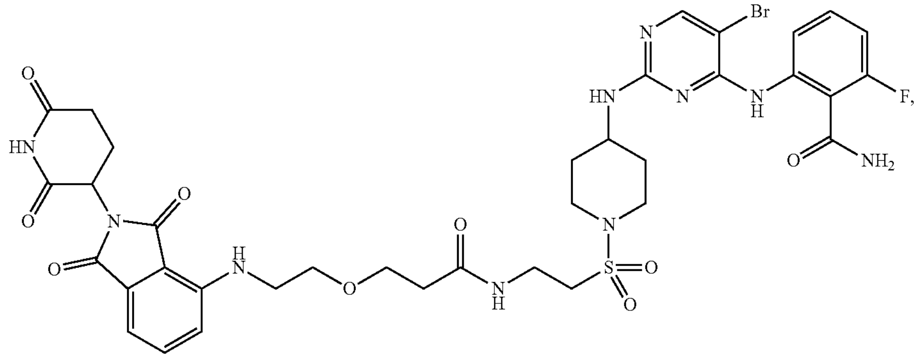
(3)
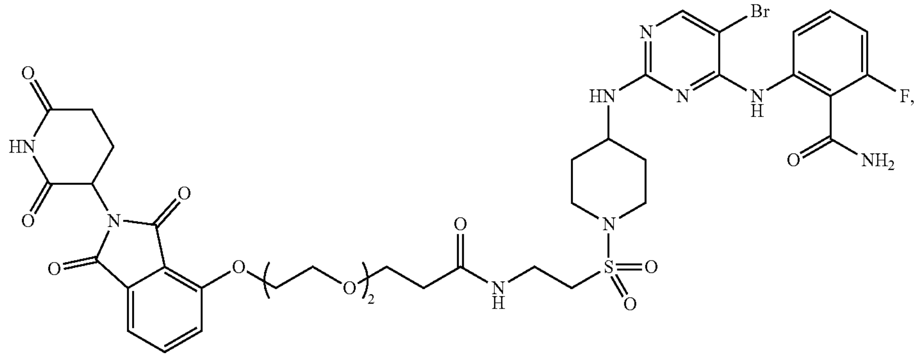
(4)
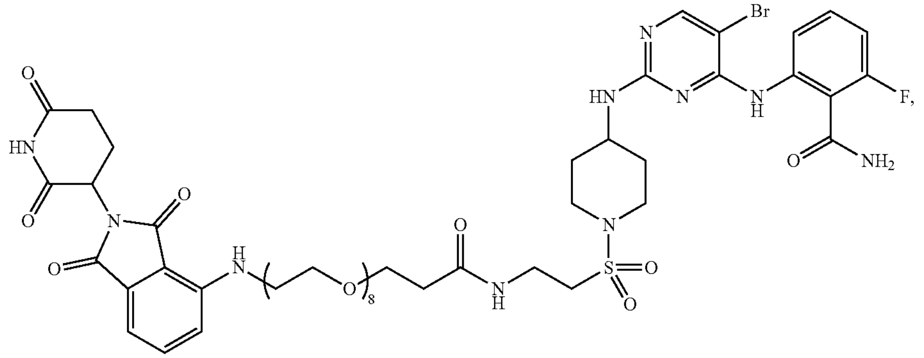
(5)
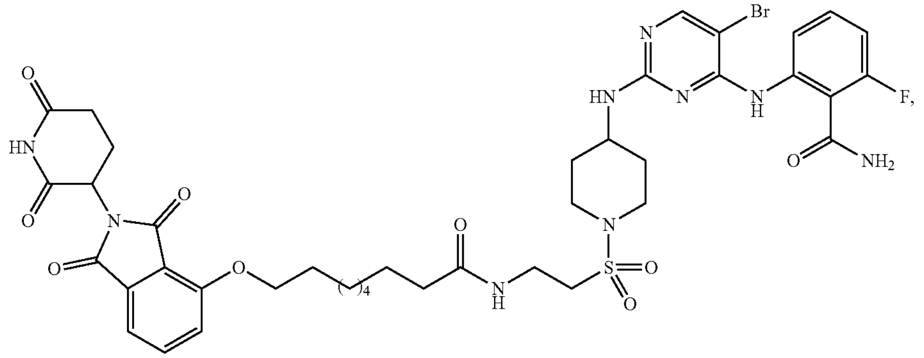

-continued
(6)
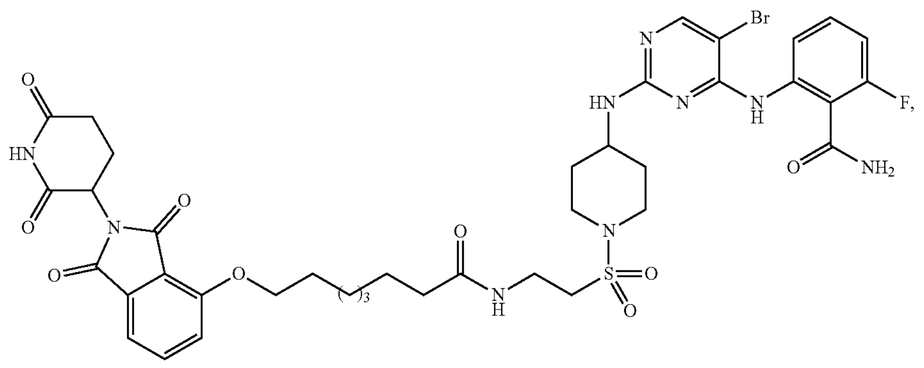
(7)
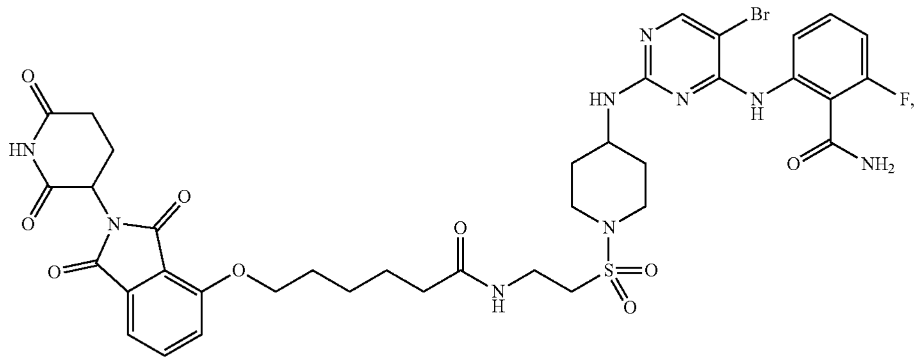
(8)
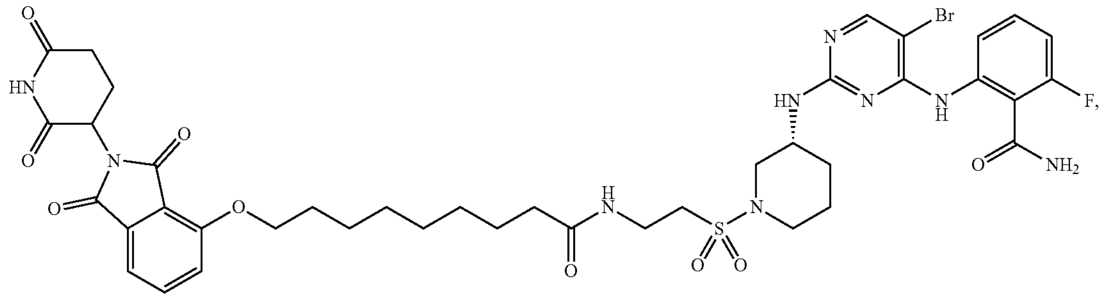
(13)
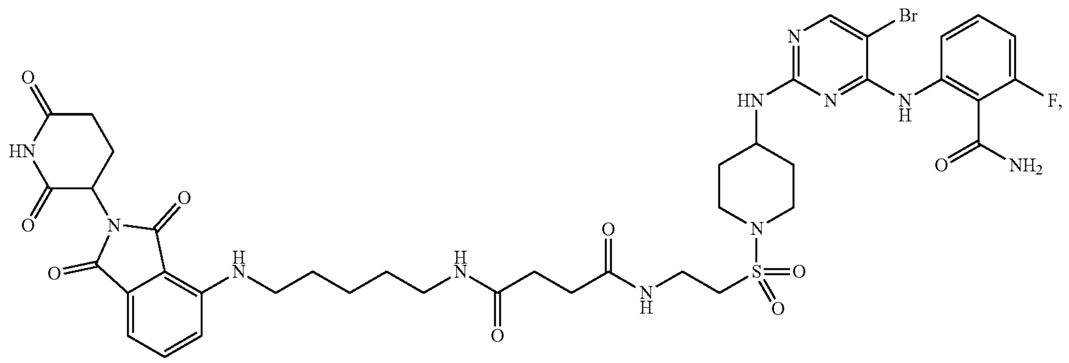

-continued
(14)
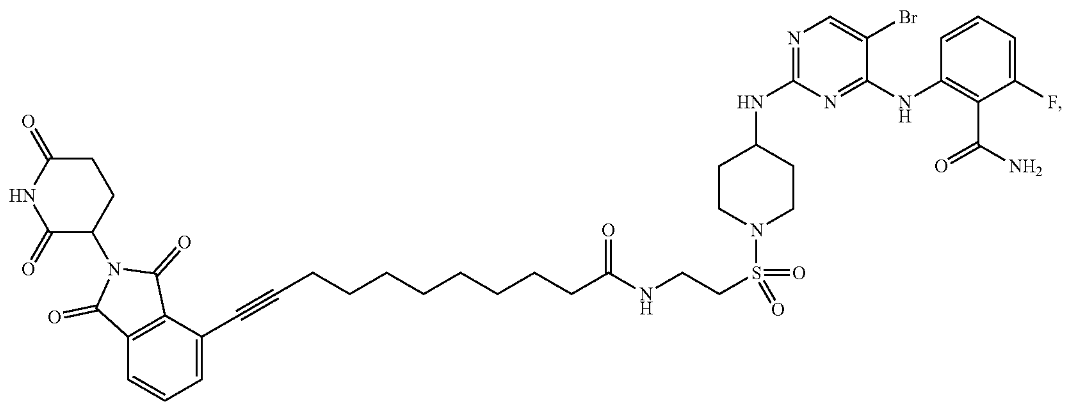
(15)
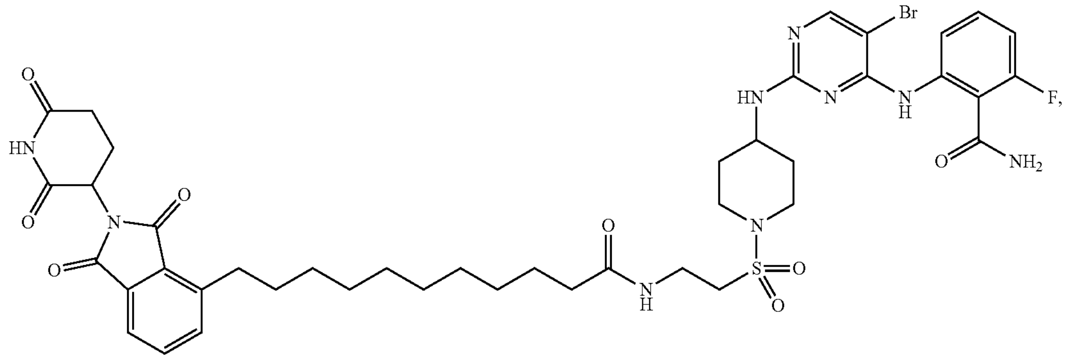
(16)
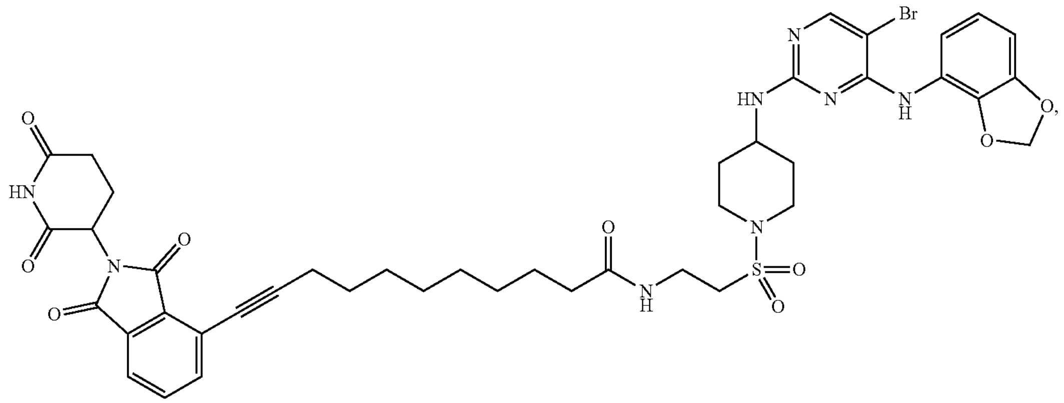
(17)
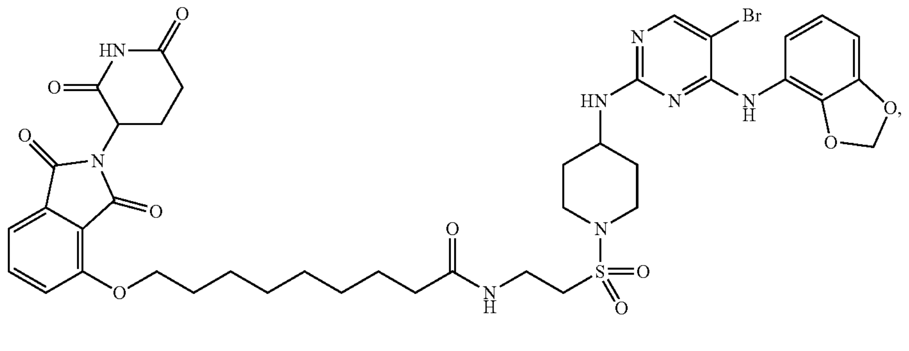

-continued
(18)
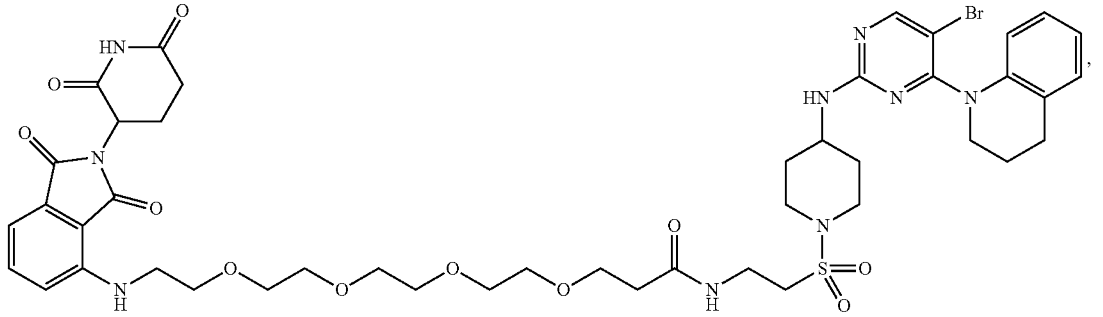
(19)
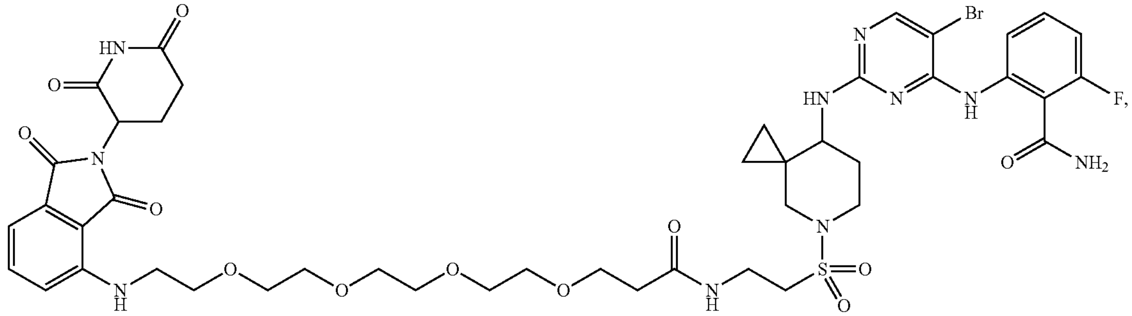
(20)
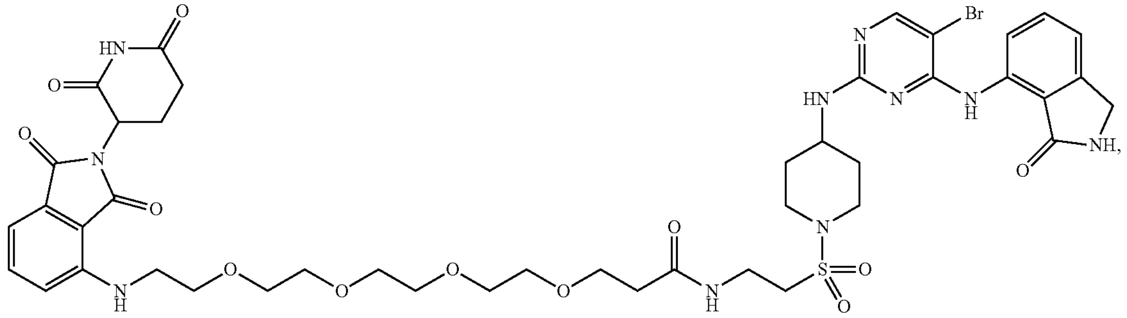
(21)
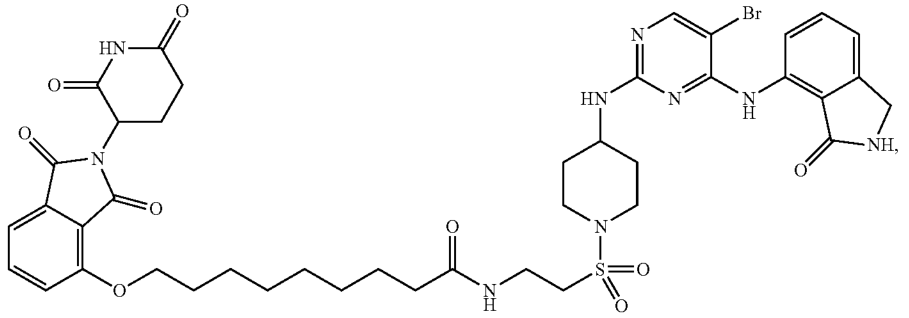
(22)
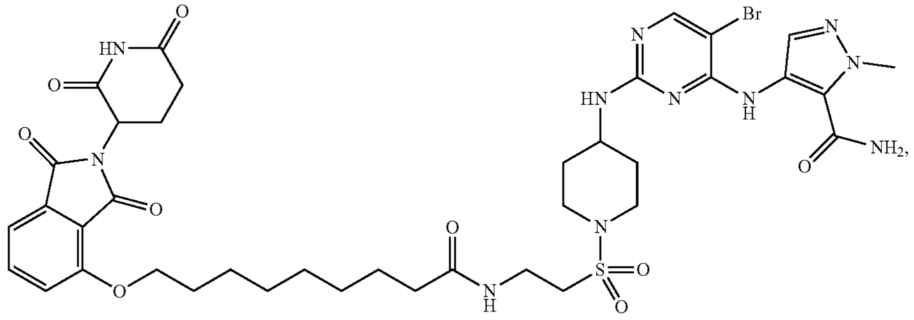

-continued
(23)
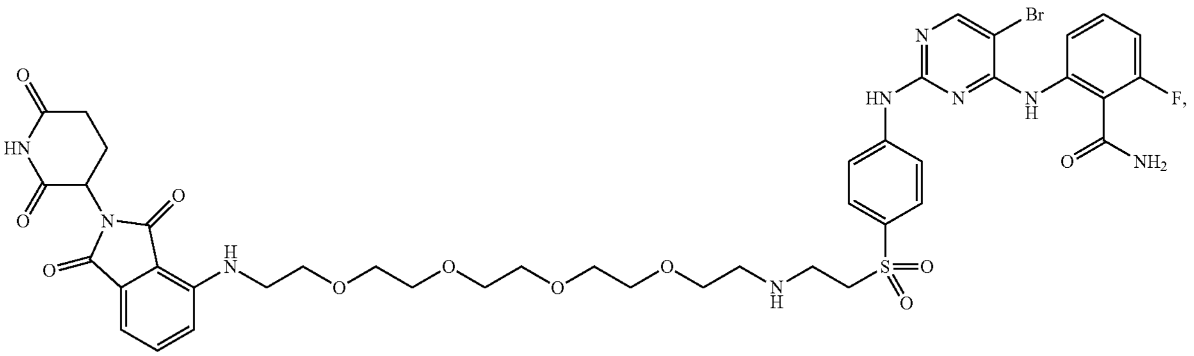
(24)
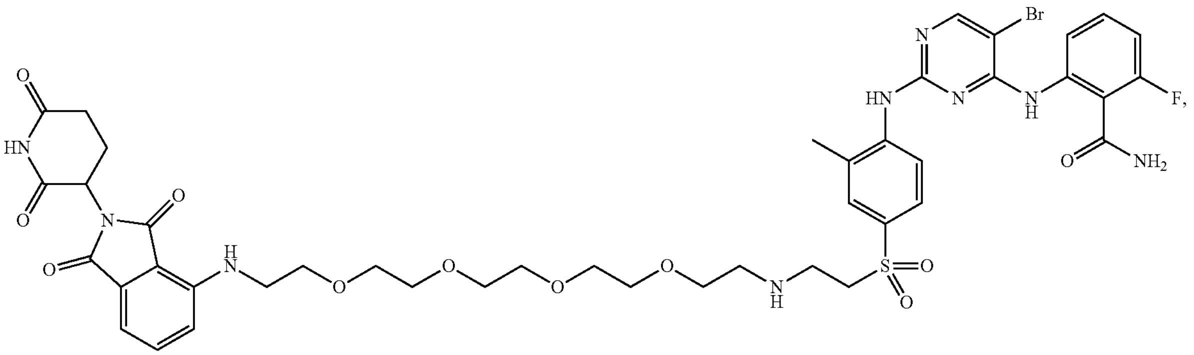
(25)
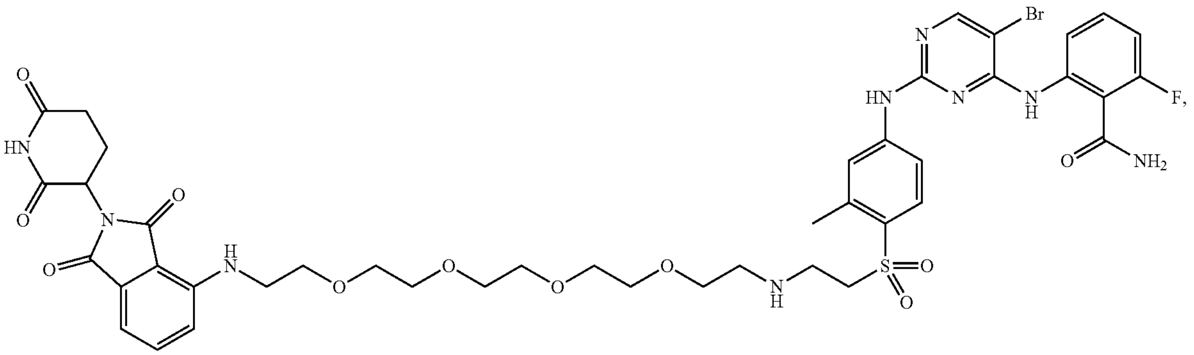
(26)
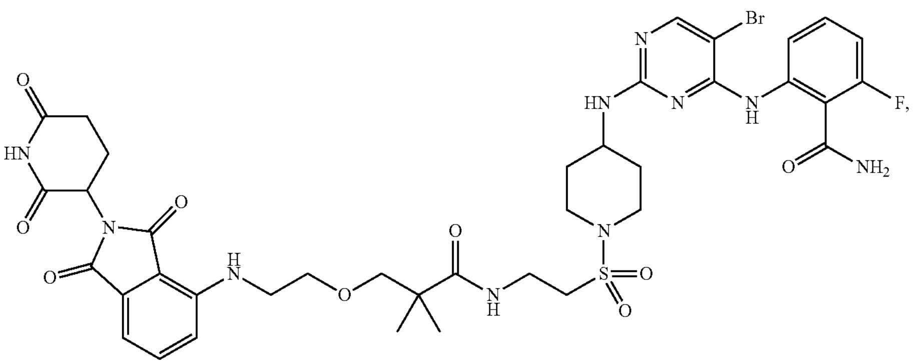

-continued
(27)
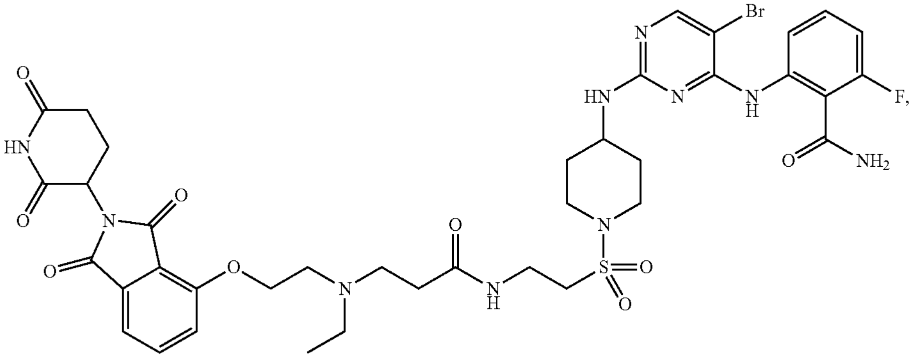
(28)
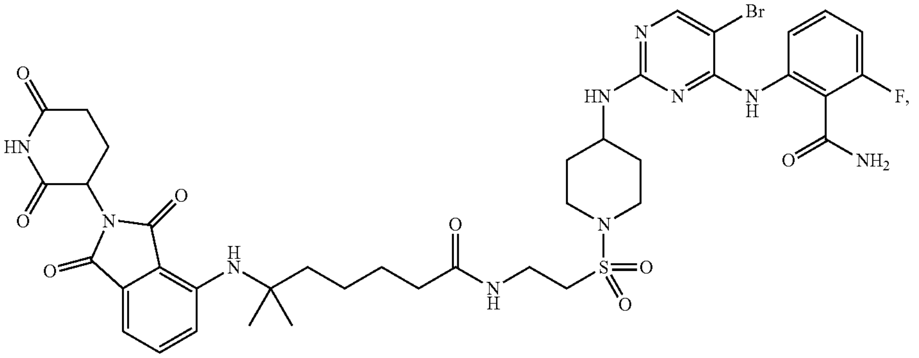
(29)
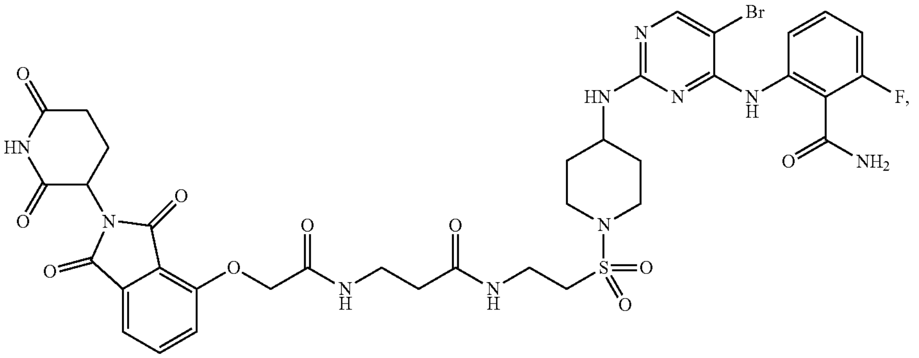
(30)
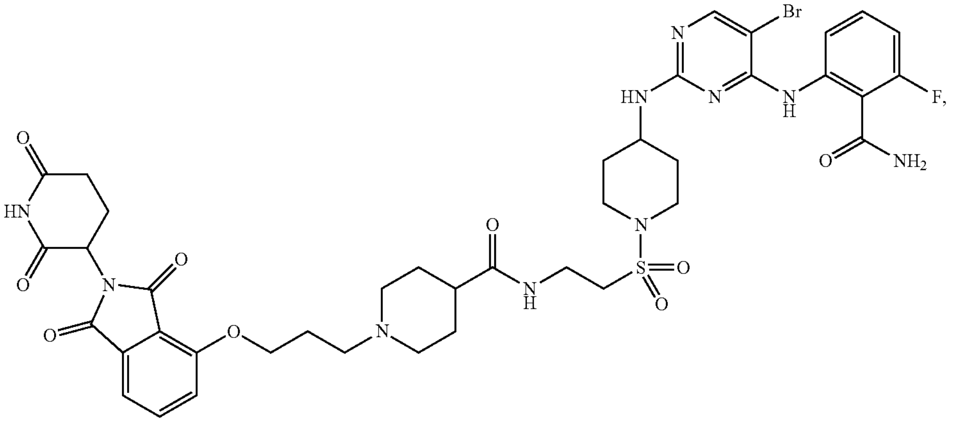

-continued
(31)
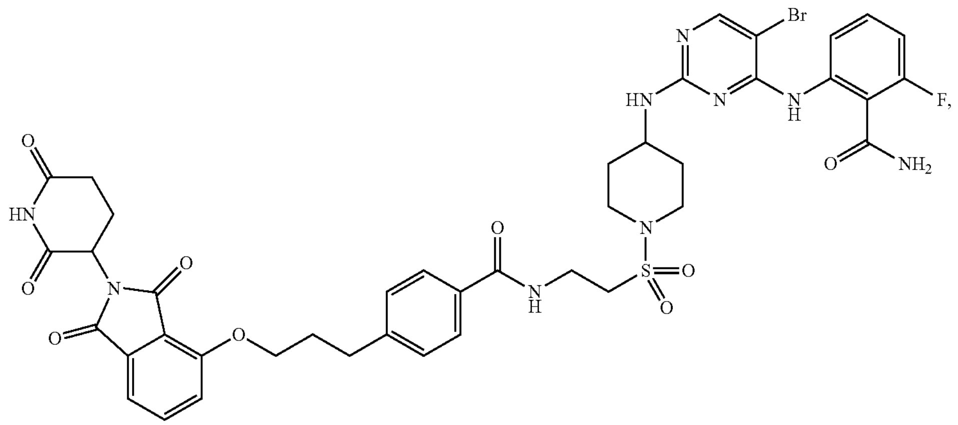
(32)
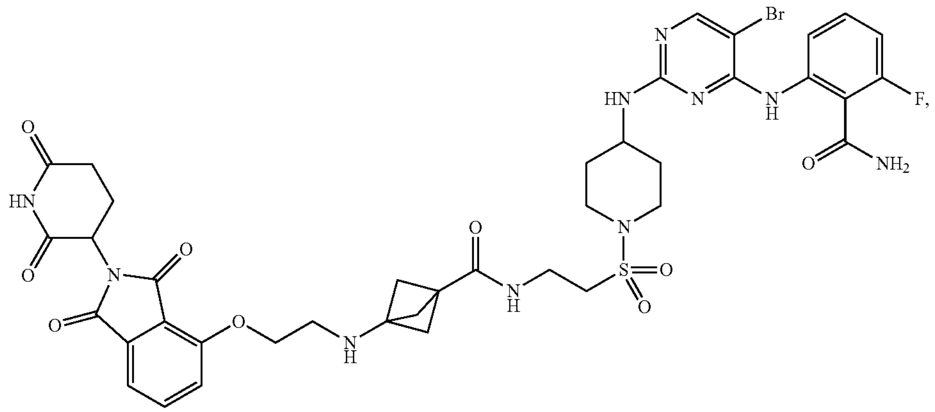
(33)
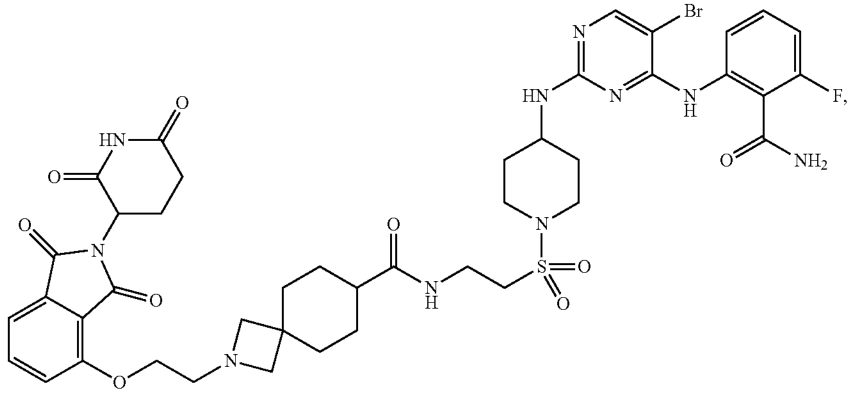

-continued
(34)
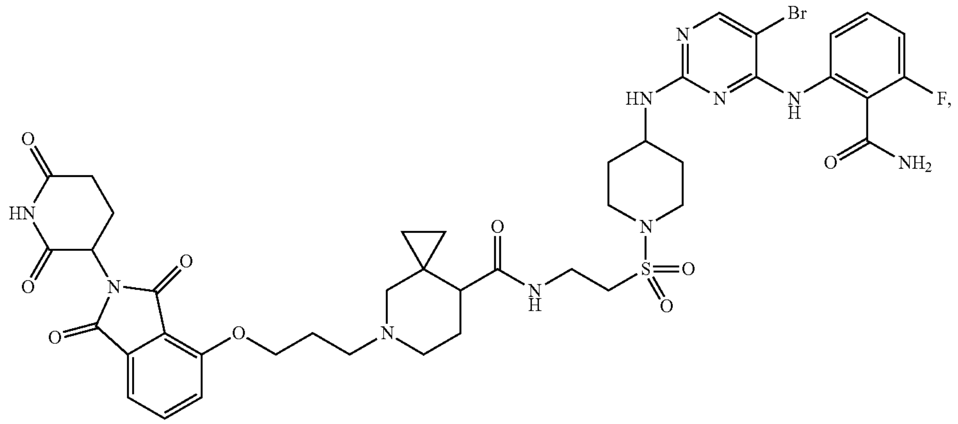
(35)
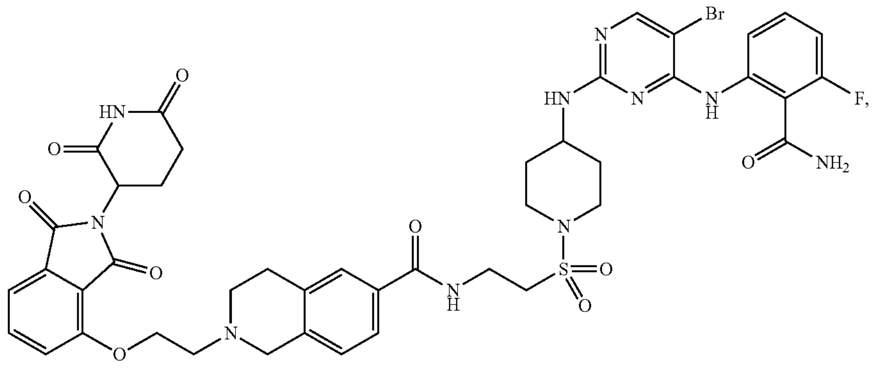
(36)
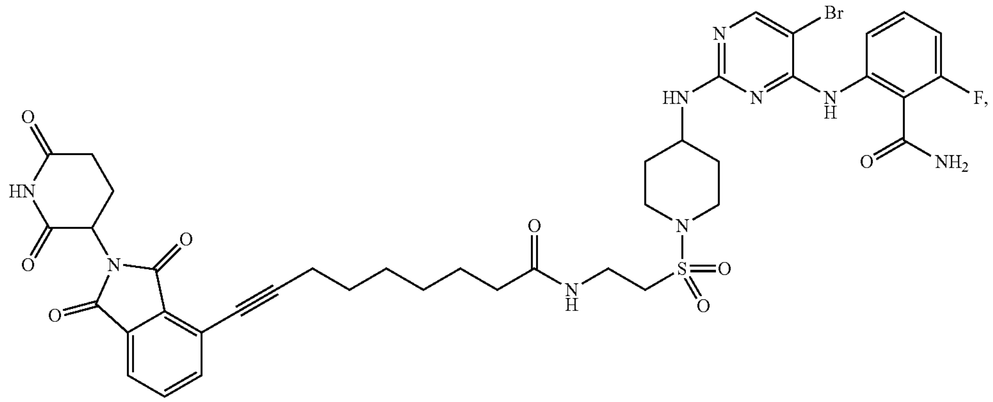
(37)
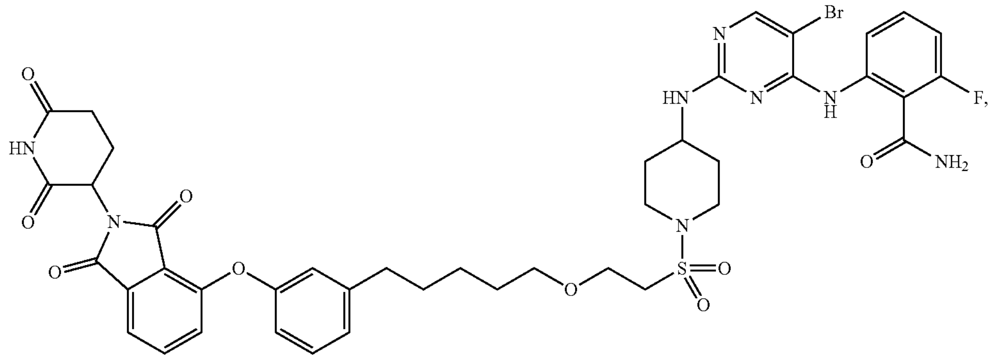

-continued
(38)
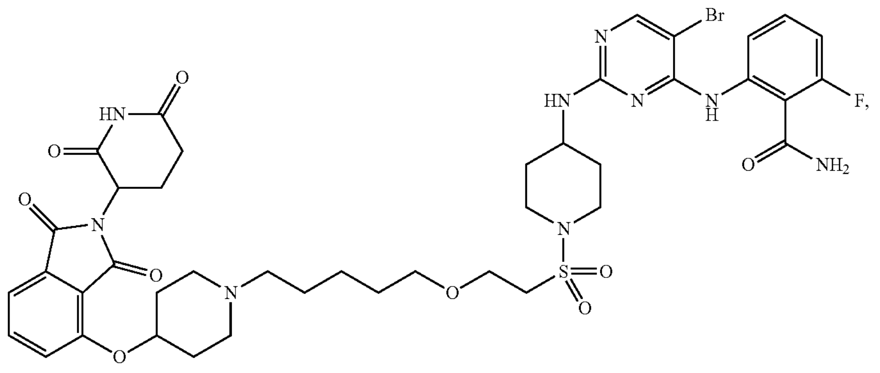
(39)
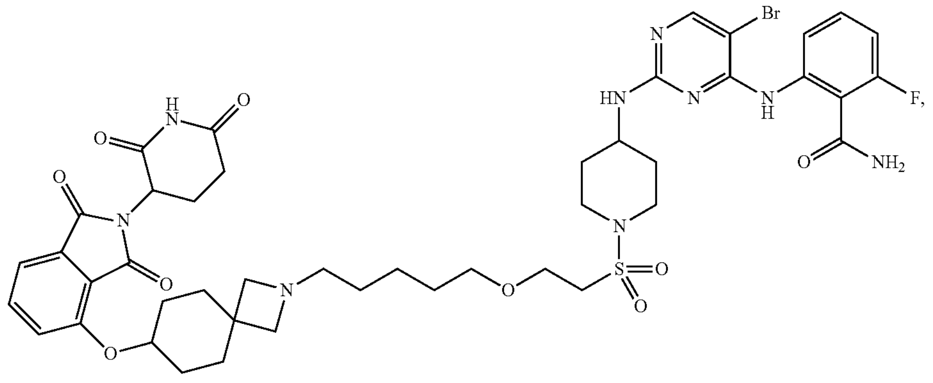
(40)
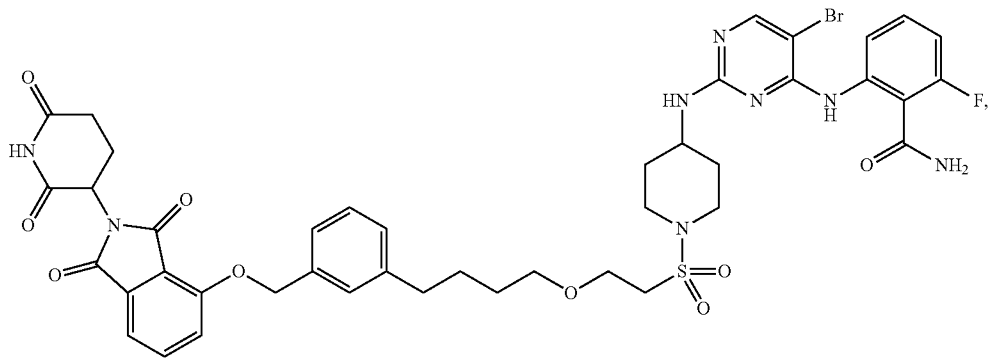
(41)
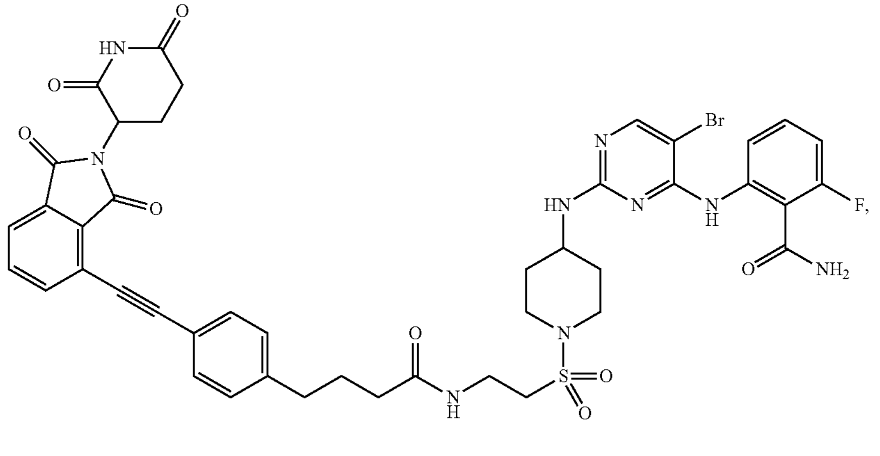

-continued
(42)
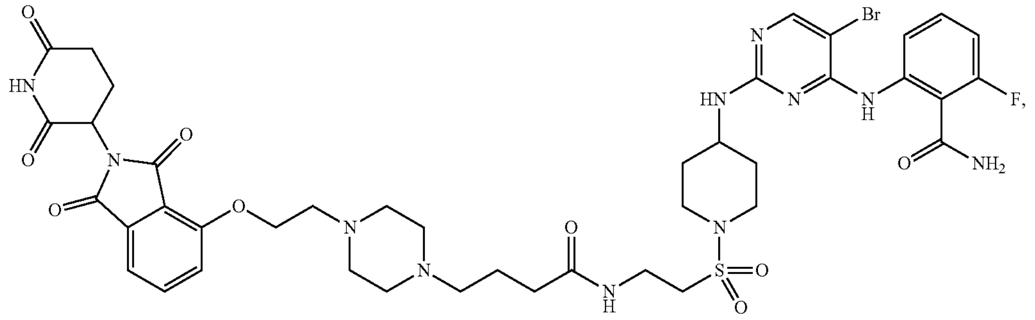
(43)
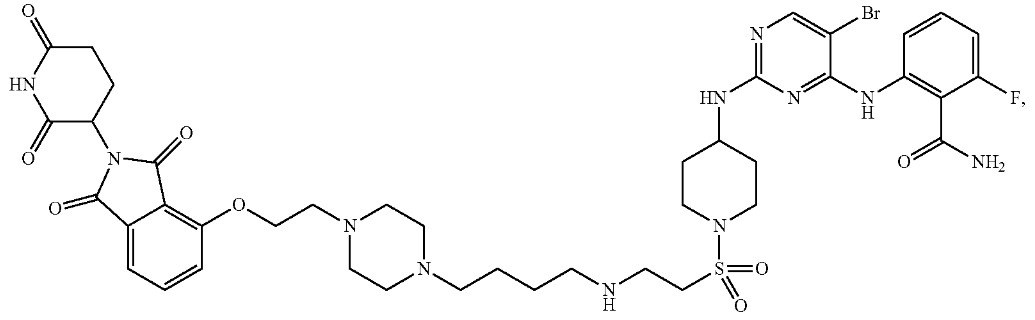
(44)
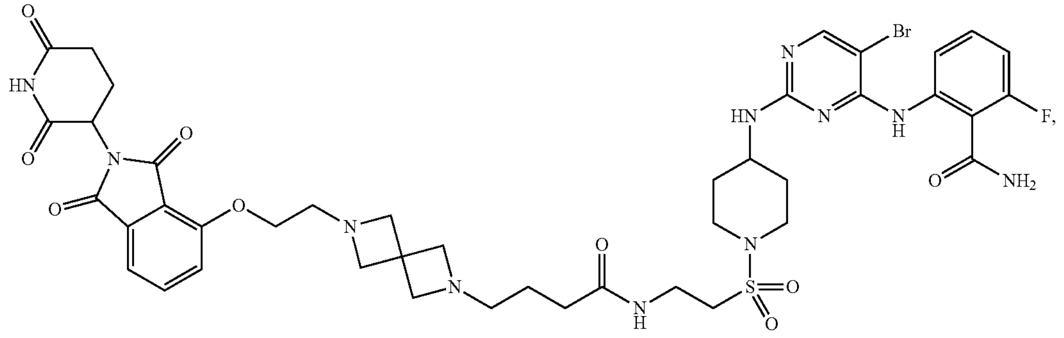
(45)
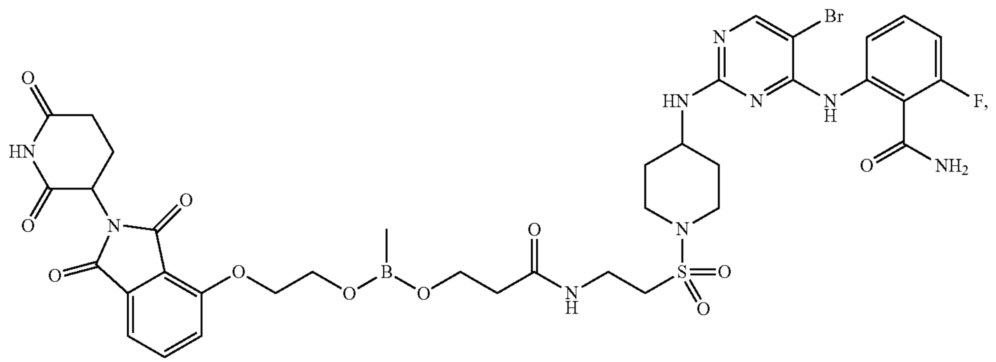

-continued (46)

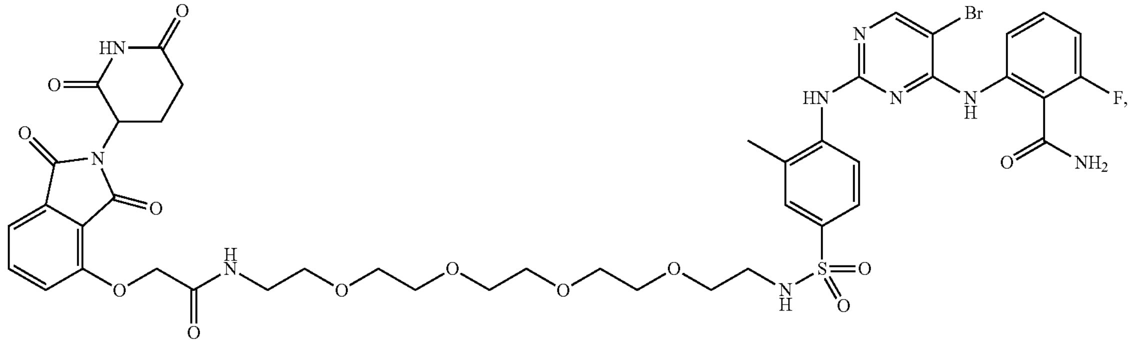

(47)

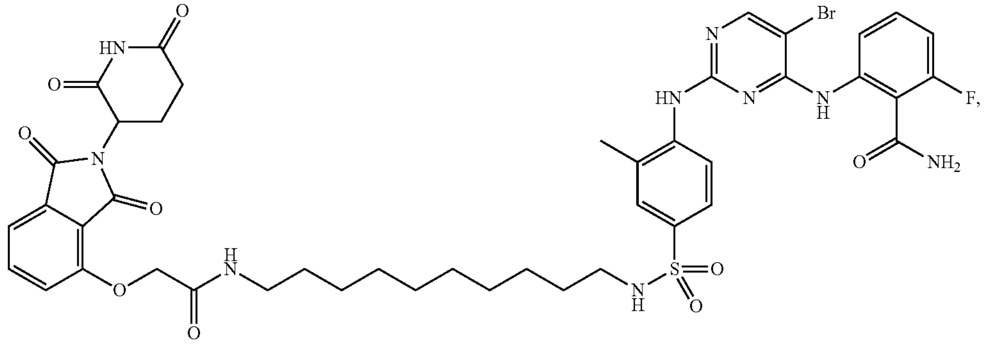

(48)

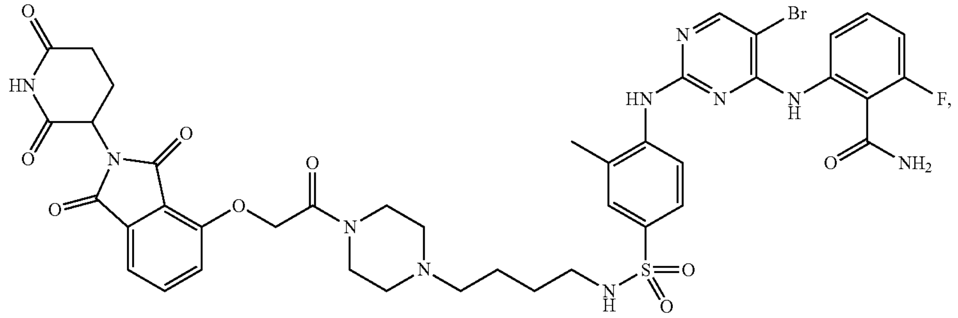

or a pharmaceutically acceptable salt, or stereoisomer thereof.

24. A pharmaceutical composition, comprising a therapeutically effective amount of the bifunctional compound of claim 1, or pharmaceutically acceptable salt or stereoisomer thereof, and a pharmaceutically acceptable carrier.

25. A method of treating cancer, comprising administering to a subject in need thereof a therapeutically effective amount of the bifunctional compound of claim 1, or a pharmaceutically acceptable salt or stereoisomer thereof, wherein the cancer is ovarian cancer or T-cell leukemia.

26. The method of claim 25, wherein the cancer is T-cell leukemia.

27. The method of claim 25, wherein the cancer is ovarian cancer.

* * * * *